US009220788B2

(12) United States Patent
Davis et al.

(10) Patent No.: US 9,220,788 B2
(45) Date of Patent: Dec. 29, 2015

(54) NANOPARTICLE AND POLYMER FORMULATIONS FOR THYROID HORMONE ANALOGS, ANTAGONISTS, AND FORMULATIONS AND USES THEREOF

(75) Inventors: Paul J. Davis, West Sand Lake, NY (US); Faith B. Davis, West Sand Lake, NY (US); Shaker A. Mousa, Wynantskill, NY (US); Gennadi V. Glinksy, Loudonville, NY (US); Aleck Hercbergs, Beechwood, OH (US)

(73) Assignee: NANOPHARMACEUTICALS LLC, Rensselaer, NY (US)

( * ) Notice: Subject to any disclaimer, the term of this patent is extended or adjusted under 35 U.S.C. 154(b) by 0 days.

(21) Appl. No.: 12/816,287

(22) Filed: Jun. 15, 2010

(65) Prior Publication Data

US 2011/0052715 A1 Mar. 3, 2011

Related U.S. Application Data

(60) Provisional application No. 61/187,799, filed on Jun. 17, 2009, provisional application No. 61/219,993, filed on Jun. 24, 2009, provisional application No. 61/222,289, filed on Jul. 1, 2009, provisional application No. 61/237,178, filed on Aug. 26, 2009, provisional application No. 61/327,909, filed on Apr. 26, 2010.

(51) Int. Cl.
| A61K 9/50 | (2006.01) |
| A61K 47/48 | (2006.01) |
| A61K 41/00 | (2006.01) |
| B82Y 5/00 | (2011.01) |

(52) U.S. Cl.
CPC ........... *A61K 47/482* (2013.01); *A61K 41/0038* (2013.01); *A61K 47/4823* (2013.01); *A61K 47/48176* (2013.01); *A61K 47/48215* (2013.01); *A61K 47/48284* (2013.01); *A61K 47/48315* (2013.01); *A61K 47/48915* (2013.01); *B82Y 5/00* (2013.01); *Y10T 428/2982* (2015.01)

(58) Field of Classification Search
CPC .................. A61K 41/0038; A61K 47/48176; A61K 47/482; A61K 47/48215; A61K 47/48284; A61K 47/48315; A61K 47/48915; A61K 47/4823; Y10T 428/2982; B82Y 5/00
See application file for complete search history.

(56) References Cited

U.S. PATENT DOCUMENTS

| 3,625,214 A | 12/1971 | Higuchi |
| 4,205,058 A | 5/1980 | Wagner et al. |
| 4,650,751 A | 3/1987 | Siegel et al. |
| 4,789,734 A | 12/1988 | Pierschbacher |
| 4,801,504 A | 1/1989 | Burdick et al. |
| 4,801,575 A | 1/1989 | Pardridge |
| 4,906,474 A | 3/1990 | Langer et al. |
| 4,925,673 A | 5/1990 | Steiner et al. |
| 4,968,590 A | 11/1990 | Kuberasampath et al. |
| 5,011,486 A | 4/1991 | Aebischer et al. |
| 5,091,513 A | 2/1992 | Huston et al. |
| 5,104,895 A | 4/1992 | Spinelli et al. |
| 5,158,978 A | 10/1992 | Rubin |
| 5,225,204 A | 7/1993 | Chen et al. |
| 5,231,000 A | 7/1993 | Majocha et al. |
| 5,304,121 A | 4/1994 | Sahatjian |
| 5,410,016 A | 4/1995 | Hubbell et al. |
| 5,438,126 A | 8/1995 | DeGroot et al. |
| 5,482,719 A | 1/1996 | Guillet et al. |
| 5,571,840 A | 11/1996 | Mayor et al. |
| 5,591,709 A | 1/1997 | Lindenbaum |
| 5,593,688 A | 1/1997 | Baldeschwieler |
| 5,648,506 A | 7/1997 | Desai et al. |
| 5,766,635 A | 6/1998 | Spenleuhauer et al. |
| 6,139,870 A | 10/2000 | Verrecchia |
| 6,316,412 B1 | 11/2001 | Ginsberg et al. |
| 6,414,037 B1 | 7/2002 | Pezzuto et al. |
| 6,482,406 B1 | 11/2002 | Stewart |
| 6,515,100 B2 | 2/2003 | Harris |
| 6,534,676 B2 | 3/2003 | Morkin et al. |
| 6,596,712 B2 | 7/2003 | Zasloff et al. |
| 6,677,473 B1 | 1/2004 | Madison et al. |
| 6,740,680 B1 | 5/2004 | Danforth, Jr. et al. |
| 6,818,620 B2 | 11/2004 | Bhatnagar |
| 6,821,947 B2 | 11/2004 | Iozzo |
| 6,936,274 B2 | 8/2005 | Hanshew, Jr. |
| 7,166,155 B2 | 1/2007 | Ishikawa |
| 7,358,085 B2 | 4/2008 | Zhang et al. |

(Continued)

FOREIGN PATENT DOCUMENTS

| CA | 2673133 A1 | 11/2008 |
| CN | 1126589 A | 7/1996 |

(Continued)

OTHER PUBLICATIONS

Parveen et al. (J. Drug Targeting, Feb. 2008, 16 (2), 108-123).*
K. Avgoustakis et al. PLGA-mPEG nanoparticles of cisplatin: in vitro nanoparticle degradation, in vitro drug release and in vivo drug residence in blood properties, J. Contr. Rel. 2002, 79, 123-135.*
McCarty et al. "Promises and Pitfalls of Anti-Angiogenic Therapy in Clinical Trials." *Trends Mol. Med.* 9.2(2003):53-58.

(Continued)

*Primary Examiner* — Johann R Richter
*Assistant Examiner* — Genevieve S Alley
(74) *Attorney, Agent, or Firm* — Schmeiser, Olsen & Watts, LLP

(57) ABSTRACT

Disclosed are methods of treating subjects having conditions related to angiogenesis including administering an effective amount of a polymeric nanoparticle form of thyroid hormone agonist, partial agonist or an antagonist thereof, to promote or inhibit angiogenesis in the subject. Nanoparticle forms of thyroid hormone or thyroid hormone analogs as well as uses thereof are also disclosed.

31 Claims, 72 Drawing Sheets

(56) References Cited

U.S. PATENT DOCUMENTS

| | | | |
|---|---|---|---|
| 7,638,558 | B2 | 12/2009 | Brietenkamp et al. |
| 7,785,632 | B2 | 8/2010 | Mousa et al. |
| 7,807,621 | B2 | 10/2010 | Mazar et al. |
| 8,026,209 | B2 | 9/2011 | Gaillard et al. |
| 8,071,134 | B2 | 12/2011 | Mousa et al. |
| 8,242,171 | B2 | 8/2012 | Sinclair et al. |
| 8,518,451 | B2 | 8/2013 | Mousa et al. |
| 8,668,926 | B1 | 3/2014 | Davis et al. |
| 8,802,240 | B2 | 8/2014 | Davis et al. |
| 2001/0021763 | A1 | 9/2001 | Harris |
| 2001/0046521 | A1 | 11/2001 | Zasloff et al. |
| 2002/0049247 | A1 | 4/2002 | Chen |
| 2002/0137676 | A1 | 9/2002 | Hsiang et al. |
| 2002/0151594 | A1 | 10/2002 | Morkin et al. |
| 2003/0027940 | A1 | 2/2003 | Lang et al. |
| 2003/0138557 | A1 | 7/2003 | Allison |
| 2003/0147945 | A1* | 8/2003 | Tardi et al. .................... 424/450 |
| 2003/0157098 | A1 | 8/2003 | Laug |
| 2003/0162758 | A1 | 8/2003 | Schwartz et al. |
| 2003/0165576 | A1 | 9/2003 | Fujii et al. |
| 2004/0013728 | A1 | 1/2004 | Oh et al. |
| 2004/0033259 | A1 | 2/2004 | Hanshew et al. |
| 2005/0124862 | A1 | 6/2005 | Mousa et al. |
| 2005/0158376 | A1 | 7/2005 | Sardi et al. |
| 2005/0171027 | A1 | 8/2005 | Sinclair et al. |
| 2005/0222387 | A1 | 10/2005 | Debatin et al. |
| 2005/0249721 | A1 | 11/2005 | Houston et al. |
| 2005/0272817 | A1 | 12/2005 | Heino |
| 2006/0166303 | A1 | 7/2006 | Spanuth |
| 2006/0210539 | A1 | 9/2006 | Zhang et al. |
| 2007/0117841 | A1 | 5/2007 | Ozes et al. |
| 2007/0190160 | A1 | 8/2007 | Turos et al. |
| 2008/0124280 | A1 | 5/2008 | Mousa et al. |
| 2008/0193377 | A1 | 8/2008 | Line et al. |
| 2009/0022806 | A1 | 1/2009 | Mousa et al. |
| 2009/0175862 | A1 | 7/2009 | Silverio et al. |
| 2010/0112079 | A1 | 5/2010 | Mousa et al. |
| 2010/0159021 | A1 | 6/2010 | Davis et al. |
| 2010/0209382 | A1 | 8/2010 | Alexander-Bridges et al. |
| 2010/0255108 | A1 | 10/2010 | Lin et al. |
| 2011/0052715 | A1 | 3/2011 | Davis et al. |
| 2011/0142941 | A1 | 6/2011 | Davis et al. |
| 2012/0258069 | A1 | 10/2012 | Alexander-Bridges et al. |
| 2012/0315320 | A1 | 12/2012 | Davis et al. |
| 2014/0072635 | A1 | 3/2014 | Mousa et al. |
| 2014/0072646 | A1 | 3/2014 | Mousa et al. |
| 2014/0199375 | A1 | 7/2014 | Mousa et al. |

FOREIGN PATENT DOCUMENTS

| | | | |
|---|---|---|---|
| WO | 9500135 | | 1/1995 |
| WO | WO-9500135 | A1 | 1/1995 |
| WO | 9640048 | | 12/1996 |
| WO | WO-9640048 | A2 | 12/1996 |
| WO | 9833942 | | 8/1998 |
| WO | WO-9833942 | A1 | 8/1998 |
| WO | 9856771 | | 12/1998 |
| WO | WO-9856771 | A2 | 12/1998 |
| WO | 9958119 | A1 | 11/1999 |
| WO | 9962549 | | 12/1999 |
| WO | WO-9962549 | A1 | 12/1999 |
| WO | 0064431 | A1 | 11/2000 |
| WO | WO-0064431 | A1 | 11/2000 |
| WO | 0078815 | A1 | 12/2000 |
| WO | WO-0078815 | A1 | 12/2000 |
| WO | WO-0113031 | A2 | 2/2001 |
| WO | 0113936 | A1 | 3/2001 |
| WO | WO-0113936 | A1 | 3/2001 |
| WO | 0176589 | A1 | 10/2001 |
| WO | 0203914 | A2 | 1/2002 |
| WO | WO-0203914 | A2 | 1/2002 |
| WO | 0249501 | A2 | 6/2002 |
| WO | WO-0249501 | A2 | 6/2002 |
| WO | 02060389 | A2 | 8/2002 |
| WO | WO-02060389 | A2 | 8/2002 |
| WO | 03075741 | A2 | 9/2003 |
| WO | WO-03075741 | A2 | 9/2003 |
| WO | 2004013728 | A2 | 2/2004 |
| WO | 2004069201 | A2 | 8/2004 |
| WO | 2005027895 | A2 | 3/2005 |
| WO | WO-2005027895 | A2 | 3/2005 |
| WO | 2006003014 | A2 | 1/2006 |
| WO | WO-2006003014 | A2 | 1/2006 |
| WO | 2006031922 | A2 | 3/2006 |
| WO | WO-2006031922 | A2 | 3/2006 |
| WO | 2007035612 | A2 | 3/2007 |
| WO | WO 2008/051291 | * | 5/2008 |
| WO | WO-2008051291 | A2 | 5/2008 |
| WO | 2008140507 | A2 | 11/2008 |
| WO | WO 2008/014507 | * | 11/2008 |
| WO | WO-2008140507 | A2 | 11/2008 |
| WO | 2010120506 | A1 | 10/2010 |
| WO | 2010148007 | A2 | 12/2010 |

OTHER PUBLICATIONS

Nickoloff et al. "Aberrant Production of Interleukin-8 and Thrombospondin-1 by Psoriatic Keratinocytes Mediates Angiogenesis." *Am. J. Pathol.* 144.4(1994):820-828.

Thompson et al. "The Clinical Manipulation of Angiogenesis: Pathology, Side-Effects, Surprises, and Opportunities with Novel Human Therapies." *J. Pathol.* 190(2000):330-337.

Velasco et al. "Dermatological Aspects of Angiogenesis." *Brit. J. Dermatol.* 147(2002):841-852.

Glinskii et al., "Modification of survival pathway gene expression in human breast cancer cells by tetraiodothyroacetic acid (tetrac)", *Cell Cycle*, 8(21):3562-3570 (2009).

Yalcin et al., "Tetraiodothyroacetic Acid (Tetrac) and Nanoparticulate Tetrac Arrest Growth of Medullary Carcinoma of the Thyroid", *J. Clin. Endocrinol. Metab.*, 95(4):1972-1980 (2010).

Igarashi et al. "Techniques Supporting Angiogenesis Therapy 2: DDS Technique Supporting Regenerative Medicine." *Inflamm. Immun.* 10.6(2002):652-658.

Kobayashi et al. "Drug Delivery Catheter." *Surg. Front.* 9.1(2002):55-57.

Office Action (Mail Date Feb. 25, 2014) for U.S. Appl. No. 13/156,047, filed Jun. 8, 2011.

Office Action (Mail Date Mar. 12, 2014) for U.S. Appl. No. 12/947,389, filed Nov. 16, 2010.

Notice of Allowance (Mail Date Feb. 6, 2014) for U.S. Appl. No. 13/345,194, filed Jan. 6, 2012.

A.D.A.M. Medical Encyclopedia, www.ncbi.nlm.nih.gov/pubmedhealth/PMH0001308/, downloaded Jul. 12, 2012. 6 pages.

Application No. PCT/US2005/032813, International Search Report dated Dec. 22, 2006. 6 pages.

Application No. PCT/US2007/009026, International Search Report dated Nov. 7, 2008. 5 pages.

Application No. PCT/US2009/069104, International Search Report dated Mar. 4, 2010 5 pages.

Application No. PCT/US2007/026167, International Search Report dated Oct. 30, 2008. 3 pages.

Application No. PCT/US2010/038700, International Search Report dated Mar. 21, 2011. 4 pages.

Application No. PCT/US2006/036243, International Search Report dated Jul. 30, 2007. 7 pages.

Application No. PCT/US2010/029371, International Search Report dated Aug. 24, 2010. 5 pages.

Balestrazzi et al., "Leaf-associated bacteria from transgenic white poplar producing resveratrol-like compounds: isolation, molecular characterization, and evaluation of oxidative stress tolerance", Can. J. Microbiol., 55:829-840 (2009) 12 pages.

Balin-Gauthier et al., "In vivo and in vitro antitumor activity of oxaliplatin in combination with cetuximab in human colorectal tumor cell lines expressing different level of EGFR", Cancer Chemother. Pharmacol., 57:709-718 (2006) 8 pages.

Baur et al., "Resveratrol improves health and survival of mice on a high-calorie diet", Nature, 444:337-342 (2006) 6 pages.

(56) References Cited

OTHER PUBLICATIONS

Baur et al., "Therapeutic potential of resveratrol: the in vivo evidence", Nat. Rev. Drug Discov., 5:493-506 (2006) 14 pages.
Bergstrom et al., "Iodine-123 labelled Z-(R,R)-IQNP: a potential radioligand for visualization of M1 and M2 muscarinic acetylcholine receptors in Alzheimer's disease", Eur. J. Nucl. Med., 26(11):1482-1485 (1999).
Beum et al., "Binding of Rituximab, Trastuzumab, Cetuximab, or mAb T101 to Cancer Cells Promotes Trogocytosis Mediated by THP-1 Cells and Monocytes", J. Immunol., 181:8120-8132 (2008) 13 pages.
Bokemeyer et al., "Fluorouracil, Leucovorin, and Oxaliplatin With and Without Cetuximab in the First-Line Treatment of Metastatic Colorectal Cancer", J. Clin. Oncol., 27(5):663-671 (2009) 9 pages.
Brachmann et al., "The SIR2 gene family, conserved from bacteria to humans, functions in silencing, cell cycle progression, and chromosome stability", Genes Dev. 9:2888-2902 (1995) 15 pages.
Brockhoff et al., "Differential impact of Cetuximab, Pertuzumab and Trastuzumab on BT474 and SK-BR-3 breast cancer proliferation", Cell Prolif., 40:488-507 (2007) 20 pages.
Bulitta et al., "Development and Qualification of a Pharmacodynamic Model for the Pronounced Inoculum Effect of Ceftazidime against Pseudomonas aeruginosa", Antimicrob. Agents Chemother., 53(1):46-56 (2009) 11 pages.
D'Arezzo et al., "Rapid Nongenomic Effects of 3,5,3'-Triiodo-L Thyronine on the Intracellular pH of L-6 Myoblasts are Mediated by Intracellular Calcium Mobilization and Kinase Pathways", Endocrinol., 145(12):5694-5703 (2004) 10 pages.
Database BIOSIS [Online] Bioscience Information Service, Philadelphia, PA, US; Nov. 16, 2003, Mousa et al., "Discovery of pro-angiogenic effects of thyroid hormone and analogs", Accession No. PREV200400161659 (Abstract).
Davis et al., "Cell-surface receptor for thyroid hormone and tumor cell proliferation", Expert Reviews in Endicrinology and Metabolism, 1(6):753-761 (2006) 10 pages.
Davis et al., "Translational implications of nongenomic actions of thyroid hormone initiated at its integrin receptor", Am. J. Physiol. Endocrinol. Metab., 297:E1238-E1246 (2009) 9 pages.
Drusano et al., "Pharmacodynamics of Abacavir in an In Vitro Hollow-Fiber Model System", Antimicrob. Agents Chemother., 46(2):464-470 (2002) 7 pages.
Frye, R.A., "Characterization of Five Human cDNAs with Homonology to the Yeast SIR2. Gene: Sir2-like Proteins (Sirtuins) Metabolize NAD and May Have Protein ADP-Ribosyltransferase Activity", Biochem. Biophys. Res. Comm., 260:273-279 (1999) 7 pages.
Fujii et al., "Crystal Structure of Trimestatin, a Disintegrin Containing a Cell Adhesion Recognition Motif RGD", J. Mol. Biol., 332:1115-1122 (2003) 8 pages.
GenBank Accession No. AF083106, Apr. 14, 2000 5 pages.
GenBank Accession No. AF083107, Mar. 21, 2001. 3 pages.
GenBank Accession No. NM_012238, Apr. 25, 2010. 8 pages.
GenBank Accession No. NM_030593, Mar. 14, 2010. 8 pages.
GenBank Accession No. NP_036370, Apr. 25, 2010. 6 pages.
GenBank Accession No. NP_501912, Nov. 13, 2008. 4 pages.
GenBank Accession No. P53685, Apr. 20, 2010. 8 pages.
Grant, D.B., "Monitoring TSH concentrations during treatment for gongenital hypothyroidism", Arch. Disease Childhood, 66:669-670 (1991) 2 pages.
Office Action (Mail Date Sep. 4, 2014) for U.S. Appl. No. 12/947,389, filed Nov. 16, 2010.
Office Action (Mail Date Oct. 16, 2014) for U.S. Appl. No. 12/644,493, filed Dec. 22, 2009.
Office Action (Mail Date Jul. 13, 2012) for U.S. Appl. No. 12/751,375, filed Mar. 31, 2010.
Abdollahi et al., "Inhibition of $\alpha v \beta 3$ Integrin Survival Signaling Enhances Antiangiogenic and Antitumor Effects of Radiotherapy", Clin. Cancer Res., 11 (17):6270-6279 (2005).

Albert et al., "Integrin $\alpha v \beta 3$ Antagonist Cilengitide Enhances Efficacy of Radiotherapy in Endothelial Cell and Non-Small-Cell Lung Cancer Models", Int. J. Radial. Oncol. Biol. Phys., 65(5):1536-1543 (2006).
Alexis et al., "Nonocclusive Common Carotid Artery Thrombosis in the Rat Results in Reversible Sensorimotor and Cognitive Behavioral Deficits", Stroke, 26:2338-2346 (1995).
Ali et al., "Angiogenesis as a potential biomarker in prostate cancer chemoprevention trials", Urology, 57(Suppl 4A):143-147 (2001).
Ali et al., "Apoptosis-inducing effect of erlotinib is potentiated by 3,3'-diindolylmethane in vitro and in vivo using an orthotopic model of pancreatic cancer", Mol. Cancer Ther., 7(6):1708-1719 (2008).
Ali et al., "High levels of oestrogen receptor-$\alpha$ in tumorigenesis: inhibition of cell growth and angiogenic factors", Cell Prolif., 34(4):223-231 (2001).
Allen, A.R., "Surgery of experimental lesion of spinal cord equivalent to crush injury of fracture dislocation of spinal column", J. Am. Med. Assoc., 57(11):878-880 (1911).
Almog et al., "Transcriptional Switch of Dormant Tumors to Fast-Growing Angiogenic Phenotype", Cancer Res., 69(3):836-844 (2009).
Amirkhosravi et al., "Antimetastatic effect of tinzaparin, a low-molecular-weight heparin", J. Thromb. Haemost., 1:1972-1976 (2003).
Amirkhosravi et al., "Inhibition of tumor cell-induced platelet aggregation and lung metastasis by the oral GpIIb/IIIa antagonist XV454", J. Thrombosis Haemost., 90:549-554 (2003).
Ando et al., "Induction by carbon-ion irradiation of the expression of vascular endothelial growth factor in lung carcinoma cells", Int. J. Radiat. Biol., 76(8):1121-1127 (2000).
Audus et al., "Bovine Brain Microvessel Endothelial Cell Monolayers as a Model System for the Blood-Brain Barrier", in Biological Approaches to the Controlled Delivery of Drugs, Ann. N.Y. Acad. Sci., 507:9-18 (1987).
Avis, K.E., "Parenteral Preparations", in Remington's Pharmaceutical Sciences, 15$^{th}$ Ed., Ch. 84, Mack Publishing Co., Easton, Pennsylvania, pp. 1461-1487 (1975).
Bederson et al., "Rat Middle Cerebral Artery Occlusion: Evaluation of the Model and Development of a Neurologic Examination", Stroke, 17 (3):472-476 (1986).
Belenky et al., "NAD$^+$ metabolism in health and disease", Trends Biochem. Sci., 32(1):12-19 (2007).
Ben-Hur et al., "Thermally Enhanced Radioresponse of Cultured Chinese Hamster Cells: Inhibition of Repair of Sublethal Damage and Enhancement of Lethal Damage", Radiat Res., 58:38-51 (1974).
Benedetti et al., "Life Tables and Survivor Functions", in BMDP Statistical Software Manual, BMDP Statistical Software, Inc. vol. 2, p. 573 and 689-718 (1988).
Bennett et al., "A peptide derived from $\alpha$-fetoprotein prevents the growth of estrogen-dependent human breast cancers sensitive and resistant to tamoxifen", Proc. Natl. Acad. Sci. USA, 99(4):2211-2215 (2002).
Bergers et al., "Modes of resistance to anti-angiogenic therapy", Nat. Rev. Cancer, 8(8):592-603 (2008).
Bergh et al., "Integrin $\alpha v \beta 3$ Contains a Cell Surface Receptor Site for Thyroid Hormone that is Linked to Activation of Mitogen-Activated Protein Kinase and Induction of Angiogenesis", Endocrinology, 146(7):2864-2871 (2005).
Bergstrom et al., "Iodine-123 labelled Z-(R,R)-IQNP: a potential radioligand for visualization of $M_1$ and $M_2$ muscarinic acetylcholine receptors in Alzheimer's disease", Eur. J. Nucl. Med., 26(11):1482-1485 (1999).
Bergstrom et al., "Reduction of fibrinogen adsorption on PEG-coated polystyrene surfaces", J. Biomed. Mat. Res., 26:779-790 (1992).
Bhat et al., "NCAM-180, the largest component of the neural cell adhesion molecule, is reduced in dysmyelinating quaking mutant mouse brain", Brain Res., 452:373-377 (1988).
Blaszczyk-Thurin et al., "An Experimental Vaccine Expressing Wild-Type p53 Induces Protective Immunity Against Glioblastoma Cells with High Levels of Endogenous p53", Scand. J. Immunol., 56:361-375 (2002).
Blight, A.R., "Macrophages and Inflammatory Damage in Spinal Cord Injury", J. Neurotrauma, 9(Suppl. 1):S83-S91 (1992).

(56) References Cited

OTHER PUBLICATIONS

Blood et al., "Tumor interactions with the vasculature: angiogenesis and tumor metastasis", *Bioch. Biophys. Acta*, 1032:89-118 (1990).
Bornebroek et al., "Potential for imaging cerebral amyloid deposits using $^{123}$I-labelled serum amyloid P component and SPET", *Nucl. Med. Commun.*, 17:929-933 (1996).
Bozarth et al., "An improved method for the quantitation of cellular migration: Role of αvβ3 integrin in endothelial and smooth muscle cell migration", *Meth. Cell Sci.*, 19(3):179-187 (1997).
Braughler et al., "Involvement of Lipid Peroxidation in CNS Injury", *J. Neurotrauma*, 9(Suppl. 1):S1-S7 (1992).
Breier et al., "The role of vascular endothelial growth factor in blood vessel formation", *Trends Cell Biol.*, 6:454-456 (1996).
Bridoux et al., "Semisynthesis and pharmacological activities of Tetrac analogs: Angiogenesis modulators", *Bioorg. Med. Chem. Lett.*, 19:3259-3263 (2009).
Bridoux et al., "Semisynthesis and pharmacological activities of thyroxine analogs: Development of new angiogenesis modulators", *Bioorg. Med. Chem. Lett.*, 20(11):3394-3398 (2010).
Brooks et al., "Antiintegrin αvβ3 blocks human breast cancer growth and angiogenesis in human skin", *J. Clin. Invest.*, 96(4):1815-1822 (1995).
Burgman et al., "Effect of Inhibitors of Poly(ADP-Ribose)Polymerase on the Radiation Response of HeLa S3 Cells", *Radiat. Res.*, 119:380-386 (1989).
Carmeliet et al., "Molecular Basis of Angiogenesis Role of VEGF and VE-Cadherin", *Ann. N.Y. Acad. Sci.*, 902:249-264 (2000).
Chanoine et al., "The role of transthyretin in the transport of thyroid hormone to cerebrospinal fluid and brain", *Acta Medica Austriaca*, 19(Suppl. 1):25-28 (1992).
Charness et al., "Ethanol Increases the Expression of Functional Delta-Opioid Receptors in Neuroblastoma x Glioma NG108-15 Hybrid Cells", *J. Biol. Chem.*, 261(7):3164-3169 (1986).
Charo et al., "The Vitronectin Receptor αvβ3 Binds Fibronectin and Acts in Concert with $α_5 β_1$ in Promoting Cellular Attachment and Spreading on Fibronectin", *J. Cell Biol.*, 111(6 Pt. 1):2795-2800 (1990).
Chase et al., "Principles of Radioisotope Methodology", 2nd Ed., Minneapolis, MN. Burgess Publ. Co., 1962, pp. 68, 87-90.
Chavakis et al., "Kinetics of integrin expression in the mouse model of proliferative retinopathy and success of secondary intervention with cyclic RGD peptides", *Diabetologia*, 45:262-267 (2002).
Cheng et al., "Molecular Aspects of Thyroid Hormone Actions", *Endocri. Rev.*, 31(2):139-170 (2010).
Cheresh et al., "Biosynthetic and Functional Properties of an Arg-Gly-Asp-directed Receptor Involved in Human Melanoma Cell Attachment to Vitronectin, Fibrinogen and von Willibrand Factor", *J. Biol. Chem.*, 262(36):17703-17711 (1987).
Cheresh, D. A., "Human endothelial cells synthesize and express an Arg-Gly-Asp-directed adhesion receptor involved in attachment to fibrinogen and von Willibrand factor", *Proc. Natl. Acad. Sci. U.S.A.*, 84:6471-6475 (1987).
Chiarugi et al., "*Anoikis*: A necessary death program for anchorage-dependent cells", *Biochem. Pharmacol.*, 76:1352-1364 (2008).
Chinese Office Action for Application No. 2004800331846 dated Mar. 5, 2010.
Chinese Office Action for Application No. 2004800331846, mailed Nov. 30, 2007, cites CN 1126589.
Clifton et al., "Marked Protection by Moderate Hypothermia After Experimental Traumatic Brain Injury", *J. Cereb. Blood Flow Metab.*, 11(1):114-121 (1991).
Cody et al., "Molecular modeling of the thyroid hormone interactions with αvβ3 integrin", *Steroids*, 72:165-170 (2007).
Cohen-Jonathan et al., "αvβ3 Integrin pathway controls glioma radioresistance through ILK", *Proc. Amer. Assoc. Cancer Res.*, 47:5180 (2006) (Abstract Only).
Cohen-Jonathan et al., "Radioresistance Induced by the High Molecular Forms of the Basic Fibroblast Growth Factor is Associated with an Increased $G_2$ Delay and a Hyperphosphorylation of $p34^{CDC2}$ in HeLa Cells", *Cancer Res.*, 57:1364-1370 (1997).

Cox et al., "The repair of potentially lethal damage in X-irradiated cultures of normal and ataxia telangiectasia human fibroblasts", *Int. J. Radiat. Biol.*, 39(4):357-365 (1981).
Cristofanilli et al., "Thyroid Hormone and Breast Carcinoma. Primary Hypothyroidism is Associated with a Reduced Incidence of Primary Breast Carcinoma", *Cancer*, 103(6)1122-1128 (2005).
Davis et a., "Promotion by thyroid hormone of cytoplasm-to-nucleus shuttling of thyroid hormone receptors", *Steroids*, 73:1013-1017 (2008).
Davis et al., "Acting via a Cell Surface Receptor, Thyroid Hormone is a Growth Factor for Glioma cells", *Cancer Res.*, 66(14):7270-7275 (2006).
Davis et al., "Mechanisms of nongenomic actions of thyroid hormone", *Frontiers Neuroendocrinol.*, 29:211-218 (2008).
Davis et al., "Proangiogenic Action of Thyroid Hormone is Fibroblast Growth Factor-Dependent and is Initiated at the Cell Surface", *Circ. Res.*, 94:1500-1506 (2004).
Davis et al., "Thyroxine Promotes Association of Mitogen-activated Protein Kinase and Nuclear Thyroid Hormone Receptor (TR) and Causes Serine Phosphorylation of TR", *J. Biol. Chem.*, 275(48):38032-38039 (2000).
De la Cruz et al., "Effect of Aspirin Plus Dipyridamole on the Retinal Vascular Pattern in Experimental Diabetes Mellitus", *J. Pharmacol. Exp. Ther.*, 280(1):454-459 (1997).
De Ryck et al., "Neocortical localization of tactile/proprioceptive limb placing reactions in the rat", *Brain Res.*, 573(1):44-60 (1992).
Deardorff, D.L., "Isotonic Solutions", in *Remington's Pharmaceutical Sciences*, $15_{th}$ Ed., Chapter 79, Mack Publishing Co., Easton, pp. 1405-1412 (1975).
DeFesi et al., "3,5,3'—Triiodothyronine Effects on the Growth Rate and Cell Cycle of Cultured GC Cells", *Endocrinol.*, 108(1):259-267 (1981).
Demediuk et al., "Traumatic Spinal Cord Injury in Rats Causes Increases in Tissue Thromboxane But Not Peptidoleukotrienes", *J. Neurosci. Res.*, 20:115-121 (1988).
Di Chiro et al., "Glucose utilization of cerebral gliomas measured by [$^{18}$F] fluorodeoxyglucose and positron emission tomography", *Neurol.*, 32:1323-1329 (1982).
Dietrich et al., "Post-traumatic brain hypothermia reduces histopathological damage following concussive brain injury in the rat", *Acta Neuropathol.*, 87(3):250-258 (1994).
Ding et al., "Radioprotection of Hematopoietic Tissue by Fibroblast Growth Factors in Fractionated Radiation Experiments", *Acta Oncol.*, 36(3):337-340 (1997).
Dixon et al., "A fluid percussion model of experimental brain injury in the rat", *J. Neurosurg.*, 67(1):110-119 (1987).
Dupont et al., "Antiangiogenic and antimetastatic properties of Neovastat (Æ-941), an orally active extract derived from cartilage tissue", *Clin. Exp. Metastasis*, 19:145-153 (2002).
Edwards et al., "Trypsinized BHK21 cells aggregate in the presence of metabolic inhibitors and in the absence of divalent cations", *J. Cell Sci.*, 19(3):653-667 (1975).
Elkind et al., "Radiation Response of Mammalian Cells Grown in Culture. I. Repair of X-Ray Damage in Surviving Chinese Hamster Cells", *Radiat. Res.*, 13:556-593 (1960).
Elvin et al., "Cell Adhesiveness and the Cell Cycle: Correlation in Synchronized Balb/c 3T3 Cells", *Biol. Cell*, 48:1-10 (1983).
Ely and Berne, "Protective Effects of Adenosine in Myocardial Ischemia", *Circulation*, 85:893-904 (1992).
Ethier et al., "Adenosine stimulates proliferation of human endothelial cells in culture", *Am. J. Physiol.*, 265:H31-H138 (1993).
Everts et al., "Uptake of 3,3',5,5'-Tetraiodothyroacetic Acid and 3,3',5'-Triiodothyronine in Cultured Rat Anterior Pituitary Cells and Their Effects on Thyrotropin Secretion", *Endocrinol.*, 136(10):4454-4461 (1995).
Faden et al., "Endogenous Opioid Immunoreactivity in Rat Spinal Cord Following Traumatic Injury", *Ann. Neurol.*, 17(4):386-390 (1985).
Faden, A.I., "Experimental Neurobiology of Central Nervous System Trauma", *Crit. Rev. Neurobiol.*, 7(3/4):175-186 (1993).

(56) References Cited

OTHER PUBLICATIONS

Feeney et al., "Amphetamine, Haloperidol, and Experience Interact to Affect Rate of Recovery After Motor Cortex Injury", *Science*, 217(4562):855-857 (1982).
Fei et al., "P53 and radiation responses", *Oncogene*, 22:5774-5783 (2003).
Felding-Habermann et al., "Integrin activation controls metastasis in human breast cancer", *Proc. Natl. Acad. Sci. U.S.A.*, 98(4):1853-1858 (2001).
Feng et al., "Fibrin and Collagen Differentially Regulate Human Dermal Microvascular Endothelial Cell Integrins: Stabilization of $\alpha v/\beta 3$ mRNA by Fibrin", *J. Invest. Dermatol.*, 113(6):913-919 (1999).
Fife et al., "Effects of tetracyclines on angiogenesis in vitro", *Cancer Lett.*, 153:75-78 (2000).
Folkman, J., "Angiogenesis in cancer, vascular, rheumatoid and other disease", *Nat. Med.*, 1(1):27-31 (1995).
Freese et al., "Characterization and mechanism of glutamate neurotoxicity in primary striatal cultures", *Brain Res.*, 521(1/2):254-264 (1990).
Gavrieli et al., "Identification of Programmed Cell Death In Situ via Specific Labeling of Nuclear DNA Fragmentation", *J. Cell. Biol.*, 119(3):493-501 (1992).
GenBank Accession No. NM_002210, Jun. 15, 2008.
Geng et al., "A Specific Antagonist of the p110δ Catalytic Component of Phosphatidylinositol 3'-Kinase, IC486068, Enhances Radiation-Induced Tumor Vascular Destruction", *Cancer Res.*, 64:4893-4899 (2004).
Ginis et al., "Hypoxia affects tumor cell invasiveness in vitro: the role of hypoxia-activated ligand HAL1/13 (Ku 86 autoantigen)", *Cancer Lett.*, 154:163-174 (2000).
Gladson, C. L., "Expression of Integrin $\alpha v\beta 3$ in Small Blood Vessels of Glioblastoma Tumors", *J. Neuropath. Exp. Neurol.*, 55(11):1143-1149 (1996).
Glinsky et al., "Classification of Human Breast Cancer Using Gene Expression Profiling as a Component of the Survival Predictor Algorithm", *Clin. Cancer Res.*, 10:2272-2283 (2004).
Glinsky et al., "Gene expression profiling predicts clinical outcome of prostate cancer", *J. Clin. Invest.*, 113(6):913-923 (2004).
Glinsky et al., "Microarray analysis identifies a death-from-cancer signature predicting therapy failure in patients with multiple types of cancer", *J. Clin. Invest.*, 115(6):1503-1521 (2005).
Glinsky et al., "Microarray Analysis of Xenograft-Derived Cancer Cell Lines Representing Multiple Experimental Models of Human Prostate Cancer", *Mol Carcinog.*, 37:209-221 (2003).
Goldstein et al., "Influence of Lesion Size and Location on Amphetamine-Facilitated Recovery of Beam-Walking in Rats", *Behav. Neurosci.*, 104(2):320-327 (1990).
Goldstein, A., "Estimating the Error Variance and the Confidence Interval for a Regression Line", in *Biostatistics*, The MacMillan Co., New York, pp. 139-146 (1964).
Goodman, M.M., "Automated Synthesis of Radiotracers for PET Applications", in *Clinical Positron Emission Tomography*, Mosby Yearbook, K.F. Hubner et al., Chapter 14, pp. 110-122 (1992).
Grant, D.B., "Monitoring TSH concentrations during treatment for congenital hypothyroidism", *Arch. Disease Childhood*, 66:669-670 (1991).
Gregoriadis, G., "Lipsomes", in *Drug Carriers in Biology and Medicine*, Academic Press, Ch. 14, pp. 287-341 (1979).
Guigon et al., "Regulation of β-Catenin by a Novel Nongenomic Action of Thyroid Hormone β Receptor", *Mol. Cell. Biol.*, 28(14):4598-4608 (2008).
Hahn et al., "Plateau-phase cultures of mammalian cells: An in vitro model for human cancer", *Curr. Top. Radiat. Res. Q.*, 8:39-83 (1972).
Halks-Miller et al., "CCR1 Immunoreactivity in Alzheimer's Disease Brains", *Society for Neuroscience Meeting*, 24:787.6 (1998) (Abstract Only).

Hansebout, R. R., "A Comprehensive Review of Methods of Improving Cord Recovery After Acute Spinal Cord Injury", in *Early Management of Acute Spinal Cord Injury*, Tator, Ed., Raven Press, New York, pp. 181-196 (1982).
Hartert, H., "Blutgerinnungsstudien Mit Der Thrombelastogeraphie, Einem Neuen Untersuchungsverfahren", *Klinische Wochenschrift*, 26(37/38):577-583 (1948) (German Language Only).
Heller et al., "Inhibition of potentially lethal damage recovery by altered pH, glucose utilization and proliferation in plateau growth phase human glioma cells", *Int. J. Radiat. Biol.*, 66(1):41-47 (1994).
Hercbergs et al., "GL261 brain tumor cells: responses to single or fractionated x-irradiation with the $\alpha v\beta 3$ integrin tyroxine receptor antag-onist tetrac (tetraiodothyroacetic acid)", 20th EORTC-NCI-AACR Symposium on Molecular Targets and Cancer Therapeutics, Geneva, Switzerland, Oct. 2008.
Hercbergs et al., "GL261 brain tumor cells: responses to single or fractionated x-irradiation with the $\alpha v\beta 3$ integrin tyroxine receptor antag-onist tetras (tetraiodothyroacetic acid)", *Eur. J. Cancer*, 6(12):172 (Abstract Only), Oct. 2008.
Hercbergs et al., "Propylthiouracil-induced Chemical Hypothyroidism with High-Dose Tamoxifen Prolongs Survival in Recurrent High Grade Glioma: A Phase I/II Study", *Anticancer Res.*, 23:617-626 (2003).
Hercbergs, A., "The Thyroid Gland as an Intrinsic Biologic Response-Modifier in Advanced Neoplasia—A Novel Paradigm", *in vivo*, 10:245-247 (1996).
Hermanson, "Modification with Synthetic Polymers", in *Bioconjugate Tech.*, Ch. 15, Academic Press, San Diego, CA, pp. 617-618 (1996).
Hoff et al., "Medullary Thyroid Carcinoma", *Hematol. Oncol. Clin. North Am.*, 21(3):475-488 (2007).
Horuk et al., "Expression of Chemokine Receptors by Subsets of Neurons in the Central Nervous System", *J. Immunol.*, 158:2882-2890 (1997).
Hubner, K. F., "University of Tennessee Biomedical Imaging Center and Transfer of Technology to the Clinical Floor", in *Clinical Positron Emission Tomography*, Mosby Yearbook, K.F. Hubner et al., pp. 4-16 (1992).
Hudlicka et al., "Factors involved in capillary growth in the heart", *Mol. Cell. Biochem.*, 147:57-68 (1995).
Illario et al., "Fibronectin-Induced Proliferation in Thyroid Cells is Mediated by $\alpha v\beta 3$ Integrin through Ras/Raf-1/MEK/ERK and Calcium/CaMKII Signals", *J. Clin. Endocrinol. Metab.*, 90(5):2865-2873 (2005).
Ingerman-Wojenski et al., "Evaluation of electrical aggregometry: comparison with optical aggregometry, secretion of ATP, and accumulation of radiolabeled platelets", *J. Lab. Clin. Med.*, 101(1):44-52 (1983).
International Search Report for PCT/US2004/030583, mailing date Mar. 7, 2005.
Iwata et al., "A new, convenient method for the preparation of 4-[18F]fluorobenzyl halides", *Applied Radiation and Isotopes*, 52(1):87-92 (2000).
Jain, K. K., "Strategies and technologies for drug delivery systems", *TIPS*, 19:155-157 (1998).
Janssen et al., "Pathogenesis of Spinal Cord Injury and Newer Treatments—A Review", *Spine*, 14(1):23-32 (1989).
Jeffrey et al., "The preparation and characterisation of poly(lactide—co—glycolide) microparticles. 1. Oil-in-water emulsion solvent evaporation", *Int. J. Pharm.*, 77:169-175 (1991).
Jordan et al., "Thyroid Status is a Key Modulator of Tumor Oxygenation: Implication for Radiation Therapy", *Radiat. Res.*, 168:428-432 (2007).
Kapiszewska et al., "The Effects of Reduced Temperature and/or Starvation Conditions on the Radiosensitivity and Repair of Potentially Lethal Damage and Sublethal Damage in L5178Y-R and L5178Y-S Cells", *Radiat Res.*, 113:458-472 (1988).
Kastan et al., "A Mammalian Cell Cycle Checkpoint Pathway Utilizing p53 and *GADD45* is Defective in Ataxia-Telangiectasia", *Cell*, 71:587-597 (1992).
Kerr et al., "Novel Small Molecule αv Integrin Antagonists: Comparative Anti-Cancer Efficacy with Known Angiogenesis Inhibitors", *Anticancer Res.*, 19:959-968 (1999).

(56) References Cited

OTHER PUBLICATIONS

Kerr et al., "Small molecule αv integrin antagonists: novel anticancer agents", *Exp. Opin. Invest. Drugs*, 9(6):1271-1279 (2000).
Kim et al., "Regulation of Angiogenesis in Vivo, by Ligation of Integrin α5 β1 with the Central Cell-Binding Domain of Fibronectin", *Am. J. Pathol.*, 156(4):1345-1362 (2000).
Kimelberg, H.K., "Astrocytic Edema in CNS Trauma", *J. Neurotrauma*, 9(Suppl. 1):S71-S81 (1992).
Kitevska et al., "Caspase-2: controversial killer or checkpoint controller?", *Apoptosis*, 14:829-848 (2009).
Kleczkowska et al., "Differential poly(ADP-ribose) metabolism in repair-proficient and repair-deficient murine lymphoma cells", *Mut. Res.*, 235:93-99 (1990).
Klunk et al., "Development of Small Molecule Probes for the Beta-Amyloid Protein of Alzheimer's Disease", *Neurobiol. Aging*, 15(6):691-698 (1994).
Koyama et al., "Recent Status and Future Perspectives in Therapeutic Angiogenesis", *Prog. Med.*, 22(12):3070-3076 (2002) (English Abstract Only).
Kramer et al., "Human Microvascular Endothelial Cells Use $\beta_1$ and $\beta_3$ Integrin Receptor Complexes to Attach to Laminin", *J. Cell Biol.*, 111:1233-1243 (1990).
Kumar et al., "Enhancing Effect of Thyroxine on Tumor Growth and Metastases in Syngeneic Mouse Tumor Systems", *Cancer Res.*, 39:3515-3518 (1979).
Kuroki et al., "Diabetic retinopathy—The mechanisms of the ocular neovascularization and the development of anti-angiogenic drugs-", *Nippon Rinsho*, 57(3):584-589 (1999) (English Abstract Only).
Kwok et al., "Differences in EGF related radiosensitisation of human squamous carcinoma cells with high and low numbers of EGF receptors", *Br. J. Cancer*, 64:251-254 (1991).
Lawler et al., "Cell Attachment to Thombospondin: The Role of ARG—GLY—ASP, Calcium and Integrin Receptors", *J. Cell Biol.*, 107(6 Pt. 1):2351-2361 (1988).
Letterio et al., "Maternal Rescue of Transforming Growth Factor-β1 Null Mice", *Science*, 264:1936-1938 (1994).
Lin et al., "Androgen-induced human breast cancer cell proliferation is mediated by discrete mechanisms in estrogen receptor-α-positive and -negative breast cancer cells", *J. Steroid Biochem. Mol. Biol.*, 113:182-188 (2009).
Lin et al., "Identification of the Putative MAP Kinase Docking Site in the Thyroid Hormone Receptor-β1 DNA-Binding Domain: Functional Consequences of Mutations at the Docking Site", *Biochem.*, 42:7571-7579 (2003).
Lin et al., "L-Thyroxine vs. 3,5,3'-triiodo-L-thyronine and cell proliferation: activation of mitogen-activated protein kinase and phosphatidylinositol 3-kinase", *Am. J. Physiol. Cell Physiol.*, 296:C980-C991 (2009).
Lin et al., "Resveratrol is pro-apoptotic and thyroid hormone is anti-apoptotic in glioma cells: both actions are integrin and ERK mediated", *Carcinogenesis*, 29(1):62-69 (2008).
Lin et al., "The pro-apoptotic action of stilbene-induced COX-2 in cancer cells: Convergence with the anti-apoptotic effect of thyroid hormone", *Cell Cycle*, 8(12):1877-1882 (2009).
Lin et al., "Thyroid hormone is a MAPK-dependent growth factor for thyroid cancer cells and is anti-apoptotic", *Steriods*, 72:180-187 (2007).
Liu et al., "Calcineurin is a Common Target of Cyclophilin-Cyclosporin A and FKBP-FK506 Complexes", *Cell*, 66:807-815 (1991).
Lorger et al., "Activation of tumor cell integrin αvβ3 controls angiogenesis and metastatic growth in the brain", *Proc. Natl. Acad. Sci. U.S.A.*, 106(26):10666-10671 (2009).
Lyons et al., "The Expression of an N-CAM Serum Fragment is Positively Correlated with Severity of Negative Features in Type II Schizophrenia", *Biol. Psychiatry*, 23:769-775 (1988).
Mahmood et al., "An $N_2S_2$ Tetradentate Chelate for Solid-Phase Synthesis: Evaluation in Solution and Solid Phase and Characterization of Technetium-99 Complexes", *Technetium, Rhenium and Other Metals in Chemistry and Nuclear Medicine*, 5:71-76 (1999).

Mangale et al., "Identification of genes regulated by an interaction between αvβ3 integrin and vitronectin in murine decidua", *Reprod. Fertil. Dev.*, 20:311-319 (2008).
Markgraf et al., "Sensorimotor and cognitive consequences of middle cerebral artery occlusion in rats", *Brain Res.*, 575(2):238-246 (1992).
Masson-Gadais et al., "Integrin αvβ3 requirement for VEGFR2-mediated activation of SAPK2/p38 and Hsp90-dependent phosphorylation of focal adhesion kinase in endothelial cells activated by VEGF", *Cell Stress Chaperones*, 8(1):37-52 (2003).
Meneses et al., "Recombinant angiostatin prevents retinal neovascularization in a murine proliferative retinopathy model", *Gene Therapy*, 8(8):646-648 (2001).
Mezosi et al., "Nongenomic effect of thyroid hormone on free-radical production in human polymorphonuclear leukocytes", *J. Endocrinol.*, 185:121-129 (2005).
Mishkin et al., "Increased Survival of Rats Bearing Morris Hepatoma 7800 after Induction of Hypothyroidism", *Cancer Res.*, 39:2371-2375 (1979).
Miyaguchi et al., "Correlation of Epidermal Growth Factor Receptor and Radiosensitivity in Human Maxillary Carcinoma Cell Lines", *ActaOtolaryngol.*, 118:428-431 (1998).
Moeller et al., "Cytosolic Action of Thyroid Hormone Leads to Induction of Hypoxia-Inducible Factor-1α and Glycolytic Genes", *Molec. Endo.*, 19(12):2955-2963 (2005).
Mohamed at al., "Wound Healing Properties of Cimetidine In Vitro", *Drug Intell. Clin. Pharm.*, 20(12):973-975 (1986).
Monferran et al., "αvβ3 and αvβ5 integrins control glioma cell response to ionising radiation through ILK and RhoB", *Int. J. Cancer*, 123:357-364 (2008).
Morand et al., "Effect of Iodide on Nicotinamide Adenine Dinucleotide Phosphate Oxidase Activity and Duox2 Protein Expression in Isolated Porcine Thyroid Follicles", *Endo.*, 144(4):1241-1248 (2003).
Moreno et al., "Thyroid Economy—Regulation, Cell Biology, Thyroid Hormone Metabolism and Action: The Special Edition: Metabolic Effects of Thyroid Hormones. Metabolic Effects of Thyroid Hormone Derivatives", *Thyroid*, 18(2):239-253 (2008).
Mousa et al., "Cellular and Molecular Mechanisms of Nicotine's Pro-Angiogenesis Activity and Its Potential Impact on Cancer", *J. Cell. Biochem.*, 97:1370-1378 (2006).
Mousa et al., "Discovery of Pro-Angiogenic Effects of Thyroid Hormone Analogs", *Blood*, 102(11):4015 (2003) (Abstract Only).
Mousa et al., "Pro-angiogenesis action of thyroid hormone and analogs in a three-dimensional in vitro microvascular endothelial sprouting model", *Int. Angiol.*, 25(4):407-413 (2006).
Mousa et al., "Proangiogenesis Action of the Thyroid Hormone Analog 3,5-Diiodothyropropionic Acid (DITPA) is Initiated at the Cell Surface and is Integrin Mediated", *Endocrinol.*, 147(4):1602-1607 (2006).
Mousa et al., "Tetraiodothyroacetic (tetrac) inhibits angiogenesis", In: *Program of the 77th Annual Meeting of the American Thyroid Association*, Phoenix, AZ, 2006: Abstract 108.
Mousa et al., "Tetraiodothyroacetic acid, a small molecule integrin ligand, blocks angiogenesis induced by vascular endothelial growth factor and basic fibroblast growth factor", *Angiogenesis*, 11:183-190 (2008).
Mousa et al., "The Proangiogenic Action of Thyroid Hormone Analogue GC-1 is Initiated at an Integrin", *J. Cardiovasc. Pharmacol.*, 46(3):356-360 (2005).
Mousa, S.A., "Mechanisms of Angiogenesis: Potential Therapeutic Targets", in *Angiogenesis Inhibitors and Stimulators : Potential Therapeutic Implications*, Landes Bioscience, Georgetown, Texas, Chapter I, pp. 1-12 (2000).
Muller et al., "The Double Life of the Ku Protein: Facing the DNA Breaks and the Extracellular Environment", *Cell Cycle*, 4(3):438-441 (2005).
Nehls et al., "A microcarrier-based cocultivation system for the investigation of factors and cells involved in angiogenesis in three-dimensional fibrin matrices in vitro", *Histochem. Cell Biol.*, 104(6):459-466 (1995).
Nehls et al., "A Novel, Microcarrier-Based in Vitro Assay for Rapid and Reliable Quantification of Three-Dimensional Cell Migration and Angiogenesis", *Microvasc. Res.*, 50(3):311-322 (1995).

(56) References Cited

OTHER PUBLICATIONS

Neises et al., "Esterification of Carboxylic Acids with Dicylohexylcarbodiimide/4-Dimethylaminopyridine: tert-Butyl Ethyl Fumarate", *Org. Synth.*, 7:93 (1990); 63:183 (1985).
Newcomb et al., "Radiation Sensitivity of GL261 Murine Glioma Model and Enhanced Radiation Response by Flavopiridol", *Cell Cycle,*: 5(1):93-99 (2006).
Nilsson et al., "Evidence for Multiple Thyroxine-binding Sites in Human Prealbumin", *J. Biol. Chem.*, 246(19):6098-6105 (1971).
Ning et al., "Anti-integrin monoclonal antibody CNTO 95 enhances the therapeutic efficacy of fractionated radiation therapy in vivo", *Mol. Cancer Ther.*, 7(6):1569-1578 (2008).
Okada et al., "A Quantitative in vivo Method of Analyzing Human Tumor-induced Angiogenesis in Mice Using Agarose Microencapsulation and Hemoglobin Enzyme-linked Immunosorbent Assay", *Jpn. J. Cancer Res.*, 86(12):1182-1188 (1995).
Pages et al., "Signaling Angiogenesis via p42/p44 MAP Kinase Cascade", *Ann. N.Y. Acad. Sci.*, 902:187-200 (2000).
Painter et al., "Membrane initiation of DNA synthesis", *Nature*, 270:543 (1977).
Panter et al., "Pretreatment with NMDA antagonists limits release of excitatory amino acids following traumatic brain injury", *Neurosci. Lett.*, 136(2):165-168 (1992).
Pardridge, W. M., "Receptor-Mediated Peptide Transport through the Blood-Brain Barrier", *Endocrine Rev.*, 7(3):314-330 (1986).
Penno et al., "Rapid and quantitative in vitro measurement of cellular chemotaxis and invasion", *Meth. Cell Sci.*, 19:189-195 (1997).
Plow et al., "Ligand Binding to Integrins", *J. Biol. Chem.*, 275(29):21785-21788 (2000).
Powell, J., "The Serial Analysis of Gene Expression", *Meth. Mol. Biol.*, 99:297-319 (2000).
Pujol et al., "Letter to the Editors: Prevention of thyroid neoplasm recurrence with Triac and levothyroxine", *Clin. Endocrinol.*, 46:121-122 (1997).
Raue et al., "Multiple Endocrine Neoplasia Type 2", *Horm. Res.*, 68(Suppl.5):101-104 (2007).
Rebbaa et al., "Novel function of the thyroid hormone analog tetraiodothyroacetic acid: a cancer chemosensitizing and anti-cancer agent", *Angiogenesis*, 11(3):269-276 (2008).
Reinholt et al., "Osteopontin—a possible anchor of osteoclasts to bone", *Proc. Natl. Acad. Sci. U.S.A.*, 87:4473-4475 (1990).
Remsen et al., "Antibodies to the Neural Cell Adhesion Molecule Disrupt Functional Recovery in Injured Nerves", *Exp. Neurol.*, 110:268-273 (1990).
Ren et al., "Regulation of tumor angiogenesis by thrombospondin-1", *Biochim. Biophys. Acta*, 1765:178-188 (2006).
Risau, W., "Mechanisms of angiogenesis", *Nature*, 386:671-674 (1997).
Sahni et al., "Stimulation of endothelial cell proliferation by FGF-2 in the presence of fibrinogen requires $\alpha v\beta 3$", *Blood*, 104(12):3635-3641 (2004).
Saito et al., "Vector-mediated delivery of $^{125}$ I-labeled β-amyloid peptide $A\beta^{1-40}$ through the blood-brain barrier and binding to Alzheimer disease amyloid of the $A\beta^{1-40}$ /vector complex", *Proc. Natl. Acad. Sci. USA* 92:10227-10231 (1995).
Samuels et al., "Depletion of L-3-5-3'-Triiodothyronine and L-Thyroxine in Euthyroid Calf Serum for Use in Cell Culture Studies of the Action of Thyroid Hormone", *Endo.*, 105(1):80-85 (1979).
SAS/STAT Guide for Personal Computers, Version 6 Edition, p. 717 (1987).
Sato et al., "Neovascularization: General Remarks", *Biotherapy*, 15(6):631-636 (2001) (English Abstract Only).
Scanlan et al., "3-Iodothyronamine is an endogenous and rapid-acting derivative of thyroid hormone", *Nat. Med.*, 10(6):638-642 (2004).
Scanlan et al., "Selective thyromimetics: Tissue-selective thyroid hormone analogs", *Curr. Opin. Drug Discov. Dev.*, 4(5):614-622 (2001).

Schlange et al., "Autocrine WNT signaling contributes to breast cancer cell proliferation via the canonical WNT pathway and EGFR transactivation", *Breast Cancer Res.*, 9:R63 (2007) (15 pages).
Schlumberger et al., "New therapeutic approaches to treat medullary thyroid carcinoma", *Nat. Clin. Prac. Endocrinol. Metab.*, 4(1):22-32 (2008).
Schnell et al., "Expression of alpha v beta 3 integrin in patients with high and low grade glioma", *Proc. Amer. Assoc. Cancer Res.*, 47:226 (2006) (Abstract Only).
Schnell et al., "Expression of Integrin $\alpha v\beta 3$ in Gliomas Correlates with Tumor Grade and is not Restricted to Tumor Vasculature", *Brain Pathol.*, 18:378-386 (2008).
Schreiber et al., "Hormone delivery systems to the brain—transthyretin", *Exp. Clin. Endocrinol Diabetes*, 103(2):75-80 (1995).
Schueneman et al., "SU11248 Maintenance Therapy Prevents Tumor Regrowth after Fractionated Irradiation of Murine Tumor Models", *Cancer Res.*, 63:4009-4016 (2003).
Shih et al., "Disparate Effects of Thyroid Hormone on Actions of Epidermal Growth Factor and Transforming Growth Factor-β Are Mediated by 3,5'-Cyclic Adenosine 5'-Monophosphate-Dependent Protein Kinase II", *Endo.*, 145(4):1708-1717 (2004).
Shih et al., "Thyroid Hormone Promotes Serine Phosphorylation of p53 by Mitogen-Activated Protein Kinase", *Biochem.*, 40:2870-2878 (2001).
Shinohara et al., "Enhanced radiation damage of tumor vasculature by mTOR inhibitors", *Oncogene*, 24:5414-5422 (2005).
Skovronsky et al., "In vivo detection of amyloid plaques in a mouse model of Alzheimer's disease", *Proc. Natl. Acad. Sci. U.S.A.*, 97(13):7609-7614 (2000).
Skuli et al., "$\alpha v\beta 3/\alpha v\beta 5$ Integrins-FAK-RhoB: A Novel Pathway for Hypoxia Regulation in Glioblastoma", *Cancer Res.*, 69(8):3308-3316 (2009).
Song et al., "Formulation and characterization of biodegradable nanoparticles for intravascular local drug delivery", *J. Controlled Rel.*, 43:197-212 (1997).
Sunwoo et al., "Novel Proteasome Inhibitor PS-341 Inhibits Activation of Nuclear Factor-κ B, Cell Survival, Tumor Growth, and Angiogenesis in Squamous Cell Carcinoma", *Clin. Cancer Res.*, 7:1419-1428 (2001).
Szatmari et al., "Detailed characterization of the mouse glioma 261 tumor model for experimental glioblastoma therapy", *Cancer Sci.*, 97(6):546-553 (2006).
Szumiel, I., "$Ca^{2+}$, $Mg^{2+}$ and (Adenosine Diphosphate Ribose)$_n$ in Cellular Response to Irradiation", *J. theor. Biol.*, 101:441-451 (1983).
Takemaru et al., "Chibby, a nuclear β-catenin-associated antagonist of the Wnt/Wingless pathway", *Nature*, 422:905-909 (2003).
Tanaka et al., *J. Soc. Gastroenterological Surgery*, 27(2):360 (1996) (In Japanese).
Tang et al., "Thyroid Hormone Causes Mitogen-Activated Protein Kinase-Dependent Phosphorylation of the Nuclear Estrogen Receptor", *Endocrinol.*, 145(7):3265-3272 (2004).
Tator et al., "Review of the secondary injury theory of acute spinal cord trauma with emphasis on vascular mechanisms", *J. Neurosurg.*, 75(1):15-26 (1991).
Theodossiou et al, "Propylthiouracil-Induced Hypothyroidism Reduces Xenograft Tumor Growth in Athymic Nude Mice", *Cancer*, 86:1596-1601 (1999).
Thraves et al., "Radiosensitization of Human Fibroblasts by 3-Aminobenzamide: An Inhibitor of Poly(ADP-Ribosylation)", *Radiat Res.*, 104:119-127 (1985).
Tomanek et al., "A Thyroid Hormone Analog Stimulates Angiogeneis in the Post-infarcted Rat Heart", *J. Mol. Cell. Cardiol.*, 30:923-932 (1998).
Tomanek et al., "Angiogenesis: New Insights and Therapeutic Potential", *Anatomical Record (New Anat.)*, 261:126-135 (2000).
Tomanek et al., "Early Coronary Angiogenesis in Response to Thyroxine Growth Characteristics and Upregulation of Basic Fibroblast Growth Factor", *Circ. Res.*, 82(5):587-593 (1998).
Tomanek et al., "Growth of the Coronary Vasculature in Hypertrophy: Mechanisms and Model Dependence", *Cell. Mol. Biol. Res.*, 40(2):129-136 (1994).

(56) References Cited

OTHER PUBLICATIONS

Toms et al., "Thyroid Hormone Depletion Inhibits Astrocytoma Proliferation via a p53-Independent Induction of p21 (WAF/1CIP1)", *Anticancer Res.*, 18:289-293 (1998).
Tuttle et al., "Recombinant Human TSH-Assisted Radioactive Iodine Remnant Ablation Achieves Short-Term Clinical Recurrence Rates Similar to Those of Traditional Thyroid Hormone Withdrawal", *J. Nucl. Med.*, 49(5):764-770 (2008).
Utsumi et al., "Potentially Lethal Damage Versus Sublethal Damage: Independent Repair Processes in Actively Growing Chinese Hamster Cells", *Radiat. Res.*, 77:346-360 (1979).
Van Waes et al., "Effects of the novel αv integrin antagonist SM256 and cis-platinum on growth of murine sguamous cell carcinoma PAM LY8", *Int. J. Oncol.*, 16(6):1189-1195 (2000).
Varnes et al., "The Effect of pH on Potentially Lethal Damage Recovery in A549 Cells", *Radiat Res.*, 108:80-90 (1986).
Wang et al., "DITPA stimulates bFGF, VEGF, angiopoietin, and Tie-2 and facilitates coronary arteriolar growth", *Am. J. Physiol. Heart Circ. Physiol.*, 284:H613-H618 (2003).
Wang et al., "Integrin-associated Protein Stimulates αvβ1-dependent Chemotaxis via Gi-mediated Inhibition of Adenylate Cyclase and Extracellular-regulated Kinases", *J. Cell Biol.*, 147:389-399 (1999).
Wen et al., "Prognostic Value of EGFR and TGF-α in Early Laryngeal Cancer Treated With Radiotherapy", *Laryngoscope*, 106(7):884-888 (1996).
Werdelin et al., "Neuropeptides and neural cell adhesion molecule (NCAM) in CSF from patients with ALS", *Acta Neurol. Scand.*, 79(3):177-181 (1989).
Wilkinson, J. H., "Synthesis of some Possible Metabolites of Thyroxine and Triiodothyronine", *Biochem. J.*, 63:601-605 (1956).
Xia et al., "Chemokines/chemokine receptors in the central nervous system and Alzheimer's disease", *J. NeuroVirol.*, 5:32-41 (1999).
Yalcin et al., "Tetraidothyroacetic Acid (Tetrac) and Tetrac Nanoparticles Inhibit Growth of Human Renal Cell Carcinoma Xenografts", *Anticancer Res.*, 10:3825-3831 (2009).
Yanase et al., "Role of N-methyl-D-aspartate receptor in acute spinal cord injury", *J. Neurosurg.*, 83:884-888 (1995).
Yang et al., "Rab7b, a novel lysosome-associated small GTPase, is involved in monocytic differentiation of human acute promyelocytic leukemia cells", *Biochem. Biophys. Res. Commun.*, 318:792-799 (2004).
Young, W., "Role of Calcium in Central Nervous System Injuries", *J. Neurotrauma*, 9(Suppl. 1):S9-S25 (1992).
Yu et al., "The Corepressor Silencing Mediator for Retinoid and Thyroid Hormone Receptor Facilitates Cellular Recovery from DNA Double-Strand Breaks", *Cancer Res.*, 66(18):9316-9322 (2006).
Zhang et al., "Quantitative PET Imaging of Tumor Integrin αvβ3 Expression with 18F-FRGD2", *J. Nucl. Med.*, 47:113-121 (2006).
Zhen et al., "Synthesis and Amyloid Binding Properties of Rhenium Complexes: Preliminary Progress Toward a Reagent for SPECT Imaging of Alzheimer's Disease Brain", *J. Med. Chem.*, 42:2805-2815 (1999).
Zhuang et al., "$^{99m}$Tc-Labeled MIBG Derivatives: Novel $^{99m}$Tc Complexes as Myocardial Imaging Agents for Sympathetic Neurons", *Bioconjugate Chem.*, 10:159-168 (1999).
Hercbergs, et al., "Radiosensitization of GL261 glioma cells by tetraiodothyroacetic acid (tetrac)", *Cell Cycle*, 8(16):2586-2591 (2009) 6 pages.
Jonker et al., "Cetuximab for the Treatment of Colorectal Cancer", *N. Engl. J. Med.*, 357(20):2040-2048 (2007) 9 pages.
Kalofonos et al., "Monoclonal Antibodies in the Management of Solid Tumors", *Curr. Top. Med. Chem.*, 6:1687-1705 (2006) 19 pages.
Kim et al., "Soluble Flt-1 gene delivery using PEI-g-PEG-RGD conjugate for anti-angiogenesis", *J. Control Release*, 106:224-234 (2005) 11 pages.
Koutras et al., "Antiproliferative effect of exemestane in lung cancer cells", *Mol. Cancer*, 8(1):109 (2009) 12 pages.
Lameloise et al., "Differences between the effects of thyroxine and tetraiodothyroacetic acid on TSH suppression and cardiac hypertrophy", *Eur. J. Endocrinol.*, 144:145-154 (2001) 10 pages.
Li et al., "Requirement of hypoxia-inducible factor-1α down-regulation in mediating the antitumor activity of the anit-epidermal growth factor receptor monoclonal antibody cetuximab", *Mol. Cancer Ther.*, 7(5):1207-1217 (2008) 11 pages.
Lin et al., "Integrin αβ3 contains a receptor site for resveratrol", *FASEB J.* 20(10): 1742-1744 (2006) 3 pages.
Lin et al., "Resveratrol Causes COX-2- and p53-Dependent Apoptosis in Head and Neck Squamos Cell Cancer Cells", *J. Cell Biochem.*, 104:2131-2142 (2008) 12 pages.
Lin et al., "Resveratrol Induced Serine Phosphorylation of p53 Causes Apoptosis in a Mutant p53 Prostate Cancer Cell Line", *J. Urol.*, 168:748-755 (2002) 8 pages.
Louie et al., "Pharmacodynamics of Levofloxacin in a Murine Pneumonia Model of Pseudomonas aeruginosa Infection: Determination of Epithelial Lining Fluid Targets", *Antimicrob Agents Chemother.*, 53(8):3325-3330 (2009) 6 pages.
Moreno et al., "Metabolic Effects of Thyroid Hormone Derivatives", *Thyroid*, 18(2):239-253 (2008) 15 pages.
Mousa et al., "Discovery of pro-angiogenic effects of thyroid hormone analogs", Database Biosis (Online) Biosciences Information Service, Database Accession No. PREV20040016169 (Nov. 16, 2003).
Mousa, et al., "Pro-angiogenesis action of thyroid hormone and analogs in a three-dimensional in vitro microvascular endothelial sprouting model", *Int. Angiol.*, 25(4):407-413 (2006).
Mousa, S.A., et al., "Effect of Resveratrol on Angiogenesis and Platelet/Fibrin-Accelerated Tumor Growth in the Chick Chorioallantoic Membrane Model," *Nutr. Cancer*, 52(1):59-65 (2005) 7 pages.
Ndiaye et al., "Red wine polyphenol-induced, endothelium-dependent NO-mediated relaxation is due to the redox-sensitive PI3-kinase / Akt-dependent phosphorylation of endothelial NO-synthase in the isolated porcine coronary artery", *FASEB J.*, 19(3):455-457 (2005) 3 pages.
Oak et al., "Antiangiogenic properties of natural polyphenols from red wine and green tea", *J. Nutr. Biochem.*, 16:1-8 (2005) 8 pages.
Panyam, et al., "Biodegradable nanoparticles for drug and gene delivery to cells and tissues", *Advanced Drug Delivery Reviews*, 55: 329-347 (2009) 19 pages.
Park et al., "Effects of Tetramethoxystilbene on Hormone-Resistant Breast Cancer Cells: Biological and Biochemical Mechanisms of Action", *Cancer Res.*, 67:5717-5726 (2007) 10 pages.
Patel, D.K., "Clinical Use of Anti-Epidermal Growth Factor Receptor Monoclonal Antibodies in Metastatic Colorectal Cancer", *Pharacotherapy*, 28(11 Pt.2):31S-41S (2008) 12 pages.
Pirola, et al., "Resveratrol: One Molecule, Many Targets", *IUBMB Life*, vol. 60, Issue 5, pp. 323-332. 10 pages, May 2008.
Prichard et al., "Concurrent Cetuximab and Bevacizumab Therapy in a Murine Orthotopic Model of Anaplastic Thyroid Carcinoma", *Laryngoscope*, 117:674-679 (2007) 7 pages.
Rayalam et al., "Resveratrol induces apoptosis and inhibits adipogenesis in 3T3-L1 adipocytes", *Phytother. Res.*, 22:1367-1371 (2008) 5 pages.
Shih et al., "Inhibitory effect of epidermal growth factor on resveratrol-induced apoptosis in prostate cancer cells is mediated by protein kinase C-α", *Mol. Cancer Ther*, 3:1355-1363 (2004) 9 pages.
Stefani et al., "The Effect of Resveratrol on a Cell Model of Human Aging", *Ann. NY Acad. Sci.*, 1114:407-418 (2007) 12 pages.
Strieth, et al., "Antiangiogenic combination tumor therapy blocking α-integrins and VEGF-receptor-2 increases therapeutic effects in vivo", *Int. J. Cancer*, 119:423-431 (2006) 9 pages.
Tang et al., "Resveratrol-induced Cyclooxygenase-2 facilitates p53-dependent apoptosis in human breast cancer cells", *Mol. Cancer Ther.*, 5(8):2034-2042 (2006) 9 pages.
Tol et al., "Chemotherapy, Bevacizumab, and Cetuximab in Metastatic Colorectal Cancer", *N. Engl. J. Med.*, 360(6):563-572 (2009) 10 pages.
Tzirogiannis et al., "Enhanced Proliferation of Human Lung Adenocarcinoma and Small Cell Lung Carcinoma Cells Directed

(56) References Cited

OTHER PUBLICATIONS from the Cell Surface by Thyroid Hormone", in 89th Annual Meeting, The Endocrine Society (2007) Abstract Only 3 pages.

VanCutsem et al., "Cetuximab and Chemotherapy as Initial Treatment for Metastatic Colorectal Cancer", N. Engl. J. Med., 360:1408-1417 (2009) 10 pages.

Yalcin et al., "Tetraidothyroacetic Acid (Tetrac) and Tetrac Nanoparticles Inhibit Growth of Human Renal Cell Carcinoma Xenografts", Anticancer Res., 29:3825-3832 (2009) 7 pages.

Yalcin et al., "Tetraiodothyroacetic Acid and Tetraiodothyroacetic Acid Nanoparticle Effectively Inhibit the Growth of Human Follicular Thyroid Cell Carcinoma", Thyroid, 20(3):281-286 (2010) 6 pages.

Yang, et al., "Enhanced inhibition of adipogenesis and induction of apoptosis in 3T3-L1 adipocytes with combinations of resveratrol and quercetin", Life Sci., 82:1032-1039 (2008) 8 pages.

Yonkers et al., "Sensory Neuron Sodium Current Requires Nongenomic Actions of Thyroid Hormone During Development", J. Neurophysiol., 100:2719-2725 (2008) 7 pages.

Yu et al., "Osteopontin Gene is Expressed in the Dermal Papilla of Pelage Follicles in a Hair-Cycle-Dependent Manner", J. Invest. Dermatol., 117:1554-1558 (2001) 5 pages.

Zhang et al., "Oestrogen inhibits resveratrol-induced post-translational modification of p53 and apoptosis in breast cancer cells", Br. J. Cancer, 91:178-185 (2004) 8 pages.

Surks, Martin I. et al. "Subclinical Thyroid Disease; Scientific Review and Guidelines for Diagnosis and Management." Journal of the American Medical Association, Jan. 14, 2004, vol. 291, No. 2, pp. 228-238; especially pp. 230-231.

NCI Cancer Drug Information, Cetuximab, 2006, http://www.cancer.gov/cancertopics/druginfo/cetuximab,downloaded07/18/14.

Gu et al. 2007, Nanotoday 2:14-21.

Office Action (Mail Date Jun. 21, 2011) for U.S. Appl. No. 12/947,389—Filing Date Nov. 16, 2010.

Office Action (Mail Date Apr. 4, 2014) for U.S. Appl. No. 12/947,389, filed Nov. 16, 2010.

Office Action (Mail Date Oct. 17, 2012) for U.S. Appl. No. 12/947,389, filed Nov. 16, 2010.

Office Action (Mail Date May 12, 2015) for U.S. Appl. No. 14/078,713, filed Nov. 13, 2013.

Office Action (Mail Date Mar. 24, 2015) for U.S. Appl. No. 13/975,725, filed Aug. 26, 2013.

Office Action (Mail Date Oct. 5, 2012) for U.S. Appl. No. 12/644,493, filed Dec. 22, 2009.

Office Action (Mail Date Apr. 16, 2015) for U.S. Appl. No. 13/156,047, filed Jun. 8, 2011.

Office Action (Mail Date Jan. 12, 2015) for U.S. Appl. No. 12/751,375, filed Mar. 31, 2010.

Office Action (Mail Date Jun. 3, 2015) for U.S. Appl. No. 12/751,375, filed Mar. 31, 2010.

Office Action (Mail Date Jun. 11, 2015) for U.S. Appl. No. 14/242,041, filed Apr. 1, 2014.

Office Action (Mail Date Oct. 15, 2013) for U.S. Appl. No. 13/345,194, filed Jan. 6, 2012.

Application No. PCT/US2010/038700, Supplemental European Search Report dated Apr. 20, 2015, 7 pages.

J Wood, K Bonjean, S Ruetz, A Bellahcene, L Devy, JM Foidart, V Castronovo, JR Green. "Novel Antiangiogenic Effects of the u Bisphosphonate Compound Zoledronic Acid." The Journal of Pharmacology and Experimental Therapeutics, vol. 302, No. 3, 2002, pp. 1055-1061.

M Yalcin, DJ Bharali, L Lansing, E Dyskin, SS Mousa, A Hercbergs, FB Davis, PJ Davis, SA Mousa. "Tetraidothyroacetic Acid v (Tetrac) and Tetrac Nanoparticles Inhibit Growth of Human Renal Cell Carcinoma Xenografts." Anticancer Research, vol. 29, 2009, pp. 3825-3832.

\* cited by examiner $T_4$ and $T_3$ stimulate angiogenesis in the chorioallantoic membrane model

| Treatment | Angiogenesis Index |
|---|---|
| PBS | 63 ± 10 |
| $T_3$ (1 nM) | 121 ± 18** |
| $T_4$ (0.1 μM) | 155 ± 11** |

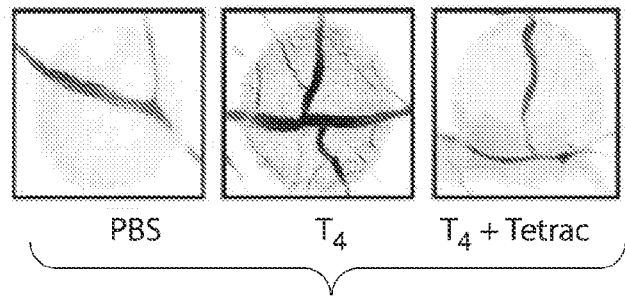
FIG. 3A
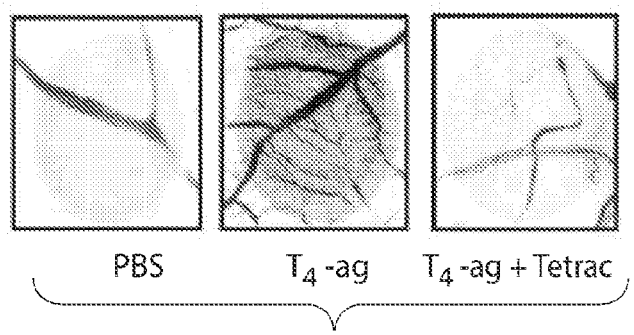
FIG. 3B
Summary of effects of $T_4$, $T_4$-agarose and tetrac on angiogenesis
| Treatment | Angiogenesis Index |
|---|---|
| PBS | 67 ± 9 |
| $T_4$ (0.1 μM) | 156 ± 16** |
| Tetrac (0.1 μM) | 76 ± 9 |
| $T_4$ + tetrac | 66 ± 6 |
| $T_4$-agarose (0.1 μM) | 194 ± 28** |
| $T_4$-agarose + tetrac | 74 ± 7 |
FIG. 3C Effects of FGF2 and T$_4$ on angiogenesis

| Treatment | Angiogenesis Index |
|---|---|
| PBS | 86  11 |
| FGF2 (0.5 μg/ml) | 126  17* |
| FGF2 (1.0 μg/ml) | 172  9** |
| T$_4$ (0.5 μM) | 115  4* |
| T$_4$ + FGF2 (0.5 μg/ml) | 167  10** |

Effect of FGF2 antibody on angiogenesis stimulated by $T_4$ and FGF2

| Treatment | Angiogenesis Index |
|---|---|
| PBS | 92 ± 10 |
| FGF2 (1.0 µg/ml) | 187 ± 17** |
| FGF2 + FGF2-ab | 118 ± 7 |
| $T_4$ (0.1 µM) | 142 ± 12* |
| $T_4$ + FGF2-ab | 96 ± 10 |

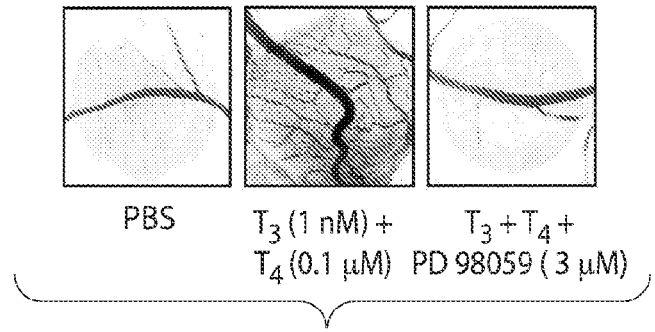
FIG. 6A
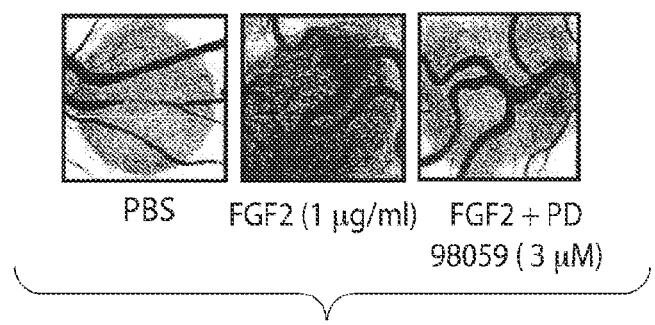
FIG. 6B
Effects of PD 98059 on angiogenesis
stimulated by $T_4$ and FGF2
| Treatment | Angiogenesis Index |
|---|---|
| PBS | 63  10 |
| $T_3$ (1 nM) + $T_4$ (0.1 μM) | 153  15* |
| $T_3$ + $T_4$ + PD 98059 (3 μM) | 50  10 |
| PBS | 86  11 |
| FGF2 (1 μg/ml) | 191  15** |
| FGF2 + PD 98059 (3 μM) | 110  16 |
FIG. 6C

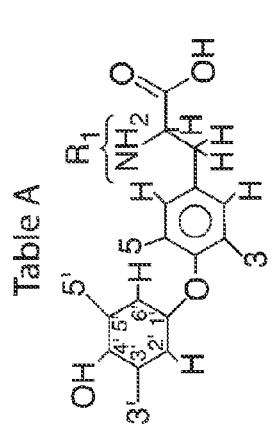

Table B

| $R_1$ | $R_2$ | $R_3$ | 5' | Analogue |
|---|---|---|---|---|
| $CH_2CH$ | H | $CO_2H$ | I | 3,5,3',5'-tetraiodo-thyropropionic acid |
| $CH_2$ | H | $CO_2H$ | I | 3,5,3',5'-tetraiodo-thyroacetic acid |
| $CH_2$ | H | $CO_2H$ | H | 3,5,3'-triiodothyroa-cetic acid |
| $CH_2CH$ | $NH_2$ | $COC_2H_5$ | I | L-$T_4$ ethylester |
| $CH_2CH$ | $NH_2$ | H | H | 3,5,3'-triiodothyrona-mine |

FIG. 10B

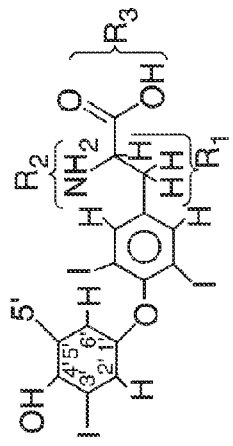

Table A

| 3' | 5' | 3 | 5 | $R_1$ | Analogue |
|---|---|---|---|---|---|
| I | I | I | I | $NH_2$ | L-$T_4$ |
| I | H | I | I | $NH_2$ | L-$T_3$ |
| I | I | I | H | $NH_2$ | r$T_3$ |
| H | H | I | I | $NH_2$ | 3,5-L-$T_2$ |
| I | I | H | H | $NH_2$ | 3',5'-L-$T_2$ |
| I | H | I | H | $NH_2$ | 3,3'-L-$T_2$ |
| I | H | H | H | $NH_2$ | 3'-L-$T_3$ |
| Br | Br | Br | Br | $NH_2$ | 3,5,3'-tetra-bromo-L-thyronine |
| H | H | Br | Br | $NH_2$ | 3,5,3',-dibromo-L-thyronine |
| Isop[a] | H | Me[b] | Me | $NH_2$ | DIMIT |
| Isop | H | Me | Me | $NH-COCH_3$ | N-acetyl DIMIT |

[a] Isop, isopropyl
[b] Me, methyl

FIG. 10A

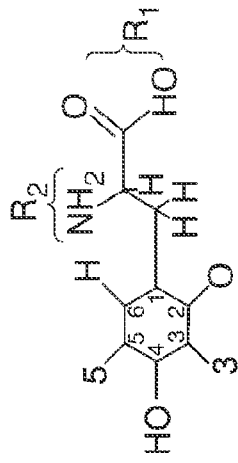

Table D

| 3 | 5 | R1 | R3 | Analogue |
|---|---|---|---|---|
| I | I | COOH | NH₂ | 3,5-diiodo-L-tyrosine |
| Br | Br | COOH | NH₂ | 3,5-dibromo-L-tyrosine |
| Me | Me | COOH | NH₂ | 3,5-dimethyl-DL-tyrosine |
| NO₂ | NO₂ | COOH | NH₂ | 3,5-dinitro-L-tyrosine |
| I | H | COOH | NH₂ | 3-iodo-l-tyrosine |
| NO₂ | H | COOH | NH₂ | 3-nitro-L-tyrosine |
| H | H | COOH | NH₂ | L-tyrosine |
| I | I | H | NH₂ | 3,5-diiodotyramine |
| H | H | H | NH₂ | tyramine |
| I | I | COOH | H | 3-(3,5-diiodo-4-hydroxy-phenyl) propionic acid |
| H | H | COOH | H | 3-(p-hydroxy-phenyl) propionic acid |

FIG. 10D

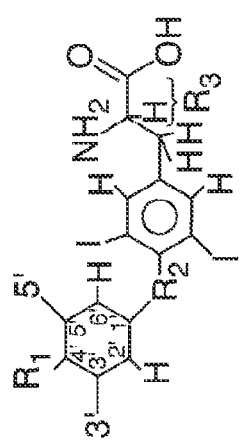

Table C

| R₁ | R₂ | R₃ | 3' | 5' | 3 | 5 | Analogue |
|---|---|---|---|---|---|---|---|
| H | O | L | H | H | I | I | 4'-deoxy T₂ |
| OH | S | L | H | H | I | I | S-bridged T₃ |
| OH | O | D | H | I | I | I | D-T₄ |
| OH | O | D | H | H | I | I | D-T₃ |

FIG. 10C

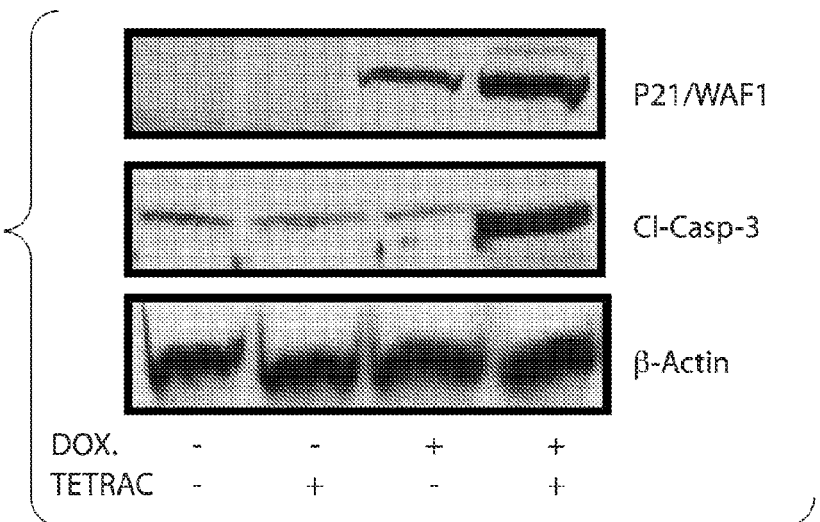
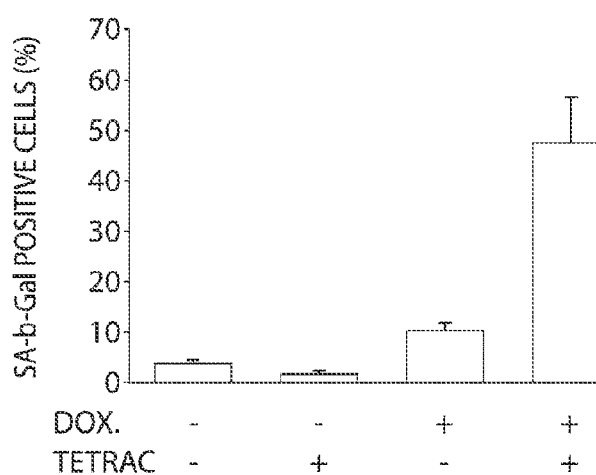
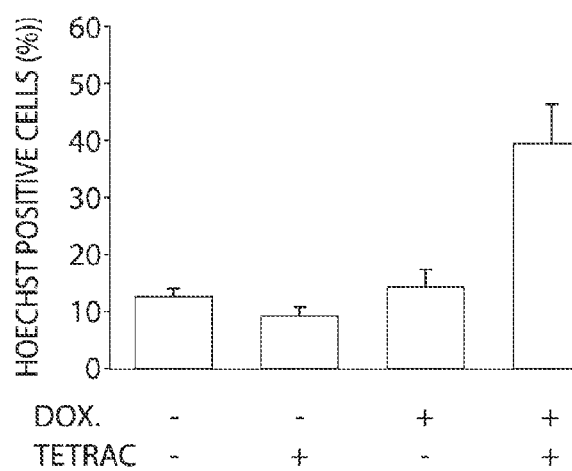

Figure S2: Syntheses of compounds 13-15. Reagents and conditions: (a) TEA (1.0 equiv.), TiPSCl (1.0 equiv.), THF, 30 min., rt, N$_2$; (b) TEA (1.0 equiv.), epibromohydrin (10.0 equiv.), THF, 12 hrs., 65°C, N$_2$ Representative images showing the effect on angiogenesis of bFGF, T₄, and 11 (pro-angiogenic); 12 (anti-angiogenic); and 15 (no activity).

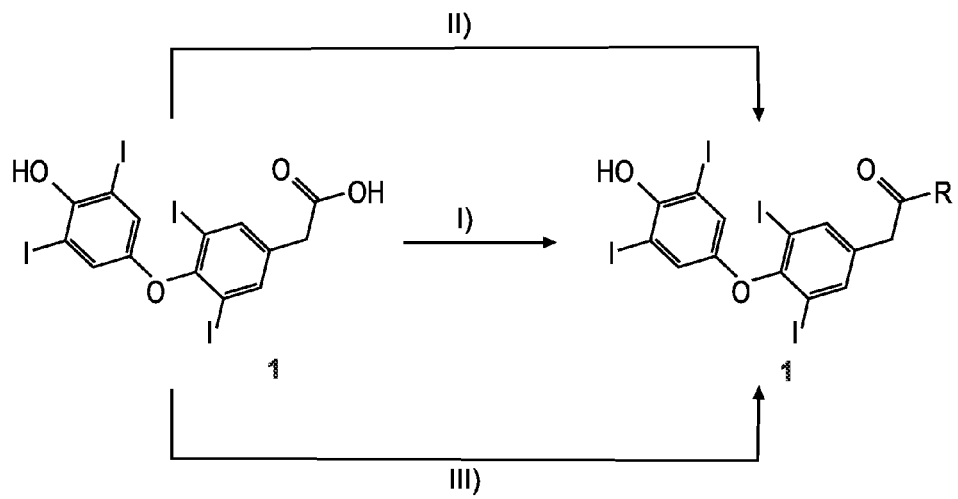
I. MeOH/DMP/CSA, MeOH, Reflux
II. ᵗBuOH (3.0 eq)/4-DMAP (0.8 eq.)/DCG (1.1 eq.), Dioxane anh., r.t., 3 hrs., N₂
III. CBzCl (1.0 eq.) or TIPSCl(1.0 eq.)/TEN (1.0 eq.), THF anh., r.t., 10 min., N₂
2. R= OMe
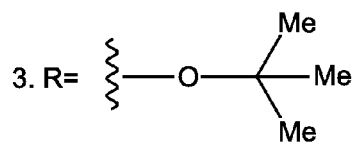
3. R=
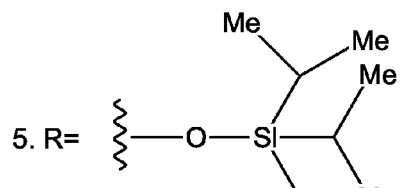
5. R=
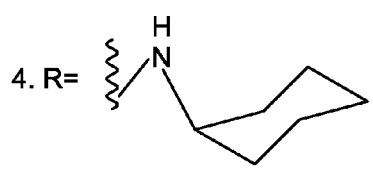
4. R=
FIG. 25

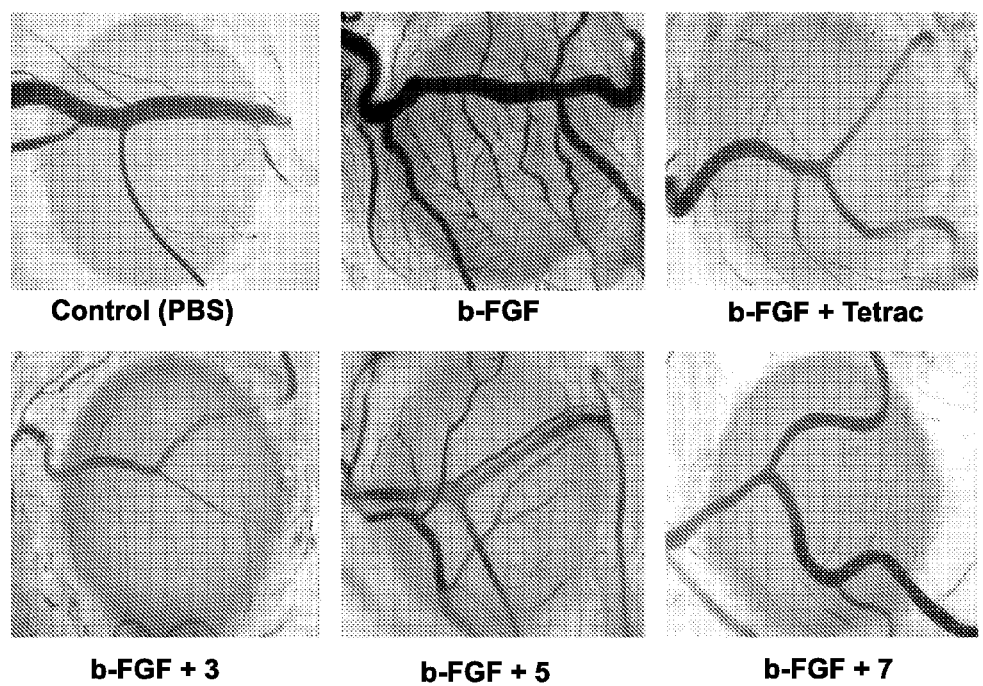
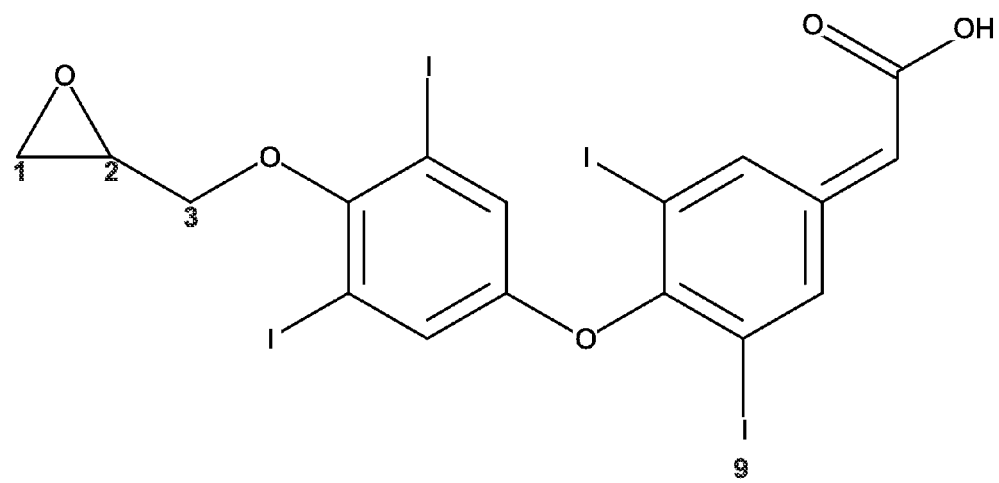
FIG. 28

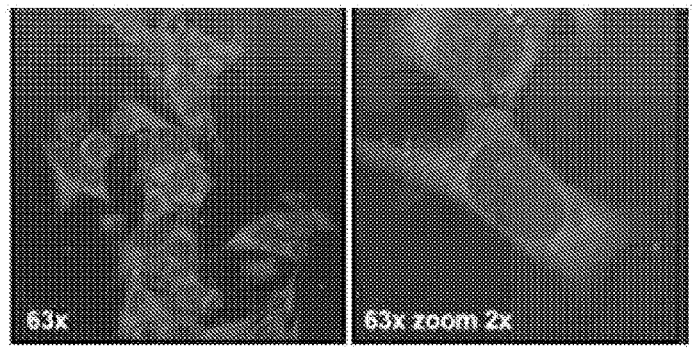
Confocal Images showing the uptake of Cy3-PLGA-Tetrac nanoparticles in MTC cell
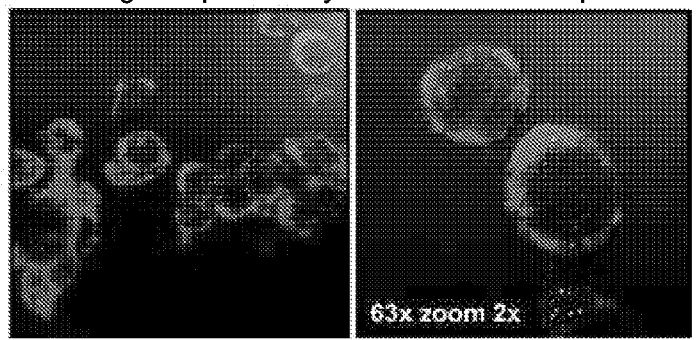
Confocal Images showing the uptake of Cy3-Tetrac in MTC cell
FIG. 36
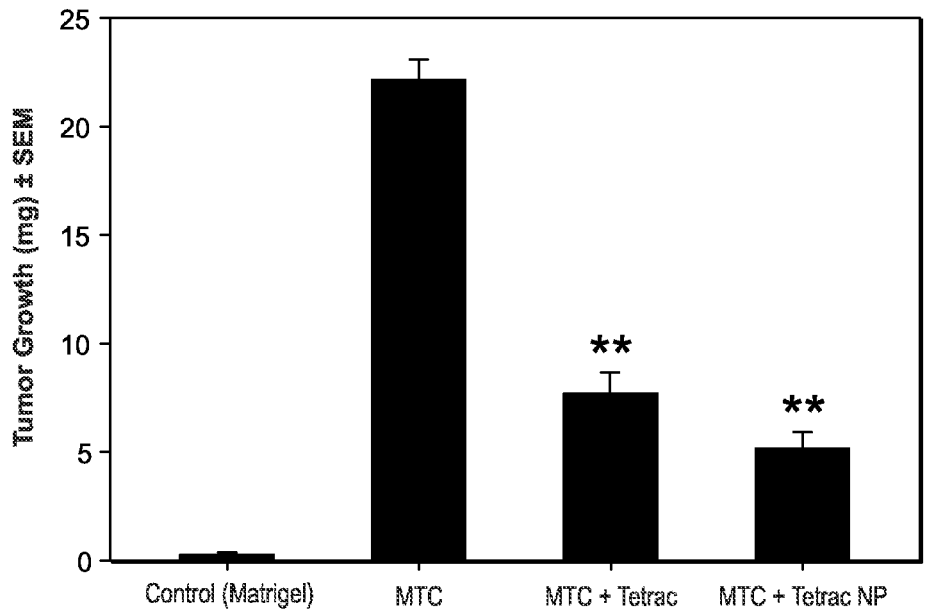
FIG. 37A

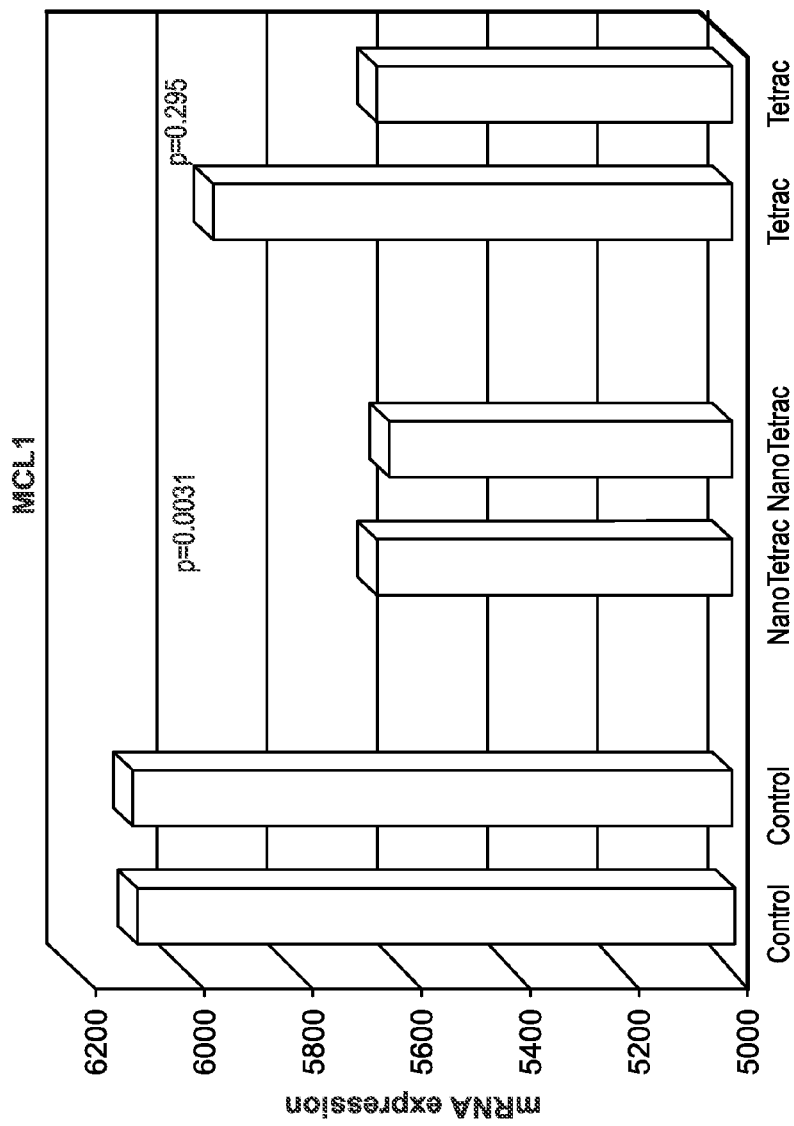

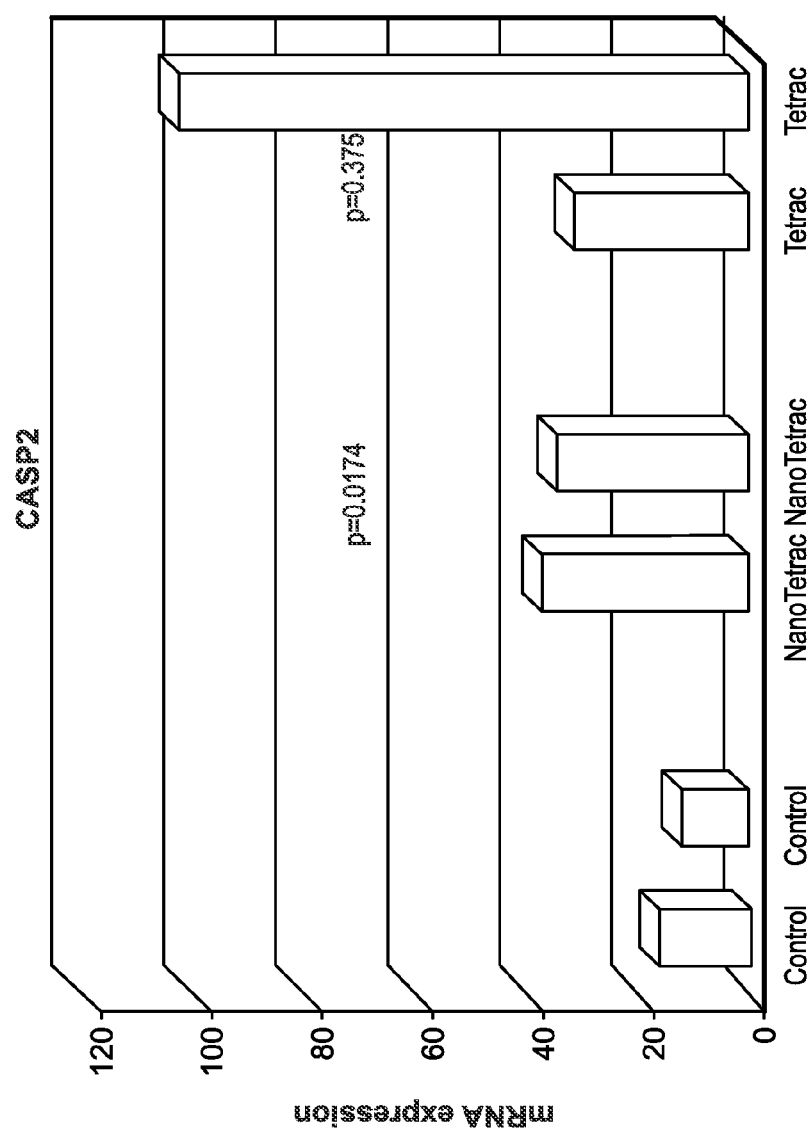

PLG-Amino-Tetrac

GL261 responses to graded doses of 250 kVp x-rays. Control cells are denoted by ●, and tetrac treated cells (2 uM) by ○. A one hour exposure to tetrac prior to irradiation was given. The dose enhancement factor produced by terrac at 2(Gy(a typical radiotherapeutic dose) is 2.5.

We have also plotted the log of the mean fluorescence index for αvβ3 protein verses the content of TGF-β1 protein in eight different human colon cancer cells. This is shown in the next plot where the correlation between the log MFI and TGF-β1 is positive (CC = 0.979, P < 0.001).

Lastly, we have correlated the log MFI of the αvβ3 protein in the membrane of 8 different human colon cancer cells with the alpha x-ray parameter. This correlation is also positive and is extremely strong (CC = 0.907, P = 0.002).

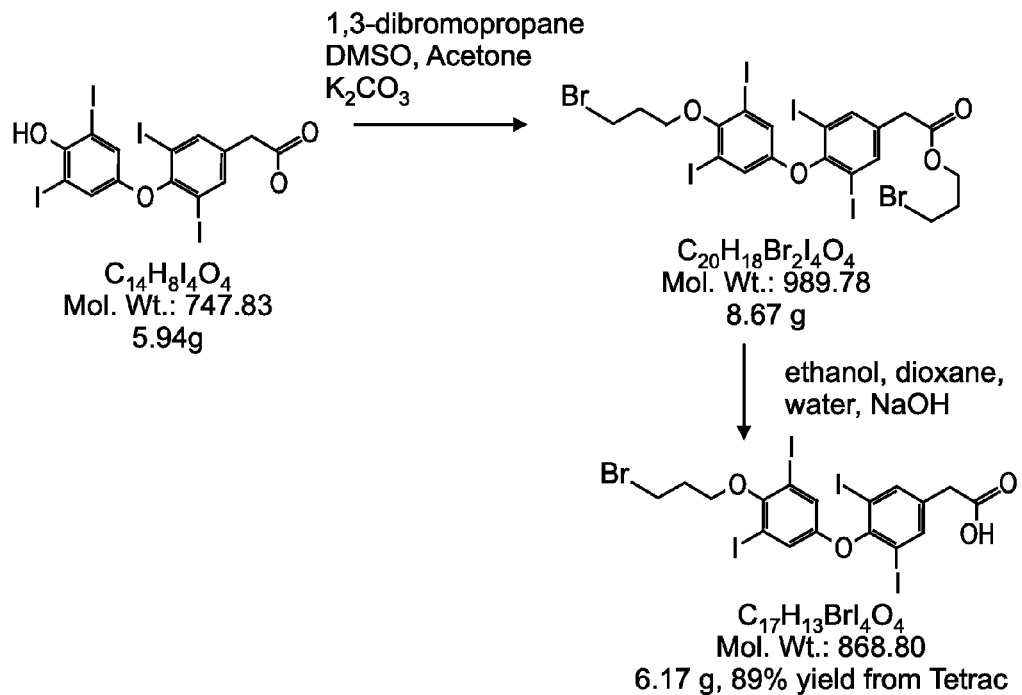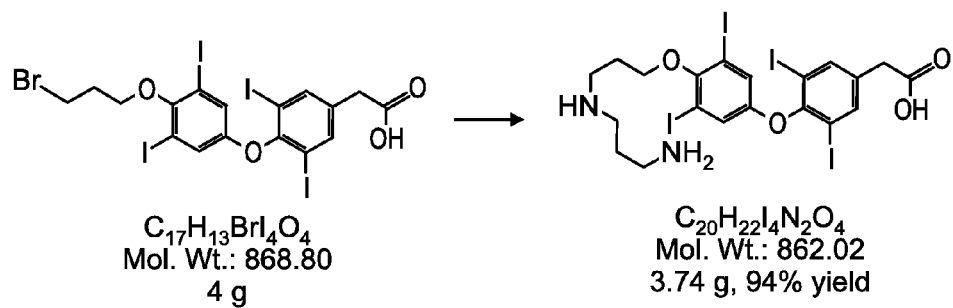
FIG. 66A

Preparation of Activated PLGA was scaled up:

6g

Activated PLGA
4.55g, 76% yield
(1.5 g in stock)

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Chemically Synthesized Primer Sequence

<400> SEQUENCE: 1
tggtatgtgg cactgaaacg                                                  20

<210> SEQ ID NO 2
<211> LENGTH: 20
<212> TYPE: DNA
<213> ORGANISM: Artificial Sequence
<220> FEATURE:
<223> OTHER INFORMATION: Chemically Synthesized Primer Sequence

<400> SEQUENCE: 2
ctcaatgacc tggcgaagac                                                  20

<210> SEQ ID NO 3
<211> LENGTH: 22
<212> TYPE: DNA
<213> ORGANISM: Artificial Sequence
<220> FEATURE:
<223> OTHER INFORMATION: Chemically Synthesized Primer Sequence

<400> SEQUENCE: 3
aaggtcatcc ctgagctgaa cg                                               22

<210> SEQ ID NO 4
<211> LENGTH: 22
<212> TYPE: DNA
<213> ORGANISM: Artificial Sequence
<220> FEATURE:
<223> OTHER INFORMATION: Chemically Synthesized Primer Sequence

<400> SEQUENCE: 4
gggtgtcgct gttgaagtca ga                                               22
```

NANOPARTICLE AND POLYMER FORMULATIONS FOR THYROID HORMONE ANALOGS, ANTAGONISTS, AND FORMULATIONS AND USES THEREOF

RELATED APPLICATIONS

This application claims priority to U.S. Ser. No. 61/187,799, filed Jun. 17, 2009; U.S. Ser. No. 61/219,993, filed Jun. 24, 2009; U.S. Ser. No. 61/222,289, filed Jul. 1, 2009; U.S. Ser. No. 61/237,178, filed Aug. 26, 2009; and U.S. Ser. No. 61/327,909, filed Apr. 26, 2010. Each of these applications is herein incorporated by reference in its entirety.

FIELD OF THE INVENTION

This invention relates to nanoparticle and polymer conjugate forms of thyroid hormone, thyroid hormone analogs and derivatives thereof. Methods of using such compounds and pharmaceutical compositions containing same are also disclosed. The invention also relates to methods of preparing such compounds.

REFERENCE TO A "SEQUENCE LISTING"

The sequence listing material in the text file entitled "5021191_1.txt" (1,477 bytes), which was created on Nov. 3, 2010, is herein incorporated by reference in its entirety.

BACKGROUND OF THE INVENTION

Thyroid hormones, such as L-thyroxine (T4) and 3,5,3'-triiodo-L-thyronine (T3), and their analogs such as GC-1, DITPA, Tetrac and Triac, regulate many different physiological processes in different tissues in vertebrates. It was previously known that many of the actions of thyroid hormones are mediated by the thyroid hormone receptor ("TR"). A novel cell surface receptor for thyroid hormone (L-thyroxine, T4, T3) has been described on integrin $\alpha v\beta 3$. The receptor is at or near, but functionally and topographically distinct from, the Arg-Gly-Asp (RGD) recognition site on the integrin. The $\alpha v\beta 3$ receptor is not a homologue of the nuclear thyroid hormone receptor (TR), but activation of the cell surface receptor results in a number of nucleus-mediated events, including the recently-reported pro-angiogenic action of the hormone and fibroblast migration in vitro in the human dermal fibroblast monolayer model of wound-healing.

Tetraiodothyroacetic acid (Tetrac) is a deaminated analog of $T_4$ that has no agonist activity at the integrin, but inhibits binding of $T_4$ and $T_3$ to the integrin and the pro-angiogenic action of agonist thyroid hormone analogs at $\alpha v\beta 3$. Inhibition of the angiogenic action of thyroid hormone has been shown in the chick chorioallantoic membrane (CAM) model, in the vessel sprouting model involving human dermal microvascular endothelial cells (HDMEC), and in vivo in the mouse matrigel angiogenesis model. In the absence of thyroid hormone, Tetrac blocks the angiogenic activity of basic fibroblast growth factor (bFGF, FGF2), vascular endothelial growth factor (VEGF) and other pro-angiogenic factors. Tetrac is effective in the CAM, HDMEC, and mouse angiogenesis models. This inhibitory action of Tetrac is thought to reflect its influence on the RGD recognition site that is relevant to pro-angiogenic actions.

Evidence that thyroid hormone can act primarily outside the cell nucleus has come from studies of mitochondrial responses to T3 or T2, from rapid onset effects of the hormone at the cell membrane and from actions on cytoplasmic proteins. The description of a plasma membrane receptor for thyroid hormone on integrin $\alpha v\beta 3$ has provided some insight into effects of the hormone on membrane ion pumps, such as the Na+/H+ antiporter, and has led to the description of interfaces between the membrane thyroid hormone receptor and nuclear events that underlie important cellular or tissue processes, such as angiogenesis and proliferation of certain tumor cells.

Circulating levels of thyroid hormone are relatively stable; therefore, membrane-initiated actions of thyroid hormone on neovascularization or on cell proliferation or on membrane ion channels—as well, of course, as gene expression effects of the hormone mediated by TR mentioned above—may be assumed to contribute to "basal activity" or setpoints of these processes in intact organisms. The possible clinical utility of cellular events that are mediated by the membrane receptor for thyroid hormone may reside in inhibition of such effect(s) in the contexts of neovascularization or tumor cell growth. Indeed, it has been shown that blocking the membrane receptor for iodothyronines with tetraiodothyroacetic acid (Tetrac), a hormone-binding inhibitory analog that has no agonist activity at the receptor, can arrest growth of glioma cells and of human breast cancer cells in vitro. Tetrac is a useful probe to screen for participation of the integrin receptor in actions of thyroid hormone.

Thyroid hormone can also stimulate the proliferation in vitro of certain tumor cell lines. Murine glioma cell lines have been shown to proliferate in response to physiological concentrations of T4 by a mechanism initiated at the integrin receptor and that is MAPK-dependent. In what may be a clinical corollary, a prospective study of patients with far advanced glioblastoma multiforme (GBM) in whom mild hypothyroidism was induced by propylthiouracil showed an important survival benefit over euthyroid control patients. In 2004, it was reported that human breast cancer MCF-7 cells proliferated in response to T4 by a mechanism that was inhibited by Tetrac. (See Tang et al., Endocrinology 145:3265-72 (2004)). A recent retrospective clinical analysis by Cristofanilli et al. showed that hypothyroid women who developed breast cancer did so later in life than matched euthyroid controls and had less aggressive, smaller lesions at the time of diagnosis than controls. (See Cristofanilli et al., Cancer 103 (6):1122-28 (2005). Thus, the trophic action of thyroid hormone on in vitro models of both brain tumor and breast cancer appears to have clinical support.

The ability of tetraiodothyroacetic acid (Tetrac) to inhibit the action of T4 and T3 at the integrin is shown in FIG. 1. Tetrac blocks the binding of iodothyronines to the integrin receptor. Also shown is crosstalk between the integrin and vascular growth factor receptors clustered with the receptor as well as the epidermal growth factor receptor (EGFR). Here, the presence of thyroid hormone at the cell surface alters the function of EGFR to allow the latter to distinguish EGF from TGF-$\alpha$, another growth factor that binds to EGFR. Moreover, the receptor is able to distinguish among the different thyroid hormone analogs and to selectively activate MAPK or PI3K, depending on the particular analog that this bound to the receptor.

There is a need in the art for thyroid hormone analogs that can bind to the cell surface receptor while not being able to enter the cell. Such reformulated hormone analogs would not express intracellular actions of the hormone and, thus, if absorbed into the circulation, would not have systemic thyroid hormone analog actions.

SUMMARY OF THE INVENTION

The invention is based, in part, on the discovery that thyroid hormone, thyroid hormone analogs, as well as their polymeric and nanoparticle forms, act at the cell membrane level and have pro-angiogenic properties that are independent of the nuclear thyroid hormone effects. Accordingly, these thyroid hormone analogs, polymeric forms, and nanoparticles can be used to treat a variety of disorders. Similarly, the invention is also based on the discovery that thyroid hormone analog antagonists (and their polymeric and nanoparticle forms) inhibit the pro-angiogenic effects of such analogs, and can also be used to treat a variety of disorders. Thus, such thyroid hormone analog antagonists can be used to inhibit cancer cell proliferation.

Accordingly, in one aspect the invention features methods for treating a condition amenable to treatment by promoting angiogenesis by administering to a subject in need thereof an amount of L-T4 or L-T3 nanoparticles, or analogs thereof, effective for promoting angiogenesis. Examples of such conditions amenable to treatment by promoting angiogenesis are provided herein and can include, for example, occlusive vascular disease, coronary disease, erectile dysfunction, myocardial infarction, ischemia, stroke, peripheral artery vascular disorders, cerebrovascular ischemia, limb ischemia, and/or wounds.

Examples of thyroid hormone analogs to promote angiogenesis are also provided herein and can include, but are not limited to, triiodothyronine (T3), levothyroxine (T4), T4 or T3 N-Methyl, T4 or T3 N-Ethyl, T4 or T3 N-Triphenyl, T4 or T3 N-Propyl, T4 or T3 N-Isopropyl, T4 or T3 N-tertiary butyl, 3,5-dimethyl-4-(4'-hydroxy-3'-isopropylbenzyl)-phenoxy acetic acid (GC-1), or 3,5-diiodothyropropionic acid (DITPA). Additional analogs are shown in FIG. 10, Tables A-D and are described in Example 12, infra. These analogs can be conjugated to polyvinyl alcohol (PVA), acrylic acid ethylene co-polymer, polyethyleneglycol (PEG), methoxypolyethylene glycol-poly(lactide-co-glycolide), polyacrylic acid, polylactic acid, agarose, PEO, m-PEG, PLLA, PGA, poly-L-lysine, Human Serum Albumin, cellulose derivatives, carbomethoxy/ethyl/hydroxypropyl, hyaluronic acid, folate linked cyclodextrin/dextran, sarcosine/amino acid spaced polymer, alginate, carrageenan, polylactic acid pectin/chitosan, chitosan, dextran, collagen, polyamine, poly aniline, poly alanine, polytrytophan, poly tyrosine, polylactide-coglycolide, poly(lactic-co-glycolic acid) (PLGA), polylysyl glycolide, polyglycolide, polylactide, or co-polymers thereof. The conjugation is via covalent (i.e., ester, ether, anhydride, or sulfhydryl linkage) or non-covalent bonds depending on the polymer used.

In one embodiment the thyroid hormone, thyroid hormone analogs, or polymeric or nanoparticulate forms thereof are administered by parenteral, oral, rectal, or topical means, or combinations thereof. Parenteral modes of administration include, but are not limited to, for example, subcutaneous, intraperitoneal, intramuscular, or intravenous modes, such as by catheter. Topical modes of administration can include, but are not limited to, solutions, creams, lotions, ointments, gels and transdermal patches.

In another embodiment, the thyroid hormone and/or thyroid hormone analogs can be conjugated to a nanoparticle, microparticle, or liposome or polymeric forms thereof can be incorporated in a nanoparticle, microparticle, or liposome. The nanoparticle and/or microparticle can be made from a polymer that can include, for example, polyglycolide, polylactide, or co-polymers thereof. The liposome, nanoparticle, or microparticle has a size of about less than 250 nanometers, and can be administered via one or more parenteral routes, or via another mode of administration. In another embodiment the liposome, nanoparticle, or microparticle can be lodged in capillary beds surrounding ischemic tissue, or applied to the inside of a blood vessel via a catheter.

Thyroid hormone, thyroid hormone analogs, or polymeric or nanoparticulate forms thereof according to the invention can also be co-administered with one or more biologically active substances that can include, for example, growth factors, vasodilators, anti-coagulants, anti-virals, anti-bacterials, anti-inflammatories, immuno-suppressants, analgesics, vascularizing agents, or cell adhesion molecules, or any combinations thereof. In one embodiment, the thyroid hormone analog or polymeric form is administered as a bolus injection prior to or post-administering one or more biologically active substances.

Growth factors can include, for example, transforming growth factor alpha ("TGFα"), transforming growth factor beta ("TGFβ"), basic fibroblast growth factor, vascular endothelial growth factor, epithelial growth factor, nerve growth factor, platelet-derived growth factor, insulin-like growth factor, and vascular permeability factor. Vasodilators can include, for example, adenosine, adenosine derivatives, or combinations thereof. Anticoagulants include, but are not limited to, heparin, heparin derivatives, anti-factor Xa, antithrombin, aspirin, clopidogrel, or combinations thereof.

In another aspect of the invention, methods are provided for promoting angiogenesis along or around a medical device by coating the device with a thyroid hormone, thyroid hormone analog, or polymeric or nanoparticulate forms thereof according to the invention prior to inserting the device into a patient. The coating step can further include coating the device with one or more biologically active substance, such as, but not limited to, a growth factor, a vasodilator, an anticoagulant, or combinations thereof. Examples of medical devices that can be coated with thyroid hormone analogs or polymeric forms according to the invention include defibrillators, stents, catheters, cannulas or electrodes.

In a further aspect, the invention provides methods for treating a condition amenable to treatment by inhibiting angiogenesis by administering to a subject in need thereof an amount of an anti-angiogenesis agent effective for inhibiting angiogenesis. Examples of the conditions amenable to treatment by inhibiting angiogenesis include, but are not limited to, primary or metastatic tumors, adenoid carcinoma, breast cancer, colon cancer, glioblastoma multiforme and other brain cancers, head-and-neck cancer, hepatoma, lung cancer, lymphoma, melanoma, basal cell carcinoma, squamous cell carcinoma, myeloma, neuroblastaoma, ovarian cancer, prostate cancer, pancreatic cancer, renal cancer, sarcoma, stomach cancer, thyroid cancer, diabetic retinopathy, macular degeneration, arthritis, non-cancerous skin disorders selected from the group consisting of rosacea, poikiloderma of Civatte, angiomas, telangiectasias, and psoriasis, and related conditions. Those skilled in the art will recognize that the anti-angiogenesis compositions, agents, and formulations described herein also exhibit anti-inflammatory properties that are directed at several targets, e.g., pro-inflammatory gene expression locally in inflamed tissues as well as angiogenesis. Such anti-angiogenesis agents can act at the cell surface to inhibit the pro-angiogenesis agents.

Examples of the anti-angiogenesis agents used for inhibiting angiogenesis are also provided by the invention and include, but are not limited to, tetraiodothyroacetic acid (Tetrac), triiodothyroacetic acid (Triac), monoclonal antibody LM609, XT 199, or polymeric forms thereof. Also included are Tetrac analogs, such as those described in Example 13, infra. These analogs can be conjugated to polyvinyl alcohol, acrylic acid ethylene co-polymer, polyethyleneglycol (PEG), methoxypolyethylene glycol-poly(lactide-co-glycolide), polyacrylic acid, polylactic acid, agarose, polyglycolide, PEO, m-PEG, PVA, PLLA, PGA, poly-L-lysine, Human Serum Albumin, cellulose derivatives, carbomethoxy/ethyl/hydroxypropyl, hyaluronic acid, folate linked cyclodextrin/dextran, sarcosine/amino acid spaced polymer, alginate, carrageenan, polylactic acid pectin/chitosan, chitosan, dextran, collagen, polyamine, poly aniline, poly alanine, polytrytophan, poly tyrosine, polylactide-co-glycolide, poly(lactic-co-glycolic acid) (PLGA), polylysyl glycolide, polyglycolide, polylactide, or co-polymers thereof. The conjugation is via covalent (i.e., ester, ether, anhydride, or sulfhydryl linkage) or non-covalent bonds depending on the polymer used.

In another aspect, the invention provides for primary or adjunctive anti-proliferative treatment of certain cancers. Examples of the cancerous conditions amenable to this treatment include, but are not limited to, adenoid carcinoma, breast cancer, colon cancer, glioblastoma multiforme and other brain cancers, head-and-neck cancer, hepatoma, lung cancer, lymphoma, melanoma, basal cell carcinoma, squamous cell carcinoma, myeloma, neuroblastaoma, ovarian cancer, prostate cancer, pancreatic cancer, renal cancer, sarcoma, stomach cancer, and thyroid cancer. Examples of the agents used for anti-proliferative action are provided by the invention and include, but are not limited to other anti-proliferative agents including chemotherapeutic agents (e.g., doxorubicin, paclitaxel, cisplatin, cyclophosphamide, and gemcitabine).

In one embodiment, the anti-angiogenesis agent, or polymeric or nanoparticulate forms thereof is administered by a parenteral, oral, rectal, or topical mode, or combination thereof. Parenteral modes of administration include, for example, subcutaneous, intraperitoneal, intramuscular, or intravenous modes, such as by catheter. Topical modes of administration can include, for example, solutions, creams, lotions, ointments, gels, and transdermal patches. In another embodiment, the anti-angiogenesis agent can be co-administered with one or more anti-angiogenesis therapies or chemotherapeutic agents.

In another embodiment, the anti-angiogenic agent can be conjugated to a nanoparticle, microparticle, or liposome, or polymeric forms thereof can be incorporated into a nanoparticle, microparticle, or liposome. The nanoparticle or microparticle can be made from a polymer that can include, for example, polyglycolide, polylactide, or co-polymers thereof. The liposome, nanoparticle, or microparticle has a size of about less than 250 nanometers, and can be administered via one or more parenteral routes, or another mode of administration. In another embodiment the liposome, nanoparticle, or microparticle can be lodged in capillary beds surrounding ischemic tissue, or applied to the inside of a blood vessel via a catheter.

In yet a further aspect, the invention provides compositions (i.e., angiogenic agents) that include thyroid hormone, and analogs conjugated to a polymer. The conjugation can be through a covalent or non-covalent bond, depending on the polymer. A covalent bond can occur through an ether, ester, anhydride, or sulfhydryl linkage, for example. Examples of the thyroid hormone analogs are also provided by the instant invention and include levothyroxine (T4), triiodothyronine (T3), 3,5-dimethyl-4-(4'-hydroxy-3'-isopropylbenzyl)-phenoxy acetic acid (GC-1), 3,5-diiodothyropropionic acid (DITPA), and/or analogs thereof. In one embodiment, the polymer can include, but is not limited to, polyvinyl alcohol (PVA), acrylic acid ethylene co-polymer, polyethyleneglycol (PEG), methoxypolyethylene glycol-poly(lactide-co-glycolide), polyacrylic acid, polylactic acid, agarose, PEO, m-PEG, PLLA, PGA, poly-L-lysine, Human Serum Albumin, cellulose derivatives, carbomethoxy/ethyl/hydroxypropyl, hyaluronic acid, folate linked cyclodextrin/dextran, sarcosine/amino acid spaced polymer, alginate, carrageenan, polylactic acid pectin/chitosan, chitosan, dextran, collagen, polyamine, poly aniline, poly alanine, polytrytophan, poly tyrosine, polylactide-co-glycolide, poly(lactic-co-glycolic acid) (PLGA), polylysyl glycolide, polyglycolide, polylactide, or co-polymers thereof.

In another aspect, the invention also provides compositions (i.e., anti-angiogenic agents that include thyroid hormone analogs such as tetraiodothyroacetic acid (Tetrac), triiodothyroacetic acid (Triac), monoclonal antibody LM609, XT 199, and/or analogs thereof conjugated to a polymer. For example, the conjugation can be through a covalent or non-covalent bond, depending on the polymer employed. Those skilled in the art will recognize that a covalent bond can occur through an ether, ester, sulfhydrylor anhydride linkage, for example. By way of non-limiting example, the polymer may be selected from polyvinyl alcohol (PVA), acrylic acid ethylene co-polymer, polyethyleneglycol (PEG), methoxypolyethylene glycol-poly(lactide-co-glycolide), polyacrylic acid, polylactic acid, agarose, PEO, m-PEG, PLLA, PGA, poly-L-lysine, Human Serum Albumin, cellulose derivatives, carbomethoxy/ethyl/hydroxypropyl, hyaluronic acid, folate linked cyclodextrin/dextran, sarcosine/amino acid spaced polymer, alginate, carrageenan, polylactic acid pectin/chitosan, chitosan, dextran, collagen, polyamine, poly aniline, poly alanine, polytrytophan, poly tyrosine, polylactide-co-glycolide, poly(lactic-co-glycolic acid) (PLGA), polylysyl glycolide, polyglycolide, polylactide, or co-polymers thereof.

In another aspect, the invention provides for pharmaceutical formulations including pharmaceutically or therapeutically effective amounts of the angiogenic agents or anti-angiogenic agents according to the present invention in a pharmaceutically acceptable carrier. In one embodiment, the pharmaceutical formulations can also include one or more pharmaceutically acceptable excipients or carriers.

The pharmaceutical formulations according to the present invention can be encapsulated, conjugated, or incorporated in a liposome, microparticle, or nanoparticle. The liposome, nanoparticle, or microparticle has a size of between about 10 nanometers and 1000 nanometers or less than about 250 nanometers. Any of the pharmaceutical formulations according to the present invention can be administered via parenteral, oral, rectal, or topical means, or any combinations thereof. In another embodiment, the pharmaceutical formulations can be co-administered to a subject in need thereof with one or more biologically active substances including, but not limited to, growth factors, vasodilators, anti-coagulants, anti-virals, anti-bacterials, anti-inflammatories, immunosuppressants, analgesics, vascularizing agents, cell adhesion molecules, or combinations thereof.

Additional methods of the present invention include a method of increasing the chemosensitivity or radiosensitivity of cancer cells by administering to the cells Tetrac, Tetrac analogs, or nanoparticles thereof in an amount sufficient to enhance the chemosensitivity or radiosensitivity as well as methods of treating a patient suffering from the presence of a tumor, by administering Tetrac, Tetrac analogs, or nanoparticles thereof to the patient in an amount effective for enhancing the chemosensitivity or radiosensitivity of cancer cells.

Those skilled in the art will recognize that any of the nanoparticles disclosed herein can be used to induce chemosensitization of chemoresistant cancer cells. Thus, these nanoparticles can be used to suppress the development of chemotherapeutic drug resistance in cancer cells.

Likewise, any of these nanoparticles can also be used to induce radiosensitivity or oppose radioresistance of cancer cells. In general, radiosensitivity is the relative susceptibility of cells, tissues, organs or organisms to the harmful effect of ionizing radiation. Cells are least sensitive when in the S phase, then the $G_1$ phase, then $G_2$ phase and the most sensitive in the M phase of the cell cycle. Overall, X-rays are more effective on cells which have a greater reproductive activity.

The nanoparticles can be formed from a polymer either before or after conjugation of the polymer to the thyroid hormone or thyroid hormone analog. Thus, the invention provides methods of producing thyroid hormone or thyroid hormone analog nanoparticles by conjugating a polymer to the thyroid hormone or thyroid hormone analog prior to making the nanoparticles. Alternatively, the nanoparticles can first be synthesized from a polymer prior to binding the thyroid hormone or thyroid hormone analog to the synthesized nanoparticles. Those skilled in the art will recognize that, in either embodiment, the thyroid hormone or thyroid hormone analog can be T4, T3, T4 or T3 N-Methyl, T4 or T3 N-Ethyl, T4 or T3 N-Triphenyl, T4 or T3 N-Propyl, T4 or T3 N-Isopropyl, T4 or T3-N-Tertiary butyl, GC-1, DIPTA, Tetrac, Triac, and/or any other analogs thereof.

In some embodiments, a linker between about 4 and 15 atoms long is used between the polymer (or the pre-synthesized nanoparticle) and the thyroid hormone or thyroid hormone analog. For example, the linker may be attached to the thyroid hormone or thyroid hormone analog via a covalent or non-covalent bond. Moreover, the point of attachment for the linker may be the outer ring hydroxyl of the thyroid hormone or thyroid hormone analog. One non-limiting example of a suitable linker is shown in FIG. 35.

By way of non-limiting example, the polymer may be polyvinyl alcohol (PVA), acrylic acid ethylene co-polymer, polyethyleneglycol (PEG), methoxypolyethylene glycol-poly(lactide-co-glycolide), polyacrylic acid, polylactic acid, agarose, PEO, m-PEG, PLLA, PGA, poly-L-lysine, Human Serum Albumin, cellulose derivatives, carbomethoxy/ethyl/hydroxypropyl, hyaluronic acid, folate linked cyclodextrin/dextran, sarcosine/amino acid spaced polymer, alginate, carrageenan, polylactic acid pectin/chitosan, chitosan, dextran, collagen, polyamine, poly aniline, poly alanine, polytrytophan, poly tyrosine, polylactide-co-glycolide, poly(lactic-co-glycolic acid) (PLGA), polylysyl glycolide, polyglycolide, polylactide, or co-polymers thereof.

In various embodiments, the amount of thyroid hormone or thyroid hormone analog in the nanoparticle is between 0.1 and 25%. For example, the amount of thyroid hormone conjugated to the nanoparticle may be about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, or 25% The determination of the preferred (or optimal) percentage of thyroid hormone or thyroid hormone analog per nanoparticle is well within the routine skill of those in the art. The results of preliminary studies suggest that lower concentrations of thyroid hormone or thyroid hormone analogs may be more active than either unmodified thyroid hormone or thyroid hormone analogs or nanoparticles having a higher density.

Moreover, in one embodiment, the nanoparticles produced according to these methods may have a diameter between 10 and 1000 nm. In another embodiment, the diameter of the nanoparticles is less than 250 nm.

The invention also provides compositions of thyroid hormone or thyroid hormone analog nanoparticles wherein the thyroid hormone or thyroid hormone analog is conjugated to a polymer via a linker and then the polymer is formed into the nanoparticle. Alternatively, the thyroid hormone or thyroid hormone analogs are attached to the polymers that have already been formed into the nanoparticles via a linker. For example, the linker can be between 4 and 15 atoms (i.e., 4, 5, 6, 7, 8, 9, 10, 11, 12, 13, 14, or 15) long and may be attached to the thyroid hormone or thyroid hormone analog via a covalent or non-covalent bond. Moreover, the point of attachment for the linker may be the outer ring hydroxyl of the thyroid hormone or thyroid hormone analog. Those skilled in the art will recognize that the reason for using a linker is to expose Tetrac (or Triac) properly to the receptor site on the integrin. If there is no linker present, then the ligand will not protrude adequately from the surface of the nanoparticle to fully occupy the receptor site. The outer ring hydroxyl group is used for linker attachment because the hydroxyl group is not primarily involved in ligand-integrin interaction.

In any of the compositions described herein, the thyroid hormone or thyroid hormone analog (other than Tetrac, which does not have an $NH_2$ moiety) can have a protecting group at the $NH_2$ moiety or at the carboxyl moiety of Tetrac. Examples of suitable protecting groups include, but are not limited to N-Methyl, N-Ethyl, N-Triphenyl, N-Propyl, N-Isopropyl, N-tertiary butyl, and/or any other functional group known in the art. Those skilled in the art will recognize that that OTIPS protecting group can also be used in the compositions described herein.

In any of these compositions, the thyroid hormone or thyroid hormone analog can be selected from T4, T3, T4 or T3 N-Methyl, T4 or T3 N-Ethyl, T4 or T3 N-Triphenyl, T4 or T3 N-Propyl, T4 or T3 N-Isopropyl, T4 or T3-N-Tertiary butyl, GC-1, DIPTA, Tetrac, Triac, analogs thereof, or any combination thereof.

Likewise, for any of the compositions described herein, suitable polymers include, but are not limited to polyvinyl alcohol (PVA), acrylic acid ethylene co-polymer, polyethyleneglycol (PEG), methoxypolyethylene glycol-poly(lactide-co-glycolide), polyacrylic acid, polylactic acid, agarose, PEO, m-PEG, PLLA, PGA, poly-L-lysine, Human Serum Albumin, cellulose derivatives, carbomethoxy/ethyl/hydroxypropyl, hyaluronic acid, folate linked cyclodextrin/dextran, sarcosine/amino acid spaced polymer, alginate, carrageenan, polylactic acid pectin/chitosan, chitosan, dextran, collagen, polyamine, poly aniline, poly alanine, polytrytophan, poly tyrosine, polylactide-co-glycolide, poly(lactic-co-glycolic acid) (PLGA), polylysyl glycolide, polyglycolide, polylactide, or co-polymers thereof.

Those skilled in the art will also recognize that, in these compositions, the amount of thyroid hormone or thyroid hormone analog in the nanoparticle is preferably between 0.1 and 25%. Moreover, in these compositions, the nanoparticles have a diameter between 10 and 1000 nm or preferably less than 250 nm.

Also provided are pro-angiogenic formulations containing any of the pro-angiogenic compositions described herein and one or more pharmaceutically acceptable carriers, wherein the thyroid hormone or thyroid hormone analog is selected from the group consisting of T4, T3, T4 or T3 N-Methyl, T4 or T3 N-Ethyl, T4 or T3 N-Triphenyl, T4 or T3 N-Propyl, T4 or T3 N-Isopropyl, T4 or T3-N-Tertiary butyl, GC-1, and DIPTA. Such pro-angiogenic formulations may also contain one or more biologically active substances selected from the group consisting of TGF-beta, basic fibroblast growth factor (FGF2), epithelial growth factor (EGF), transforming growth factors alpha and beta (TGF-α and β), nerve growth factor (NGF), platelet-derived growth factor (PDGF), vascular endothelial growth factor/vascular permeability factor (VEGF/VPF), anti-virals, anti-bacterials, anti-inflammatory, immuno-suppressants, analgesics, vascularizing agents, and cell adhesion molecules. These formulations can be used to treat a condition amenable to treatment by promoting angiogenesis in a subject in a subject by administering to the subject a therapeutically effective amount of the pro-angiogenic formulation. For example, conditions amenable to treatment by promoting angiogenesis can include occlusive vascular disease, coronary disease, erectile dysfunction, myocardial infarction, ischemia, stroke, peripheral artery vascular disorders, cerebrovascular, limb ischemia, and wounds.

Likewise, the invention also provides anti-angiogenic formulations containing any of the anti-angiogenic compositions described herein and one or more pharmaceutically acceptable carriers, wherein the thyroid hormone analog is selected from the group consisting of Tetrac and Triac. Such anti-angiogenic compositions may also contain one or more chemotherapeutic drugs selected from a group consisting of doxorubicin, etoposide, cyclophosphamide, 5-fluorouracil, cisplatin, trichostatin A, paclitaxel, gemcitabine, taxotere, cisplatinum, carboplatinum, irinotecan, topotecan, adriamycin, bortezomib, and atoposide. Such formulations can be used to treat a condition amenable to treatment by inhibiting angiogenesis in a subject by administering to the subject a therapeutically effective amount of the anti-angiogenic formulation. For example,
conditions amenable to treatment by inhibiting angiogenesis can include primary or metastatic tumors, adenoid carcinoma, breast cancer, colon cancer, glioblastoma multiforme and other brain cancers, head-and-neck cancer, hepatoma, lung cancer, lymphoma, melanoma, basal cell carcinoma, squamous cell carcinoma, myeloma, neuroblastaoma, ovarian cancer, prostate cancer, pancreatic cancer, renal cancer, sarcoma, stomach cancer, thyroid cancer, diabetic retinopathy, macular degeneration, arthritis, non-cancerous skin disorders, rosacea, poikiloderma of Civatte, angiomas, telangiectasias, and psoriasis.

These anti-angiogenic formulations can also be used to suppress growth of cancer cells which are resistant to drug therapy, comprising administering to a subject in need thereof an amount of the formulation effective for suppressing the growth. For example, the therapy-resistant cancer cells are selected from the group consisting of a primary or metastatic tumors, adenoid carcinoma, breast cancer, colon cancer, glioblastoma multiforme and other brain cancers, head-and-neck cancer, hepatoma, lung cancer, lymphoma, melanoma, basal cell carcinoma, squamous cell carcinoma, myeloma, neuroblastaoma, ovarian cancer, prostate cancer, pancreatic cancer, renal cancer, sarcoma, stomach cancer, and thyroid cancer. In various embodiments, the drug therapy comprises administration of conventional or novel chemotherapeutic drugs, including, for example, (but not limited to) doxorubicin, etoposide, cyclophosphamide, 5-fluorouracil, cisplatin, trichostatin A, paclitaxel, gemcitabine, taxotere, cisplatinum, carboplatinum, irinotecan, topotecan, adriamycin, bortezomib and atoposide or novel derivatives of the foregoing agents. In other embodiments, these methods further involve
administering a chemotherapeutic drug such as doxorubicin, etoposide, cisplatin, and/or trichostatin A.

In other embodiments, the invention provides methods of treating a patient suffering from the presence of a tumor, by administering the anti-angiogenic formulations of the invention to the patient in an amount effective for enhancing the chemosensitivity of cancer cells.

Those skilled in the art will recognize that any of the anti-angiogenic formulations described herein can also be administered in combination (i.e., at the same time or sequentially) with cetuximab in order to increase chemosensitivity.

Those skilled in the art will recognize that thyroid hormone receptor on the cell surface can radiosensitize cancer cells. The integrin is not expressed on normal cells. As such, normal cells will not become radiosensitized. Moreover, the exposure of cancer cells to Tetrac only needs to be brief (i.e., 60 minutes or less) in order to achieve radiosensitization.

Also provided are methods of increasing radiosensitivity or opposing resistance of cancer cells by administering to a subject in need thereof an amount of Tetrac, Tetrac nanoparticles or analogs thereof (or any of the anti-angiogenic formulations described herein), effective for increasing the radiosensitivity of the cancer cells. Specifically, the cancer cells can be selected from the group consisting of a primary or metastatic tumor, breast cancer, thyroid cancer, neuroblastoma, glioma and glioblastoma multiforme and other brain cancers, colon cancer, head-and-neck cancers, melanoma and basal cell and squamous cell carcinomas of the skin, sarcoma, ovarian cancer, prostate cancer, kidney cancer, hepatoma, lung cancer, pancreatic cancer, stomach cancer, myeloma, and lymphoma. More particularly, the cancer cells are brain cancer cells.

In one embodiment, the Tetrac or Tetrac nanoparticles (or any of the anti-angiogenic formulations described herein) are administered to the subject before being subjected to radiation therapy. Those skilled in the art will recognize that the Tetrac or Tetrac nanoparticles (or any of the anti-angiogenic formulations described herein) decreases a recovery of sub-lethal damage repair of the cancer cells. In addition, the Tetrac or Tetrac nanoparticles (or any of the anti-angiogenic formulations described herein) decrease a recovery of potentially lethal damage repair of the cancer cells.

Further, arteriovenous malformation (AVM) can be treated with radiation as well. Therefore, in accordance with this embodiment, patients being treated with radiation for AVM may also be given an amount of Tetrac, Tetrac nanoparticles or analogs thereof, in an amount effective to increase the radiosensitivity of the cancer cells.

Moreover, in some embodiments, Tetrac, Tetrac nanoparticles, or analogs thereof can be used in combination with thyrotropin (TSH) administration or the treatment of thyroid cancer remnants with radioiodine (RAI). Specifically, recombinant human TSH (rhTSH, Thyrogen) (Genzyme) can be used in connection with the Tetrac, Tetrac nanoparticles, or analogs thereof. (See, R M Tuttle et al., J Nucl Med 49:764-770, 2008, which is herein incorporated by reference in its entirety).

The details of one or more embodiments of the invention have been set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural references unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference in their entirety.

BRIEF DESCRIPTION OF THE DRAWINGS

FIG. 2 shows the effects of L-T4 and L-T3 on angiogenesis quantitated in the chick CAM assay.

FIG. 3 shows that Tetrac inhibits stimulation of angiogenesis by T4 and agarose-linked T4 (T4-ag). In FIG. 3A, a 2.5-fold increase in blood vessel branch formation is seen in a representative CAM preparation exposed to 0.1 μmol/L T4 for 3 days. In 3 similar experiments, there was a 2.3-fold increase. This effect of the hormone is inhibited by Tetrac (0.1 μmol/L), a T4 analog shown previously to inhibit plasma membrane actions of T4.13 Tetrac alone does not stimulate angiogenesis (C). In FIG. 3B, T4-ag (0.1 μmol/L) stimulates angiogenesis 2.3-fold, an effect also blocked by Tetrac. FIG. 3C is a summary of the results of 3 experiments that examine the actions of Tetrac, T4-ag, and T4 in the CAM assay. Data (means±SEM) were obtained from 10 images for each experimental condition in each of 3 experiments. **P<0.001 by ANOVA, comparing T4-treated and T4-agarose-treated samples with PBS-treated control samples.

FIG. 4 is a comparison of the proangiogenic effects of FGF2 and T4.

FIG. 5 shows the effect of anti-FGF2 on angiogenesis caused by T4 or exogenous FGF2.

FIG. 6 shows the effect of PD 98059, a MAPK (ERK1/2) signal transduction cascade inhibitor, on angiogenesis induced by T4, T3, and FGF2. In FIG. 6A, angiogenesis stimulated by T4 (0.1 μmol/L) and T3 (1 nmol/L) together is fully inhibited by PD 98059 (3 μmol/L). As shown in FIG. 6B, Angiogenesis induced by FGF2 (1 μg/mL) is also inhibited by PD 98059, indicating that the action of the growth factor is also dependent on activation of the ERK1/2 pathway. T4 initiates its proangiogenic effect at the cell membrane. The results shown in FIGS. 6A and B are consistent with 2 roles played by MAPK in the proangiogenic action of thyroid hormone: ERK1/2 transduces the early signal of the hormone that leads to FGF2 elaboration and transduces the subsequent action of FGF2 on angiogenesis. FIG. 6C shows a summary of results of 3 experiments, represented by A and B, showing the effect of PD98059 on the actions of T4 and FGF2 in the CAM model. *P<0.01; **P<0.001, indicating results of ANOVA on data from 3 experiments.

FIG. 7 shows that T4 and FGF2 activate MAPK in ECV304 endothelial cells. Cells were prepared in M199 medium with 0.25% hormone-depleted serum and treated with T4 (0.1 μmol/L) for 15 minutes to 6 hours. Cells were harvested and nuclear fractions prepared as described previously. Nucleoproteins, separated by gel electrophoresis, were immunoblotted with antibody to phosphorylated MAPK (pERK1 and pERK2, 44 and 42 kDa, respectively), followed by a second antibody linked to a luminescence-detection system. A β-actin immunoblot of nuclear fractions serves as a control for gel loading in each part of this figure. Each immunoblot is representative of 3 experiments.

FIG. 10 depicts various thyroid hormone analogs capable of conjugation with various polymers. FIGS. 10 A-D show substitutions required to achieve various thyroid hormone analogs, which can be conjugated to create polymeric or nanoparticulate forms of thyroid hormones or thyroid hormone analogs of the invention.

FIG. 15 shows the effect of Tetrac on expression of classical drug resistance genes and on drug transport.

FIG. 16 demonstrates that Tetrac forces drug resistant cancer cells to undergo senescence and apoptosis. In FIG. 16A, SKN-SH/R cells were subjected to treatment doxorubicin (Dox) alone, Tetrac alone, or the combination of both for 24 h. Expression of p21/WAF1, cleaved caspase-3 (Cl-Casp-3) and beta action were measured by Western blot using specific antibodies. In FIG. 16B, the cells were seeded in 24 well plates and treated as mentioned above and expression of the senescence associated beta galactosidase (SA-β-Gal.) was assayed as described in the methods section. In FIG. 16C, the cells were seeded on cover slips and treated with the drugs as above for 24 h, after which they were fixed and stained with Hoechst and the percentage of positive cells graphed. The data represent average of 3 determinations±SE.

FIG. 25 is a schematic showing the synthesis of various Tetrac analogs.

FIG. 28 shows representative illustrations for the anti-angiogenesis effects of Tetrac and Tetrac analogs 3 (tert-butyl-2-(4-(4-hydroxy-3,5-diiodophenoxy)-3,5-diiodophenyl)acetate), 5 (Triisopropylsilyl-2-(4-(4-hydroxy-3,5-diiodophenoxy)-3,5-diiodophenyl)acetate), and 7 (triisopropylsilyl-2-(4-(3,5-diiodo-4-(oxiran-2-ylmethoxy) phenoxy)-3,5-diiodophenyl)acetate).

FIG. 36 shows representative confocal images illustrating the differences in distribution between Tetrac and Tetrac NP in human medullary thyroid cancer cells. Cy3-labeled Tetrac NP (PLGA-Tetrac nanoparticles) is on the cell surface (upper panel), whereas Cy3-labeled Tetrac is distributed homogenously in cytoplasm and over the nucleus (lower panel).

mouse xenograft volume over time, compared to control. Data represent mean tumor volume (mm³)±SD, n=6 animals per group. A: right flank; B: left flank tumor cell implants. *P<0.01, two treatment groups versus control.

Figure 39:
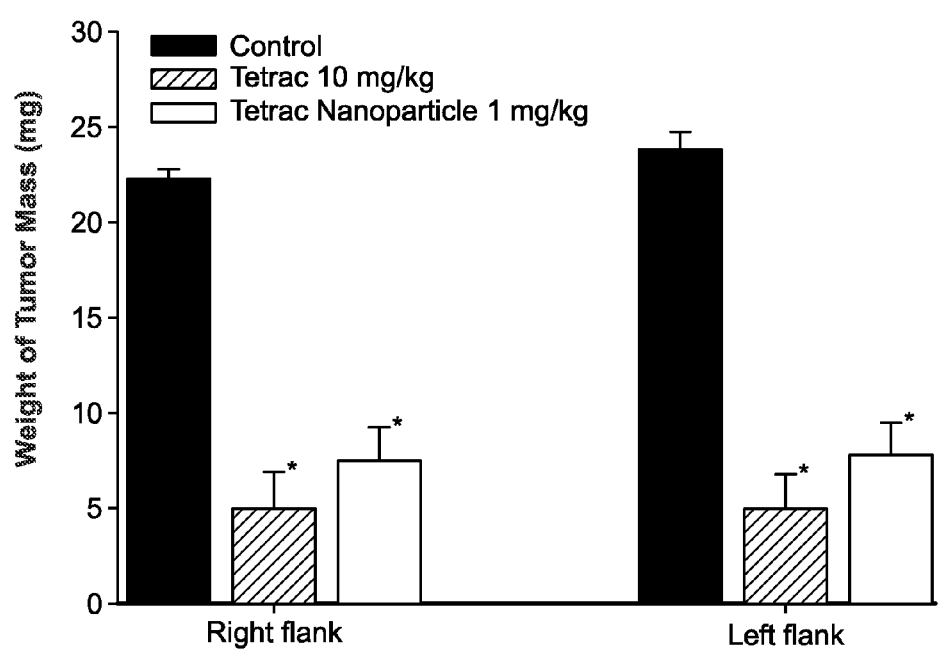

FIG. 39 shows the effect of Tetrac and Tetrac nanoparticle treatment on MTC tumor mass at time of sacrifice, compared to untreated control. Data represent mean tumor mass (mg) ±SD, n=6 animals per group. *P<0.01, treatment groups vs. control.

Figure 40:
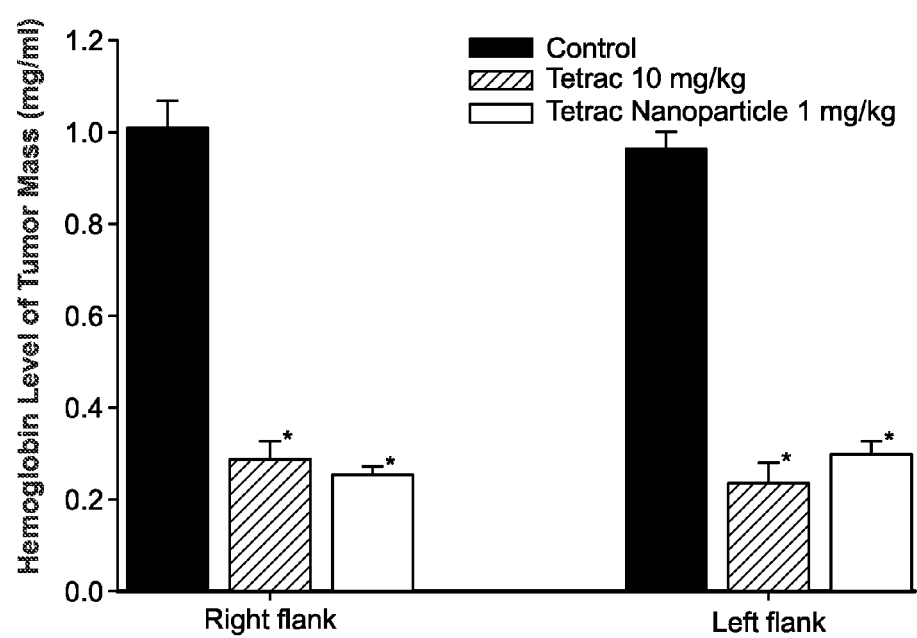

FIG. 40 shows the effect of Tetrac and Tetrac nanoparticle on MTC tumor mass hemoglobin level, compared to control. Data represent mean hemoglobin level (mg/mL)±SD, n=6 animals per group. *P<0.01, treatment groups vs. control.

Figure 41:
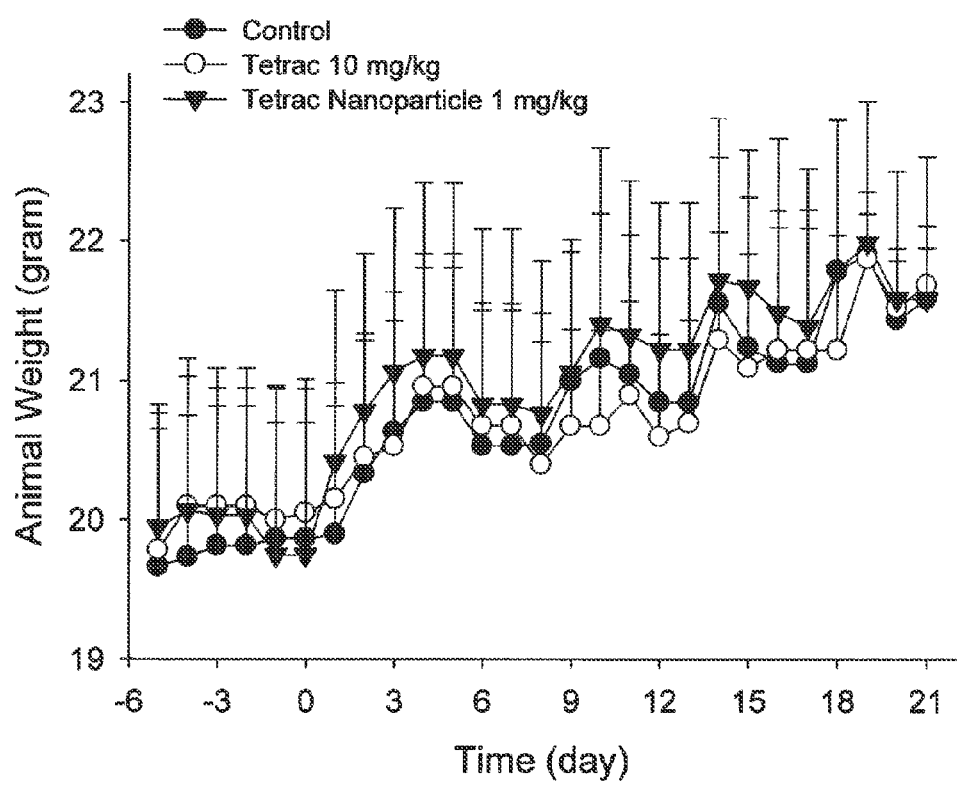

FIG. 41 shows the effect of Tetrac and Tetrac nanoparticle treatment on mean body weight of xenografted (MTC tumor cells) animals over time, compared to control. Data represent mean body weight (gm)±SD, n=6 animals per group.

Figure 42:
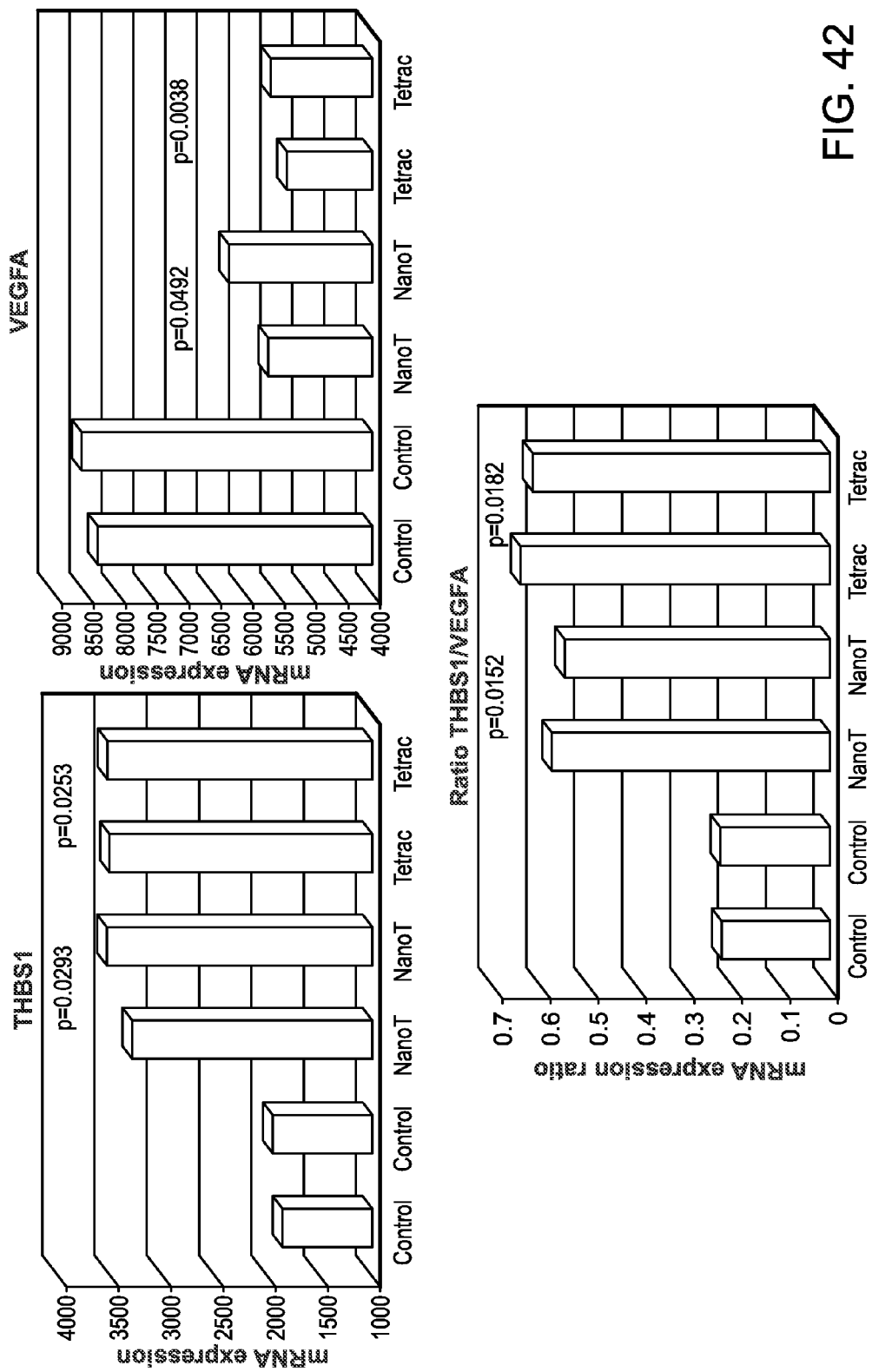

FIG. 42 shows duplicate RNA microarray results from human MTC cells treated with unmodified Tetrac or Tetrac nanoparticles (NanoT) that demonstrate significantly increased expression of thrombospondin (THBS1) (upper left panel) and VEGFA (upper right panel) in response to both agents. Tetrac and NP decreased VEGF expression. The lower panel describes the ratio between the expression profiles.

Figure 43:
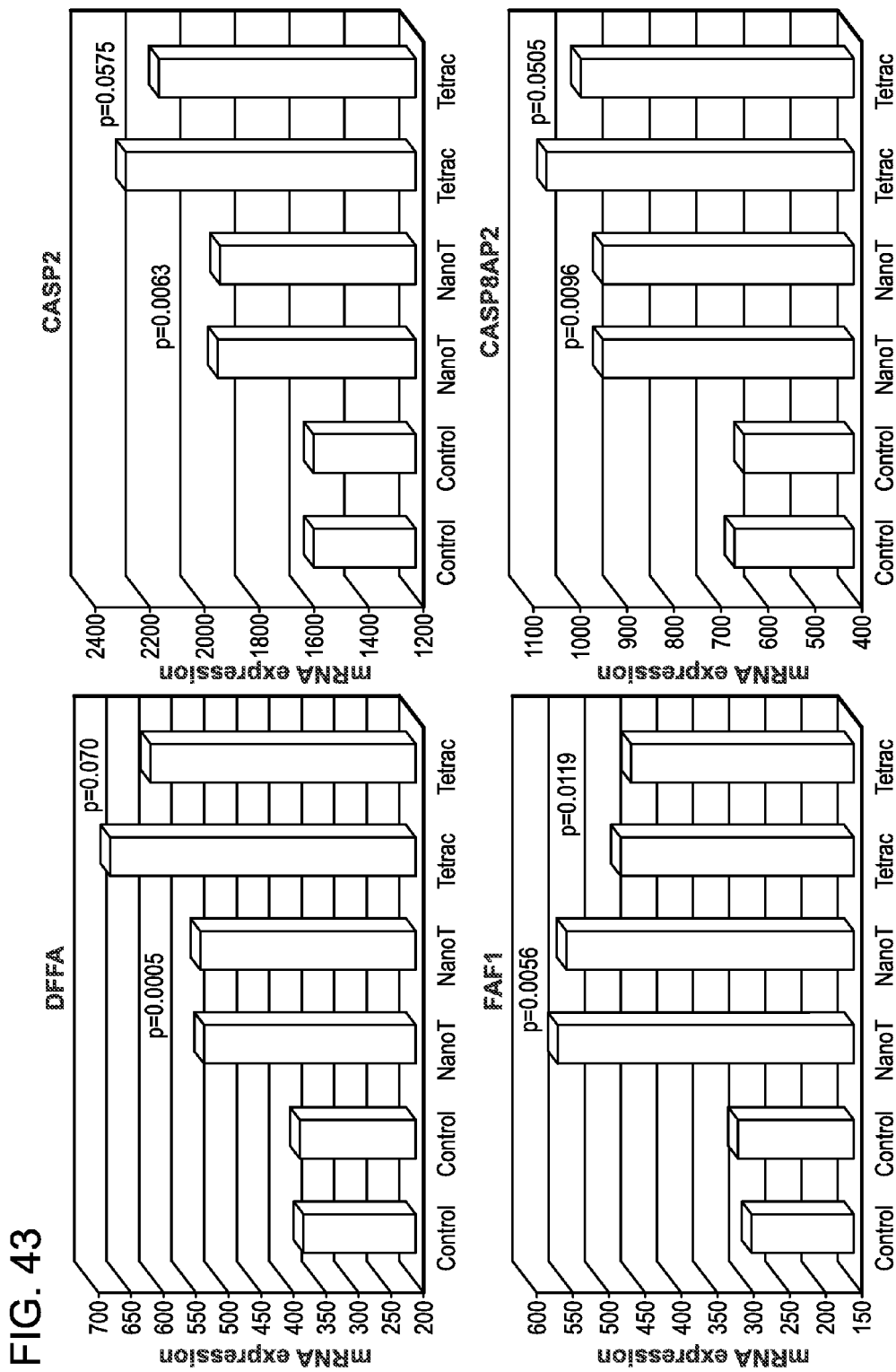

FIG. 43 shows duplicate RNA microarray results from treated MTC cells, unmodified Tetrac and Tetrac NP (NanoT) similarly induce expression of apoptosis-relevant genes: DFFA (upper left panel), caspase-2 (CASP2) (upper right panel), fas associated factor 1 (FAFI) (lower left panel), and caspase-8 associated protein-2 (CASP8Ap2) (lower right panel).

Figure 44:
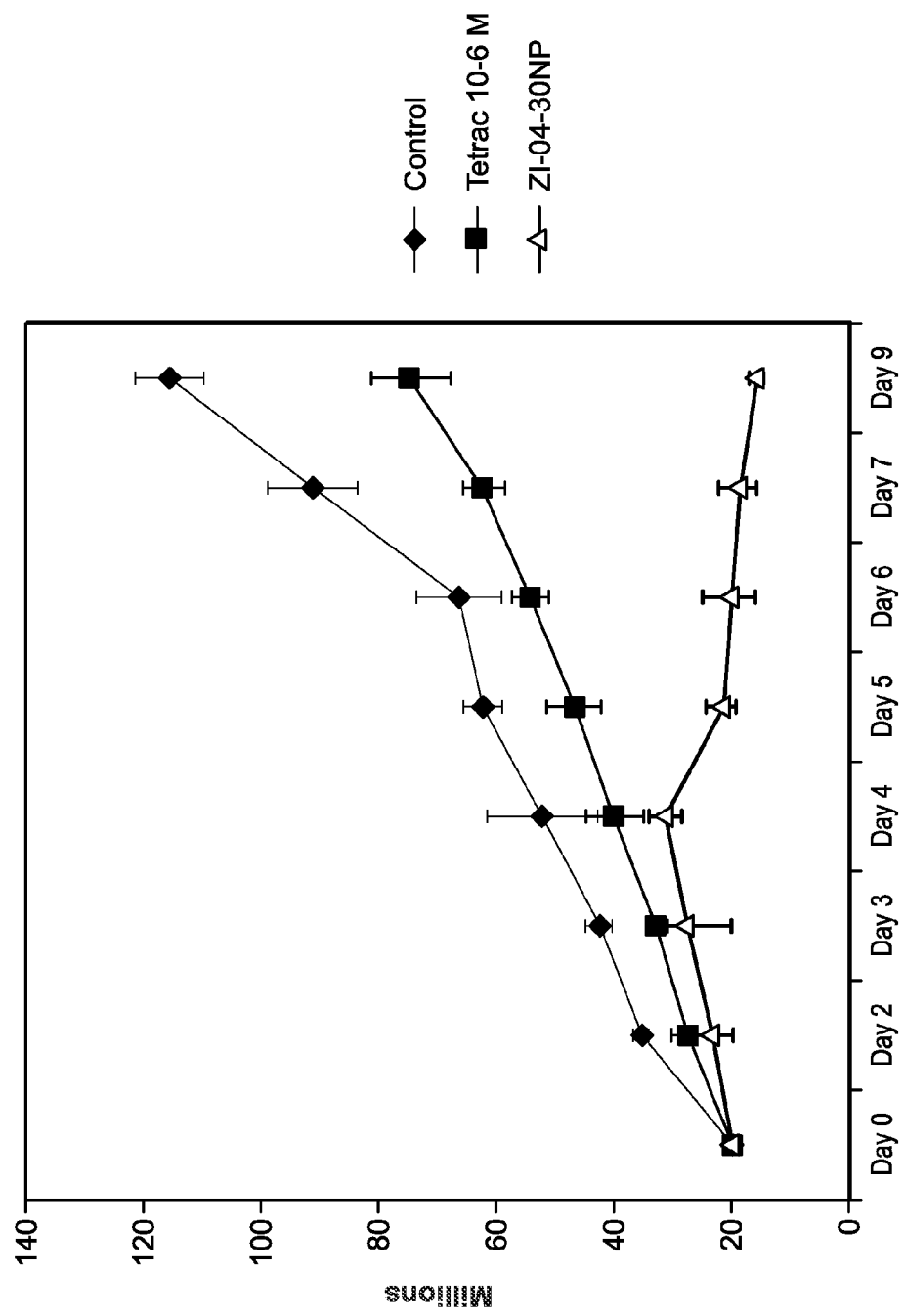

FIG. 44 shows the effects of Tetrac formulations on MDA-MB-231 cell proliferation (cell count) in a perfusion bellows cell culture system. Control cells proliferated throughout the 9 day study. Added at day 0 were unmodified Tetrac ($10^{-6}$ M) and Tetrac nanoparticulate (lot ZI-04-30NP) (Tetrac equivalent in the nanoparticulate preparation was $10^{-6}$ M). Tetrac reduced cell proliferation by more than 30% and the nanoparticulate formulation fully suppressed cell proliferation.

Figure 45A:
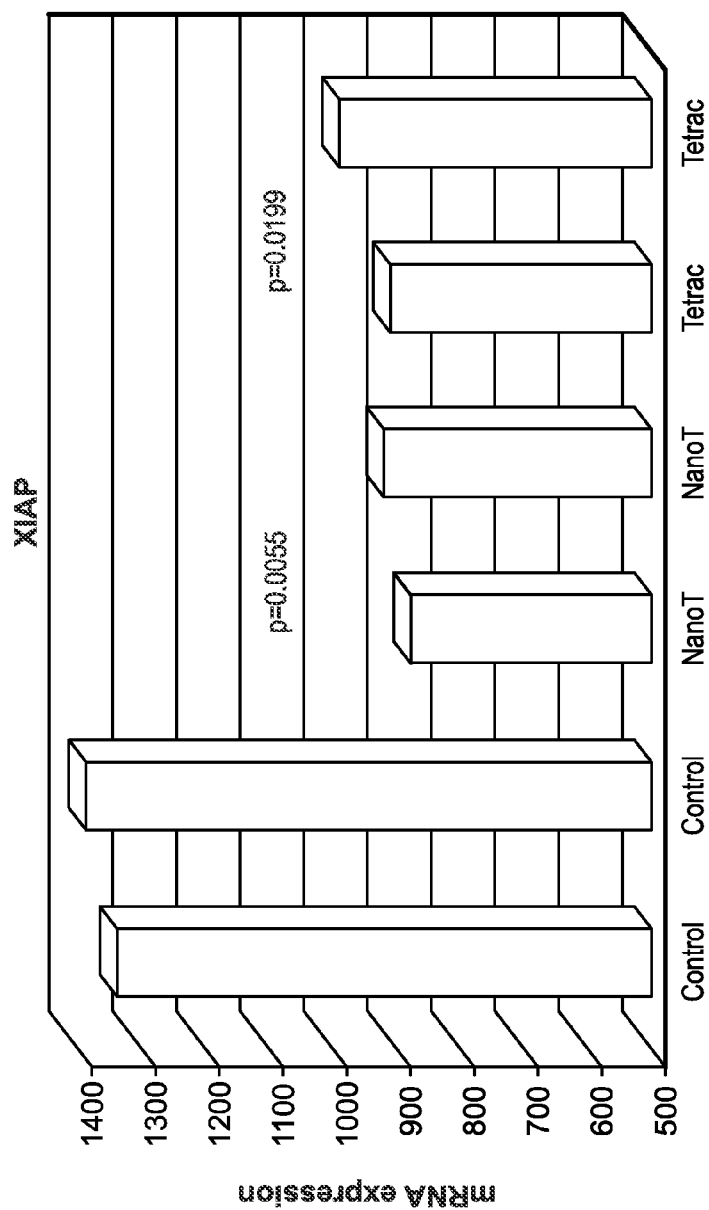

FIG. 45A demonstrates the downregulation of expression of XIAP (X-linked inhibitor of apoptosis) in MDA-MB-231 human breast cancer cells by treatment of cells with unmodified Tetrac ("Tetrac") or nanoparticulate Tetrac ("NanoT"). Results shown are of two independent replicates of each treatment. The two Tetrac formulations were equally effective. FIG. 45B shows the downregulation of expression of MCL1 (myeloid cell leukemia sequence 1) in MDA-MB-231 cells by NanoT (nanoparticulate Tetrac). Effect of unmodified Tetrac was not significant. The gene product is an inhibitor of apoptosis. Results shown are from two independent replicates of the two treatments. NanoT and Tetrac were both effective in gene downregulation.

Figure 46B:
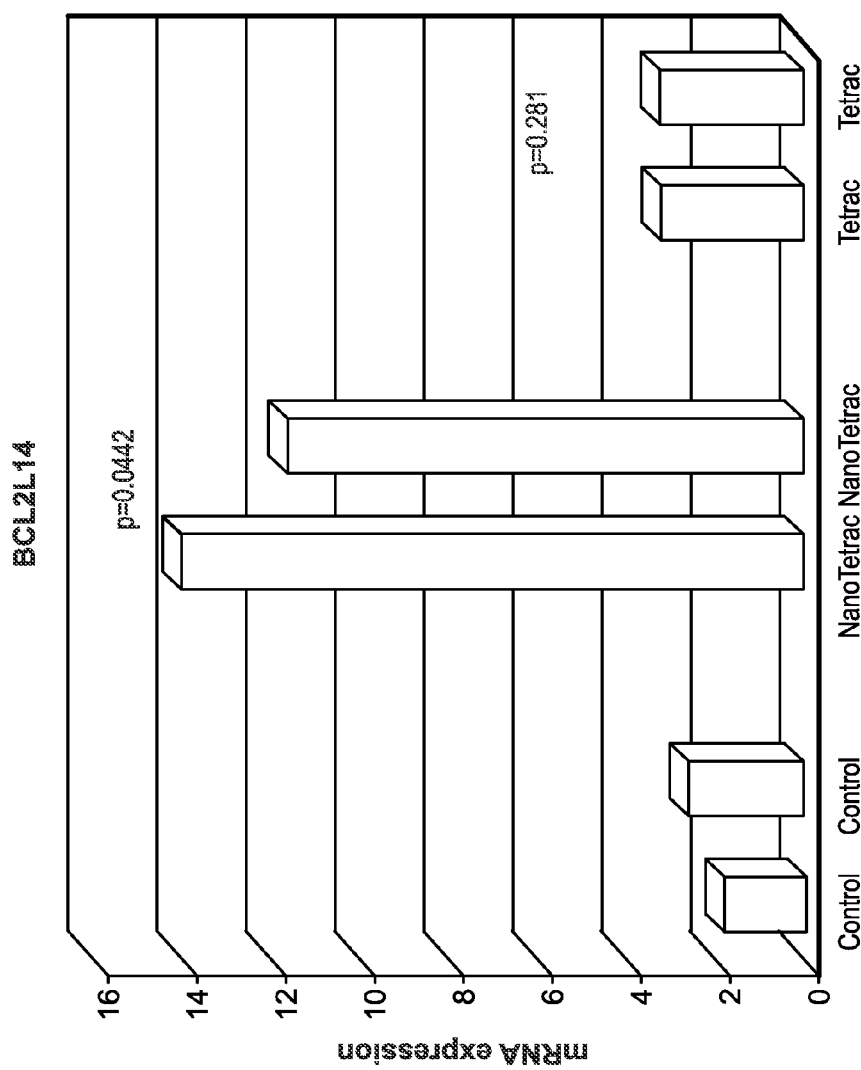

FIG. 46A shows the upregulation of caspase 2 (CASP2) gene expression in human MDAMB-231 cells by Tetrac nanoparticles ("NanoT"). Effect of unmodified Tetrac was not significant. The gene product supports apoptosis. Results are from two independent replicates of the treatments. Both treatments caused expression of the gene. FIG. 46B shows the upregulation of BCL2LI4 (Bcelllymphoma-2) gene expression in MDA-MB-231 cells by nanoparticulate Tetrac ("NanoTetrac®"). Unmodified Tetrac ("Tetrac") did not significantly stimulate gene expression. The gene product is a facilitator of apoptosis. Results shown are of two independent replicates of Tetrac and nanoparticulate Tetrac treatments.

Figure 47:
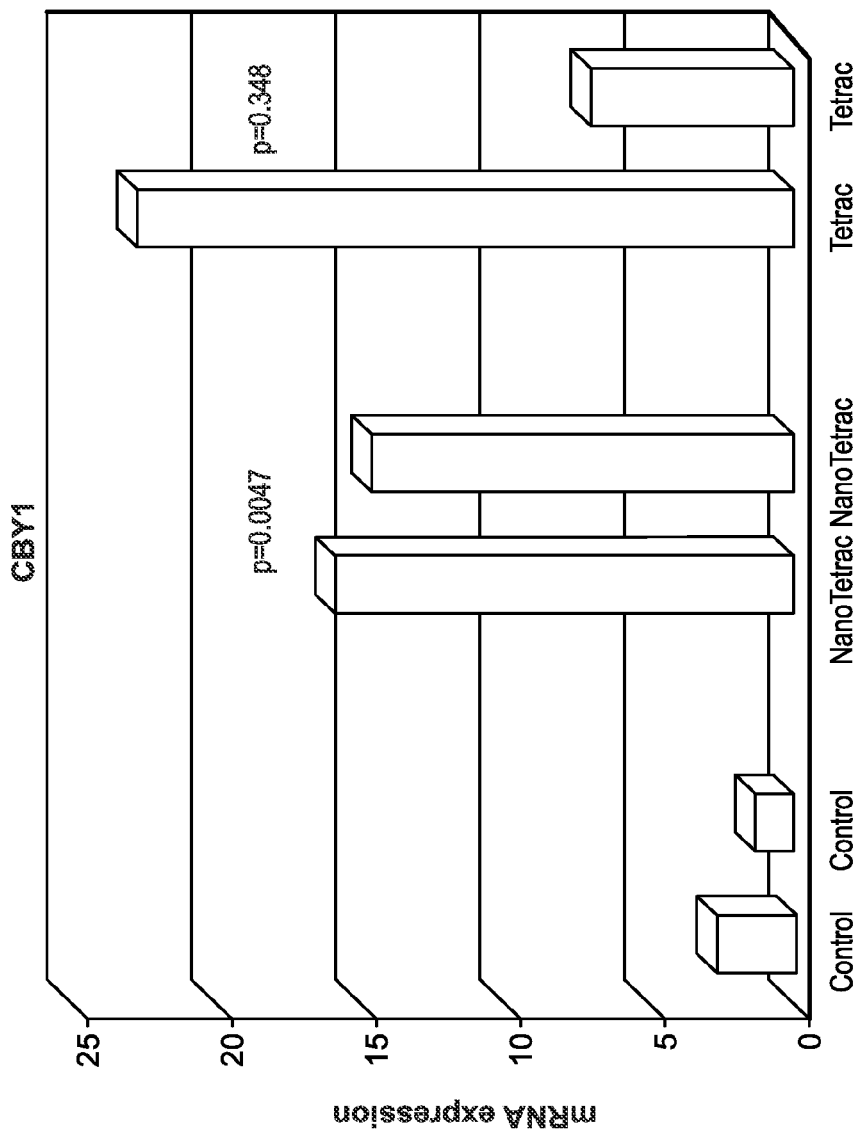

FIG. 47 shows the upregulation of chibby homolog 1 (CBY1) gene expression by nanoparticulate Tetrac ("NanoTetrac®") and unmodified Tetrac ("Tetrac") in MDA-MB-231 breast cancer cells. The gene product interacts with (3-catenin to interfere with oncogenic transcription of the catenin. Results shown are of two independent replicates of Tetrac and nanoparticulate Tetrac treatments of cells.

Figure 48:
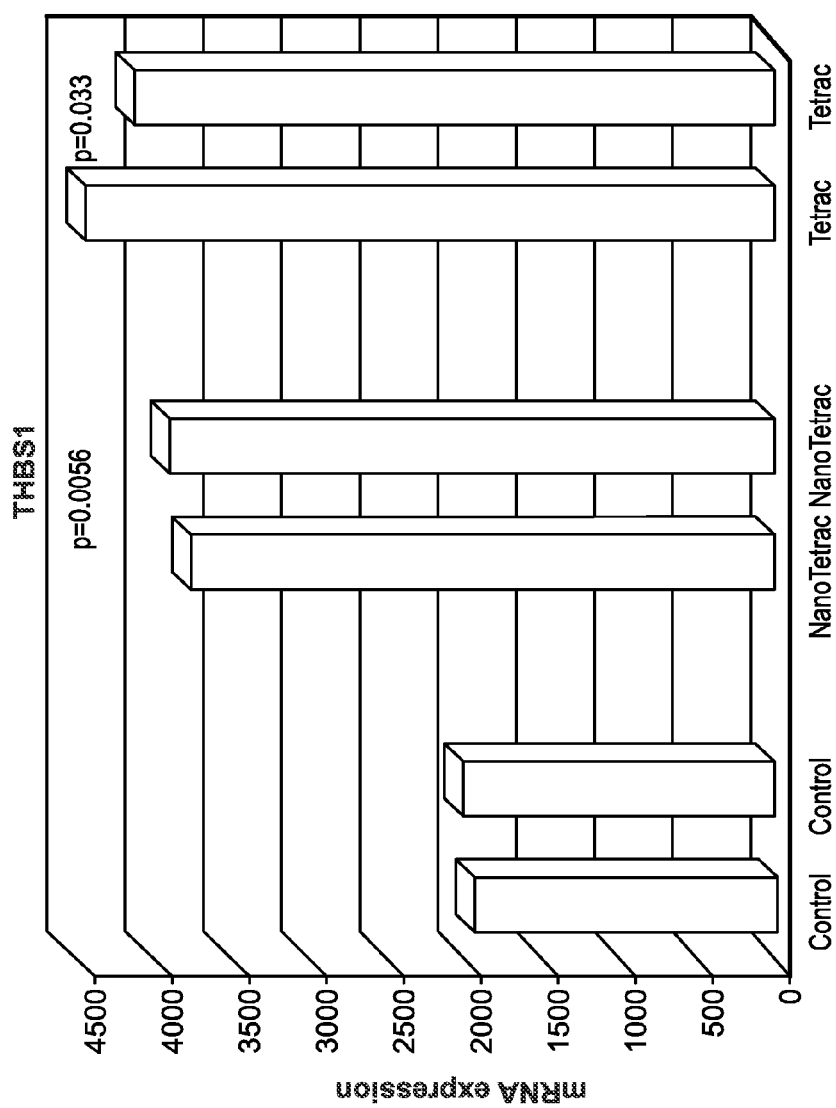

FIG. 48 shows the upregulation in MDA-MB-231 cells of THBSI (thrombospondin 1) gene expression by nanoparticulate Tetrac ("NanoTetrac") and unmodified Tetrac ("Tetrac"). THBS1 (thromobospondin-1) is an angiogenesis inhibitor. Results presented are of two independent replicates of Tetrac and Tetrac nanoparticle treatment of cells.

Figure 49:
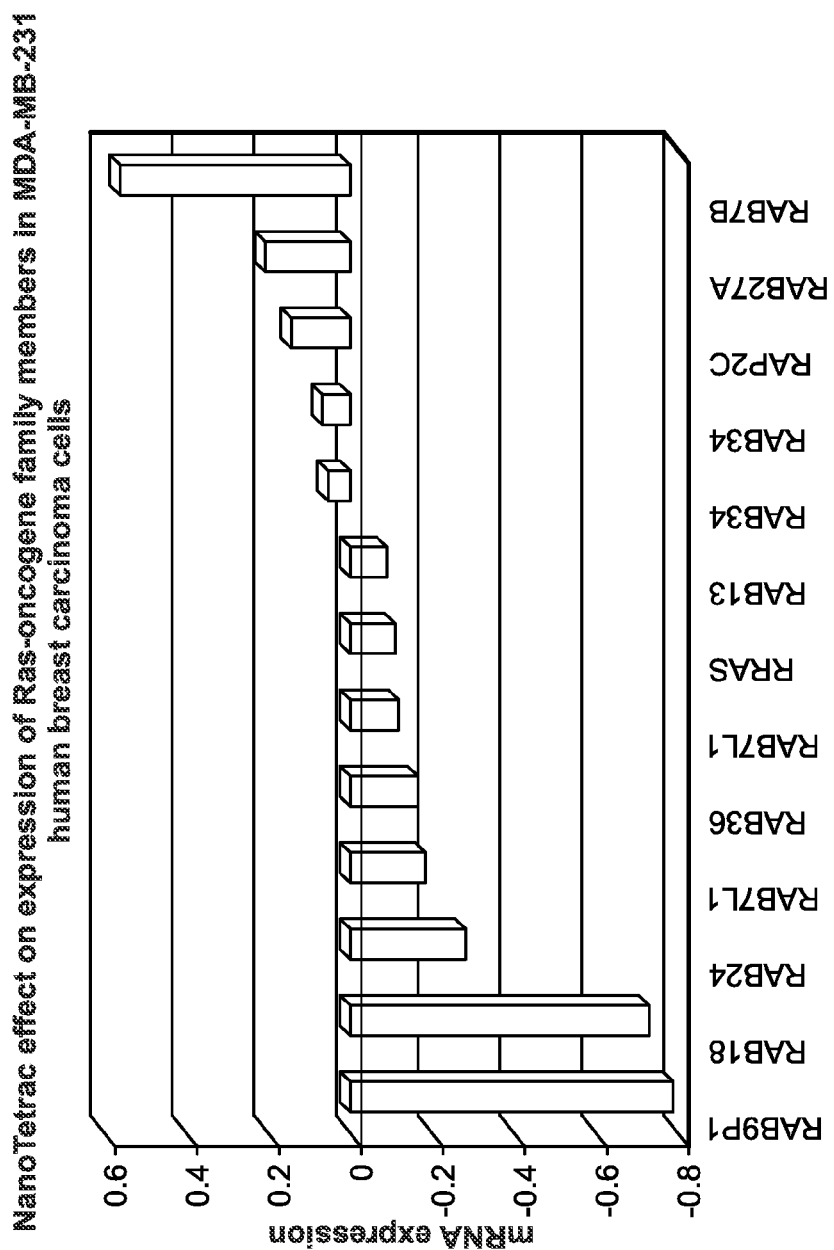

FIG. 49 shows the effect of nanoparticulate Tetrac ("NanoTetrac®") treatment on Rasoncogene family members in MDA-MB-231 human breast cancer cells. There are 13 differentially regulated family members, 8 of which are downregulated by NanoTetrac®. The most substantially upregulated family member, RAB7B, is a differentiating factor in monocytes in promyelocytic leukemia.

Figure 50:
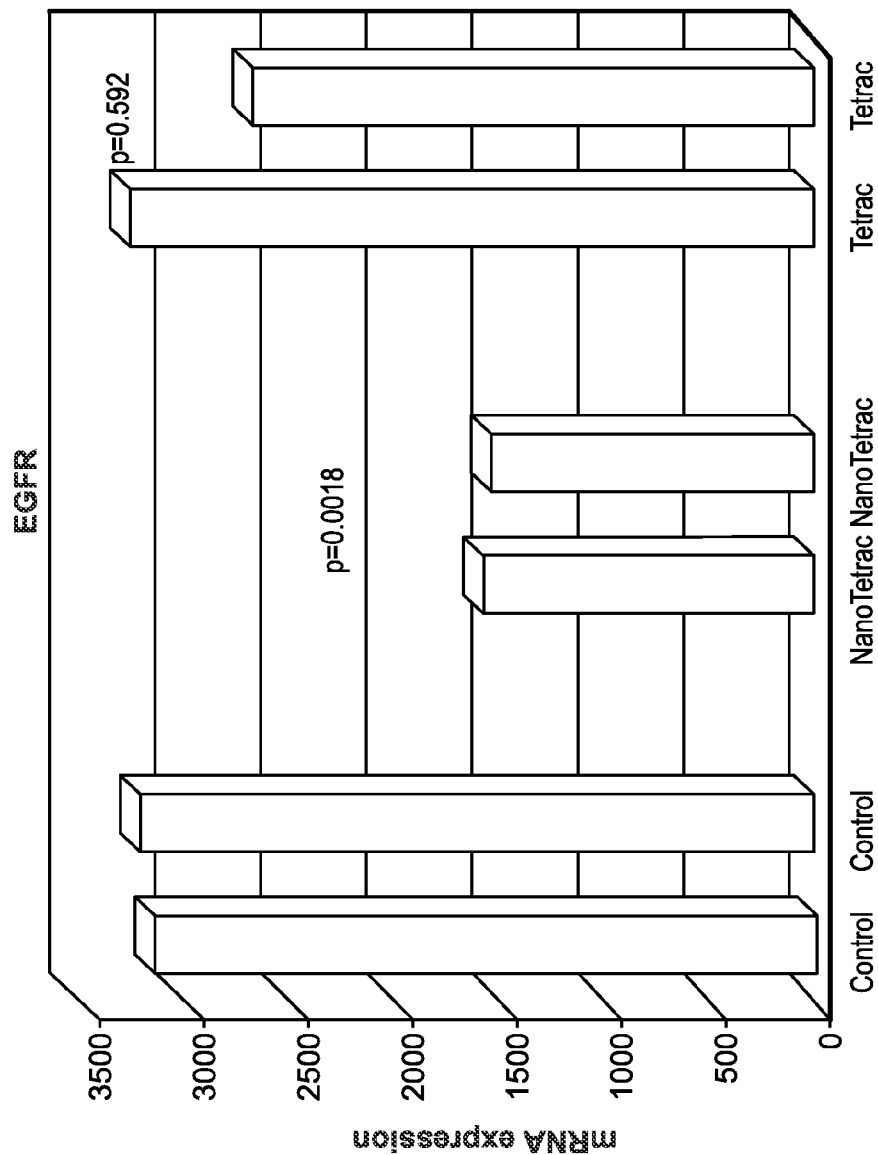

FIG. 50 demonstrates that nanoparticulate Tetrac ("NanoTetrac®") downregulates epidermal growth factor receptor (EGFR) in human breast cancer MDA-MB-231 cells. Unmodified Tetrac ("Tetrac") was ineffective. Results shown are of two independent replicates of Tetrac and nanoparticulate Tetrac treatment of cells.

Figure 51:
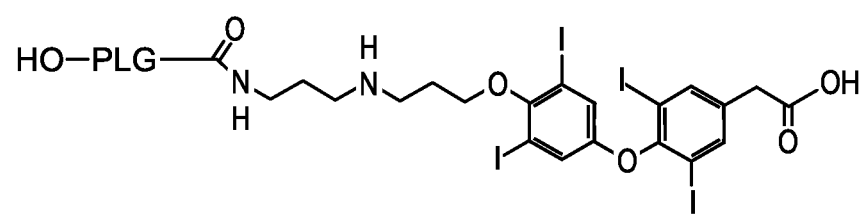

FIG. 51 is a diagram showing the structure of PLGA-Amino-Tetrac, which can be prepared according to the conjugation method described in Example 14, infra.

Figure 52:
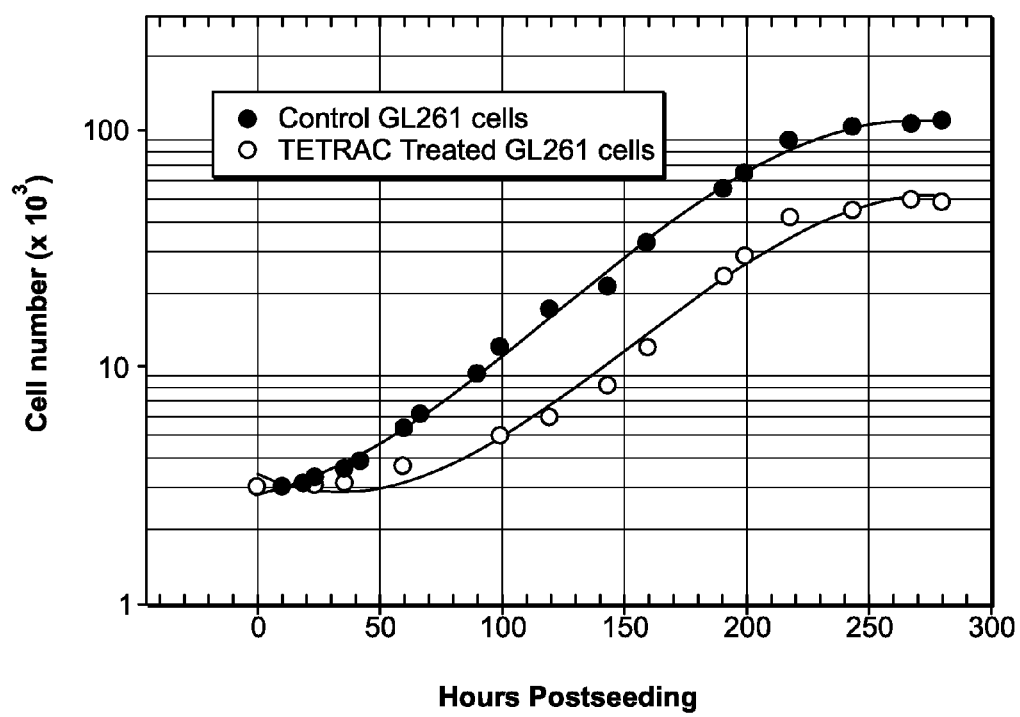

FIG. 52 is a graph of the growth curve of GL261 cells without and with 2 μm Tetrac. The Tetrac was left on the cell monolayer for the duration of the experiment and caused suppression of the cell growth.

Figure 53:
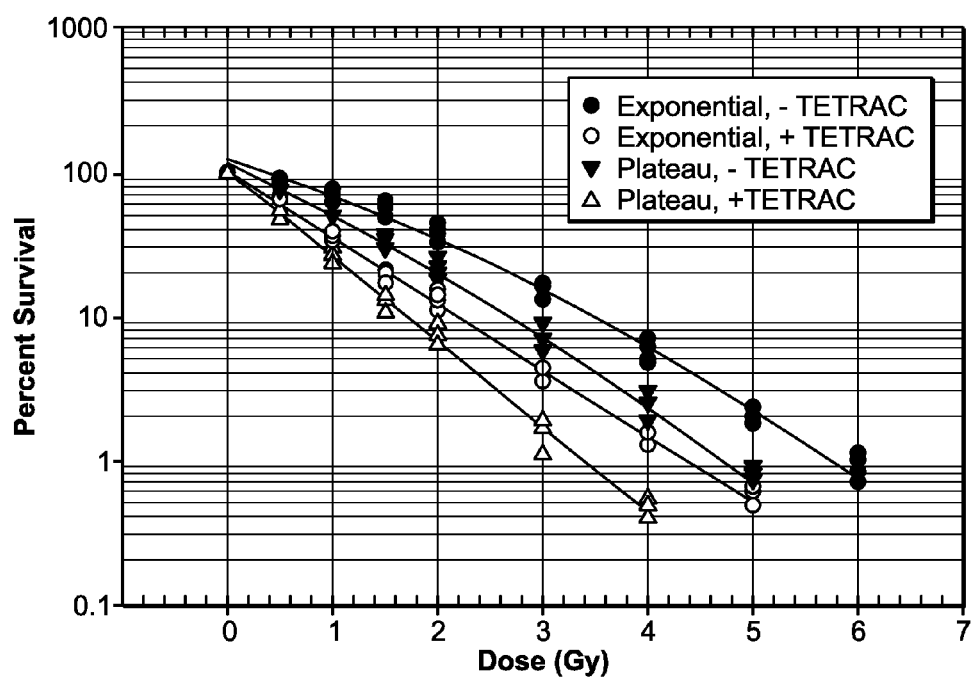

FIG. 53 shows the survival of GL261 murine brain tumor cells after exposure to graded doses of 250 kVp x-rays. The data is shown for 4 experiments for exponential and plateau phase cells (without and with Tetrac).

Figure 54:
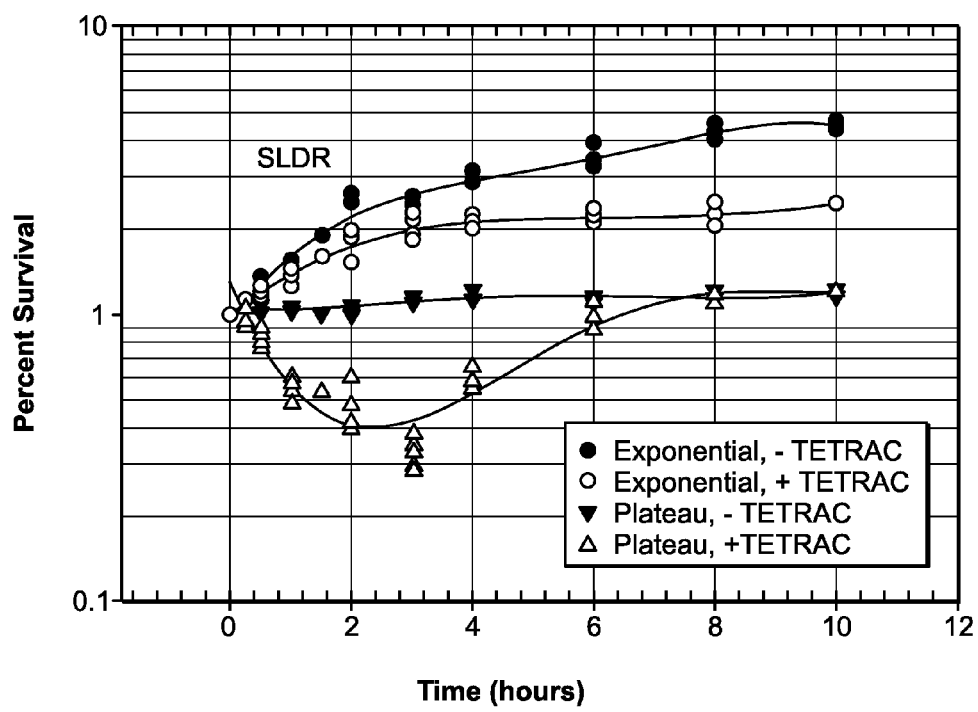

FIG. 54 shows the sublethal damage repair (SLDR) in GL261 cells after doses of x-rays sufficient to reduce survival to 10%. The doses were split into two equal fractions and were given as an increasing function of time between the two split doses. Data is shown for 4 experiments with exponential and plateau phase cells, without and with Tetrac (2 μM).

Figure 55:
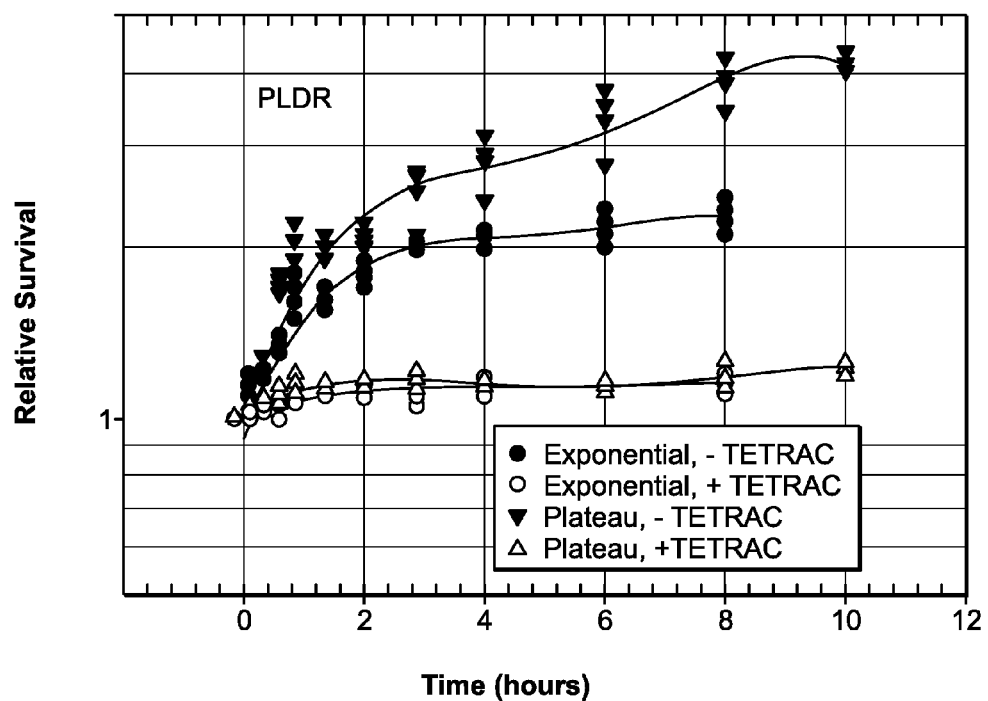

FIG. 55 shows the potentially lethal damage repair (PLDR) in GL261 cells after doses of x-rays that are sufficient to reduce cell survival to 10%. The dose was given as one single fraction at time zero, and cells were trypsinized and re-plated as a function of time after this initial dose. Data is shown for 4 experiments with exponential and plateau phase cells, without and with Tetrac.

Figure 56:
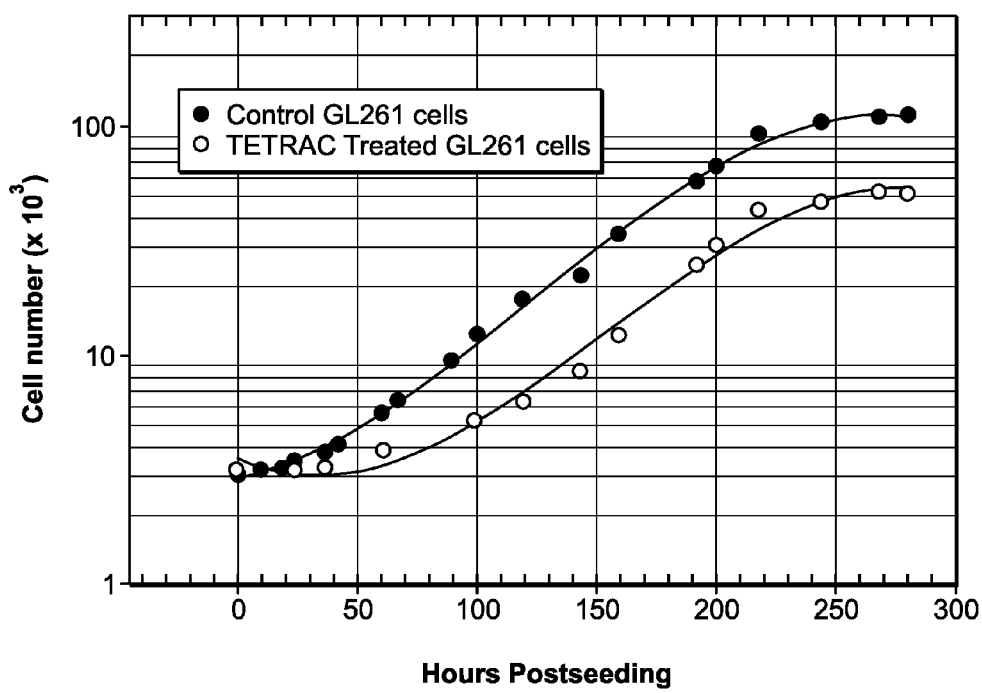

FIG. 56 shows that the treatment of GL261 brain tumor cells with 2 uM Tetrac slows their growth. In particular, it increases the latency and decreases the maximum saturation density. There is no significant change in the mean rate of growth during the log growth phase.

Figure 57:
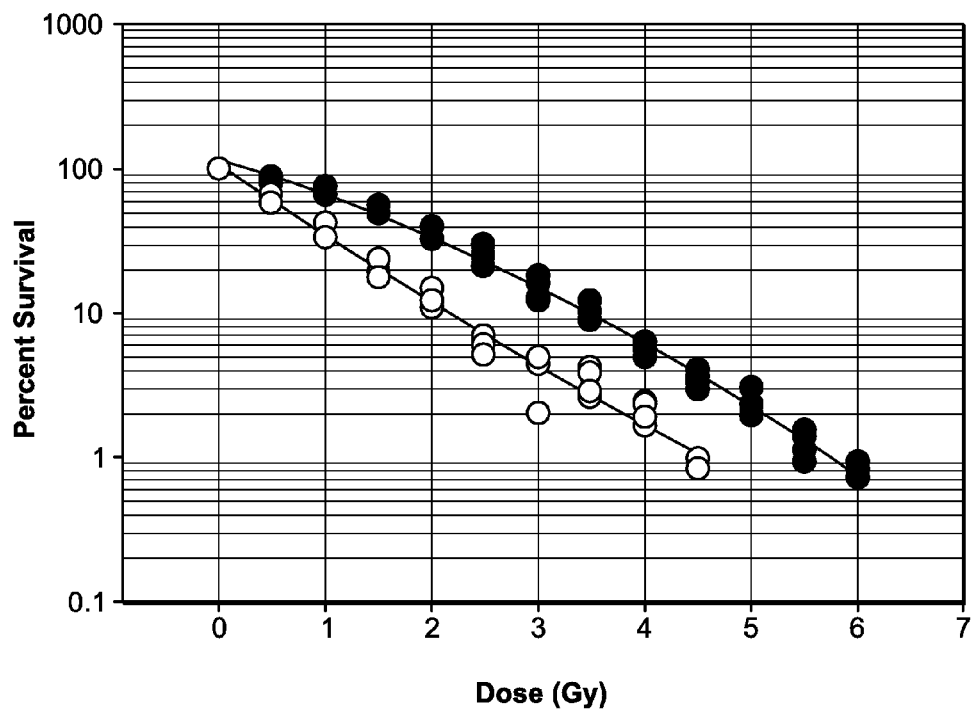

FIG. 57 shows GL261 cell responses to graded doses of 250 kVp x-rays. Control cells are denoted by • and Tetrac treated cells (2 uM) by ○. The cells were given a one hour exposure to Tetrac (2 μM) prior to irradiation. The dose enhancement factor produced by Tetrac at 2Gy (a typical radiotherapeutic dose) is 2.5. Treatment with Tetrac increased the sensitivity of the cells to radiation.

Figure 58:
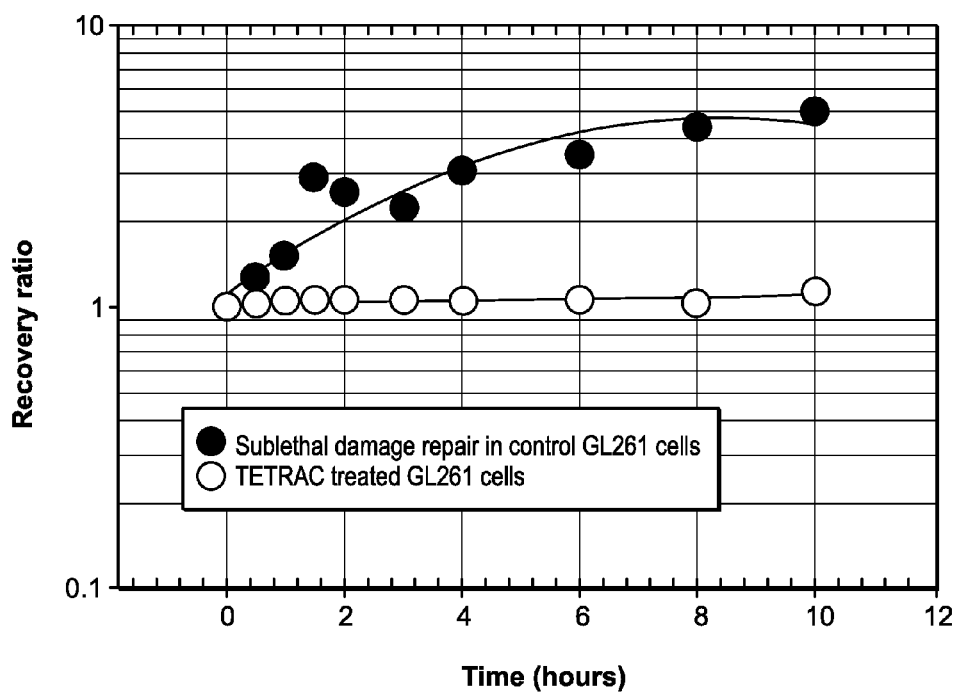

FIG. 58 shows the effects of Tetrac (2 uM) on cellular repair due to x-ray damage. At 6 to 8 hours post-irradiation, control cells repaired x-ray damage by a factor of 4 to 5. In contrast, Tetrac treated cells showed no repair of x-ray damage.

Figure 59:
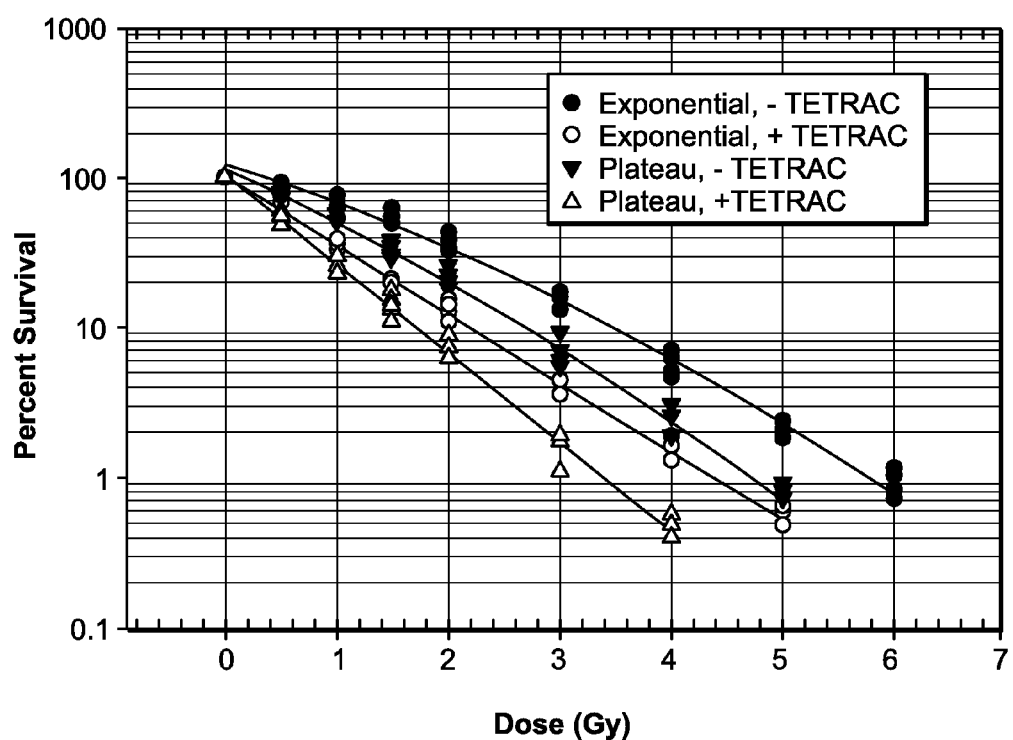

FIG. 59 shows the effects of Tetrac (2 uM) on irradiated exponentially growing or on plateau phase GL261 cells. Tetrac reduced the percentage survival of both exponential and plateau phase cells.

Figure 60:
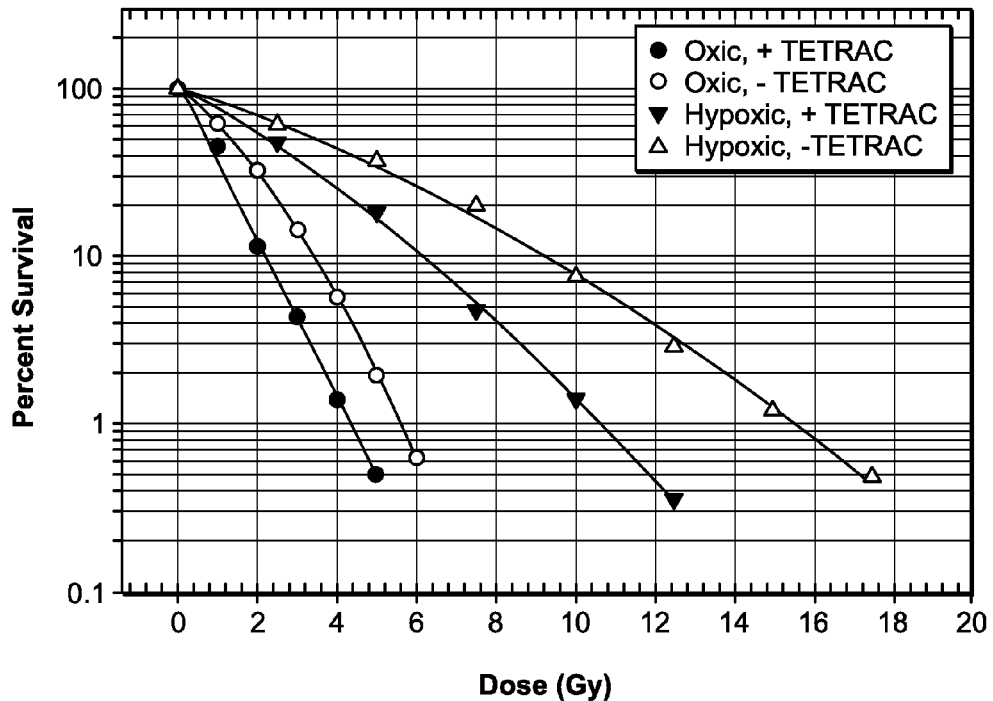

FIG. 60 demonstrates the effect of Tetrac (2 µM) on hypoxic or oxic GL261 cells that were exposed to graded doses of 250 kVp x-rays. Tetrac was found to sensitize both oxic and hypoxic cells equally. This is important for radiation therapy, as solid tumors often contain a proportion of viable hypoxic cells.

Figure 61:
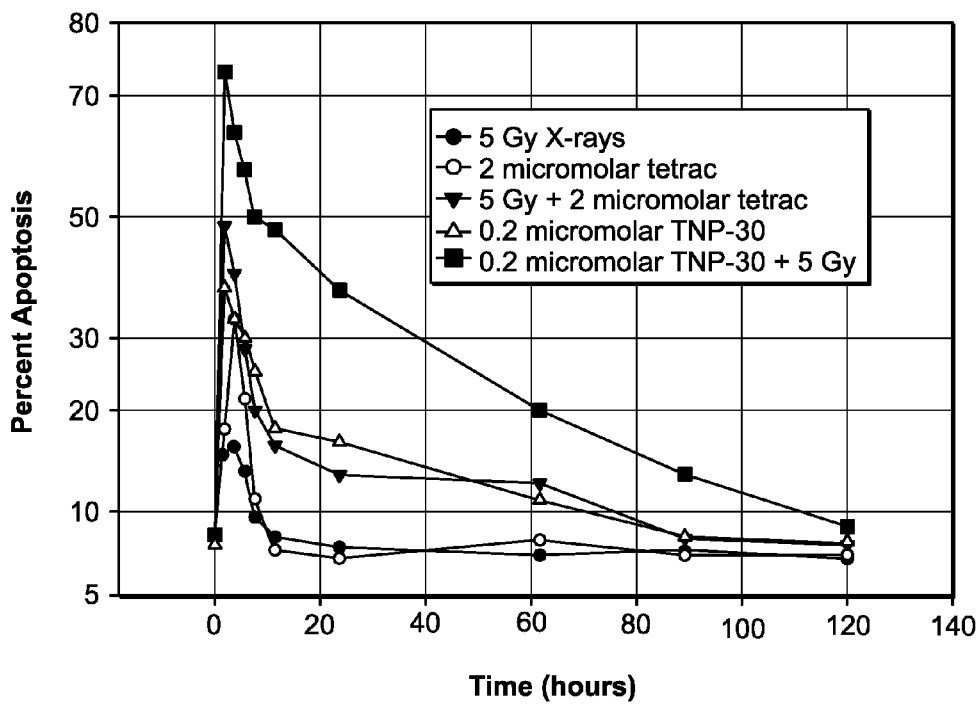

FIG. 61 is a comparison of apoptosis on Tetrac (2 µM) and T-NP (0.2 µM) treated GL261 cells that were or were not exposed to 5 Gy x-rays. The effects of Tetrac and T-NP plus 5 Gy of x-rays on apoptosis appear to be supra-additive.

Figure 62:
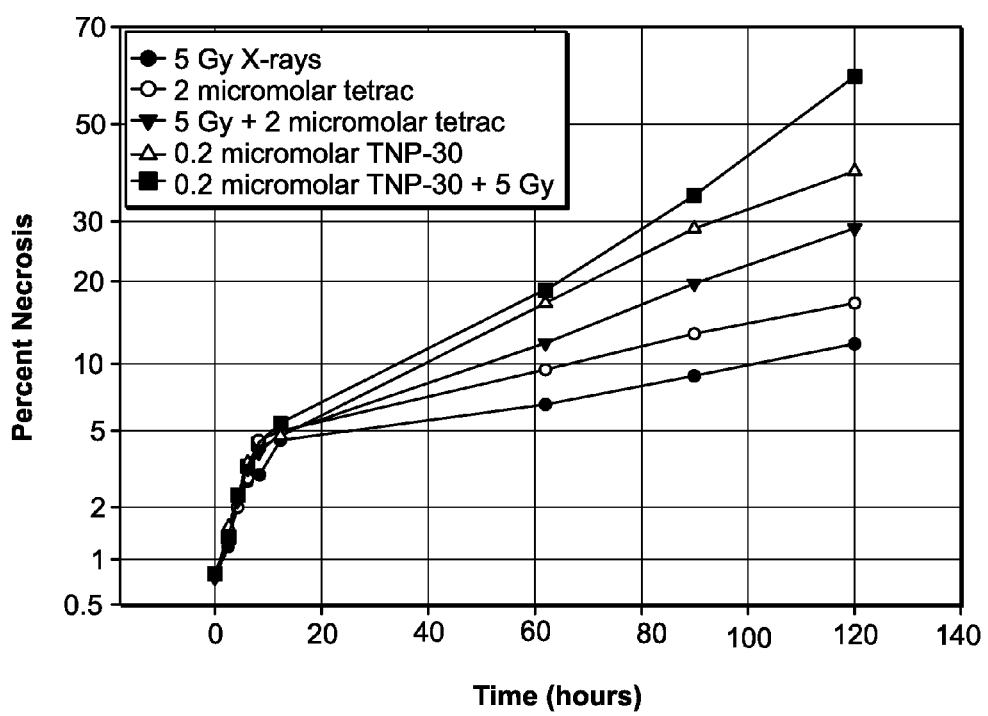

FIG. 62 shows the effects of Tetrac (2 µM) and T-NP (0.2 µM) on necrosis in GL261 tumor cells. By comparing the necrotic percentage at 120 hours, the effects were found to be essentially additive.

Figure 63:
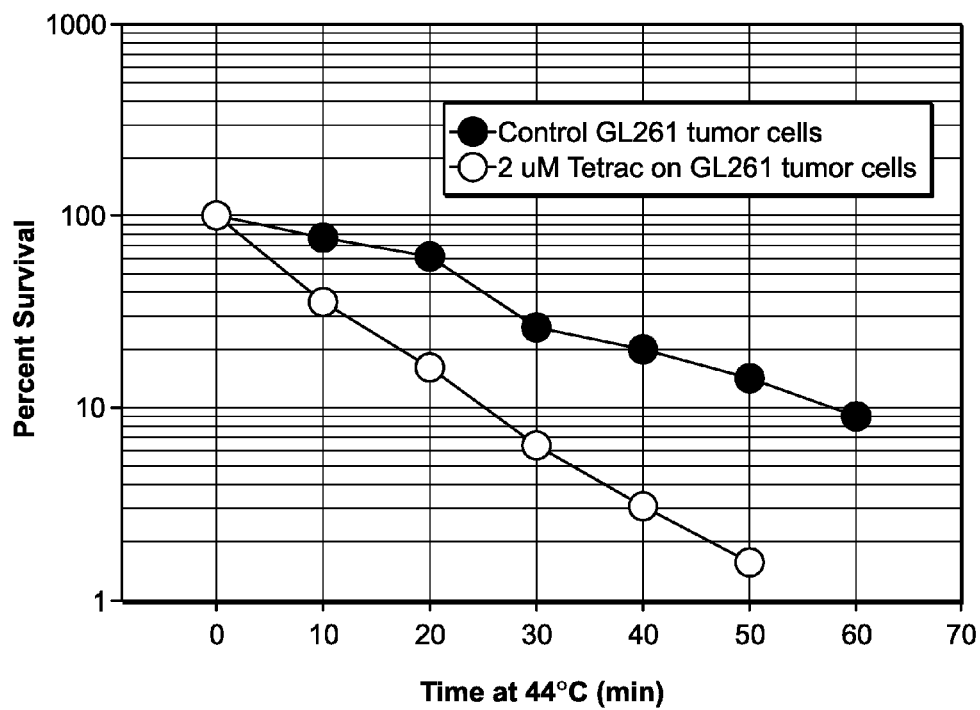

FIG. 63 shows the effects of Tetrac-treated hyperthermic GL261 cells that were propagated at 44° C. hyperthermia. Tetrac (2 uM) sensitizes GL261 tumor cells to graded times at 44° C. hyperthermia. By comparing controls to Tetrac-treated cells at 20 minutes at 44° C., it was found that the sensitization is by a factor of 3.8.

Figure 64:
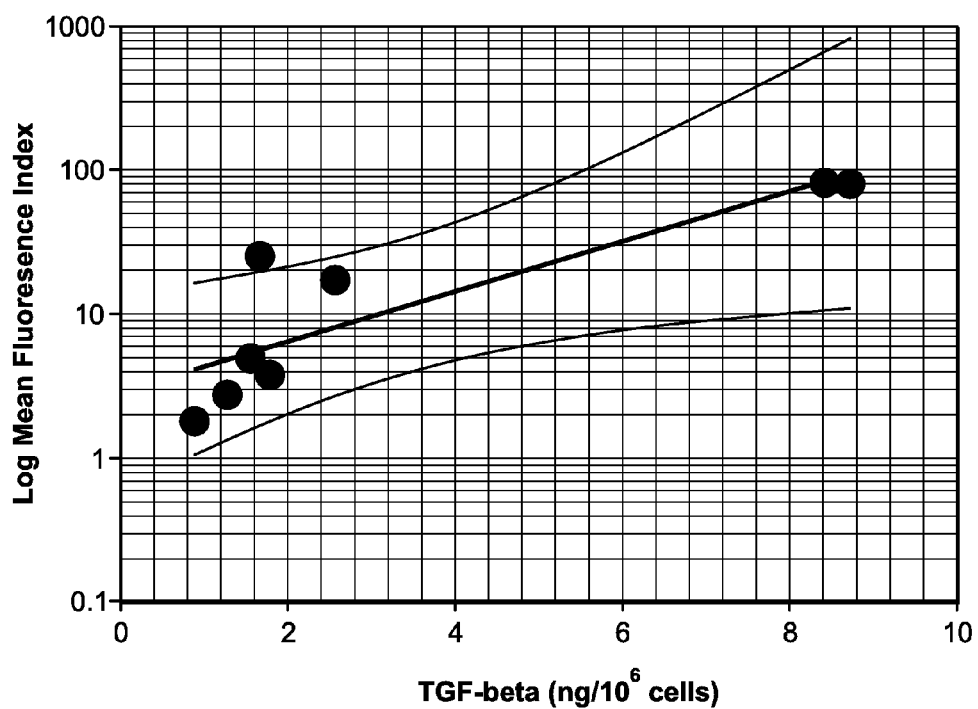

FIG. 64 is a log plot of the mean fluorescence index (MFI) for $\alpha v \beta 3$ protein versus the content of TGF-$\beta 1$ protein in eight different human colon cancer cells.

Figure 65:
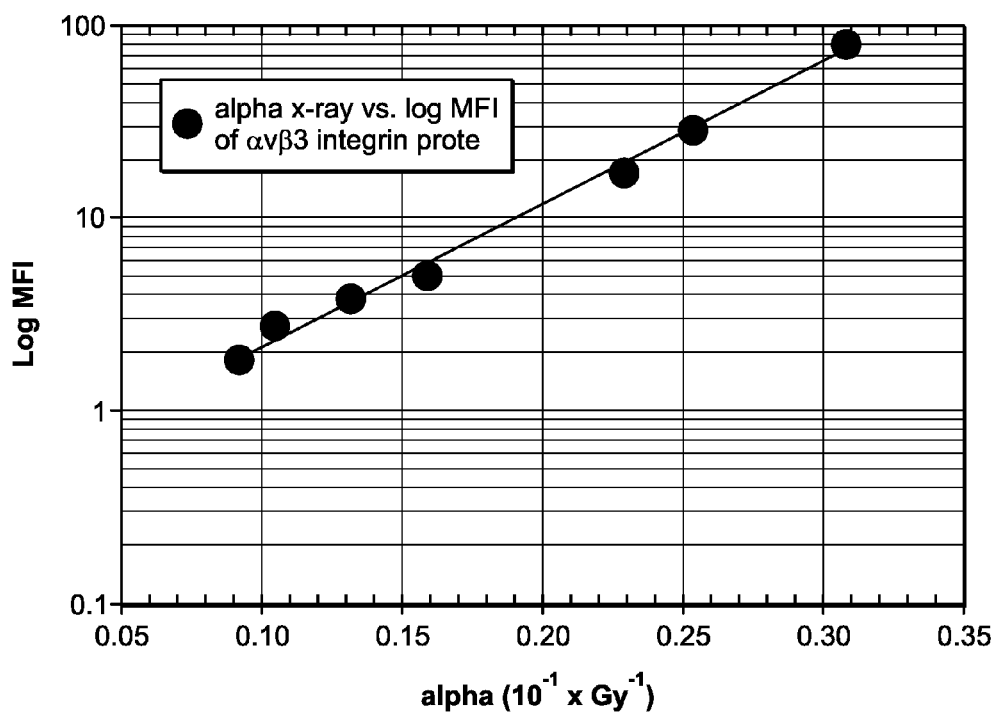

FIG. 65 shows the correction of the log MFI of the $\alpha v \beta 3$ protein in the membrane of 8 different human colon cancer cells with the alpha x-ray parameter. This correlation is also positive and is extremely strong (CC=0.907, P=0.002).

Figure 66B:
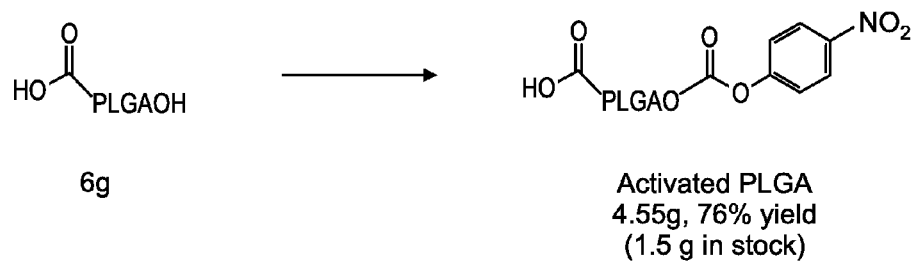
Figure 66C:
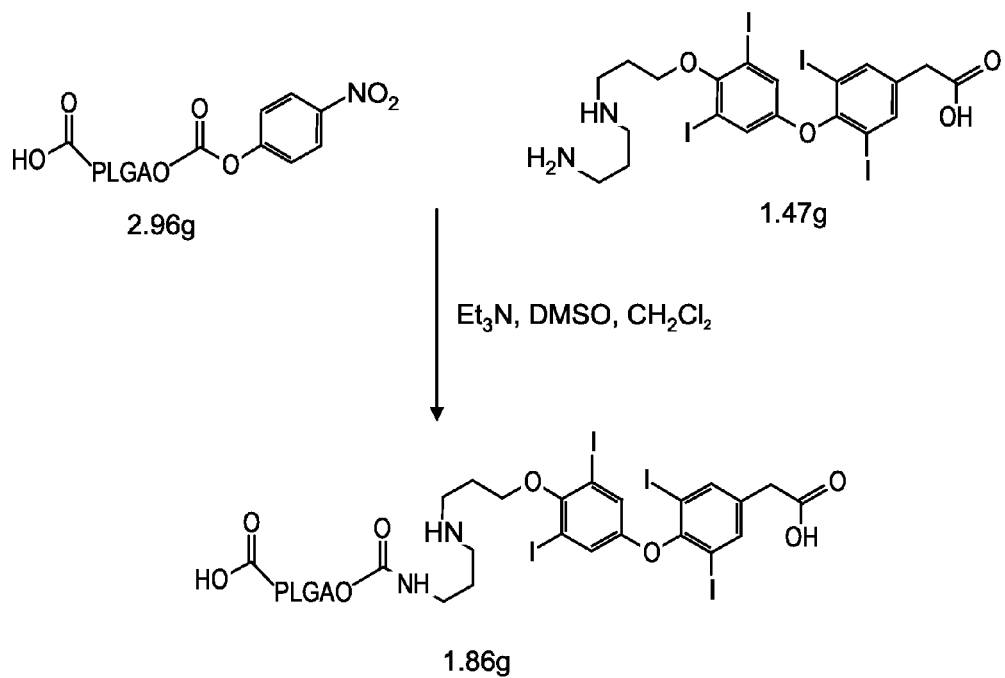

FIG. 66 shows the preparation of Tetrac-PLGA Nanoparticles. FIG. 66A shows the preparation of aminopropyl-Tetrac. FIG. 66B shows the preparation of Activated PLGA. FIG. 66C shows the preparation of PLGA-Tetrac.

DETAILED DESCRIPTION OF THE INVENTION

Disclosed herein are a new class of thyroid hormone molecules that act on the cell-surface, termed "Thyro-integrin molecules." These molecules selectively activate the receptor on the cell surface. Thyroid hormone is pro-angiogenic, acting via a mechanism that is mitogen-activated protein kinase (MAPK/ERK1/2)- and fibroblast growth factor (FGF2)-dependent.

Effects of the hormone on tumor cells are mediated by a novel cell surface receptor on integrin $\alpha v \beta 3$. The discovery that thyroid hormone acts by means of this receptor located at the plasma membrane of cells has led to the discovery that polymer-conjugated thyroid hormone analogs and nanoparticulate thyroid hormone analogs can bind to the cell surface receptor while not being able to enter the cell.

Within the scope of the present invention are nanoparticulate thyroid hormone analogs and polymer conjugates thereof that cannot gain access to the cell interior and whose activities must therefore be limited to the integrin receptor. In some embodiments, the nanoparticulate hormone analogs are poly (lactic-co-glycolic) acid or polylactide-co-glycolide derivatives, either esters or the more stable ether-bond formulations. Agarose-T4 is a model of the nanoparticulate that has been shown to be fully active at the integrin receptor. The reformulated hormone analogs described herein will not express intracellular actions of the hormone and, thus, if absorbed into the circulation, will not have systemic thyroid hormone analog actions.

The molecules of the present invention can thus selectively activate the integrin receptor. When this receptor is activated, a cascade of changes in protein mediators takes place, culminating in a signal, which can modify the activity of nuclear transactivator proteins, such as STAT proteins, p53 and members of the superfamily of nuclear hormone receptors.

Nongenomic actions of thyroid hormone are those which are independent of intranuclear binding of hormone by the nuclear T3 receptor (TR). These actions are initiated largely at the cell surface. By conjugating known thyroid hormone analogs to synthetic polymers, a new family of hormones is created that acts exclusively at the cell surface receptor, but allows endogenous hormone to continue to enter the cell and act on mitochondria or directly on nuclear TR. Depending upon the hormone analog that is conjugated, angiogenesis or wound-healing can be supported or actions on tumor cell growth or angiogenesis can be antagonized.

Tetrac is capable of inducing apoptosis in C6 glioma cells and in thyroid cancer cells (BHP 2-7). Thus, at least part of the decrease in proliferation of cancer cells when they are exposed to Tetrac is programmed cell death (apoptosis). When proliferation slows in studies of any cancer cells, the issue is whether the cells survive in a cell cycle arrest mode or whether they die. Cell death is more desirable than cell cycle arrest when treating cancer cells.

L-thyroxine (T4) and 3,5,3'-triiodo-L-thyronine (T3) cause proliferation of small cell and non-small cell human lung carcinoma lines and do so via a mechanism that requires the presence in the tumor cells of estrogen receptor-alpha (ER$\alpha$). Tetrac is a probe for the involvement of the cell surface receptor for thyroid hormone on integrin $\alpha v \beta 3$ in the cellular actions of T4 and T3. Tetrac, either free or as a nanoparticle, blocks this proliferative action of T4 and T3 on lung carcinoma cells, which indicates that the cell surface receptor for thyroid hormone on integrin $\alpha v \beta 3$ mediates the T4 and T3 effects. The proliferative actions of T4 and T3 have been blocked on lung cancer cells with anti-$\alpha$V and anti-beta3 and with RGD peptide. These observations further support the role of the integrin receptor for thyroid hormone in promotion by T4 and T3 of proliferation of lung cancer cells.

Thus, Tetrac, either free or as the nanoparticle, is an attractive strategy for management of various cancers. In addition to its anti-proliferative action, Tetrac, either free or as the nanoparticle, is anti-angiogenic, inhibiting new blood vessel growth that supports carcinoma growth. Thus, Tetrac has at least two discrete actions that are relevant to inhibition of tumor growth.

Described in detail below are formulations and uses of the thyroid hormone polymer conjugates and nanoparticles within the scope of the present invention.

DEFINITIONS

For convenience, certain terms used in the specification, examples and claims are collected here. Unless otherwise defined, all technical and scientific terms used herein have the same meaning as commonly understood by one of ordinary skill in the art to which this invention pertains.

As used herein, the term "angiogenic agent" includes any compound or substance that promotes or encourages angiogenesis, whether alone or in combination with another substance. Examples include, but are not limited to, T3, T4, T3 or T4-agarose, polymeric analogs of T3 or T4, 3,5-dimethyl-4-(4'-hydroxy-3'-isopropylbenzyl)-phenoxy acetic acid (GC-1), and/or DITPA. In contrast, the terms "anti-angiogenesis agent" or anti-angiogenic agent" refer to any compound or substance that inhibits or discourages angiogenesis, whether alone or in combination with another substance.

Examples include, but are not limited to, Tetrac, Triac, XT 199, and mAb LM609, and/or polymeric or nanoparticulate forms thereof.

As used herein, the term "myocardial ischemia" is defined as an insufficient blood supply to the heart muscle caused by a decreased capacity of the heart vessels. Also as used herein, the term "coronary disease" is defined as diseases/disorders of cardiac function due to an imbalance between myocardial function and the capacity of coronary vessels to supply sufficient blood flow for normal function. Specific coronary diseases/disorders associated with coronary disease which can be treated with the compositions and methods described herein include, but are not limited to, myocardial ischemia, angina pectoris, coronary aneurysm, coronary thrombosis, coronary vasospasm, coronary artery disease, coronary heart disease, coronary occlusion and coronary stenosis.

As used herein the term "occlusive peripheral vascular disease" (also known as peripheral arterial occlusive disorder) is a vascular disorder-involving blockage in the carotid or femoral arteries, including the iliac artery. Blockage in the femoral arteries causes pain and restricted movement. A specific disorder associated with occlusive peripheral vascular disease is diabetic foot, which affects diabetic patients, and often results in amputation of the foot.

As used herein the terms "regeneration of blood vessels," "angiogenesis," "revascularization," and "increased collateral circulation" (or words to that effect) are considered synonymous.

The term "pharmaceutically acceptable" when referring to a natural or synthetic substance means that the substance has an acceptable toxic effect in view of its much greater beneficial effect, while the related the term, "physiologically acceptable," means the substance has relatively low toxicity. Moreover, the term, "co-administered" means two or more drugs are given to a patient at approximately the same time or in close sequence so that their effects run approximately concurrently or substantially overlap. Those skilled in the art will recognize that this term includes sequential as well as simultaneous drug administration.

"Pharmaceutically acceptable salts" refers to pharmaceutically acceptable salts of thyroid hormone analogs, polymeric forms, and derivatives, which salts are derived from a variety of organic and inorganic counter ions well known in the art and include, by way of example only, sodium, potassium, calcium, magnesium, ammonium, tetra-alkyl ammonium, and the like; and when the molecule contains a basic functionality, salts of organic or inorganic acids, such as hydrochloride, hydrobromide, tartrate, mesylate, acetate, maleate, oxalate and the like can be used as the pharmaceutically acceptable salt. The term also includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, propionic acid, pyruvic acid, maleic acid, malonic acid, succinic acid, fumaric acid, tartaric acid, citric acid, benzoic acid, mandelic acid, methanesulfonic acid, ethanesulfonic acid, p-toluenesulfonic acid, salicylic acid, and the like. Particularly preferred salts of compounds of the invention are the monochloride salts and the dichloride salts.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, zinc, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Ureido" refers to a radical of the formula —N(H)—C(O)—NH$_2$.

It is understood from the above definitions and examples that for radicals containing a substituted alkyl group any substitution thereon can occur on any carbon of the alkyl group. The compounds of the invention, or their pharmaceutically acceptable salts, may have asymmetric carbon atoms in their structure. The compounds of the invention and their pharmaceutically acceptable salts may therefore exist as single enantiomers, diastereoisomers, racemates, and mixtures of enantiomers and diastereomers. All such single enantiomers, diastereoisomers, racemates and mixtures thereof are intended to be within the scope of this invention. Absolute configuration of certain carbon atoms within the compounds, if known, are indicated by the appropriate absolute descriptor R or S.

Separate enantiomers can be prepared through the use of optically active starting materials and/or intermediates or through the use of conventional resolution techniques, e.g., enzymatic resolution or chiral HPLC.

As used herein, the phrase "nerve growth factors" or "neurogenesis factors" refers to proteins, peptides or other molecules having a growth, proliferative, differentiative, or trophic effect on cells of the CNS or PNS. Such factors may be used for inducing proliferation or differentiation and can include, for example, any trophic factor that allows cells of the CNS or PNS to proliferate, including any molecule which binds to a receptor on the surface of the cell to exert a trophic, or growth-inducing effect on the cell. Preferred factors include, but are not limited to, nerve growth factor ("NGF"), epidermal growth factor ("EGF"), platelet-derived growth factor ("PDGF"), insulin-like growth factor ("IGF"), acidic fibroblast growth factor ("aFGF" or "FGF-1"), basic fibroblast growth factor ("bFGF" or "FGF-2"), and transforming growth factor-alpha and -beta ("TGF-α" and "TGF-β").

"Subject" includes living organisms such as humans, monkeys, cows, sheep, horses, pigs, cattle, goats, dogs, cats, mice, rats, cultured cells therefrom, and transgenic species thereof. In a preferred embodiment, the subject is a human. Administration of the compositions of the present invention to a subject to be treated can be carried out using known procedures, at dosages and for periods of time effective to treat the condition in the subject. An effective amount of the therapeutic compound necessary to achieve a therapeutic effect may vary according to factors such as the age, sex, and weight of the subject, and the ability of the therapeutic compound to treat the foreign agents in the subject. Dosage regimens can be adjusted to provide the optimum therapeutic response. For example, several divided doses may be administered daily or the dose may be proportionally reduced as indicated by the exigencies of the therapeutic situation.

"Administering" includes routes of administration which allow the compositions of the invention to perform their intended function, e.g., promoting or inhibiting angiogenesis. A variety of routes of administration are possible including, but not necessarily limited to parenteral (e.g., intravenous, intra-arterial, intramuscular, subcutaneous injection), oral (e.g., dietary), topical, nasal, rectal, or via slow releasing microcarriers depending on the disease or condition to be treated. Oral, parenteral and intravenous administration are preferred modes of administration. Formulation of the compound to be administered will vary according to the route of administration selected (e.g., solution, emulsion, gels, aerosols, capsule). An appropriate composition comprising the compound to be administered can be prepared in a physiologically acceptable vehicle or carrier and optional adjuvants and preservatives. For solutions or emulsions, suitable carriers include, for example, aqueous or alcoholic/aqueous solutions, emulsions or suspensions, including saline and buffered media, sterile water, creams, ointments, lotions, oils, pastes and solid carriers. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See generally, *Remington's Pharmaceutical Science*, 16th Edition, Mack, Ed. (1980)).

"Effective amount" includes those amounts of pro-angiogenic or anti-angiogenic compounds which allow it to perform its intended function, e.g., promoting or inhibiting angiogenesis in angiogenesis-related disorders as described herein. The effective amount will depend upon a number of factors, including biological activity, age, body weight, sex, general health, severity of the condition to be treated, as well as appropriate pharmacokinetic properties. For example, dosages of the active substance may be from about 0.01 mg/kg/day to about 500 mg/kg/day, advantageously from about 0.1 mg/kg/day to about 100 mg/kg/day. A therapeutically effective amount of the active substance can be administered by an appropriate route in a single dose or multiple doses. Further, the dosages of the active substance can be proportionally increased or decreased as indicated by the exigencies of the therapeutic or prophylactic situation.

"Pharmaceutically acceptable carrier" includes any and all solvents, dispersion media, coatings, antibacterial and antifungal agents, isotonic and absorption delaying agents, and the like which are compatible with the activity of the compound and are physiologically acceptable to the subject. An example of a pharmaceutically acceptable carrier is buffered normal saline (0.15 M NaCl). The use of such media and agents for pharmaceutically active substances is well known in the art. Except insofar as any conventional media or agent is incompatible with the therapeutic compound, use thereof in the compositions suitable for pharmaceutical administration is contemplated. Supplementary active compounds can also be incorporated into the compositions.

"Additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, e.g., in *Remington's Pharmaceutical Sciences*.

A "patient," "individual," "subject" or "host" refers to either a human or a non-human animal.

The term "modulation" is art-recognized and refers to upregulation (i.e., activation or stimulation), downregulation (i.e., inhibition or suppression) of a response, or any combination thereof.

The terms "prophylactic" or "therapeutic" treatment are art-recognized and refer to the administration of one or more drugs or compounds to a host. If administration occurs prior to clinical manifestation of the unwanted condition (e.g., disease or other unwanted state of the host animal), the treatment is prophylactic, i.e., it protects the host against developing the unwanted condition. If administration occurs after the manifestation of the unwanted condition, the treatment is therapeutic, i.e., it is intended to diminish, ameliorate or maintain the existing unwanted condition or other side effects.

The terms "systemic administration," "administered systemically," "peripheral administration" and/or "administered peripherally", as used herein, are all art-recognized and refer to the administration of a subject composition, therapeutic or other material other than directly into the central nervous system, such that it enters the patient's system and, thus, is subject to metabolism and other like processes.

Likewise, the terms "parenteral administration" and "administered parenterally" are also art-recognized and refer to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and/or intrasternal injection and infusion.

As used herein, "treating" a condition or disease refers to curing as well as ameliorating at least one symptom of the condition or disease.

The term "therapeutic agent" is art-recognized and refers to any chemical moiety that is a biologically, physiologically, or pharmacologically active substance that acts locally or systemically in a subject. This term also refers to any substance intended for use in the diagnosis, cure, mitigation, treatment or prevention of disease or in the enhancement of desirable physical or mental development and/or conditions in an animal or human.

The term "synthetic" is art-recognized and refers to production by in vitro chemical or enzymatic synthesis.

Throughout this application, the terms "nanoparticle", "nano-'X'", "nano 'X'", "nanoparticulate", "nanoparticulate form", "X-NP", "NP-X", and the like are used interchangeably to refer to a modification of any of the active compound(s) of the invention (i.e., the thyroid hormone or thyroid hormone analogs described herein), where the active compound(s) are covalently bound (e.g., by an ester, ether, anhydride, or sulfur linkage) with or without a linker to a polymer wherein the polymer is formulated into a nanoparticle, wherein the active compound is located on the surface of the nanoparticle and wherein the nanoparticle is between 10 nm and 1000 nm in size, and preferably less than 250 nm in size. Conjugation of the thyroid hormone or thyroid hormone analogs via covalent bond or non-covalent bond to a polymer increases the half life of the compound and/or insures that the compound does not gain access to the interior of the cells (thus, limiting their action to the integrin binding site).

Thyro-Integrin Molecules

Disclosed herein is a class of thyroid hormone or thyroid hormone analog molecules that work on the cell-surface termed "Thyro-integrin molecules." These molecules selectively activate the cell surface receptor for thyroid hormone (L-thyroxine, T4; T3) that has been described on integrin αvβ3. This receptor is at or near the Arg-Gly-Asp (RGD) recognition site on the integrin. The αvβ3 receptor is not a homologue of the nuclear thyroid hormone receptor (TR), but activation of the cell surface receptor results in a number of nucleus-mediated events, including the reported pro-angiogenic action of the hormone and fibroblast migration in vitro in the human dermal fibroblast monolayer model of wound-healing.

Integrin αvβ3 is a heterodimeric plasma membrane protein with several extracellular matrix protein ligands containing an amino acid sequence Arg-Gly-Asp ("RGD"). Using purified integrin, it was discovered that integrin αvβ3 binds T4 and that this interaction is perturbed by αvβ3 antagonists. Radioligand-binding studies revealed that purified αvβ3 binds T4 with high affinity (EC50, 371 pM), and appears to bind T4 preferentially over T3. This is consistent with previous reports that show MAPK activation and nuclear translocation, as well as hormone-induced angiogenesis, by T4, compared to T3. Integrin αvβ3 antagonists inhibit binding of T4 to the integrin and, importantly, prevent activation by T4 of the MAPK signaling cascade. This functional consequence-MAPK activation of hormone-binding to the integrin, together with inhibition of the MAPK-dependent pro-angiogenic action of thyroid hormone by integrin αvβ3 antagonists, allowed the identification of the iodothyronine-binding site on the integrin as a receptor. It should be noted that 3-iodothyronamine, a thyroid hormone derivative, has been shown by Scanlan et al. to bind to a trace amine receptor (TAR I), but the actions of this analog interestingly are antithetic to those of T4 and T3. (See Nat Med 10:638-42 (2004)).

It is known that the hormone-binding domain on integrin αvβ3 contains two thyroid hormone-binding sites. (See Lin et al., Am J Physiol Cell Physiol 298:C980-C991 (2009), which is herein incorporated by reference). One of these, Site 1, is RGD peptide-sensitive and unrelated to cell proliferation. The RGD recognition site is involved in the protein-protein interactions linking the integrin to extracellular matrix (ECM) proteins such as vitronectin, fibronectin, and laminin. Site 2 is RGD peptide-insensitive and relates to tumor cell proliferation and angiogenesis. Thus, the thyroid hormone site (site 2) is not identical with (and is distinct from) the RGD recognition site on the integrin. As discussed in Lin et al., (Am. J. Physiol Cell Physiol 296:C980-C991 (2009)), the thyroid hormone receptor and RGD recognition site on the integrin are proximal to one another and have some overlapping functions. However, the thyroid hormone site has distinctive roles with regards to gene expression, crosstalk with adjacent vascular growth factor receptors, and tumor cell proliferation.

Also initiated at the cell surface integrin receptor is the complex process of angiogenesis, monitored in either a standard chick blood vessel assay, with human endothelial cells in a sprouting assay, or in vivo mouse matrigel model of angiogenesis. This hormone-dependent process requires MAPK activation and elaboration of basic fibroblast growth factor (bFGF; FGF2) that is the downstream mediator of thyroid hormone's effect on angiogenesis. Tetrac blocks this action of T4 and T3, as does RGD peptide and small molecules that mimic RGD peptide. It is possible that desirable neovascularization can be promoted with local application of thyroid hormone analogs, e.g., in wound-healing, or that undesirable angiogenesis, such as that which supports tumor growth, can be antagonized in part with Tetrac.

Accordingly, the modulation by T4 of the laminin-integrin interaction of astrocytes may be a consequence of binding of the hormone to the integrin. The possibility thus exists that at the cell exterior thyroid hormone may affect the liganding by integrin αvβ3 of extracellular matrix proteins in addition to laminin.

Actions of T4 that are nongenomic in mechanism have been well documented. A number of these activities are MAPK-mediated. The initial steps in activation of the MAPK cascade by thyroid hormone, including activation of protein kinase C, have been shown to be sensitive to GTPγS and pertussis toxin, which indicates that the plasma membrane receptor for thyroid hormone is G protein-sensitive. It should be noted that certain cellular functions mediated by integrin αvβ3 have been shown by others to be G protein-modulated. For example, site-directed mutagenesis of the RGD binding domain abolishes the ability of the nucleotide receptor P2Y2 to activate $G_o$, while the activation of $G_q$, was not affected. Wang et al., J Cell Biol 147:389-400 (1999) demonstrated that an integrin-associated protein, IAP/CD47, induced smooth muscle cell migration via $G_i$-mediated inhibition of MAPK activation.

In addition to linking the binding of T4 and other analogs by integrin αvβ3 to activation of a specific intracellular signal transduction pathway, the liganding of the hormone by the integrin is critical to induction by T4 of MAPK-dependent angiogenesis. In the CAM model, significant vessel growth occurs after 48-72 h of T4 treatment, indicating that the plasma membrane effects of T4 can result in complex transcriptional changes. Thus, what is initiated as a nongenomic action of the hormone—transduction of the cell surface T4 signal—interfaces with genomic effects of the hormone that culminate in neovascularization. The integrin is a signal transducing protein connecting signals from extracellular matrix (ECM) proteins to the cell interior (outside-in) or from cytoplasm and intracellular organelles to ECM (inside-out). Binding of L-thyroxine (T4) or 3,5,3'-triiodo-L-thyronine (T3) to heterodimeric αvβ3 results in activation of mitogen-activated protein kinase (MAPK; ERK1/2). Activated MAPK (phosphoMAPK, pMAPK) translocates to the cell nucleus where it phosphorylates transactivator proteins such as Ser-142 of thyroid hormone receptor-β1 (TRβ1), which results in shedding by TR of corepressor proteins and recruitment of coactivators, estrogen receptor-α(ERα) (in a MAPK-mediated manner); or signal transducer and activator of transcription-1α (STAT1α). Among the genes consequently transcribed are basic fibroblast growth factor (bFGF), which mediates thyroid hormone-induced angiogenesis) and other proliferation factors important to cell division of tumor cells. Findings in several cell lines all support the participation of the integrin in functional responses of cells to thyroid hormone.

Identification of αvβ3 as a membrane receptor for thyroid hormone indicates clinical significance of the interaction of the integrin and the hormone and the downstream consequence of angiogenesis. For example, αvβ3 is over-expressed in many tumors, and this over-expression appears to play a role in tumor invasion and growth. Relatively constant circulating levels of thyroid hormone can facilitate tumor-associated angiogenesis. T4 has been shown to have pro-angiogenic action in the CAM model (see, WO2008/140507, incorporated by reference). In addition, human dermal microvascular endothelial cells also form new blood vessels when exposed to thyroid hormone. (See WO2008/140507). Local delivery of αvβ3 antagonists or Tetrac around tumor cells might inhibit thyroid hormone-stimulated angiogenesis. Although Tetrac lacks many of the biologic activities of thyroid hormone, it does gain access to the interior of certain cells. Thus, anchoring of Tetrac, or specific RGD antagonists, to non-immunogenic substrates (e.g., agarose or polymers) would exclude the possibility that the compounds could cross the plasma membrane, yet retain the ability to prevent T4-induced angiogenesis. Such polymer conjugated thyroid hormones and thyroid hormone analogs represent a family of thyroid hormone analogs that have specific cellular effects, but do not gain access to the cell interior.

Accordingly, integrin αvβ3 is both a cell surface receptor for thyroid hormone (L-thyroxine, T4) and the initiation site for T4-induced activation of intracellular signaling cascades. αvβ3 dissociably binds radiolabeled T4 with high affinity. Radioligand-binding is displaced by tetraiodothyroacetic acid (Tetrac), αvβ3 antibodies and by an integrin RGD recognition site peptide. CV-1 cells lack nuclear thyroid hormone receptor but bear plasma membrane αvβ3, and treatment of these cells with physiological concentrations of T4 activates the MAPK pathway, an effect inhibited by Tetrac, RGD peptide and αvβ3 antibodies. Inhibitors of T4-binding to the integrin also block the MAPK-mediated pro-angiogenic action of T4. T4-induced phosphorylation of MAPK is blocked by siRNA knockdown of αv and (33. These findings indicate that T4 binds to αvβ3 near the RGD recognition site and show that hormone-binding to αvβ3 has physiologic consequences.

The compositions of the present invention are based, in part, on the discovery that thyroid hormone, thyroid hormone analogs, and their polymeric or nanoparticulate forms, act at the cell membrane level and have pro-angiogenic properties that are independent of the nuclear thyroid hormone effects. Accordingly, these thyroid hormone analogs and polymeric forms (i.e., angiogenic agents) can be used to treat a variety of disorders. Similarly, the invention is also based on the discovery that thyroid hormone analog antagonists inhibit the pro-angiogenic effect of such analogs, and can also be used to treat a variety of disorders. These compositions and methods of use therefore are described in detail below.

Compositions

Disclosed herein are angiogenic and anti-angiogenic agents comprising thyroid hormones, analogs thereof, polymer conjugations, and nanoparticles of the hormones and their analogs. The disclosed compositions can be used for promoting angiogenesis to treat disorders wherein angiogenesis is beneficial. Additionally, the inhibition of these thyroid hormones, analogs and polymer conjugations can be used to inhibit angiogenesis to treat disorders associated with such undesired angiogenesis. As used herein, the term "angiogenic agent" includes any compound or substance that promotes or encourages angiogenesis, whether alone or in combination with another substance.

Pro-angiogenic agents of the present invention are thyroid hormone agonists and include thyroid hormone, analogs, and derivatives either alone or in covalent or non-covalent conjugation with polymers, microparticles, liposomes, or nanoparticles. Examples include, but are not limited to, T3, T4, T3 or T4-agarose, polymeric analogs of T3, T4, 3,5-dimethyl-4-(4'-hydroxy-3'-isopropylbenzyl)-phenoxy acetic acid (GC-1), DITPA, and/or analogs thereof. Anti-angiogenic agents of the present invention include thyroid hormone antagonists, analogs, and derivatives either alone or in covalent or non-covalent conjugation with polymers, microparticles, liposomes, or nanoparticles. Examples of such anti-angiogenic thyroid hormone antagonists include, but are not limited to, Tetrac, Triac, XT 199, mAb LM609, and/or analogs thereof as well as combinations thereof.

Examples of representative thyroid hormone agonists, antagonists, analogs and derivatives are shown below, and are also shown in FIG. 10, Tables A-D. Table A shows T2, T3, T4, and bromo-derivatives. Table B shows side chain modifications. Table C shows hydroxy groups, diphenyl ester linkages, and D-configurations. Table D shows tyrosine analogs. The structures of some of the representative compounds are illustrated below:

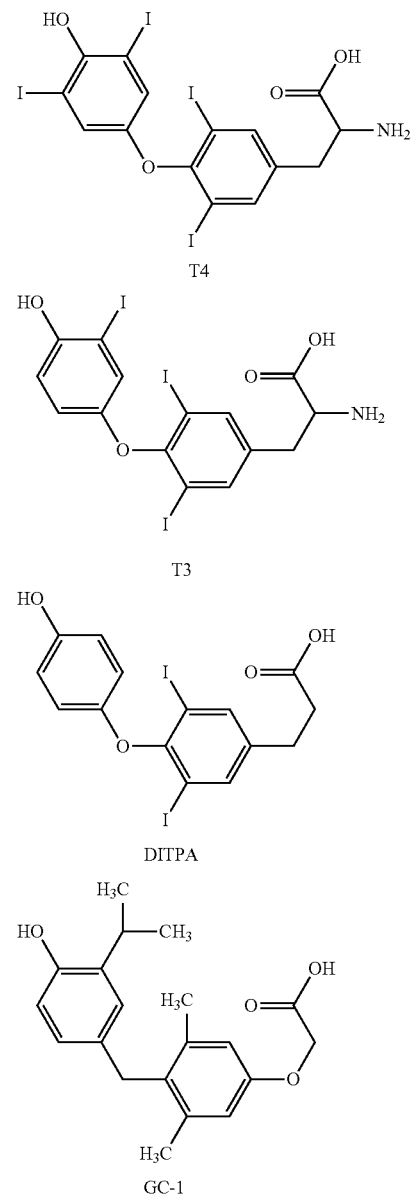

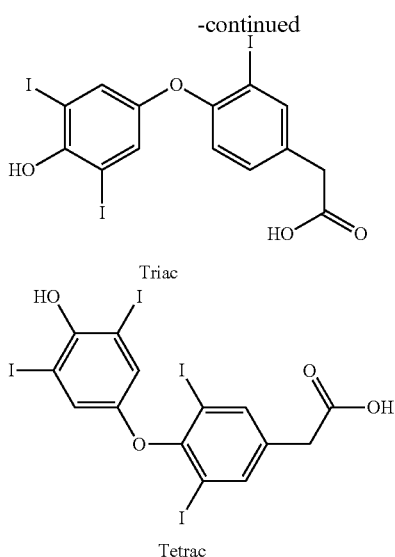

Triac

Tetrac

The details of the synthesis of additional thyroid hormone analogs are provided in Examples 12-14, infra.

Polymer Conjugations

Polymer conjugations are used to improve drug viability. While many old and new therapeutics are well-tolerated, many compounds need advanced drug discovery technologies to decrease toxicity, increase circulatory time, or modify biodistribution. One strategy for improving drug viability is the utilization of water-soluble polymers. Various water-soluble polymers have been shown to modify biodistribution, improve the mode of cellular uptake, change the permeability through physiological barriers, and/or modify the rate of clearance through the body. To achieve either a targeting or sustained-release effect, water-soluble polymers have been synthesized that contain drug moieties as terminal groups, as part of the backbone, or as pendent groups on the polymer chain.

Representative compositions of the present invention include thyroid hormone or analogs thereof conjugated to polymers. Conjugation with polymers can be either through covalent (i.e., ester, ether, sulfhydryl, or anhydride linkages) or non-covalent linkages. (See WO2008/140507, incorporated herein by reference, for specific examples).

Another representative polymer conjugation includes thyroid hormone or its analogs conjugated to polyethylene glycol (PEG). Attachment of PEG to various drugs, proteins and liposomes has been shown to improve residence time and decrease toxicity. PEG can be coupled to active agents through the hydroxyl groups at the ends of the chains and via other chemical methods. PEG itself, however, is limited to two active agents per molecule. In a different approach, copolymers of PEG and amino acids were explored as novel biomaterials which would retain the biocompatibility properties of PEG, but which would have the added advantage of numerous attachment points per molecule and which could be synthetically designed to suit a variety of applications.

Those skilled in the art will recognize that, while the nanoparticles can be linked to the thyroid hormone or thyroid hormone analog via the side chain carboxyl, there are certain features of thyroid hormone or thyroid hormone analog structure that must be emphasized in the design of the nanoparticles. First, inner ring side chain modifications importantly alter activity of the molecule. For example, agonist T4 becomes antagonist Tetrac at the integrin receptor hormone-binding Site 2 with the deamination of the side chain. Similarly, agonist T3 becomes antagonist Triac with deamination of the side chain. Therefore, construction of the nanoparticle via the side chain is not optimal, whereas construction of the nanoparticle via the outer ring hydroxyl is desirable.

Second, the 5' position of the outer ring of the thyroid hormone or thyroid hormone analogs must be exposed to the receptor pocket, thereby enabling the receptor to distinguish between T4 and T3. Appropriate receptor recognition is crucial for the transduction of the distinctive intracellular signals generated by each thyroid hormone analog.

Third, the ether bond between the inner and outer rings of the thyroid hormone analog is not essential, as evidenced by the fact that GC-1 is an agonist. (See Mousa et al., J Cardiovasc Pharmacol 46:356-60 (2005), incorporated herein by reference). However, an intervening carbon atom is required when the ether bond is absent.

Finally, because DITPA has been shown to be an agonist (see Mousa et al., Endocrinology 147:1602-07 (2006), incorporated herein by reference), those skilled in the art will recognize that the outer ring 3' iodine is not required. Similarly, the 3' position does not need to be modified.

Additionally, those skilled in the art will recognize that, while it is possible to use the inner ring side chain of the thyroid hormone or thyroid hormone analogs to bind the nanoparticle, this would not be an optimal construct.

A variety of synthetic, natural and biopolymeric origin side groups with efficient biodegradable backbone polymers can be conjugated to thyroid hormone analogs. Poly alkyl glycols, polyesters, poly anhydride, poly saccharide, and poly amino acids are available for conjugation. Representative examples of conjugated thyroid hormone analogs are known in the art, for example in WO2008/140507, which is incorporated by reference in its entirety.

Biodegradable and biocompatible polymers have been designated as probable carriers for long term and short time delivery vehicles including non hydrolysable polymeric conjugates. PEGs and PEOs are the most common hydroxyl end polymers with a wide range of molecular weights to choose for the purpose of solubility (easy carrier mode), degradation times and ease of conjugation. One end protected Methoxy-PEGs can also be employed as a straight chain carrier capable of swelling and thereby reducing the chances of getting protein attached or stuck during the sub-cellular transportation. Certain copolymers of ethylene and vinyl acetate, i.e. EVAc which have exceptionally good biocompatibility, low crystallinity and hydrophobic in nature are ideal candidate for encapsulation mediated drug delivery carrier.

Polymers with demonstrated high half-life and in-system retention properties can be employed for conjugation purpose. Among the most common and recommended are biodegradable polymers from lactic and glycolic acids. Specifically, polylactide-co-glycolide is desirable because of the ability to derivatize the free carboxylic acid end to form covalent bonds with linkers attached to the thyroid hormone or analogs thereof and of the ease of formation and stability of nanoparticles derived from these polymers. The outer ring hydroxyl (or phenolate) must be the linking site to the hormone molecules via an ether bond. However, as described herein, the linker is bound to the nanoparticle via an amide bond imbedded in the nanoparticle.

The naturally occurring polysaccharides from cellulose, chitin, dextran, ficoll, pectin, carrageenan (all subtypes), and alginate and some of their semi-synthetic derivatives are ideal carriers due to its high biocompatibility, bio systems familiar degradation products (mono saccharide from glucose and fructose), hydrophilic nature, solubility, protein immobilization/interaction for longer term stability of the polymer matrix. This provides a shell for extra protection for polymer matrix from degradation over time and adding to the effective half life of the conjugate.

Proteins and polypeptides from serum albumin, collagen, gelatin and poly-L-lysine, poly-L-alanine, poly-L-serine are natural amino acids based drug carrier with advantage of biodegradation, biocompatibility and moderate release times of the carrier molecule. Poly-L-serine is of further interest due to its different chain derivatives, e.g., poly serine ester, poly serine imine and conventional poly serine polymeric backbone with available sites for specific covalent conjugation.

Synthetic hydrogels from methacrylate derived polymers have been frequently used in biomedical applications because of their similarity to the living tissues. The most widely used synthetic hydrogels are polymers of acrylic acid, acrylamide and 2-hydroxyethyl methacrylate (HEMA). The poly HEMA (pHEMA) are inexpensive, biocompatible, available primary alcohol side chain elongation functionality for conjugation and fit for ocular, intraocular and other ophthalmic applications which makes them perfect drug delivery materials. The pHEMA are immune to cell attachment and provides zero cell motility which makes them an ideal candidate for an internal delivery system.

Synthetic thyroid analog DITPA conjugation library design program has been achieved with the development of crude DITPA conjugated products. PVA and PEG hydrophilic polymer coupling can also be mediated through dicycolhexyl carbodiimide and by other coupling reagents of hydrophilic and hydrophobic nature.

Another representative polymer conjugation includes thyroid hormone or its analogs in non-covalent conjugation with polymers.

A. Polymer Conjugate Synthesis of TRs Agonist or Antagonist and Nanoparticles

There are two functional groups in the TRs agonist or antagonist molecules: a carboxylic acid and a hydroxyl group. To synthesize the TRs agonist or antagonist/polymer conjugates, the reaction site can be either of the two. However, those skilled in the art will appreciate that various features of thyroid hormone analog structure must be emphasized and maintained when constructing the thyroid hormone analog nanoparticles in order to insure that appropriate activity can be achieved. Two possible synthesis routes are summarized below:

1) With the carboxylic acid group located on the α, β or γ position relative to the inner phenyl ring. The acid group can be activated and then reacted with hydroxyl and amino groups to form ester and amide. The candidate polymers can include PVA, PEG-NH$_2$, poly(lysine), polylactide, polyglycolide, poly(lactic-co-glycolic acid), poly(lactide-co-glycolide), and related polymers.
2) The hydroxyl group located on the outer phenyl.

Representative thyroid agonists (Pro-angiogenic) include T3, T4, DITPA, GC-1 and analogs and derivatives thereof. Illustrative embodiments are shown in WO2008/140507 (incorporated by reference). Likewise, representative thyroid antagonists (anti-angiogenic) are also shown in WO2008/140507.

B. Polymer Conjugate Synthesis of T4 and Nanoparticles Thereof

There are three functional groups in T4 molecules: one carboxylic acid group, one amine group and one hydroxyl group. To synthesize the T4/polymer conjugates, the reaction site can be any one of the three.

1) With carboxylic acid group. The acid group can be activated and reacted with a hydroxyl or an amine group to form an ester or an amide. Due to the high reactivity of amine group in the T4, the amine group should be protected before the conjugating reaction, and then de-protected reaction. Otherwise, the self polymerization will form the T4 oligomers. The candidate polymers can include PVA, PEG-NH$_2$, poly(lysine), polylactide, polyglycolide, poly(lactic-co-glycolic acid), poly(lactide-co-glycolide) and related polymers.
2) With the amine group. The amine group can react with a polymer, activated carboxylic acid, or halogen group. If the polymer has a large amount of excess of activated carboxylic acid, the reaction can proceed directly. Poly (methylacrylic acid) and poly(acrylic acid) can be used in this way.
3) With the hydroxyl group. The polymer can be directly attached to the T4 or can be attached by means of a linker. Due to the existence of a higher reactive amine group, the direct reaction of T4 with a polymer with carboxylic acid is difficult. This amine group must be protected before the reaction and de-protected after the conjugating reaction. The common protected group can be acetate (Ac) or BOC group.

The T4 polymer conjugates, nanopolymers and nanoparticles can be used in a variety of indications including, but not limited to, aneurism, surgery (including dental, vascular, or general), heart attack (e.g., acute myocardial infarction) to be delivered using devices such as a defibrillator and other means, topical applications such as ointments, cream, spray, or sheets (such as for skin applications), or immobilized on a stent or other medical device and implanted at the tissue site for sustained local delivery in myocardial infarction, stroke, or peripheral artery disease patients to achieve collateral artery formation over an extended period of time ranging from weeks to months.

C. Polymer Conjugate Synthesis of GC-1 and Nanoparticles Thereof

There are two functional groups in GC-1 molecules: one carboxylic acid group, and one hydroxyl group. To synthesize the GC-1/polymer conjugates, the reaction site can be anyone of the two.

1) With carboxylic acid group. The acid group can be activated and reacted with a hydroxyl or an amine group to form an ester or an amide. The candidate polymers can include PVA, PEG-NH$_2$, poly(lysine), poly(arginine), polylactide, polyglycolide, poly(lactic-co-glycolic acid), poly(lactide-co-glycolide), and related polymers.
2) With the hydroxyl group. The polymer can be directly attached to the GC-1 molecule or can be attached by means of a linker.

D. Polymer Conjugate Synthesis of Tetrac and Nanoparticles Thereof

There are two functional groups in Tetrac molecules: one carboxylic acid group, and one hydroxyl group. To synthesize the Tetrac/polymer conjugates, the reaction site can be either one.

1) With carboxylic acid group. The acid group can be activated and reacted with a hydroxyl or an amine group to form an ester, ether, or an amide. The candidate polymers can include PVA, PEG-NH$_2$, poly(lysine), polylactide, polyglycolide, poly(lactic-co-glycolic acid), poly (lactide-co-glycolide), and related polymers.
2) With hydroxyl group. The polymer can be directly attached to Tetrac or can be attached by means of a linker.

Nanoparticles

Nanotechnology can be used for the creation of useful materials and structures sized at the nanometer scale. One drawback with biologically active substances is fragility. Nanoscale materials can be combined with such biologically active substances to dramatically improve the durability of the substance, create localized high concentrations of the substance and reduce costs by minimizing losses. Therefore, additional polymeric conjugations include nanoparticle formulations of thyroid hormones and analogs thereof. In such an embodiment, nano-polymers and nanoparticles can be used as a matrix for local delivery of thyroid hormone and its analogs. This will aid in time controlled delivery into the cellular and tissue target.

The present invention also provides nanoparticle formulations of thyroid hormones or thyroid hormone analogs containing hydrophobic anti-oxidant, anti-inflammatory, vasodilators, anti-infectives, and anti-angiogenesis compounds. This invention also provides sustained release and long residing ophthalmic formulation, so that the release of the entrapped drug can be controlled and the process of preparing the same.

Within the scope of the present invention are nanoparticulate thyroid hormones or thyroid hormone analogs ($T_4$, T3, GC-1, DITPA, Tetrac, and Triac) that cannot gain access to the cell interior and whose activities must, therefore, be limited to the integrin receptor. In one preferred embodiment, the nanoparticulate hormone analogs are poly(lactic-co-glycolic acid) or poly(lactide-co-glycolide), either esters or the more stable ether-bond formulations. The thyroid hormones or thyroid hormone analogs can be conjugated to the polymer directly or via a linker. Agarose-$T_4$ or PLGA-Tetrac are models of the nanoparticulate that have been shown to be fully active at the integrin receptor. The reformulated thyroid hormones or thyroid hormone analogs will not express intracellular actions of the thyroid hormones or thyroid hormone analogs and, thus, if absorbed into the circulation, will not have systemic thyroid hormone agonist or antagonist actions.

As used herein, the term "nanoparticle" refers to particles between about 1 nm and less than 1000 nm in diameter. In suitable embodiments, the diameter of the nanoparticles of the present invention will be less than 500 nm in diameter, and more suitably less than about 250 nm in diameter, or less than 220 nm. In certain such embodiments, the nanoparticles of the present invention will be between about 10 nm and about 200 nm, between about 30 nm and about 180 nm, or between about 50 nm and about 150 nm in diameter. Alternatively, the nanoparticles of the present invention will be between about 150 nm and about 250 nm or between about 180 nm and about 220 nm. In certain embodiments, the nanoparticles of the present invention are 155 nm, 156 nm, 157 nm, 158 nm, 159 nm, 160 nm, 161 nm, 162 nm, 163 nm, 164 nm, 165 nm, 166 nm, 167 nm, 168 nm, 169 nm, 170 nm, 171 nm, 172 nm, 173 nm, 174 nm, 175 nm, 176 nm, 177 nm, 178 nm, 179 nm, 180 nm, 181 nm, 182 nm, 183 nm, 184 nm, 185 nm, 186 nm, 187 nm, 188 nm, 189 nm, 190 nm, 191 nm, 192 nm, 193 nm, 194 nm, 195 nm, 196 nm, 197 nm, 198 nm, 199 nm, 200 nm, 201 nm, 202 nm, 203 nm, 204 nm, 205 nm, 206 nm, 207 nm, 208 nm, 209 nm, 210 nm, 211 nm, 212 nm, 213 nm, 214 nm, 215 nm, 216 nm, 217 nm, 218 nm, 219 nm, or 220 nm. As used herein, when referring to any numerical value, "about" means a value of ±10% of the stated value (e.g. "about 200 nm" encompasses a range of diameters from 180 nm to 220 nm, inclusive).

A key element in the nanoparticle formation is the linkage bridge between the thyroid hormones or thyroid hormone analogs (or other therapeutic molecules) and the nanoparticles. The thyroid hormone or thyroid hormone analog (or other therapeutic compound) can be conjugated to the nanoparticle by means of an ether (—O—) or sulfhydryl linkage (sulfur (—S—)) through the alcohol moiety of the thyroid hormone or thyroid hormone analog (or any other therapeutic molecule). Conjugations through the alcohol moiety have more activity than conjugations through the COOH moiety of the thyroid hormone or thyroid hormone analog (or other therapeutic molecule).

Figure 35:
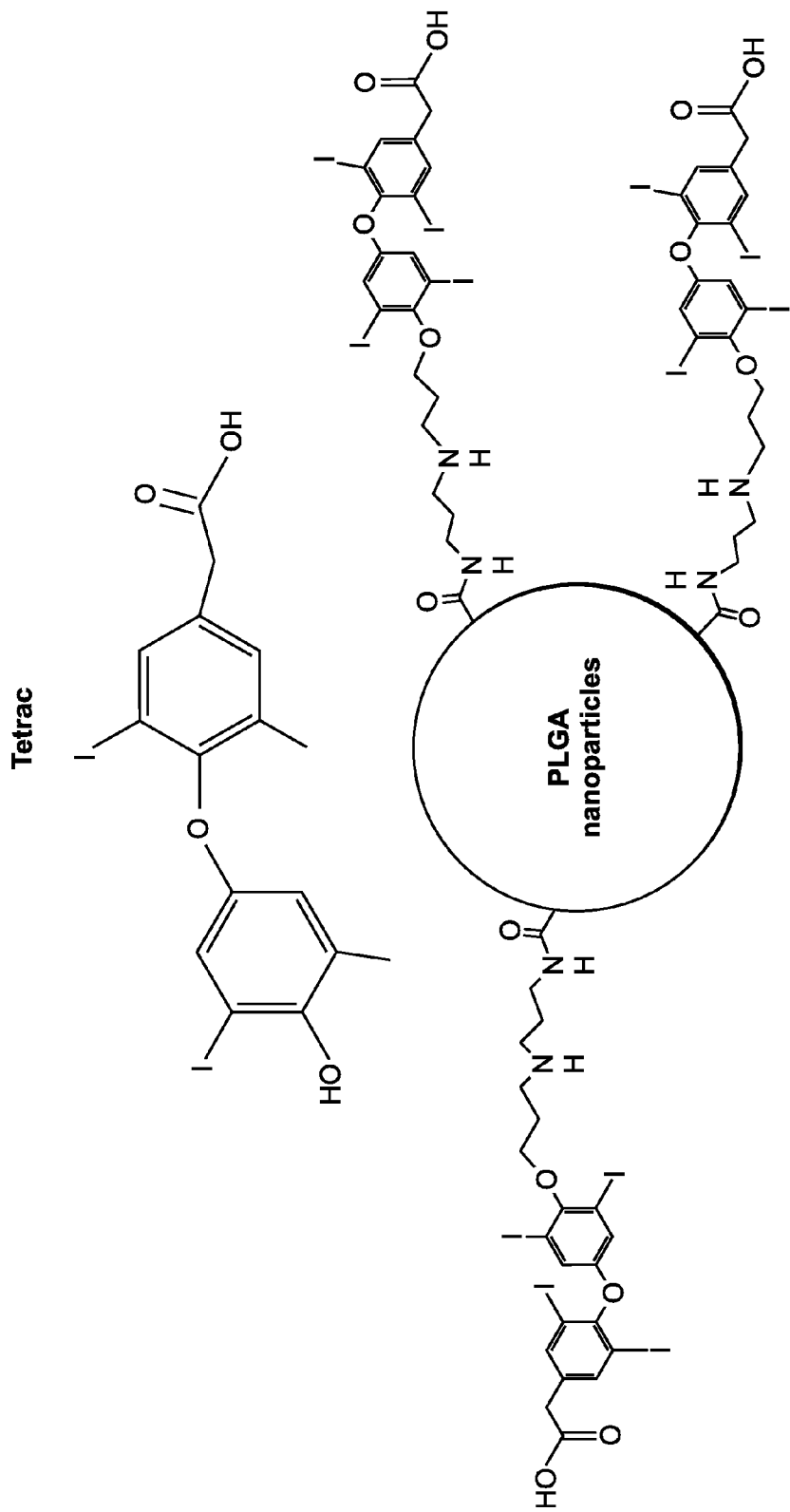
FIG. 35 is a non-limiting example of a suitable linker for use in any of the nanoparticles of the invention.

In some embodiments, a linker of between 4 and 15 atoms (i.e., 4, 5, 6, 7, 8, 9, 10, 11, 12, 13, 14, or 15) is used between the thyroid hormone or thyroid hormone analog and the polymer. When a linker is used, the amide bond for the linker must be imbedded in the nanoparticle to prevent lysis of that bond by circulating peptidases. One non-limiting example of a suitable linker is shown in FIG. 35.

The $NH_2$ group of thyroid hormone analogs, such as T3 and T4, can also be blocked with a protecting group (R group). Suitable R groups within the scope of the present invention include BOC, acetyl, methyl, ethyl, or isopropyl. For unmodified T4, R=H. Additionally, when the thyroid hormone is T4 or T3 having a protecting group at the $NH_2$, the suitable protecting group at the $NH_2$ of T4 or T3 can include, for example, N-Methyl, N-Ethyl, N-Triphenyl, N-Propyl, N-Isopropyl, N-tertiary butyl as well as any other functional groups known in the art.

Nanoparticles within the present invention may have up to approximately 100 molecules of thyroid hormone analogs per nanoparticle. By way of non-limiting example, the ratio of thyroid hormones or thyroid hormone analogs or other therapeutic molecules per nanoparticle ranges from a ratio of 1 thyroid hormone or thyroid hormone analog molecule per 1 nanoparticle (shown also as 1:1) up to 100 thyroid hormone or thyroid hormone analogs or other therapeutic molecules per nanoparticle (shown also as 100:1). More preferably, the range is from 1:15-30:1 (i.e., 15:1-30:1) thyroid hormones or thyroid hormone analogs or other therapeutic molecules per nanoparticle, and more preferably from 20:1-25:1 thyroid hormone analog or other therapeutic molecules per nanoparticle. In various embodiments, the density of the thyroid hormone or thyroid hormone analogs in the nanoparticles is between 0.1 and 25%.

Determination of the optimal or preferred density of the thyroid hormone or thyroid hormone analog bound to the nanoparticles is within the routine skill level in the art. For example, those skilled in the art will recognize that TTR can be used as the basis for a displacement assay in order to quantify the amount of Tetrac bound to nanoparticles. Specifically, such assays involve in vitro displacement of radiolabeled T4 from TTR by Tetrac or Tetrac nanoparticles (Tetrac NP). The affinity of TTR for Tetrac is 100 times greater than that for T4. Amounts of nanoparticulate Tetrac in unknown suspensions (i.e., biologic fluids) are then calculated from the displacement of radiolabeled T4. Bound/free separation of radiolabeled T4 is achieved by acid precipitation of TTR and centrifugation. Briefly, different concentrations of Tetrac or Tetrac NP, ranging from $10^{-6}$ to $10^{-10}$ M, are added to incubation tubes containing TTR and $^{125}$I-L-thyroxine (T4). The tubes are mixed and incubated for 16 hours at 4° C. The bound and free hormones are separated by adding dextran-coated charcoal (DCC) to each tube, which is then centrifuged at 12,000×g for 2 min. at 4° C. Bound [$I^{125}$] T4 in the supernatant is measured by scintillation counting.

In accordance with the present invention, nanoparticle conjugates are provided where a nanoparticle is conjugated to a plurality of thyroid hormones or thyroid hormone analogs or a nanoparticle is prepared from thyroid hormone or thyroid hormone analog polymer conjugates. Suitable nanoparticles within the scope of the present invention can include PEG-PLGA, poly(lactic-co-glycolic acid), or poly(lactide-co-glycolide), nanoparticles conjugated with T4, T3, DITPA, GC-1, Tetrac, or Triac. These nanoparticles may optionally contain one or more additional therapeutic compounds, including but not limited to resveratrol, estrogen, androgen and progesterone, such that the nanoparticles can be used to target the one or more additional therapeutic compounds to the cell surface receptor on αvβ3. Additionally, temozolomide can be encapsulated within the nanoparticles. Furthermore, due to the presence of free —COOH group(s) on the surface of the nanoparticles, these nanoparticles can also be conjugated to different targeting moieties and can be delivered to a desired site. A few cell lines have been targeted by using specific antibody attached to the nanoparticles for tumor specific site directed delivery. Additional embodiments of nanoparticles within the resent invention include T4, T3, DITPA, GC-1, or Tetrac collagen conjugated nanoparticles containing calcium phosphate as well as T4, T3, DITPA, GC-1, Tetrac, or Triac conjugated with mono- or di-PEGOH via a stable ether linkage.

Furthermore, the thyroid hormone agonists, partial agonists, or antagonists can be immobilized on the cell surface of the nanoparticles via a chemical linkage (i.e., an ester linkage, anhydride, sulfhydryl, or an ether linkage), either directly or via a linker.

Uses of Thyroid Hormone Analogs

The thyroid hormone analogs of the present invention include T3, T4, GC-1, DITPA, Tetrac, Triac and polymer conjugates and nanoparticles thereof. T3, T4, GC-1 and DITPA and their conjugates and nanoparticles thereof are pro-angiogenic, and are also referred to herein as thyroid hormone agonists. Tetrac and Triac and their conjugates and nanoparticles thereof are anti-angiogenic and anti-proliferative, and are also referred to herein as thyroid hormone antagonists.

Pro-angiogenic thyroid hormone analogs of the present invention can be used to treat disorders of the skin. These disorders include wound healing and non-cancer skin conditions. Wound healing encompasses surgical incisions, burns, and traumatic injury. T4, T3, GC-1 and DITPA, both unmodified and as nanoparticles, can be used for wound healing. These thyroid hormone analogs work by angiogenesis and by enhancing fibroblast and white blood cell migration into the area of the wound. T4, modified and as a nanoparticle, in addition, has platelet aggregating activity that is relevant to early wound healing.

The actions of T4, T3, GC-1 and DITPA nanoparticles are limited to the cell surface. Because they do not enter the cell, they avoid systemic side effects when they escape the local application site. Examples of these intracellular systemic side effects include the mild hyperthyroid state and, specifically at pituitary thyrotropic cells, suppression of thyrotropin (TSH) release.

The thyroid hormone analogs of the present invention, including T3, T4, GC-1, DITPA, and polymer conjugates and nanoparticles thereof, can also be used to treat atherosclerosis, including coronary or carotid artery disease, ischemic limb disorders, and ischemic bowel disorders. Preferred embodiments are T3, GC-1, DITPA polymeric forms or nanoparticles thereof. Additionally, the compositions of the present invention can be used in combination with biodegradable and non-biodegradable stents or other matrices.

Non-cancer skin disorders that can be treated by compositions of the present invention, specifically Tetrac, Triac and other anti-angiogenic and anti-proliferative thyroid hormone analogs, both unmodified and as nanoparticles or polymer conjugates, include, but are not limited to, rosacea, angiomas, telangiectasias, poikiloderma of Civatte and psoriasis. Examples of cancerous skin disorders that can be treated by compositions of the present invention are basal cell carcinoma, squamous cell carcinoma of the skin and melanoma. Compositions to be used for such purposes are Tetrac, Triac and other anti-angiogenic and anti-proliferative thyroid hormone analogs, both unmodified and as nanoparticles or polymer conjugates. For skin disorders, the compositions of the present invention can be administered as topical cutaneous applications, such as solutions, creams, lotions, sprays, incorporated into gauze pads or into synthetic sheets or transdermal patches.

The thyroid hormone analogs of the present invention, including Tetrac, Triac and other anti-proliferative and anti-angiogenic thyroid hormone analogs, both unmodified (when applied topically (i.e., for the treatment of rosacea and minor burns)) and as nanoparticles or polymer conjugates can also be used to treat cancers of organs in addition to the skin. These cancers include, but are not limited to, adenoid carcinoma, breast cancer, colon cancer, glioblastoma multiforme and other brain cancers, head-and-neck cancer, hepatoma, lung cancer, lymphoma, melanoma, basal cell carcinoma, squamous cell carcinoma, myeloma, neuroblastaoma, ovarian cancer, prostate cancer, pancreatic cancer, renal cancer, sarcoma, stomach cancer, and thyroid cancer.

Tetrac and Triac nanoparticles or polymer conjugates, administered systemically or locally, do not gain access to the interior of cells and work exclusively at the cell surface integrin receptor for thyroid hormone. This attribute of the formulations eliminates undesired side thyromimetic side effects of unmodified Tetrac and Triac, including hyperthyroidism and suppression of thyrotropin (TSH) release by pituitary thyrotropic cells. Tetrac can be administered in doses from about 200-2000 µg/day or up to about 700 µg/m$^2$. Tetrac or Tetrac nanoparticles can also be administered in a doses of from about 0.001 to 10 mg/Kg.

The thyroid hormone analogs of the present invention, including Tetrac, Triac, thyroid antagonists, and polymer conjugates and nanoparticles thereof, can also be used as cancer chemosensitizing and anti-cancer agents. Tetrac, Triac, analogs, thyroid antagonists, and polymer conjugates and nanoparticles thereof suppress the development of drug resistance, which is a causative factor of disease relapse. Tetrac enhances cellular response and reverses resistance to doxorubicin, etoposide, cisplatin and trichostatin A in resistant tumor cell lines derived from neuroblastoma, osteosarcoma and breast cancer.

The thyroid hormone analogs of the present invention, including Tetrac, Triac, thyroid antagonists, and polymer conjugates and nanoparticles thereof, can also be used to treat eye disorders, including diabetic retinopathy and macular degeneration. Tetrac and analogs can be given unmodified, as a polymer conjugate, or as nanoparticles either systemically, intra-ocular injection, or as eye drops.

The thyroid hormone analogs of the present invention can also be administered to treat disorders involving cell migration, such as those involving glia neurons, and potentiated NGFs. Such disorders to be treated include neurological diseases. Additionally, thyroid hormone analogs of the present invention can be used for hematopoietic and stem cell-related disorders. They can be administered at the time of bone marrow transplant for cells to reproduce faster. The present compositions can also be used for diagnostic imaging, including imaging for Alzheimer's by using $^{125}$Iodine labeled Tetrac nanoparticles. Since Alzheimer's plaques have transthyretin that bind Tetrac, this can be used for early detection. The compositions of the present invention can also be used in conjunction with defibrillators. They can also be used for treatment of viral agents, such as West Nile, HIV, cytomegalovirus (CMV), adenoviruses, and other viral agents.

Details of the uses for the present compositions in both promoting and inhibiting angiogenesis are described in detail below.

Promoting Angiogenesis

The pro-angiogenic effect of thyroid hormone analogs, polymeric forms, or nanoparticles thereof depends upon a non-genomic initiation, as tested by the susceptibility of the hormonal effect to reduction by pharmacological inhibitors of the MAPK signal transduction pathway. Such results indicate that another consequence of activation of MAPK by thyroid hormone is new blood vessel growth. The latter is initiated nongenomically, but of course, requires a consequent complex gene transcription program. The ambient concentrations of thyroid hormone are relatively stable. The CAM model, at the time it was tested, was thyroprival and thus may be regarded as a system, which does not reproduce the intact organism.

The availability of a chick chorioallantoic membrane (CAM) assay for angiogenesis has provided a model in which to quantitate angiogenesis and to study possible mechanisms involved in the induction by thyroid hormone of new blood vessel growth. $T_4$ exerts a pro-angiogenic effect that approximates that in the CAM model of FGF2 and that can enhance the action of suboptimal doses of FGF2. The pro-angiogenic effect of the hormone is initiated at the plasma membrane and is dependent upon activation by $T_4$ of the MAPK signal transduction pathway.

Thus, methods for treatment of occlusive peripheral vascular disease and coronary diseases, in particular, the occlusion of coronary vessels, and disorders associated with the occlusion of the peripheral vasculature and/or coronary blood vessels are disclosed. Also disclosed are compositions and methods for promoting angiogenesis and/or recruiting collateral blood vessels in a patient in need thereof. The compositions include an effective amount of thyroid hormone analogs and polymeric and nanoparticulate forms thereof. Such methods involve the co-administration of an effective amount of thyroid hormone analogs and polymeric and nanoparticulate forms thereof in low, daily dosages for a week or more with other standard pro-angiogenesis growth factors, vasodilators, anticoagulants, thrombolytics or other vascular-related therapies.

The CAM assay has been used to validate angiogenic activity of a variety of growth factors and compounds believed to promote angiogenesis. For example, $T_4$ in physiological concentrations was shown to be pro-angiogenic in this in vitro model and on a molar basis to have similar activity of FGF2. The presence of PTU did not reduce the effect of $T_4$, indicating that de-iodination of $T_4$ to generate $T_3$ was not a prerequisite in this model. A summary of the pro-angiogenesis effects of various thyroid hormone analogs is shown below.

Pro-Angiogenesis Effects of Various Thyroid Hormone Analogs in the CAM Model

| TREATMENT | ANGIOGENESIS INDEX |
| --- | --- |
| PBS (Control) | 89.4 ± 9.3 |
| DITPA (0.01 uM) | 133.0 ± 11.6 |
| DITPA (0.1 uM) | 167.3 ± 12.7 |
| DITPA (0.2 mM) | 117.9 ± 5.6 |
| GC-1 (0.01 uM) | 169.6 ± 11.6 |
| GC-1 (0.1 uM) | 152.7 ± 9.0 |
| T4 agarose (0.1 uM) | 195.5 ± 8.5 |
| T4 (0.1 uM) | 143.8 ± 7.9 |
| FGF2 (1 uM) | 155 ± 9 | n = 8 per group

The appearance of new blood vessel growth in this model requires several days, indicating that the effect of thyroid hormone was wholly dependent upon the interaction of the nuclear receptor for thyroid hormone (TR) with the hormone. Actions of iodothyronines that require intra-nuclear complexing of TR with its natural ligand, $T_3$, are by definition, genomic, and culminate in gene expression. On the other hand, the preferential response of this model system to $T_4$—rather than $T_3$, the natural ligand of TR—raised the possibility that angiogenesis might be initiated nongenomically at the plasma membrane by $T_4$ and culminate in effects that require gene transcription. Non-genomic actions of $T_4$ have been widely described, are usually initiated at the plasma membrane and may be mediated by signal transduction pathways. They do not require intra-nuclear ligand of iodothyronine and TR, but may interface with or modulate gene transcription. Non-genomic actions of steroids have also been well described and are known to interface with genomic actions of steroids or of other compounds. Experiments carried out with $T_4$ and Tetrac or with agarose-$T_4$ indicated that the pro-angiogenic effect of $T_4$ indeed very likely was initiated at the plasma membrane. Tetrac blocks membrane-initiated effects of $T_4$, but does not, itself, activate signal transduction. Thus, it is a probe for non-genomic actions of thyroid hormone. Agarose-$T_4$ is thought not to gain entry to the cell interior and has been used to examine models for possible cell surface-initiated actions of the hormone. Investigations of the pro-angiogenic effects of thyroid hormone in the chick chorioallantoic membrane ("CAM") model demonstrate that generation of new blood vessels from existing vessels was promoted two- to three-fold by either L-thyroxine ($T_4$) or 3,5,3'-triiodo-L-thyronine ($T_3$) at $10^{-7}$-$10^{-9}$ M. More interestingly, $T_4$-agarose, a thyroid hormone analog that does not cross the cell membrane, produced a potent pro-angiogenesis effect comparable to that obtained with $T_3$ or $T_4$.

In part, this invention provides compositions and methods for promoting angiogenesis in a subject in need thereof. Conditions amenable to treatment by promoting angiogenesis include, for example, occlusive peripheral vascular disease and coronary diseases, in particular, the occlusion of coronary vessels, and disorders associated with the occlusion of the peripheral vasculature and/or coronary blood vessels, erectile dysfunction, stroke, burns, and wounds. Also disclosed are compositions and methods for promoting angiogenesis and/or recruiting collateral blood vessels in a patient in need thereof. The compositions include an effective amount of polymeric forms of thyroid hormone analogs and derivatives and an effective amount of an adenosine and/or nitric oxide donor. The compositions can be in the form of a sterile, injectable, pharmaceutical formulation that includes an angiogenically effective amount of thyroid hormone-like substance as well as adenosine derivatives in a physiologically and pharmaceutically acceptable carrier, optionally with one or more excipients.

Myocardial Infarction

A major reason for heart failure following acute myocardial infarction is an inadequate response of new blood vessel formation, i.e., angiogenesis. Thyroid hormone and its analogs are beneficial in heart failure and stimulate coronary angiogenesis. The methods of the invention include, in part, delivering a single treatment of a thyroid hormone analog at the time of infarction either by direct injection into the myocardium or by simulation of coronary injection by intermittent aortic ligation to produce transient isovolumic contractions to achieve angiogenesis and/or ventricular remodeling.

Accordingly, in one aspect the invention features methods for treating occlusive vascular disease, coronary disease, myocardial infarction, ischemia, stroke, and/or peripheral artery vascular disorders by promoting angiogenesis by administering to a subject in need thereof an amount of a polymeric form of thyroid hormone, or an analog thereof, effective for promoting angiogenesis.

Examples of polymeric and nanoparticulate forms of thyroid hormone analogs are also provided herein and can include triiodothyronine (T3), levothyroxine (T4), (GC-1), 3,5-diiodothyropropionic acid (DITPA), or analogs thereof conjugated to polyvinyl alcohol (PVA), acrylic acid ethylene co-polymer, polyethyleneglycol (PEG), methoxypolyethylene glycol-poly(lactide-co-glycolide), polyacrylic acid, polylactic acid, agarose, PEO, m-PEG, PLLA, PGA, poly-L-lysine, Human Serum Albumin, cellulose derivatives, carbomethoxy/ethyl/hydroxypropyl, hyaluronic acid, folate linked cyclodextrin/dextran, sarcosine/amino acid spaced polymer, alginate, carrageenan, polylactic acid pectin/chitosan, chitosan, dextran, collagen, polyamine, poly aniline, poly alanine, polytrytophan, poly tyrosine, polylactide-co-glycolide, poly(lactic-co-glycolic acid) (PLGA), polylysyl glycolide, polyglycolide, polylactide, or co-polymers thereof.

The methods also involve the co-administration of an effective amount of thyroid hormone-like substance and an effective amount of an adenosine and/or NO donor in low, daily dosages for a week or more. One or both components can be delivered locally via catheter, locally, regionally, or systemically. Thyroid hormone analogs and derivatives in vivo can be delivered to capillary beds surrounding ischemic tissue by incorporation of the compounds in an appropriately sized nanoparticles. Thyroid hormone analogs, polymeric forms and derivatives can be targeted to ischemic tissue by covalent linkage with a suitable antibody.

The methods may be used as a treatment to restore cardiac function after a myocardial infarction. The methods may also be used to improve blood flow in patients with coronary artery disease suffering from myocardial ischemia or inadequate blood flow to areas other than the heart including, for example, occlusive peripheral vascular disease (also known as peripheral arterial occlusive disease), or erectile dysfunction.

Wound Healing

The actions of thyroid hormone that are initiated at the integrin receptor and that are relevant to wound-healing in vivo are platelet aggregation, angiogenesis and fibroblast in-migration.

Wound angiogenesis is an important part of the proliferative phase of healing. Healing of any skin wound other than the most superficial cannot occur without angiogenesis. Not only does any damaged vasculature need to be repaired, but the increased local cell activity necessary for healing requires an increased supply of nutrients from the bloodstream. Moreover, the endothelial cells which form the lining of the blood vessels are important in themselves as organizers and regulators of healing.

Thus, angiogenesis provides a new microcirculation to support the healing wound. The new blood vessels become clinically visible within the wound space by four days after injury. Vascular endothelial cells, fibroblasts, and smooth muscle cells all proliferate in coordination to support wound granulation. Simultaneously, re-epithelialization occurs to reestablish the epithelial cover. Epithelial cells from the wound margin or from deep hair follicles migrate across the wound and establish themselves over the granulation tissue and provisional matrix. Growth factors such as keratinocyte growth factor (KGF) mediate this process. Several models (e.g., sliding versus rolling cells) of epithelialization exist.

As thyroid hormones regulate metabolic rate, when the metabolism slows down due to hypothyroidism, wound healing also slows down. The role of topically applied thyroid hormone analogs or polymeric forms in wound healing therefore represents a novel strategy to accelerate wound healing in diabetics and in non-diabetics with impaired wound healing abilities. Topical administration can be in the form of solutions, creams, lotions, ointments, sprays, gels, foams, or transdermal patches. Additionally, nano-polymers and nanoparticles can be used as a matrix for local delivery of thyroid hormone and its analogs. This will aid in time-controlled delivery into the cellular and tissue target.

Accordingly, another embodiment of the invention features methods for treating wounds by promoting angiogenesis by administering to a subject in need thereof an amount of a polymeric or nanoparticle form of thyroid hormone, or an analog thereof, effective for promoting angiogenesis. For nanoparticles (e.g., $T_4$ as the PLGA formulation), when applied locally to surgical or traumatic wounds via gauze pads or adsorbed to synthetic films, will enhance wound-healing by the mechanisms described above. For small cutaneous wounds or abrasions, derivatized $T_4$ may be made available for clinical use in OTC gauze pads or films.

$T_4$ as the PLGA formulation, when applied locally to cutaneous ulcers via gauze pads or adsorbed to synthetic films, will enhance wound-healing by the mechanisms described above. Because it does not cause platelet aggregation, $T_3$ nanoparticles are less desirable for these applications.

Additional wound healing uses include, but are not limited to, the use for mucus membrane related disorders, including post-biopsy radiation-induced inflammation, GI tract ulceration, to curb internal bleeding, post-tooth extraction for dental patients on anti-coagulant therapy. For these uses, nanoparticles or polymer conjugates may be used.

Ophthalmic

The present invention is also directed to sustained release and long residing ophthalmic formulation of thyroid hormone analogs having thermo-sensitivity, muco-adhesiveness, and small particle size (10-1000 nm). Such a formulation may contain a micelle solution of random block co-polymer having hydrophobic or hydrophilic thyroid hormone antagonists. The invention also provides a process of preparing said formulations with different particle sizes and different surface charges (positive, negative or neutral) in eye drops or ointment.

Most ocular diseases are treated with topical application of solutions administered as eye drops or ointment. One of the major problems encountered with the topical delivery of ophthalmic drugs is the rapid and extensive pre-corneal loss caused by drainage and high tear fluid turn over. After instillation of an eye-drop, typically less than 2-3% of the applied drug penetrates the cornea and reaches the intra-ocular tissue, while a major fraction of the instilled dose is often absorbed systematically via the conjunctiva and nasolacrimal duct. Another limitation is the relatively impermeable corneal barrier that limits ocular absorption.

Because of the inherent problems associated with the conventional eye-drops significant efforts are directed towards new drug delivery systems for ophthalmic administration such as hydrogels, micro- and nanoparticles, liposomes, and collagen shields. Ocular drug delivery is an approach to controlling and ultimately optimizing delivery of the drug to its target tissue in the eye. Most of the formulation efforts aim at maximizing ocular drug absorption through prolongation of the drug residence time in the cornea and conjunctival sac as well as to slow drug release from the delivery system and minimizing pre-corneal drug loss without the use of gel that has the blurring effect on the vision.

To overcome the problem of blurred vision and poor bioavailability of a drug by using bulk gel in ophthalmic formulations, it has been suggested that colloidal carriers would have better effect. Nanoparticles as drug carriers for ocular delivery have been revealed to be more efficient than liposomes and in addition to all positive points of liposomes, these nanoparticles are an exceptionally stable entity and the sustained release of drug can be modulated.

There have been studies on the use of co-polymeric materials for ophthalmic drugs and particularly noteworthy are the attempts to incorporate hydrophobic drugs into the hydrophobic core of the copolymer micelles. The pharmaceutical efficacy of these formulations depends on the specific nature and properties of the co-polymeric materials and the compound used. Moreover, the long residence time and sustained release of drug on the cornea surface have not been achieved by other biocompatible formulations.

Neuronal

Contrary to traditional understanding of neural induction, the mechanisms that initiate and maintain angiogenesis are effective promoters and sustainers of neurogenesis. These methods and compositions are useful, for example, for the treatment of motor neuron injury and neuropathy in trauma, injury and neuronal disorders. This invention discloses the use of various pro-angiogenesis strategies alone or in combination with nerve growth factor or other neurogenesis factors. Pro-angiogenesis factors include polymeric or nanoparticulate thyroid hormone analogs as illustrated herein. The polymeric or nanoparticulate thyroid hormone analogs and its polymeric or nanoparticulate conjugates (alone or in combination with other pro-angiogenesis growth factors known in the art, with nerve growth factors, and/or with other neurogenesis factors) can be combined for optimal neurogenesis.

Disclosed are therapeutic treatment methods, compositions and devices for maintaining neural pathways in a mammal, including enhancing survival of neurons at risk of dying, inducing cellular repair of damaged neurons and neural pathways, and stimulating neurons to maintain their differentiated phenotype. Additionally, a composition containing polymeric or nanoparticulate thyroid hormones or thyroid hormone analogs, and combinations thereof, in the presence of anti-oxidants and/or anti-inflammatory agents demonstrate neuronal regeneration and protection.

The present invention also provides thyroid hormones, analogs, and polymeric or nanoparticulate conjugations, alone or in combination with nerve growth factors or other neurogenesis factors, to enhance survival of neurons and maintain neural pathways. Polymeric or nanoparticulate thyroid hormones or thyroid hormone analogs alone or in combination with nerve growth factors or other neurogenesis factors are capable of enhancing survival of neurons, stimulating neuronal CAM (Ca2++/calmodulin dependent kinase II) expression, maintaining the phenotypic expression of differentiated neurons, inducing the re-differentiation of transformed cells of neural origin, and stimulating axonal growth over breaks in neural processes, particularly large gaps in axons. Morphogens also protect against tissue destruction associated with immunologically-related nerve tissue damage. Finally, polymeric or nanoparticulate thyroid hormones or thyroid hormone analogs alone or in combination with nerve growth factors or other neurogenesis factors may also be used as part of a method for monitoring the viability of nerve tissue in a mammal.

The present invention also provides effects of polymeric or nanoparticulate thyroid hormones on synapse formation between cultured rat cortical neurons, using a system to estimate functional synapse formation in vitro. Exposure to $10^{-9}$ M polymeric thyroid hormones, 3,5,3'-triiodothyronine or thyroxine, caused an increase in the frequency of spontaneous synchronous oscillatory changes in intracellular calcium concentration, which correlated with the number of synapses formed. The detection of synaptic vesicle-associated protein synapsin I by immunocytochemical and immunoblot analysis also confirmed that exposure to thyroxine facilitated synapse formation. The presence of amiodarone, an inhibitor of 5'-deiodinase, or amitrole, a herbicide, inhibited the synapse formation in the presence of thyroxine. Thus, the present invention also provides a useful in vitro assay system for screening of miscellaneous chemicals that might interfere with synapse formation in the developing CNS by disrupting the polymeric thyroid system.

As a general matter, such methods may be applied to the treatment of any mammalian subject at risk of or afflicted with a neural tissue insult or neuropathy. The invention is suitable for the treatment of any primate, preferably a higher primate such as a human. In addition, however, the invention may be employed in the treatment of domesticated mammals which are maintained as human companions (e.g., dogs, cats, horses), which have significant commercial value (e.g., goats, pigs, sheep, cattle, sporting or draft animals), which have significant scientific value (e.g., captive or free specimens of endangered species, or inbred or engineered animal strains), or which otherwise have value.

The polymeric or nanoparticulate thyroid hormones or thyroid hormone analogs (alone or in combination with nerve growth factors or other neurogenesis factors) described herein enhance cell survival, particularly of neuronal cells at risk of dying. For example, fully differentiated neurons are non-mitotic and die in vitro when cultured under standard mammalian cell culture conditions, using a chemically defined or low serum medium known in the art. (See, for example, Charness, J. Biol. Chem. 26: 3164-3169 (1986) and Freese, et al., Brain Res. 521: 254-264 (1990)). However, if a primary culture of non-mitotic neuronal cells is treated with polymeric or nanoparticulate thyroid hormones or thyroid hormone analogs alone or in combination with nerve growth factor or other neurogenesis factors, the survival of these cells is enhanced significantly. For example, a primary culture of striatal basal ganglia isolated from the substantia nigra of adult rat brain was prepared using standard procedures, e.g., by dissociation by trituration with pasteur pipette of substantia nigra tissue, using standard tissue culturing protocols, and grown in a low serum medium, e.g., containing 50% DMEM (Dulbecco's modified Eagle's medium), 50% F-12 medium, heat inactivated horse serum supplemented with penicillin/streptomycin and 4 g/l glucose. Under standard culture conditions, these cells are undergoing significant cell death by three weeks when cultured in a serum-free medium. Cell death is evidenced morphologically by the inability of cells to remain adherent and by changes in their ultrastructural characteristics, e.g., by chromatin clumping and organelle disintegration. Specifically, cells remained adherent and continued to maintain the morphology of viable differentiated neurons. In the absence of thyroid hormone or thyroid hormone analog (alone or in combination with nerve growth factors or other neurogenesis factors) treatment, the majority of the cultured cells dissociated and underwent cell necrosis.

Dysfunctions in the basal ganglia of the substantia nigra are associated with Huntington's chorea and Parkinsonism in vivo. The ability of the polymeric or nanoparticulate thyroid hormones or thyroid hormone analogs alone or in combination with nerve growth factors or other neurogenesis factors defined herein to enhance neuron survival indicates that these polymeric or nanoparticulate thyroid hormones or thyroid hormone analogs alone or in combination with nerve growth factors or other neurogenesis factors will be useful as part of a therapy to enhance survival of neuronal cells at risk of dying in vivo due, for example, to a neuropathy or chemical or mechanical trauma. The present invention further provides that these polymeric or nanoparticulate thyroid hormones or thyroid hormone analogs (alone or in combination with nerve growth factors or other neurogenesis factors) provide a useful therapeutic agent to treat neuropathies which affect the striatal basal ganglia, including Huntington's chorea and Parkinson's disease. For clinical applications, the polymeric or nanoparticulate thyroid hormones or thyroid hormone analogs alone or in combination with nerve growth factors or other neurogenesis factors may be administered or, alternatively, a polymeric or nanoparticulate thyroid hormones or thyroid hormone analogs alone or in combination with nerve growth factors or other neurogenesis factors-stimulating agent may be administered.

The thyroid hormone or thyroid hormone analog compounds described herein can also be used for nerve tissue protection from chemical trauma. The ability of the polymeric or nanoparticulate thyroid hormones or thyroid hormone analogs (alone or in combination with nerve growth factors or other neurogenesis factors) described herein to enhance survival of neuronal cells and to induce cell aggregation and cell-cell adhesion in re-differentiated cells, indicates that the polymeric or nanoparticulate thyroid hormones or thyroid hormone analogs (alone or in combination with nerve growth factors or other neurogenesis factors) will be useful as therapeutic agents to maintain neural pathways by protecting the cells defining the pathway from the damage caused by chemical trauma. In particular, the polymeric or nanoparticulate thyroid hormones or thyroid hormone analogs alone or in combination with nerve growth factors or other neurogenesis factors can protect neurons, including developing neurons, from the effects of toxins known to inhibit the proliferation and migration of neurons and to interfere with cell-cell adhesion. Examples of such toxins include ethanol, one or more of the toxins present in cigarette smoke, and a variety of opiates. The toxic effects of ethanol on developing neurons induce the neurological damage manifested in fetal alcohol syndrome. The polymeric or nanoparticulate thyroid hormones or thyroid hormone analogs (alone or in combination with nerve growth factors or other neurogenesis factors) also may protect neurons from the cytotoxic effects associated with excitatory amino acids such as glutamate.

For example, ethanol inhibits the cell-cell adhesion effects induced in polymeric or nanoparticulate thyroid hormones or thyroid hormone analogs alone or in combination with nerve growth factors or other neurogenesis factors-treated NG108-15 cells when provided to these cells at a concentration of 25-50 mM. Half maximal inhibition can be achieved with 5-10 mM ethanol, the concentration of blood alcohol in an adult following ingestion of a single alcoholic beverage. Ethanol likely interferes with the homophilic binding of CAMs ($Ca^{2+}$/calmodulin dependent kinase II) between cells, rather than their induction, as polymeric or nanoparticulate thyroid hormones or thyroid hormone analogs alone or in combination with nerve growth factors or other neurogenesis factors-induced N-CAM levels are unaffected by ethanol. Moreover, the inhibitory effect is inversely proportional to polymeric or nanoparticulate thyroid hormones or thyroid hormone analogs alone or in combination with nerve growth factors or other neurogenesis factors concentration. Accordingly, it is envisioned that administration of a polymeric or nanoparticulate thyroid hormone or thyroid hormone analog alone or in combination with nerve growth factors or other neurogenesis factors or polymeric or nanoparticulate thyroid hormones or thyroid hormone analogs alone or in combination with nerve growth factor or other neurogenesis factors-stimulating agent to neurons, particularly developing neurons, at risk of damage from exposure to toxins such as ethanol, may protect these cells from nerve tissue damage by overcoming the toxin's inhibitory effects. The polymeric or nanoparticulate thyroid hormones or thyroid hormone analogs alone or in combination with nerve growth factors or other neurogenesis factors also are useful in therapies to treat damaged neural pathways resulting from a neuropathy induced by exposure to these toxins.

The in vivo activities of the polymeric or nanoparticulate thyroid hormones or thyroid hormone analogs alone or in combination with nerve growth factors or other neurogenesis factors described herein also are assessed readily in an animal model. A suitable animal, preferably exhibiting nerve tissue damage, for example, genetically or environmentally induced, is injected intracerebrally with an effective amount of a polymeric or nanoparticulate thyroid hormones or thyroid hormone analogs alone or in combination with nerve growth factor or other neurogenesis factors in a suitable therapeutic formulation, such as phosphate-buffered saline, pH 7. The polymeric or nanoparticulate thyroid hormones or thyroid hormone analogs alone or in combination with nerve growth factors or other neurogenesis factors preferably are injected within the area of the affected neurons. The affected tissue is excised at a subsequent time point and the tissue evaluated morphologically and/or by evaluation of an appropriate biochemical marker (e.g., by polymeric or nanoparticulate thyroid hormones or thyroid hormone analogs alone or in combination with nerve growth factors or other neurogenesis factors or N-CAM localization; or by measuring the dose-dependent effect on a biochemical marker for CNS neurotrophic activity or for CNS tissue damage, using for example, glial fibrillary acidic protein as the marker). The dosage and incubation time will vary with the animal to be tested. Suitable dosage ranges for different species may be determined by comparison with established animal models. Presented below is an exemplary protocol for a rat brain stab model.

Briefly, male Long Evans rats, obtained from standard commercial sources, are anesthetized and the head area prepared for surgery. The calvariae is exposed using standard surgical procedures and a hole drilled toward the center of each lobe using a 0.035K wire, just piercing the calvariae. 25 ml solutions containing either polymeric or nanoparticulate thyroid hormones or thyroid hormone analogs (alone or in combination with nerve growth factor or other neurogenesis factors (e.g., OP-1, 25 mg) or PBS) are then provided to each of the holes by Hamilton syringe. Solutions are delivered to a depth approximately 3 mm below the surface, into the underlying cortex, corpus callosum and hippocampus. The skin then is sutured and the animal recovered.

Three days post surgery, rats are sacrificed by decapitation and their brains processed for sectioning. Scar tissue formation is evaluated by immunofluorescence staining for glial fibrillary acidic protein, a marker protein for glial scarring, to qualitatively determine the degree of scar formation. Glial fibrillary acidic protein antibodies are available commercially, e.g., from Sigma Chemical Co., St. Louis, Mo. Sections also are probed with anti-OP-1 antibodies to determine the presence of OP-1. Reduced levels of glial fibrillary acidic protein are anticipated in the tissue sections of animals treated with the polymeric or nanoparticulate thyroid hormones or thyroid hormone analogs alone or in combination with nerve growth factor or other neurogenesis factors, evidencing the ability of polymeric or nanoparticulate thyroid hormones or thyroid hormone analogs alone or in combination with nerve growth factor or other neurogenesis factors to inhibit glial scar formation and stimulate nerve regeneration.

Brain Imaging, Diagnosis, and Therapies of Neurodegenerative Diseases

The present invention relates to novel pharmaceutical and radiopharmaceuticals that are useful for the early diagnosis, prevention, and treatment of neurodegenerative disease, such as, for example, Alzheimer's disease. The invention also includes novel chemical compounds having specific binding in a biological system and capable of being used for positron emission tomography (PET), single photon emission (SPECT) imaging methods, and magnetic resonance (MRI) imaging methods. The ability of T4 and other thyroid hormone analogs to bind to localized ligands within the body makes it possible to utilize such compounds for in situ imaging of the ligands by PET, SPECT, MRI, and similar imaging methods. In principle, nothing need be known about the nature of the ligand, as long as binding occurs, and such binding is specific for a class of cells, organs, tissues or receptors of interest.

PET imaging is accomplished with the aid of tracer compounds labeled with a positron-emitting isotope (Goodman, M. M. Clinical Positron Emission Tomography, Mosby Yearbook, 1992, K. F. Hubner et al., Chapter 14). For most biological materials, suitable isotopes are few. The carbon isotope, $^{11}C$, has been used for PET, but its short half-life of 20.5 minutes limits its usefulness to compounds that can be synthesized and purified quickly, and to facilities that are proximate to a cyclotron where the precursor $C^{11}$ starting material is generated. Other isotopes have even shorter half-lives. $N^{13}$ has a half-life of 10 minutes and $O^{15}$ has an even shorter half-life of 2 minutes. The emissions of both are more energetic than those of $C^{11}$. Nevertheless, PET studies have been carried out with these isotopes (Hubner, K. F., in Clinical Positron Emission Tomography, Mosby Year Book, 1992, K. F. Hubner, et al., Chapter 2). A more useful isotope, $^{18}F$, has a half-life of 110 minutes. This allows sufficient time for incorporation into a radio-labeled tracer, for purification and for administration into a human or animal subject. In addition, facilities more remote from a cyclotron, up to about a 200 mile radius, can make use of $F^{18}$ labeled compounds. Disadvantages of $^{18}F$ are the relative scarcity of fluorinated analogs that have functional equivalence to naturally-occurring biological materials, and the difficulty of designing methods of synthesis that efficiently utilize the starting material generated in the cyclotron. Such starting material can be either fluoride ion or fluorine gas. In the latter case only one fluorine atom of the bimolecular gas is actually a radionuclide, so the gas is designated F-F$^{18}$. Reactions using F-F$^{18}$ as starting material therefore yield products having only one half the radionuclide abundance of reactions utilizing K. F$^{18}$ as starting material. On the other hand, F$^{18}$ can be prepared in curie quantities as fluoride ion for incorporation into a radiopharmaceutical compound in high specific activity, theoretically 1.7 Ci/nmol using carrier-free nucleophilic substitution reactions. The energy emission of F$^{18}$ is 0.635 MeV, resulting in a relatively short, 2.4 mm average positron range in tissue, permitting high resolution PET images.

SPECT imaging employs isotope tracers that emit high energy photons (gamma-emitters). The range of useful isotopes is greater than for PET, but SPECT provides lower three-dimensional resolution. Nevertheless, SPECT is widely used to obtain clinically significant information about analog binding, localization and clearance rates. A useful isotope for SPECT imaging is $I^{123}$ α-gamma-emitter with a 13.3 hour half life. Compounds labeled with $I^{123}$ can be shipped up to about 1000 miles from the manufacturing site, or the isotope itself can be transported for on-site synthesis. Eighty-five percent of the isotope's emissions are 159 KeV photons, which is readily measured by SPECT instrumentation currently in use. The compounds of the invention can be labeled with Technetium. Technetium-99m is known to be a useful radionuclide for SPECT imaging. The T4 analogs of the invention are joined to a Tc-99m metal cluster through a 4-6 carbon chain which can be saturated or possess a double or triple bond.

Use of F$^{18}$ labeled compounds in PET has been limited to a few analog compounds. Most notably, $^{18}$F-fluorodeoxyglucose has been widely used in studies of glucose metabolism and localization of glucose uptake associated with brain activity. $^{18}$F-L-fluorodopa and other dopamine receptor analogs have also been used in mapping dopamine receptor distribution.

Other halogen isotopes can serve for PET or SPECT imaging, or for conventional tracer labeling. These include $^{75}$Br, $^{76}$Br, $^{77}$Br and $^{82}$Br as having usable half-lives and emission characteristics. In general, the chemical means exist to substitute any halogen moiety for the described isotopes. Therefore, the biochemical or physiological activities of any halogenated homolog of the described compounds are now available for use by those skilled in the art, including stable isotope halogen homolog. Astatine can be substituted for other halogen isotypes. $^{210}$At, for example, emits alpha particles with a half-life of 8.3 h. Other isotopes also emit alpha particles with reasonably useful half-lives. At-substituted compounds are therefore useful for brain therapy, where binding is sufficiently brain-specific.

Numerous studies have demonstrated increased incorporation of carbohydrates and amino acids into malignant brain cells. This accumulation is associated with accelerated proliferation and protein synthesis of such cells. The glucose analog $^{18}$F-2-fluoro-2-deoxy-D-glucose (2-FDG) has been used for distinguishing highly malignant brain cells from normal brain tissue or benign growths (DiChiro, G. et al. (1982) Neurology (NY) 32:1323-1329. However, fluorine-18 labeled 2-FDG is not the agent of choice for detecting low grade brain cells because high uptake in normal tissue can mask the presence of a brain. In addition, fluorine-18 labeled 2-FDG is not the ideal radiopharmaceutical for distinguishing cells from infectious tissue or detecting ovarian carcinoma because of high uptake of the 2-FDG radioactivity in infectious tissue and in the bladder, respectively. The naturally occurring amino acid methionine, labeled with carbon-11, has also been used to distinguish malignant tissue from normal tissue. But it too has relatively high uptake in normal tissue. Moreover, the half-life of carbon-11 is only 20 minutes; therefore C11 methionine cannot be stored for a long period of time.

Cerebrospinal fluid ("CSF") transthyretin ("TTR"), the main CSF thyroxine (T4) carrier protein in the rat and the human is synthesized in the choroid plexus ("CP"). After injection of $^{125}$I-T4 in the rat, radioactive T4 accumulates first in the CP, then in the CSF and later in the brain (Chanoine J P, Braverman L E. The role of transthyretin in the transport of thyroid hormone to cerebrospinal fluid and brain. Acta Med AusTriaca. 1992; 19 Suppl 1:25-8).

Compounds of the invention provide substantially improved PET imaging for areas of the body having amyloid protein, especially of the brain. All the available positron-emitting isotopes which could be incorporated into a biologically-active compound have short half-lives. The practical utility of such labeled compounds is therefore dependent on how rapidly the labeled compound can be synthesized, the synthetic yield and the radiochemical purity of the final product. Even the shipping time from the isotope source, a cyclotron facility, to the hospital or laboratory where PET imaging is to take place, is limited. A rough calculation of the useful distance is about two miles per minute of half-life. Thus $C^{11}$, with a half-life of 20.5 m is restricted to about a 40 mile radius from a source whereas compounds labeled with $F^{18}$ can be used within about a 200 mile radius. Further requirements of an $^{18}$F-labeled compound are that it have the binding specificity for the receptor or target molecule it is intended to bind, that non-specific binding to other targets be sufficiently low to permit distinguishing between target and non-target binding, and that the label be stable under conditions of the test to avoid exchange with other substances in the test environment. More particularly, compounds of the invention must display adequate binding to the desired target while failing to bind to any comparable degree with other tissues or cells.

A partial solution to the stringent requirements for PET imaging is to employ gamma-emitting isotopes in SPECT imaging. $I^{123}$ is a commonly used isotopic marker for SPECT, having a half-life of 13 hours for a useful range of over 1000 miles from the site of synthesis. Compounds of the invention can be rapidly and efficiently labeled with $I^{123}$ for use in SPECT analysis as an alternative to PET imaging. Furthermore, because of the fact that the same compound can be labeled with either isotope, it is possible for the first time to compare the results obtained by PET and SPECT using the same tracer.

The specificity of brain binding also provides utility for I-substituted compounds of the invention. Such compounds can be labeled with short-lived $^{123}$I for SPECT imaging or with longer-lived $^{125}$I for longer-term studies such as monitoring a course of therapy. Other iodine and bromine isotopes can be substituted for those exemplified.

In general, the radioactive imaging agents of the present invention are prepared by reacting radioactive 4-halobenzyl derivatives with piperazine derivatives. Preferred are F-18 labeled 4-fluorobenzyl derivatives for PET-imaging. A general method for the preparation of 4-fluoro-$^{18}$F-benzyl halides is described in Iwata et al., Applied Radiation and Isotopes (2000), Vol. 52, pp. 87-92.

For Single Photon Emission Computed Tomography ("SPECT"), $^{99m}$Tc-labeled compounds are preferred. A general synthetic pathway for these compounds starts with non-radioactive TH analogs within the present invention that are reacted with $^{99m}$Tc-binding chelators, e.g. $N_2$ $S_2$-Chelators. The synthesis of the chelators follows standard procedures, for example, the procedures described in A. Mahmood et al., A $N_2$ $S_2$-Tetra dentate Chelate for Solid-Phase Synthesis: Technetium, Rhenium in Chemistry and Nuclear Medicine (1999), Vol. 5, p. 71, or in Z. P. Zhuang et al., Bioconjugate Chemistry (1999), Vol. 10, p. 159.

One of the chelators is either bound directly to the nitrogen in the —N($R^4$)$R^5$ group of the non-radioactive compounds of the TH analogs of the present invention, or via a linker moiety comprising an alkyl radical having one to ten carbon atoms, wherein the alkyl radical optionally contains one to ten —C(O)— groups, one to ten —C(O)N(R)— groups, one to ten —N(R)C(O)— groups, one to ten —N(R)— groups, one to ten —N(R)$_2$ groups, one to ten hydroxy groups, one to ten —C(O)OR— groups, one to ten oxygen atoms, one to ten sulfur atoms, one to ten nitrogen atoms, one to ten halogen atoms, one to ten aryl groups, and one to ten saturated or unsaturated heterocyclic rings wherein R is hydrogen or alkyl. A preferred linker moiety is —C(O)—$CH_2$—N(H)—.

The compounds of the invention therefore provide improved methods for brain imaging using PET and SPECT. The methods entail administering to a subject (which can be human or animal, for experimental and/or diagnostic purposes) an image-generating amount of a compound of the invention, labeled with the appropriate isotope and then measuring the distribution of the compound by PET if $F^{18}$ or other positron emitter is employed, or SPECT if $I^{123}$ or other gamma emitter is employed. An image-generating amount is that amount which is at least able to provide an image in a PET or SPECT scanner, taking into account the scanner's detection sensitivity and noise level, the age of the isotope, the body size of the subject and route of administration, all such variables being exemplary of those known and accounted for by calculations and measurements known to those skilled in the art without resort to undue experimentation.

It will be understood that compounds of the invention can be labeled with an isotope of any atom or combination of atoms in the structure. While $F^{18}$, $I^{123}$, and $I^{125}$ have been emphasized herein as being particularly useful for PET, SPECT and tracer analysis, other uses are contemplated including those flowing from physiological or pharmacological properties of stable isotope homolog and will be apparent to those skilled in the art.

The invention also provides for technetium (Tc) labeling via Tc adducts. Isotopes of Tc, notably $Tc^{99m}$, have been used for brain imaging. The present invention provides Tc-complexed adducts of compounds of the invention, which are useful for brain imaging. The adducts are Tc-coordination complexes joined to the cyclic amino acid by a 4-6 carbon chain which can be saturated or possess a double or triple bond. Where a double bond is present, either E (trans) or Z (cis) isomers can be synthesized, and either isomer can be employed. Synthesis is described for incorporating the $^{99m}$Tc isotope as a last step, to maximize the useful life of the isotope.

The following methods were employed in procedures reported herein. $^{18}$F-Fluoride was produced from a Seimens cyclotron using the $^{18}$O(p,n) $^{18}$F reaction with 11 MeV protons on 95% enriched $^{18}$O water. All solvents and chemicals were analytical grade and were used without further purification. Melting points of compounds were determined in capillary tubes by using a Buchi SP apparatus. Thin-layer chromatographic analysis (TLC) was performed by using 250-mm thick layers of silica gel G PF-254 coated on aluminum (obtained from Analtech, Inc.). Column chromatography was performed by using 60-200 mesh silica gel (Aldrich Co.). Infrared spectra (IR) were recorded on a Beckman 18A spectrophotometer with NaCl plates. Proton nuclear magnetic resonance spectra (1H NMR) were obtained at 300 MHz with a Nicolet high-resolution instrument.

In another aspect, the invention is directed to a method of using a compound of the invention for the manufacture of a radiopharmaceutical for the diagnosis of Alzheimer's disease in a human. In another aspect, the invention is directed to a method of preparing compounds of the invention.

The compounds of the invention as described herein are the thyroid hormones or thyroid hormone analogs or other TTR binding ligands, which bind to TTR and have the ability to pass the blood-brain barrier. The compounds are therefore suited as in vivo diagnostic agents for imaging of Alzheimer's disease. The detection of radioactivity is performed according to well-known procedures in the art, either by using a gamma camera or by positron emission tomography (PET).

Preferably, the free base or a pharmaceutically acceptable salt form, e.g. a monochloride or dichloride salt, of a compound of the invention is used in a galenical formulation as a diagnostic agent. The galenical formulation containing the compound of the invention optionally contains any adjuvant known in the art, e.g. buffers, sodium chloride, lactic acid, surfactants etc. Sterilization by filtration of the galenical formulation under sterile conditions prior to usage is possible.

The radioactive dose should be in the range of 1 to 100 mCi, preferably 5 to 30 mCi, and most preferably 5 to 20 mCi per application. The compositions within the scope of the present invention can be used as diagnostic agents in positron emission tomography (PET).

The compounds of the present invention may be administered by any suitable route, preferably in the form of a pharmaceutical composition adapted to such a route, and in a dose effective to bind TTR in the brain and thereby be detected by gamma camera or PET. Typically, the administration is parenteral, e.g., intravenously, intraperitoneally, subcutaneously, intradermally, or intramuscularly. Intravenous administration is preferred.

Thus, for example, the invention provides compositions for parenteral administration which comprise a solution of contrast media dissolved or suspended in an acceptable carrier, e.g., serum or physiological sodium chloride solution.

Aqueous carriers include water, alcoholic/aqueous solutions, saline solutions, parenteral vehicles such as sodium chloride, Ringer's dextrose, etc. Examples of non-aqueous solvents are propylene glycol, polyethylene glycol, vegetable oil and injectable organic esters such as ethyl oleate. Other pharmaceutically acceptable carriers, non-toxic excipients, including salts, preservatives, buffers and the like, are described, for instance, in REMMINGTON'S PHARMACEUTICAL SCIENCES, 15.sup.th Ed. Easton: Mack Publishing Co., pp. 1405-1412 and 1461-1487 (1975) and THE NATIONAL FORMULARY XIV., 14.sup.th Ed. Washington: American Pharmaceutical Association (1975). Aqueous carriers, are preferred.

Pharmaceutical composition of this invention are produced in a manner known per se by suspending or dissolving the compounds of this invention—optionally combined with the additives customary in galenic pharmacy—in an aqueous medium and then optionally sterilizing the suspension or solution. Suitable additives are, for example, physiologically acceptable buffers (such as, for instance, tromethamine), additions of complexing agents (e.g., diethylenetriaminepentaacetic acid) or, if required, electrolytes, e.g., sodium chloride or—if necessary—antioxidants, such as ascorbic acid, for example.

If suspensions or solutions of the compounds of this invention in water or physiological saline solution are desirable for enteral administration or other purposes, they are mixed with one or several of the auxiliary agents (e.g., methylcellulose, lactose, mannitol) and/or tensides (e.g., lecithins, "Tween", "Myrj") and/or flavoring agents to improve taste (e.g., ethereal oils), as customary in galenic pharmacy.

The compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For the compounds according to the invention having radioactive halogens, these compounds can be shipped as "hot" compounds, i.e., with the radioactive halogen in the compound and administered in e.g., a physiologically acceptable saline solution. In the case of the metal complexes, these compounds can be shipped as "cold" compounds, i.e., without the radioactive ion, and then mixed with Tc-generator eluate or Re-generator eluate.

Inhibiting Angiogenesis

The invention also provides, in another part, compositions and methods for inhibiting angiogenesis in a subject in need thereof. Conditions amenable to treatment by inhibiting angiogenesis include, for example, primary or metastatic tumors, non-cancerous skin disorders, macular degeneration, and diabetic retinopathy. The compositions can include an effective amount of tetraiodothyroacetic acid (Tetrac), triiodothyroacetic acid (Triac), monoclonal antibody LM609, analogs thereof, or combinations thereof as well as polymeric and/or nanoparticulate forms thereof. Such anti-angiogenesis agents can act at the cell surface to inhibit the pro-angiogenesis agents. The compositions can be in the form of a sterile, injectable, pharmaceutical formulation that includes an anti-angiogenically effective amount of an anti-angiogenic substance in a physiologically and pharmaceutically acceptable carrier, optionally with one or more excipients.

Acting at the plasma membrane receptor for thyroid hormone, Tetrac inhibits the proangiogenic effects of T4 and T3 in standard assays of neovascularization (i.e., chick chorioallantoic membrane, human dermal microvascular endothelial cells). Tetrac blocks the action of agonist thyroid hormone analogs (T4, T3) on growth of human and animal cancer cells in vitro, as well as in certain in vivo models.

In a further aspect, the invention provides methods for treating a condition amenable to treatment by inhibiting angiogenesis by administering to a subject in need thereof an amount of an anti-angiogenesis agent effective for inhibiting angiogenesis. The compositions of the present invention can be used to inhibit angiogenesis associated with cancers, including adenoid carcinoma, breast cancer, colon cancer, glioblastoma multiforme and other brain cancers, head-and-neck cancer, hepatoma, lung cancer, lymphoma, melanoma, basal cell carcinoma, squamous cell carcinoma, myeloma, neuroblastaoma, ovarian cancer, prostate cancer, pancreatic cancer, renal cancer, sarcoma, stomach cancer, thyroid cancer, and liquid tumors. Thyroid hormone antagonists, like Tetrac, can be administered as polymer conjugates or as nanoparticles. In addition to lung cancer, the following human solid tumors have also been shown in xenografts to be susceptible to Tetrac: medullary carcinoma and follicular carcinoma of the thyroid, renal cell carcinoma, non-small cell lung carcinoma, prostate carcinoma, and pancreatic carcinoma. The proximity of the hormone receptor site to the RGD site on the integrin underlies the ability of Tetrac to block the pro-angiogenic activities of polypeptide endothelial growth factors, such as, but not limited to, vascular endothelial growth factor (VEGF) and basic fibroblast growth factor (bFGF).

Tetrac for Inducing Apoptosis in Glioma and Thyroid Cancer Cells

Tetrac (including the nanoparticulate and/or polymeric forms thereof) is capable of inducing apoptosis in C6 glioma cells and in thyroid cancer cells (BHP 2-7). Thus, at least part of the decrease in proliferation of cancer cells when they are exposed to Tetrac is programmed cell death (apoptosis). When proliferation slows in studies of any cancer cells, the issue is whether the cells survive in a cell cycle arrest mode or whether they die. Cell death is more desirable than cell cycle arrest.

Tetrac for Human Lung Cancer

The thyroid hormone/Tetrac effect involves the estrogen receptor (ER) in both small cell and non-small cell human lung carcinoma cells. L-thyroxine (T4) and 3,5,3'-triiodo-L-thyronine (T3) cause proliferation of small cell and non-small cell human lung carcinoma lines and do so via a mechanism that requires the presence in the tumor cells of estrogen receptor-alpha (ERα) in the tumor cells. Tetrac is a probe for the involvement of the cell surface receptor for thyroid hormone on integrin αvβ3 in the cellular actions of T4 and T3. Tetrac, either free or conjugated to a nanoparticle, blocks this proliferative action of T4 and T3 on lung carcinoma cells, which indicates that the cell surface receptor for thyroid hormone on integrin αvβ3 mediates the T4 and T3 effects. The proliferative actions of T4 and T3 on lung cancer cells are also blocked with anti-αv and anti-β3 antibodies and with RGD peptide. These observations further support the role of the integrin receptor for thyroid hormone in promotion by T4 and T3 of proliferation of lung cancer cells.

Thus, Tetrac, either free or conjugated to the nanoparticles or polymers, is an attractive and novel strategy for management of human lung carcinoma. In addition to its anti-proliferative action, Tetrac, either free or conjugated to the nanoparticles, is anti-angiogenic, inhibiting new blood vessel growth that supports lung carcinoma growth. Thus, Tetrac has at least two discrete actions that are relevant to inhibition of lung tumor growth.

In addition to lung cancer, the following human solid tumors have also been shown in xenografts to be susceptible to Tetrac: medullary carcinoma of the thyroid, follicular thyroid carcinoma, renal cell carcinoma, pancreatic carcinoma, stomach carcinoma, hepatoma, glioma and gliobastoma multiforme, ovarian carcinoma, neuroblastoma, colon carcinoma, head-and-neck carcinoma, breast carcinoma, and sarcoma.

Among the nanoparticles, preferred formulations of Tetrac are Tetrac linked by an ester, sulfhydryl, anhydride, or ether bond (with or without a linker) to PLGA, or to collagen or other polymeric molecules of sufficient size to prohibit cell entry by Tetrac, thereby limiting the actions of Tetrac to the cell surface receptor for thyroid hormone on integrin αvβ3.

Cancer-Related New Blood Vessel Growth:

Examples of additional conditions amenable to treatment by inhibiting angiogenesis include, but are not limited to, primary or metastatic tumors, including, but not limited to glioma and breast cancer. In such methods, compounds which inhibit the thyroid hormone-induced angiogenic effect are used to inhibit angiogenesis. Thyroid hormone antagonists such as Tetrac, as well as analogs, polymer conjugates, and nanoparticles thereof can also be used as an anti-angiogenic agent to inhibit angiopoeitin-2. This inhibition can help prevent cancer-related new blood vessel growth, as angiopoeitin-2 destabilizes blood vessels around tumors, making those blood vessels more susceptible to the induction of sprouts by VEGF.

Tetrac for Viral Agents

Tetrac may be used for treatment of viral agents, such as the West Nile virus, HIV, cytomegalovirus (CMV), adenoviruses, and other viral agents. Certain viral agents, such as the West Nile Virus, whose cell entry depends on the αvβ3 integrin via the RGD binding site can be treated with Tetrac. The proposed mechanism of action is that the αv monomer migrates into the cell nucleus and that this is the route of entry for many viruses to get into cells. Tetrac can be used for the treatment of viral agents because it can block this entry of the viruses into cells, by binding to the αvβ3 integrin binding site.

Diabetic Retinopathy:

Another example of the conditions amenable to treatment by inhibiting angiogenesis include, but are not limited to diabetic retinopathy, and related conditions. In such a method, compounds which inhibit the thyroid hormone-induced angiogenic effect are used to inhibit angiogenesis.

It is known that proliferative retinopathy induced by hypoxia (rather than diabetes) depends upon αv integrin expression (See Chavakis et al., Diabetologia 45:262-267 (2002)). It is proposed herein that thyroid hormone action on a specific integrin αvβ3 is permissive in the development of diabetic retinopathy. Thyroid hormone, its analogs, and polymer conjugations, act via the αvβ3 receptor to induce angiogenesis.

Dermatology—Nanoparticle Tetraiodothyroacetic Acid (Tetrac) to Diminish Size of Cutaneous Telangiectasias and Angiomas:

Thyroid hormone antagonists such as Tetrac as well as analogs, polymer conjugates, and nanoparticles thereof can also be used to treat non-cancer skin disorders. This therapeutic and/or cosmetic action of nanoparticulate Tetrac is based on its anti-angiogenic activity. Applied locally as an ointment or cream to cutaneous telangiectasias or spider angiomas, derivatized Tetrac will oppose the pro-angiogenic actions on endothelial cells of endogenous (circulating) thyroid hormone and of polypeptide vascular growth factors. Systemic effects of the locally applied hormone analog formulated as a PLGA nanoparticle will be negligible. For low-grade telangiectasias or angiomas, nanoparticulate Tetrac or unmodified Tetrac may be made available for clinical use in OTC preparations.

Because Tetrac opposes the platelet aggregation action of thyroid hormone, trauma at the site of application of Tetrac could lead to local bleeding. This is a risk with existing, untreated telangiectasias and angiomas. Successful diminution with application of Tetrac of the size of such vascular lesions will, however, reduce the risk of local ecchymoses. Additional dermatological topical applications for nanoparticle-conjugated thyroid antagonists include poikiloderma of civatte (long term exposure to sunlight leading to facial neovascularization and dilated blood vessels), acne or facial rosacea, psoriasis alone or in combination with Vitamin D analogs, and hemangiomas, birth marks, and skin cancer. Currently available anti-angiogenic agents are too expensive for use for the cutaneous lesions targeted here. Moreover, these agents may also be unsuitable for cutaneous application because they are not locally absorbed.

Tetrac for Cancer Chemosensitizing and as Anti-Cancer Agent

The invention also includes methods of suppressing growth of cancer cells that are resistant to drug therapy, by administering to a subject in need thereof an amount of Tetrac, Tetrac nanoparticle, or analogs thereof, effective for suppressing the growth. In certain embodiments, the therapy-resistant cancer cells are selected from, but not limited to, a primary or metastatic tumor, breast cancer, thyroid cancer, neuroblastoma, glioma and glioblastoma multiforme and other brain cancers, colon cancer, head-and-neck cancers, melanoma and basal cell and squamous cell carcinomas of the skin, sarcoma, ovarian cancer, prostate cancer, kidney cancer, hepatoma, lung cancer, pancreatic cancer, stomach cancer, myeloma, and lymphoma. For example, the drug therapy may be the administration of conventional and novel chemotherapeutic drugs, which can be selected from, but not limited to, doxorubicin, etoposide, cyclophosphamide, 5-fluorouracil, cisplatin, trichostatin A, paclitaxel, gemcitabine, taxotere, cisplatinum, carboplatinum, irinotecan, topotecan, adriamycin, bortezomib and atoposide or novel derivatives of the foregoing agents.

The thyroid hormone analogs of the present invention, including Tetrac, Triac, analogs of Tetrac and Triac, polymer and nanoparticle conjugates thereof, and other antagonists of the thyroid hormone receptor on integrin $\alpha v \beta 3$ can also be used as cancer chemosensitizing and anti-cancer agents. Tetrac, Triac, analogs, thyroid antagonists, and polymer conjugates and nanoparticles thereof suppress the development of drug resistance, which is a causative factor of disease relapse. Tetrac enhances cellular response and reverses resistance to doxorubicin, etoposide, cisplatin and trichostatin A in resistant tumor cell lines derived from neuroblastoma, osteosarcoma and breast cancer.

As discussed above, thyroid hormones play a key role in cancer progression. In addition, Tetrac has been shown to possess anti-cancer functions through its ability to inhibit cellular proliferation and angiogenesis. Tetrac also suppresses the development of drug resistance, which is a causative factor of disease relapse. (See FIGS. 13-17). Tetrac enhanced cellular response in vitro to doxorubicin, etoposide, cisplatin and trichostatin A in resistant tumor cell lines derived from neuroblastoma, osteosarcoma and breast cancer. The mechanism of action of Tetrac did not involve expression of classical drug resistance genes. However, radiolabeled doxorubicin uptake in cells was enhanced by Tetrac, suggesting that one or more export mechanisms for chemotherapeutic agents is inhibited. Tetrac was also found to enhance cellular susceptibility to senescence and apoptosis, suggesting that the agent may target multiple drug resistance mechanisms. Tetrac has previously been shown to inhibit tumor cell proliferation in vitro. (See Cheng et al., Endocri Rev 31:139-70 (2010); Rebba et al, Angiogenesis 11:269-76 (2008)). In vivo studies revealed that Tetrac in a pulsed-dose regimen was effective in suppressing the growth of a doxorubicin-resistant human breast tumor in the nude mouse. In this paradigm, doxorubicin-sensitivity was not restored, indicating that 1) the in vitro restoration of drug sensitivity by Tetrac may not correlate with in vivo resistance phenomena and 2) Tetrac is an effective chemotherapeutic agent in doxorubicin-resistant cells. (See Mousa et al., Angiogenesis 11:183-90 (2008)).

One of the remarkable features of cancer cells is their ability to adapt and, thus, to become resistant to virtually any type of stress. From the clinical standpoint, this is regarded as the principal cause of treatment failure and disease relapse. Therefore, there is great interest in developing approaches to prevent and/or to reverse the development of drug resistance. In recent years, a number of drug candidates (most of which are inhibitors of ion channels) have been identified and, although most were found to be very effective in reversing drug resistance in vitro, they were unable to do so in vivo, often due to their high toxicity. In the search of novel, less toxic drug resistance regulators, the thyroid hormone antagonist Tetrac has been identified as promising agent that, unlike other previously discovered drug resistance-reversing agents, exerts a dual action on drug transport and on signaling pathways that control cellular susceptibility to drug-induced proliferation arrest and apoptotic death. This, in addition to its above-described effect on tumor angiogenesis, makes Tetrac a promising anti-cancer drug candidate.

Figure 14:
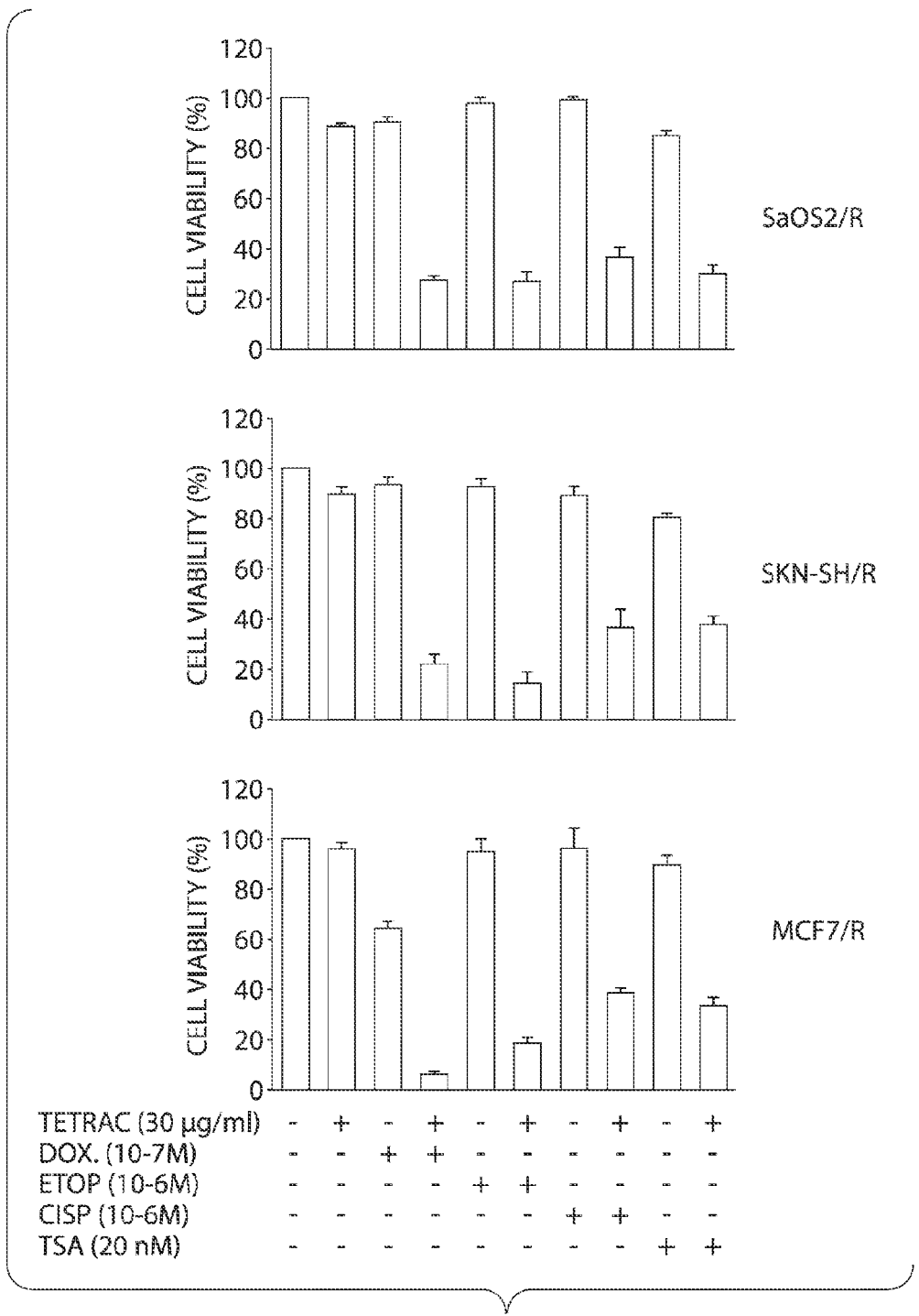
FIG. 14 demonstrates the reversal of drug resistance by Tetrac. Doxorubicin resistant SKN-SH/R, MCF7/R and SaOS2/R cells were subjected to treatment with Tetrac either alone or in combination with each of doxorubicin (Dox), etoposide (Etop), cisplatin (Cisp), or trichostatin A (TSA) at the indicated concentrations, After 4 days in cell viability was determined by the MTT assay and the data represented as average of 3 determinations±SE.
Figure 15A:
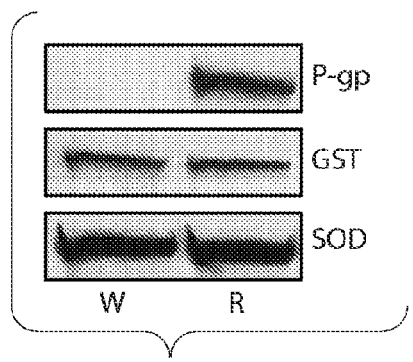
FIG. 15A is a Western blot showing the expression of P-gp, GST and SOD in wild type (W) drug sensitive and resistant (R) MCF7 cells.
Figure 15B:
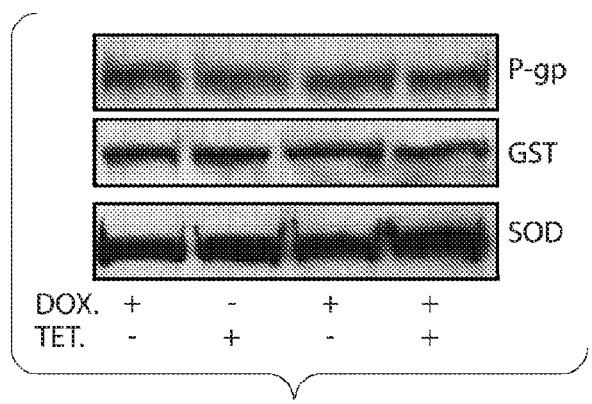
FIG. 15B shows the effect of Tetrac and doxorubicin (Dox) on expression of these genes in MCF7/R cells. The cells were treated for 24 h with each drug alone or the combination of both, after that, expression of drug resistance molecules was determined by Western blot using specific antibodies.
Figure 15C:
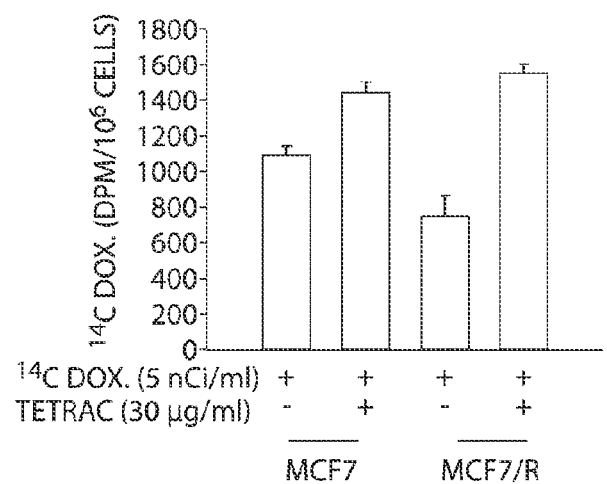
FIG. 15C shows the effect of Tetrac on intracellular accumulation of radiolabeled doxorubicin ([14C]Dox.) in drug sensitive MCF7 and resistant MCF7/R cells. The cells were incubated for 24 hours with doxorubicin in the absence or the presence of Tetrac, after that they were washed and then solubilized. Radioactivity associated with the cell lysates was counted and compared between the two cell lines either treated or not with Tetrac. The data represent an average of 3 determinations±SE.
Figure 17:
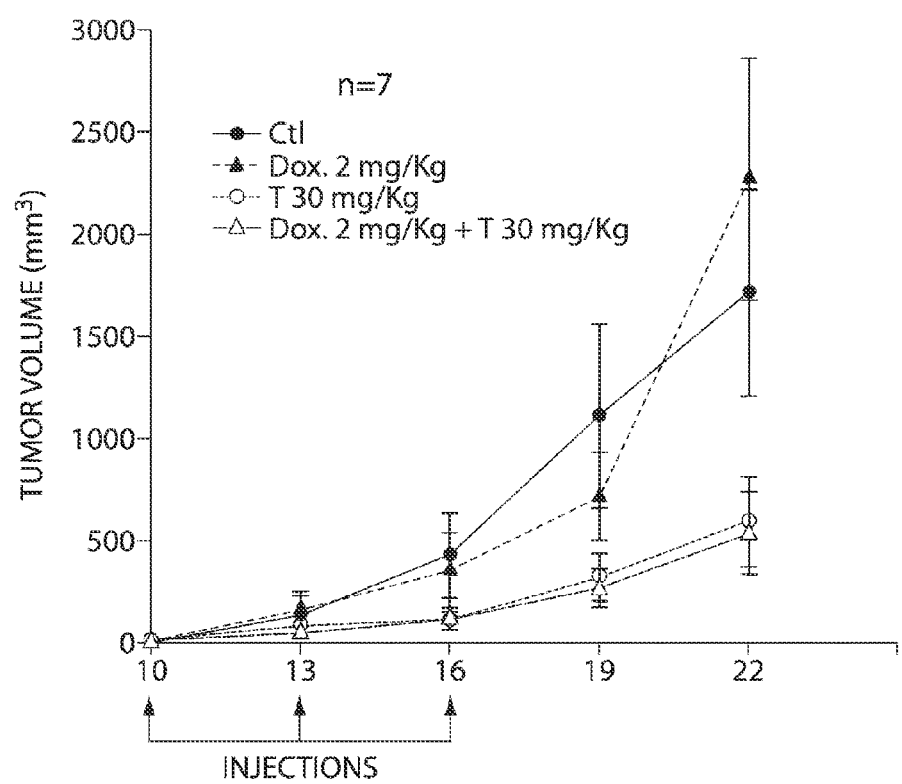
FIG. 17 shows the effect of Tetrac on growth of doxorubicin-resistant tumors in nude mice. Mice were injected with doxorubicin-resistant MCF7/R cells ($10^6$) and after 10 days, they were assigned into groups of seven mice each and challenged with doxorubicin (2 mg/kg) or Tetrac (30 mg/kg) either alone or in combination. Tumor volume was measured every 3 days for up to three weeks.
Figure 18:
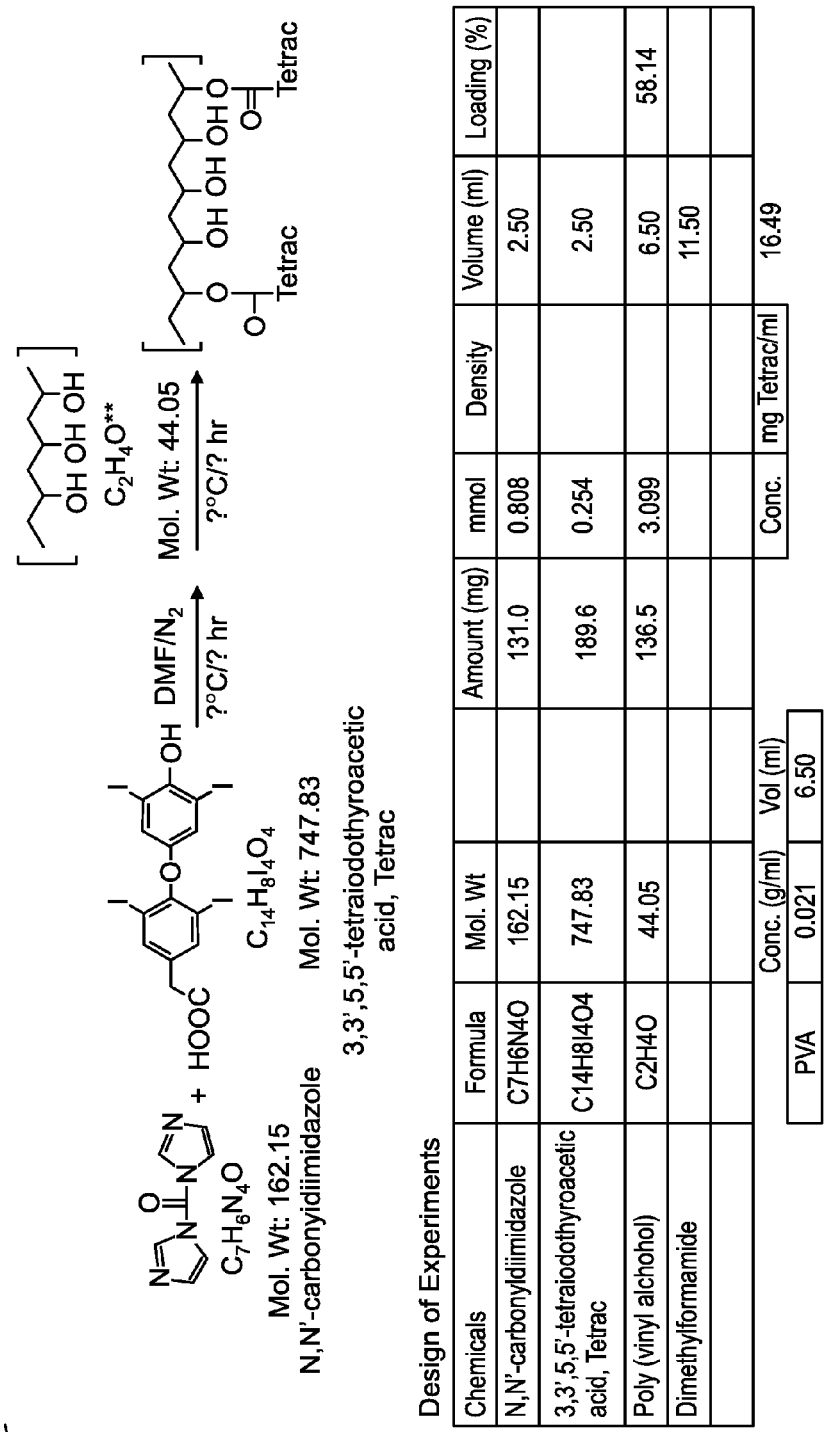
FIG. 18 is an additional representation of the conjugation of Tetrac to a polymer via an ester linkage.

The initial finding that Tetrac exerted equivalent anti-proliferative activity in vitro against drug-sensitive and drug-resistant cells (FIG. 13) suggested that this antagonist can overcome drug resistance. The cellular responses to doxorubicin, etoposide, cisplatin and TSA were significantly enhanced when these drugs were combined with Tetrac (FIG. 14). However, since the mechanisms involved in resistance to these agents are not necessarily similar, Tetrac may act by regulating more than one drug resistance pathway. To address this possibility, the effect of Tetrac on expression of P-glycoprotein, SOD, and GST-π has been studied. Expression of none of these genes was significantly altered (FIGS. 15A-B). Others have shown that agonist thyroid hormone can increase expression of P-gp. Tetrac at the concentrations used exerts its thyroid hormone antagonist activity primarily at the integrin receptor and our results thus indicate that P-gp gene expression is not modulated from the cell surface integrin receptor.

However, analysis of drug transport revealed that intracellular accumulation of radiolabeled doxorubicin increased significantly in the presence of Tetrac as compared to non-treated cells (FIG. 15C) and suggested that Tetrac may act as an inhibitor of P-gp activity. In light of the previous observation that thyroid hormones are able to bind to $\alpha v \beta 3$ integrin and to P-gp, the finding that Tetrac inhibits their binding to integrins raises the possibility that Tetrac may also interfere with their binding to P-gp. Using the same logic, Tetrac may also compete with drugs for the binding to P-gp and thus, disrupt the efficacy of this transporter. Whatever the mechanism, the finding that drug export was inhibited by Tetrac is of a fundamental importance as it sheds light on the critical role of hormone homeostasis in the regulation of cancer response to chemotherapy.

Although this finding may represent a significant advancement in understanding the mechanism by which Tetrac reverses drug resistance, it does not explain why this antagonist enhances cellular response to cisplatin, a non-p-gp substrate. Since accumulating evidence indicates that cellular ability to undergo senescence or apoptotic death play key roles in chemotherapy outcome, the effect of Tetrac on the corresponding pathways was tested. As shown in FIG. 16, cellular ability to undergo doxorubicin-induced proliferation arrest (enhanced expression of p21/WAF1) and SA-β-Gal and cell death (caspase-3 activation and chromatin condensation) were dramatically enhanced upon exposure to Tetrac, suggesting that forcing cancer cells into senescence or apoptosis may represent additional mechanisms by which Tetrac reverses drug resistance.

Increased expression of pro-apoptotic genes such as bad and bax were associated with increased response to chemotherapeutic agents in cancer of hematopoietic origins. However, in most solid tumors, a clear relationship between apoptosis and cellular response to chemotherapy was not established. In contrast, cellular ability to undergo senescence was found recently to be associated with treatment outcome of these tumors. Tetrac regulates both processes as well as the mechanisms that regulate drug transport; therefore this antagonist may have a broad use for the treatment of aggressive cancers of both hematopoietic and solid origins. An example for this is provided by the in vivo data showing that Tetrac is effective in suppressing the growth of drug resistant tumors in nude mice (FIG. 17) without any noticeable toxic effect. These findings, in addition to the fact that nanoparticulate Tetrac is also capable of suppressing angiogenesis make this hormone antagonist a compelling tool for the treatment of aggressive cancers.

Tetrac for Cancer Radiosensitivity

In general, radiosensitivity is the relative susceptibility of cells, tissues, organs or organisms to the harmful effect of ionizing radiation. Cells are least sensitive when in the S phase, then the $G_1$ phase, then $G_2$ phase and the most sensitive in the M phase of the cell cycle. Overall, x-rays are more effective on cells which have a greater reproductive activity.

It is noted that quickly dividing tumor cells are generally more sensitive than the majority of body cells are. However, this is not always true. Tumor cells can be hypoxic and, therefore, less sensitive to x-rays that mediate most of their effects through free radicals produced by ionizing oxygen. Further, the most sensitive cells are those that are undifferentiated, well nourished, divide quickly and are highly metabolically active. Amongst the body cells, the most sensitive include spermatogonia and erythroblasts, epidermal stem cells, and gastrointestinal stem cells. The least sensitive are nerve cells and muscle fibers. Highly sensitive cells also include oocytes and lymphocytes, although they are resting cells and do not meet the criteria described above.

The damage to the cell can be lethal (the cell dies) or sublethal (the cell can repair itself). Moreover, the effects on cells can be, according to the International Commission on Radiological Protection (ICRP), deterministic and stochastic. Deterministic effects have a threshold of irradiation under which they do not appear and are the necessary consequence of irradiation. The damage they cause depends on the dose: they are sublethal from 0.25 to 2 Sv (a less pronounced form of disease), lethal from 2 to 5 Sv (a certain percent of population dies in 60 days), above 5 Sv the majority of people die in 60 days and above 6 to 7 all people die. Of course, these effects depend also on many other factors, including age, sex, health etc.

Stochastic effects are coincidental and cannot be avoided. They do not have a threshold, and they can be divided into somatic and genetic effects. Among the somatic effects, secondary cancer is the most important. Secondary cancer develops because radiation causes DNA mutations directly and indirectly. Direct effects are those caused by ionizing particles and rays themselves, while the indirect are those that are caused by free radicals, generated especially in water and oxygen radiolysis.

Demonstrated herein is an increased radiosensitivity and inhibition of both sub-lethal and potentially lethal damage repair in GL261 cells by the use of Tetrac or Tetrac-Nano. Also disclosed are some mechanisms by which these results may be produced. Specifically, Tetrac and Tetrac-Nano (or analogs thereof) modifies the response of radiation and inhibits the repair of radiation damage.

GL261 brain tumor cell proliferation in vitro has been shown to be decreased by addition of the deaminated analogue of thyroxine ($T_4$), tetraiodothyroacetic acid (Tetrac). Cell proliferation was also decreased by addition of an RGD (Arg-Gly-Asp) recognition site peptide to medium containing thyroxine ($T_4$). This RGD recognition site peptide blocks the binding of $T_4$ to the $\alpha v \beta 3$ integrin receptor and suggests that Tetrac also acts by blocking the access of $T_4$ to the $\alpha v \beta 3$ integrin receptor. The acetic acid portion of Tetrac appears to anchor to the Asp of the RGD peptide site. This is a novel, specific interaction of $T_4$ with $\alpha v \beta 3$. (See Abdollahi et al., *Clin. Cancer Res.* 2005. 11:6270-79). The $\alpha v \beta 3$ integrin transduces signals via the mitogen-activated protein kinase (MAPK) pathway, and is a major adhesion receptor for proteins such as fibrinogen, vitronectin, von Willebrand factor, thombospondin, osteopontin, fibronectin, and laminin. Moreover, the $\alpha v \beta 3$ integrin receptor has been shown to be necessary for tumor-induced angiogenesis. Antagonists to the $\alpha v \beta 3$ receptor (i.e., Tetrac or Tetrac-Nano) have been shown to be anti-angiogenic and to reduce tumor growth in a mouse model of breast cancer. Tetrac is also anti-proliferative in cancer cells expressing integrin $\alpha v \beta 3$. The integrin also is known to contribute to the radioresistance of glioma cells. (See, Abdollahi et al., *Clin. Cancer Res.* 2005. 11:6270-79; Monferran et al., *Int J Cancer* 2008. 123:357-64).

It is also noted that $T_4$ is a model for the non-genomic actions of thyroid hormone (i.e. an action at the membrane, the $\alpha v \beta 3$ integrin receptor), in contrast to $T_3$ which functions primarily to activate nuclear thyroid hormone receptors which are present in the cytoplasm.

These studies provide a basis for clinical observations that induction of mild hypothyroidism by administration of propylthiouracil (PTU) improves the duration of survival by 3-fold in glioblastoma (GBM) patients. (See Hercbergs et al., *Anticancer Res* 2003. 23:617-26). This occurs because PTU inhibits thyroid hormonogenesis and reduces circulating thyroxine levels, producing hypothyroidism. Indeed, the induction of a hypothyroid state may act as a valuable therapeutic maneuver in the treatment of cancer. (See Hercbergs, *In Vivo* 1996. 10:245-47). The integrin as a treatment target in glioma has additional promise in the $\alpha v \beta 3$ receptor in hyperplastic small blood vessels and adjacent tissues of glioblastoma tumors and the expression of $\alpha v \beta 3$ has been shown to increase concurrently with the degree of malignancy in brain tumors. (See Schnell et al., *Brain Pathol* 2008. 18:378-86; Newcomb et al., *Cell Cycle* 2006. 5:93-99).

It has been shown that administration of PTU at a concentration of 0.1% to rats bearing Morris 7800 hepatoma neoplasms increased survival from 47 to 53 days in control animals to 62 to 65 days in rats drinking the PTU. This is an increase in survival of approximately 1.3 fold. Also to this point, in a transplantable liver tumor that treatment of solid tumors with 10 Gy of 250 kVp x-rays, or 10 Gy of x-rays plus 0.05% PTU in the drinking water increased the time needed to grow from approximately 270 $mm^3$ to 900 $mm^3$ from approximately 6.2 days in control tumors, to 11.2 days in x-irradiated tumors, and to 17.8 days in irradiated tumors in animals also drinking PTU. Tumors treated with PTU alone showed no difference in growth rate from control neoplasms. Mechanistically, the reduction of circulating thyroxine by PTU leads to reduced activation of the $\alpha v \beta 3$ receptor, a reduction associated with increased duration of patient survival, potentially because of a reduction in tumor angiogenesis and tumor cell proliferation. In this regard, the $\alpha v \beta 3$ integrin receptor is present in the hyperplastic small blood vessels and adjacent mesenchymal tissues of glioblastoma tumors but not in non-neoplastic brain biopsies, and the expression of the $\alpha v \beta 3$ integrin receptor has been shown to increase with the degree of malignancy in brain tumors. (See Lorger et al., Proc Natl Acad Sci 106:10666-671 (2009)).

While the GL261 murine brain tumor line has been studied in vitro to determine the effects of Tetrac on the $\alpha v \beta 3$ site, this line has not been studied in vitro in regard to its intrinsic radiosensitivity or to its radiosensitivity after modulation with agents such as Tetrac and Tetrac-Nano. However, the GL261 murine tumor cell line has been studied in vivo in regard to the radiosensitizing effects of flavopiridol (see Newcomb et al., *Cell Cycle* 2006. 5:93-99), the mTOR inhibitors rapamycin and RAD001 (see Shinohara et al., *Oncogene* 2005. 24:5414-22), the receptor tyrosine kinase inhibitors SU11248 and SU6668 (see Himmelfarb et al., *Cancer Res.* 2003.63:4009-16; Schueneman et al., *Cancer Res.* 2003. 63:4009-160), and the phosphatidylinositiol-3'-kinase antagonist IC486068 (see Geng et al., *Cancer Res.* 2004.4893-99). In terms of the relative radiosensitivity of the GL261 tumor cells in vivo, the tumor ranks ninth out of 15 tumors evaluated using the $TCD_{50}$ endpoint (radiation dose needed to control tumors in 50% of irradiated animals). (See Newcomb et al., *Cell Cycle* 2006. 5:93-99) As the GL261 tumor shows a moderate response in vivo, which is consistent with its wild-type p53 status, this implies that the in vitro radiation sensitivity of GL261 tumors would also be "moderate" in nature.

Against this background, it has been therefore documented the in vitro responses of the GL261 brain tumor line to x-irradiation. The effects of Tetrac on recovery after radiation damage using 2-dose exposures leading to estimation of the effects of Tetrac on sub-lethal damage repair (SLDR) and single dose exposures were studied when time was allowed to occur after the initial dose and before replating (potentially lethal damage repair; PLDR). Both types of repair experiments were done in both exponentially growing and in plateau phase cells to document the effects of Tetrac on cellular recovery after irradiation. It is important to note that in the experiments reported here the nongenomic action of thyroid hormone was investigated.

The clonogenic effects of Tetrac are described in the Table in Example 18, infra, which shows that Tetrac decreased the colony forming abilities of GL261 cells in the plateau phase of growth but not in the exponential phase when feeder cells were added. The fact that added Tetrac did not produce a change in the medium pH is important, as it has been shown that for PLDR, irradiation of A549 lung carcinoma cells in confluent cultures, reduced survival by a factor of about 10 from the acidic pH of 6.6 normally found in confluent cultures when the pH was adjusted to 7.6 by addition of NaOH. (See Varnes et al., *Radiat Res* 108(1):80-90 (1986)). For GL261 cell growth rates, Tetrac appears to increase the time (latency) until GL261 cell growth starts to become exponential. However, Tetrac did not affect the cell culture doubling times when the cells were in exponential growth (control GL261 cell doubling time=44.2±3.6 hours; Tetrac-treated GL261 cell doubling time=43.8±3.8 hours (±95% confidence limits)). In contrast, a decreased proliferation rate of GC cells in vitro and in WITG3 glioblostoma cells by depletion of thyroid hormones. (See Toms et al., *Anticancer Research* 18:289-94 (1998)). Finally, Tetrac decreased the final saturation density by about 50%, implying that cells were larger at 10-14 days after Tetrac exposure. This implication is confirmed as shown by the volumetric data, which shows that the Tetrac-treated exponential and plateau phase cells are 1.4 and 1.9 times larger than are the control GL261 cells.

To define how long Tetrac affected GL261 cells, the cell multiplicity (CM) factor as a function of time after a one hour exposure to Tetrac was used as a surrogate index. A decrease in the CM factor was recorded at 50% after 60 hours post Tetrac treatment. The cell multiplicity factor may not be a direct measurement of the remaining Tetrac on GL261 cells, but, rather adequately reflects the binding of Tetrac to the αvβ3 integrin receptor as supported by the measurement of cell adhesivity. However, the fact that it takes approximately 2.5 days for a 50% return of the cell multiplicity factor towards the level seen in control GL261 cells indicates that exposure to Tetrac has a marked effect on adhesivity. It has been shown in Balb/c 3T3 cells that the ratios of cell-cell adhesivity were approximately M (normalized to 1.0)>$G_1$ (0.9)>S phase cells (0.7). These data do not agree with the FCM data, where Tetrac decreases the percent of cells in the M phase and increases the percent of cells in the $G_1$ cell cycle phase. However, the FCM data agree with data on cultured GC cells that were depleted of $T_3$, and on the WITG3 glioblastoma cell line in which an increase in the percentage of cells in $G_1$, and a decrease in S and $G_2$ cell cycle phases was seen in thyroid hormone depleted cells. (See Toms et al., *Anticancer Research* 18:289-94 (1998)). It has been shown in exponentially growing BHK21 cells that use of metabolic inhibitors (e.g. cyclohexamide, sodium fluoride, potassium cyanide, rotenone, formaldehyde) inhibits aggregation, while glucose, glutamine, cyclic adenosine monophosphate (cAMP), and cytochalasin B increases aggregation. (See Edwards et al., *J Cell Sci* 19(3):6537 (1975)). In this regard it is noted that increased $T_3$ levels activate HIF-1α through PI3K. (See Moeller et al., *Proc Natl Acad Sci* 106:10666-671 (2009)).

Thus, the initial findings on the effects of Tetrac on the single dose responses of exponentially growing GL261 cells showed that Tetrac reduced the width of the "shoulder" region of the survival curve, without significantly affecting the slope ($D_0$, Gy). In FIG. 53, the graded dose survival curves for both exponentially growing and plateau phase cells is shown, without and with added Tetrac, and in the Example 18, infra, the survival parameters for the single-hit, multitarget and the linear-quadratic equations are listed. The single dose x-ray studies were then extended to include studies of the effects of Tetrac on repair of sub-lethal radiation damage (SLDR). For exponential cells, it was found that Tetrac inhibited SLDR. Indeed, the maximum recovery in control exponential GL261 cells was approximately 4.2, while that in exponentially growing Tetrac treated cells was 2.1. Therefore, the hypothesis advanced from the single dose studies of exponentially growing cells in which the Dq was found to be reduced that SLDR would also be reduced is confirmed by the split dose studies in exponentially growing cells in which inhibition of recovery was seen. However, when the plateau phase cells were examined for their SLDR expression, Tetrac inhibited SLDR almost completely, but also produced additional cell killings in the first 1 to 4 hours after the first dose. This decrease in cellular repair amounted to about a factor of 3 at three hours post-irradiation. Examples of decreased recovery and even fixation of damage) in plateau phase have been reported.

Repair of potentially lethal damage repair (PLDR) in exponentially growing cells was determined using the change in survival as a function of time after application of a single dose as the index of effect. The exponentially growing cells did not express a significant amount of PLDR (i.e. about a factor of 1.1 at 8 hours post-irradiation). This difficulty in expression of PLDR in exponential cells has been noted by other investigators. (See Gavrieli et al., *J. Cell. Biol.* 1992; 119:493-501 and Painter et al., *Nature,* 1977; 270: 543-546). PLDR in plateau phase cells increased by a factor of 2.4 from 0 to 8 hours, and Tetrac decreased this PLDR expression by a factor of 3.4.

It is noted that Tetrac has increased both cellular radiosensitivity and cellular and nuclear volumes. In effect, treatment with Tetrac increased the physical cross-sectional area available for interaction with ionizing radiation. In this regard, the fact that the presumptive target (the nucleus) becomes larger and therefore easier to hit with ionizing radiation may be of some relevance to intrinsic radiosensitivity of cells. However, the addition of Tetrac interferes with signal transduction processes, which may also impact upon cellular radiosensitivity and repair of radiation damage.

Reduced temperature and starvation conditions have been shown to produce damage fixation. Cells that exhibit damage fixation in repair situations appear to be quite radiosensitive and/or may exhibit the ataxia telangiectasia phenotype (AT). AT cells are characterized by a hypersensitivity to DNA-strand breaks produced by a mutation in the AT gene [AT-mutated; ATM] which suggests that ATM functions in a DNA damage signal transduction pathway consisting of x-irradiation→ATM→p53→DNA-PK+Ku70/Ku80→DNA DSB repair. Tetrac may interfere with this signal transduction pathway leading ultimately to tumor cell radiosensitivity.

It was found that Tetrac given at a concentration of 2 µM for one hour at 37° C., radiosensitized GL261 cells. This sensitization was primarily due to a significant increase in the $\alpha$ component as described in the linear-quadratic equation. The dose enhancement factor at 2 Gy was determined to be 2.3. As Tetrac is thought to act by blocking the binding of the thyroid hormones $T_3$ and $T_4$ to the $\alpha v \beta 3$ integrin receptor, the stoichiometry of the results are necessary to determine the meaning of the results.

In the experiments, 2 µM Tetrac was used. As the molecular weight of Tetrac is 787.8 g/m, this means that at 2 µM, there are approximately $7.3 \times 10^{17}$ molecules per ml. It is estimated that the concentrations of $T_3$ and $T_4$ in calf serum (CS) were respectively 150 and 6.8 ng/100 ml. It has been shown that $T_4$ is about 20% higher in fetal bovine serum (FBS) than in CS, while conversely, $T_3$ is about 40% higher in CS than in FBS. The levels of $T_3$ and $T_4$ in the FBS used herein were respectively approximately 900 and 82 ng/L. Using molecular weights of 651 and 777 g/mole for $T_3$ and $T_4$, this would then mean approximately $3.2 \times 10^{10}$ and $4.5 \times 10^{9}$ molecules/ml in medium containing 7.5% FBS. That is, there are many more Tetrac molecules per ml than exist either $T_3$ or $T_4$ molecules.

Additionally, the data from other tumor cell lines suggest that the mean number of $\alpha v \beta 3$ integrin receptors is about $2.2 \times 10^5$ (range 1.28 to $4.42 \times 10^5$) per cell. Therefore, Tetrac is present in excess as compared to the number of $\alpha v \beta 3$ receptors per cell. While $T_3/T_4$ levels in 7.5% FBS in medium (without Tetrac) normally saturate the $\alpha v \beta 3$ receptors in control cells, the excess of Tetrac molecules is sufficient to obviate this response. The half-time for Tetrac uptake is on the order of 10-15 min. This rapid uptake of Tetrac would account for the radiosensitization and inhibition and repair seen herein. Therefore, results reflect the blockade of the $\alpha v \beta 3$ integrin site by Tetrac, resulting in increased radiosensitivity.

Both $\alpha v \beta 3$ and $\alpha V \beta 5$ integrin sites on glioblastoma cells (U87, SF763) have been blocked using EMD121974, an RGD peptide and have been examined for sensitivity to photon irradiation. (See Monferran et al., *Int J Cancer* 2008. 123:357-64; Skuli et al., *Cancer Res* 2009. 69:3308-16). Analysis of the SF763 survival curve shape indicates that use of 85 µM EMD121974 (16 hours at 37° C.) affected the $\alpha$ component in the LQ survival equation, increasing a from approximately 0.04 to 0.18 $Gy^{-1}$, a factor of 4.4-fold. The synthetic RGD peptide, cilengitide, has also been shown to enhance the effects of radiotherapy in endothelial cell and non-small cell models of cancer. (See Albert et al., *Int J Radiat Oncol Biol Phys* 2006. 65:1536-43).

Human cancer cells (M21 melanoma, UMSCC-22B squamous carcinoma, U87 glioblastoma, and HT29 colon adenocarcinoma) have been treated with CNTO 95, a human anti-$\alpha_v$, integrin monoclonal antibody, and either $^{137}$Cs irradiation (in vitro) or x-rays (in vivo). (See Ning et al, *Mol Cancer Ther* 2008.7:1569-78). In vitro, M21 melanoma cells were sensitized to irradiation by CNTO 95 (13 µg/ml) while growing either on vitronectin or soft agar (but not on fibronectin). However, the sensitization was expressed by an increased $\beta$ value in the LQ survival formalism and not by an increase in the $\alpha$ value as shown with Tetrac or with EMD121974. (See Ning et al, *Mol Cancer Ther* 2008.7:1569-78). Such results raise the possibility of differential effects of the $\alpha v$ versus the $\beta 3$ portions of the integrin heterodimer on radiosenstivity. For the effects of CNTO 95 on in vitro apoptosis, treatment with M21 cells (20 ug/ml) increased sensitivity by a factor of 2-fold at doses of 0, 5, and 10 Gy. In vivo, CNTO 95 was most effective when irradiation was given in fractionated (not single dose) installations given before irradiation rather than after irradiation. (See Ning et al, *Mol Cancer Ther* 2008.7: 1569-78). CNTO 95 was also shown to be effective when treatment was continued by administering CNTO 95 (10 mg/kg, 3 doses per week) until completion of the studies, about 18-43 days after the start of treatment. This anti-$\alpha v$ antibody combines with $\alpha v \beta 3$, $\alpha v \beta 5$, and $\alpha v \beta 6$ integrins at different staining intensities depending on the histology of the tumor studied (i.e. for M21 melanoma maximum staining intensity was shown for $\alpha v \beta 3$ and $\alpha_v \beta_5$ integrins, while for HT29 colon adenocarcinoma the maximum staining intensities were shown for $\alpha_v \beta_5$ and $\alpha_v \beta_6$ integrins). All of these studies indicate that integrin receptors are an important site at which nongenomic responses to radiation therapy may be elicited.

Effects of Tetrac on Growth Factor Levels as Related to Intrinsic Radiosensitivity It has been shown that Tetrac blocks the activation of epidermal growth factor (EGF) and transforming growth factor-$\alpha$ (TGF-$\alpha$) in HeLa cells, and Tetrac may occlude the $\alpha v \beta 3$ integrin receptor site such that fibroblast growth factor-2 (FGF-2) and vascular endothelial growth factor (VEGF) are unable to enter cells. As increased EGF levels radiosensitize, while TGF-$\alpha$, FGF-2 and VEGF are radioprotective, growth factor blockade may provide at least part of the radiosensitization seen with Tetrac application. However, inhibition of these growth factors results in different cellular responses to radiosensitivity. Therefore, the absolute levels of each growth factor as well as their respective secretion rates are needed in a given cell line before an absolute statement can be made with regard to the application of Tetrac.

Therefore, these examples show how Tetrac affects immediate survival of GL261, to both single doses of 250 kVp x-rays and to repair of damage (sublethal and potentially lethal damage repair; SLDR, PLDR) in both exponential and plateau phase cells. The cells were exposed to 2 µM Tetrac (1 hour at 37° C.) prior to x-irradiation. At varying times after irradiation, cells were replated in medium (without Tetrac). Two weeks later, colonies were counted, and results analyzed using either the linear-quadratic (LQ) or single-hit, multitarget (SHMT) formalisms.

The results indicate that Tetrac sensitized both exponential and plateau phase cells to x-irradiation, as shown by a decrease in the quasi-threshold dose (Dq), leading to a Tetrac enhancement factor (ratio of $SF_2$ values) of 2.5. Tetrac reduced sublethal damage repair (SLDR) in exponential cells by a factor of 1.8. In plateau phase cells there was little expression of SLDR, but Tetrac produced additional cell killing at 1-4 hours after the first dose. For potentially lethal damage repair (PLDR) expression, in exponential cells, Tetrac inhibited PLDR by a factor of 1.9, and in plateau phase cells, Tetrac decreased PLDR expression by a factor of 3.4.

The data show that the decreased Dq value seen after single doses of x-rays with Tetrac treatment is also accompanied by a significant decrease in recovery of sublethal and potentially lethal damage.

Tetrac (Tetrathyroiodoacetic Acid) and its Effects on the In Vitro Sensitivity of GL261 Brain Tumor Cells to Ionizing Radiation and Hyperthermia Tetrac sensitizes tumor cells to graded single doses of x-irradiation. At a dose level of 2 Gy (the most common dose used in conventional radiation therapy), the survival of non-Tetrac treated cells is 32%, while the survival of Tetrac treated cells is 13%. The ratio of survivals at 2 Gy calculates to a dose enhancement factor of 2.5. (See FIG. 57).

However, Tetrac not only sensitizes GL261 tumor cells to ionizing radiation, it also inhibits repair of radiation produced damages. (See FIG. 58).

These two factors (radiation sensitization combined with inhibition of the repair of radiation produced damages) make Tetrac or analogs of Tetrac (i.e., Tetrac nanoparticles ("T-NPs") excellent candidates for combination with conventional radiation therapy of patient neoplasms.

Tetrac exerts similar effects on oxic and hypoxic GL261 cells. (See FIG. 60). However, once the oxic cells are destroyed, the hypoxic cells can re-oxygenate and re-enter the cell cycle and continue to proliferate. They will then undergo cell division, and repopulate the tumor. Hypoxic cells are 3 times as radioresistant as oxic cells. Therefore, hypoxic cells have a greater chance of survival than oxic cells. This effect of Tetrac, i.e., radiosensitization of hypoxic cells, is an important aspect of the overall radiosensitization of solid tumors.

Additionally, Tetrac sensitizes GL261 cells in hyperthermic conditions. Graded heat treatment of GL261 tumor cells with 44° C. was given, without and with Tetrac. Tetrac increased cell killing as compared to control cells alone, by the equivalent of about 1° C. (i.e., 44° C. plus Tetrac is the equivalent of 45° C. without Tetrac). (See FIG. 63).

The effects of Tetrac on inhibition of the repair of thermal damage (i.e., induction of thermotolerance) can also be investigated. It can be hypothesized that Tetrac would have similar effects as with ionizing radiation (e.g., inhibition of repair of heat damages).

Finally, Tetrac has also been shown to increase apoptosis and necrosis in GL261 tumor cells, and these effects have also been shown with T-NPs. The effects of Tetrac (or T-NPs) on apoptosis and necrosis range from supra-additive (apoptosis) to additive (necrosis) and provide part of the biological rationale for the application of Tetrac (or T-NPs) to radiation therapy or to hyperthermic therapy.

In summary, this data, in combination with the data regarding the effects of Tetrac on drug sensitivity, indicate that Tetrac or its analogs have an important place in the therapy of both solid and disseminated cancers with our without combined heat plus ionizing radiation.

Methods of Treatment and Formulations:

The compounds can be administered via any medically acceptable means which is suitable for the compound to be administered, including oral, rectal, topical or parenteral (including subcutaneous, intramuscular and intravenous) administration. For example, adenosine has a very short half-life. For this reason, it is preferably administered intravenously. However, adenosine $A_2$ agonists have been developed which have much longer half-lives, and which can be administered through other means. Thyroid hormones, thyroid hormone analogs, polymeric forms, and derivatives can be administered, for example, by intravenous, intramuscular, subcutaneous, oral, rectal, topical, intranasal, and/or ophthalmic administration.

In some embodiments, the thyroid hormones, thyroid hormone analogs, polymeric forms, nanoparticulate forms, and derivatives are administered via different means.

The amounts of the thyroid hormone, its analogs, polymeric forms, nanoparticulate forms, and derivatives required to be effective in stimulating angiogenesis will, of course, vary with the individual being treated and is ultimately at the discretion of the physician. The factors to be considered include the condition of the patient being treated, the efficacy of the particular adenosine $A_2$ receptor agonist being used, the nature of the formulation, and the patient's body weight. Occlusion-treating dosages of thyroid hormones, thyroid hormone analogs, its polymeric forms, nanoparticulate forms, and derivatives are any dosages that provide the desired effect.

The compounds described above are preferably administered in a formulation including thyroid hormones, thyroid hormone analogs, polymeric forms or nanoparticulate forms, and derivatives together with an acceptable carrier for the mode of administration. Any formulation or drug delivery system containing the active ingredients, which is suitable for the intended use, as are generally known to those of skill in the art, can be used. Suitable pharmaceutically acceptable carriers for oral, rectal, topical or parenteral (including subcutaneous, intraperitoneal, intramuscular and intravenous) administration are known to those of skill in the art. The carrier must be pharmaceutically acceptable in the sense of being compatible with the other ingredients of the formulation and not deleterious to the recipient thereof.

Where the agent is to be provided parenterally, such as by intravenous, subcutaneous, intramolecular, ophthalmic, intraperitoneal, intramuscular, buccal, rectal, vaginal, intraorbital, intracerebral, intracranial, intraspinal, intra-ventricular, intrathecal, intra-cisternal, intra-capsular, intranasal or by aerosol administration, the agent preferably comprises part of an aqueous or physiologically compatible fluid suspension or solution. Thus, the polymeric or nanoparticulate thyroid hormones or thyroid hormone analogs are in a carrier or vehicle is physiologically acceptable so that in addition to delivery of the desired agent to the patient, it does not otherwise adversely affect the patient's electrolyte and/or volume balance. The fluid medium for the agent thus can comprise normal physiologic saline (e.g., 9.85% aqueous NaCl, 0.15M, pH 7-7.4).

Formulations suitable for parenteral administration conveniently include sterile aqueous preparation of the active compound, which is preferably isotonic with the blood of the recipient. Thus, such formulations may conveniently contain distilled water, 5% dextrose in distilled water or saline. Useful formulations also include concentrated solutions or solids containing the active ingredient, which upon dilution with an appropriate solvent give a solution suitable for parental administration above.

Useful solutions for parenteral administration may be prepared by any of the methods well known in the pharmaceutical art, described, for example, in REMINGTON'S PHARMACEUTICAL SCIENCES (Gennaro, A., ed.), Mack Pub., 1990. Formulations of the therapeutic agents of the invention may include, for example, polyalkylene glycols such as polyethylene glycol, oils of vegetable origin, hydrogenated naphthalenes, and the like. Formulations for direct administration, in particular, may include glycerol and other compositions of high viscosity to help maintain the agent at the desired locus. Biocompatible, preferably bioresorbable, polymers, including, for example, hyaluronic acid, collagen, tricalcium phosphate, polybutyrate, lactide, and glycolide polymers and lactide/glycolide copolymers, may be useful excipients to control the release of the agent in vivo. Other potentially useful parenteral delivery systems for these agents include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or citric acid for vaginal administration. Suppositories for rectal administration may also be prepared by mixing the polymeric or nanoparticulate thyroid hormones or thyroid hormone analogs with a non-irritating excipient such as cocoa butter or other compositions which are solid at room temperature and liquid at body temperatures.

Formulations for rectal administration may be presented as a suppository with a conventional carrier, e.g., cocoa butter or Witepsol S55 (trademark of Dynamite Nobel Chemical, Germany), for a suppository base.

Formulations for topical administration to the skin surface may be prepared by dispersing the polymeric or nanoparticulate thyroid hormones or thyroid hormone analogs alone or in combination with other factors with a dermatologically acceptable carrier such as a lotion, cream, geal, ointment or soap. Particularly useful are carriers capable of forming a film or layer over the skin to localize application and inhibit removal. For topical administration to internal tissue surfaces, the agent may be dispersed in a liquid tissue adhesive or other substance known to enhance adsorption to a tissue surface. For example, hydroxypropyl cellulose or fibrinogen/thrombin solutions may be used to advantage. Alternatively, tissue-coating solutions, such as pectin-containing formulations may be used.

For oral administration, a compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Alternatively, the compound may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biology and Medicine, pp. 287-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres, or a composition of microspheres, implanted for slow release over a period of time ranging from days to months. (See, for example, U.S. Pat. Nos. 4,906,474, 4,925,673 and 3,625,214, and Jein, TIPS 19:155-157 (1998), the contents of which are hereby incorporated by reference.)

In one embodiment, the thyroid hormones, thyroid hormone analogs, polymeric or nanoparticulate forms, and adenosine derivatives can be formulated into a liposome or microparticle, which is suitably sized to lodge in capillary beds following intravenous administration. When the liposome or microparticle is lodged in the capillary beds surrounding ischemic tissue, the agents can be administered locally to the site at which they can be most effective. Suitable liposomes for targeting ischemic tissue are generally less than about 200 nanometers and are also typically unilamellar vesicles, as disclosed, for example, in U.S. Pat. No. 5,593,688 to Baldeschweiler, entitled "Liposomal targeting of ischemic tissue," the contents of which are hereby incorporated by reference.

Preferred microparticles or nanoparticles are those prepared from biodegradable polymers, such as polyglycolide, polylactide and copolymers thereof. Those of skill in the art can readily determine an appropriate carrier system depending on various factors, including the desired rate of drug release and the desired dosage.

In one embodiment, the formulations are administered via catheter directly to the inside of blood vessels. The administration can occur, for example, through holes in the catheter. In those embodiments wherein the active compounds have a relatively long half life (on the order of 1 day to a week or more), the formulations can be included in biodegradable polymeric hydrogels, such as those disclosed in U.S. Pat. No. 5,410,016 to Hubbell et al. These polymeric hydrogels can be delivered to the inside of a tissue lumen, and the active compounds released over time as the polymer degrades. If desirable, the polymeric hydrogels can have microparticles or liposomes which include the active compound dispersed therein, providing another mechanism for the controlled release of the active compounds.

The formulations may conveniently be presented in unit dosage form and may be prepared by any of the methods well known in the art of pharmacy. All methods include the step of bringing the active compound into association with a carrier, which constitutes one or more accessory ingredients. In general, the formulations are prepared by uniformly and intimately bringing the active compound into association with a liquid carrier or a finely divided solid carrier and then, if necessary, shaping the product into desired unit dosage form.

Any of the formulations can optionally include one or more additional components, such as various biologically active substances such as growth factors (including TGF-β, basic fibroblast growth factor (FGF2), epithelial growth factor (EGF), transforming growth factors alpha and beta (TGFα and β), nerve growth factor (NGF), platelet-derived growth factor (PDGF), and vascular endothelial growth factor/vascular permeability factor (VEGF/VPF)), antiviral, antibacterial, anti-inflammatory, immuno-suppressant, analgesic, vascularizing agent, and/or cell adhesion molecule.

In addition to the aforementioned ingredients, the formulations may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

Polymeric or nanoparticulate thyroid hormones or thyroid hormone analogs, alone or in combination with nerve growth factors or other neurogenesis factors, inducers, or agonists of polymeric or nanoparticulate thyroid hormones or thyroid hormone analogs alone or in combination with nerve growth factors or other neurogenesis factors, receptors of the present invention may be administered by any route which is compatible with the particular polymeric or nanoparticulate thyroid hormone analog alone or in combination with nerve growth factors or other neurogenesis factors, inducer, or agonist employed. (See WO2008/140507, incorporated herein by reference).

Where the polymeric or nanoparticulate thyroid hormones or thyroid hormone analogs alone or in combination with nerve growth factors or other neurogenesis factors is intended for use as a therapeutic for disorders of the CNS, an additional problem must be addressed: overcoming the blood-brain barrier, the brain capillary wall structure that effectively screens out all but selected categories of substances present in the blood, preventing their passage into the brain. The blood-brain barrier can be bypassed effectively by direct infusion of the polymeric or nanoparticulate thyroid hormones or thyroid hormone analogs into the brain, or by intranasal administration or inhalation of formulations suitable for uptake and retrograde transport by olfactory neurons. Alternatively, the polymeric or nanoparticulate thyroid hormones or thyroid hormone analogs can be modified to enhance its transport across the blood-brain barrier. (See WO2008/140507).

Any of the compounds provided herein may also be associated with molecules capable of targeting the polymeric or nanoparticulate thyroid hormones or thyroid hormone analogs to a desired tissue. For example, an antibody, antibody fragment, or other binding protein that interacts specifically with a surface molecule on cells of the desired tissue, may be used. Useful targeting molecules may be designed, for example, using the single chain binding site technology disclosed in U.S. Pat. No. 5,091,513. Targeting molecules can be covalently or non-covalently associated with the polymeric or nanoparticulate thyroid hormones or thyroid hormone analogs.

Each nanoparticle contain between 1 and 100 thyroid hormone or thyroid hormone analog molecules immobilized on the nanoparticle surface via chemical bonding. The nanoparticle can also encapsulate one or more additional chemotherapeutic agents, or other known pro-angiogenesis agents, anti-angiogenesis agents, or other biologically active or therapeutic molecules. Thus, the nanoparticle contains inside the one or more chemotherapeutic agents, pro- or anti-angiogenesis agents, or other biologically active or therapeutic molecules, and the thyroid hormones or thyroid hormone analogs are immobilized on the surface of the nanoparticles via stable chemical bonding. The surface of the nanoparticles can also contain a site-directing moiety such $\alpha v \beta 3$ ligand bonded to the surface via stable chemical bonding.

The effective dose can be administered in a single dose or in a plurality (two or more) of installment doses, as desired or considered appropriate under the specific circumstances. A bolus injection or diffusible infusion formulation can be used. If desired to facilitate repeated or frequent infusions, implantation of a semi-permanent stent (e.g., intravenous, intraperitoneal, intracisternal or intracapsular) may be advisable.

The polymeric or nanoparticulate thyroid hormones or thyroid hormone analogs may be administered alone or in combination with other molecules known to be beneficial in the treatment of any of the conditions described herein. For example, various well-known growth factors, hormones, enzymes, therapeutic compositions, antibiotics, and/or other bioactive agents can also be administered with the polymeric or nanoparticulate thyroid hormones or thyroid hormone analogs. Thus, various known growth factors such as NGF, EGF, PDGF, IGF, FGF, VEGF, TGF-$\alpha$, and TGF-$\beta$, as well as enzymes, enzyme inhibitors, antioxidants, anti-inflammatory agents, free radical scavenging agents, antibiotics and/or chemoattractant/chemotactic factors, can be included in the polymeric or nanoparticulate thyroid hormones or thyroid hormone analogs.

The following examples are intended to further illustrate certain embodiments of the invention and are not intended to limit the scope of the invention.

Examples 1-7

The following materials and methods were used for Examples 1-7. All reagents were chemical grade and purchased from Sigma Chemical Co. (St. Louis, Mo.) or through VWR Scientific (Bridgeport, N.J.). Cortisone acetate, bovine serum albumin (BSA) and gelatin solution (2% type B from bovine skin) were purchased from Sigma Chemical Co. Fertilized chicken eggs were purchased from Charles River Laboratories, SPAFAS Avian Products & Services (North Franklin, Conn.). T4, 3,5,3'-triiodo-L-thyronine (T3), tetraiodothyroacetic acid (Tetrac), T4-agarose, 6-N-propyl-2-thiouracil (PTU), RGD-containing peptides, and RGE-containing peptides were obtained from Sigma; PD 98059 from Calbiochem; and CGP41251 was a gift from Novartis Pharma (Basel, Switzerland). Polyclonal anti-FGF2 and monoclonal anti-$\beta$-actin were obtained from Santa Cruz Biotechnology and human recombinant FGF2 and VEGF from Invitrogen. Polyclonal antibody to phosphorylated ERK1/2 was from New England Biolabs and goat anti-rabbit IgG from DAKO. Monoclonal antibodies to $\alpha v \beta 3$ (SC73 12) and $\alpha$-tubulin (E9) were purchased from Santa Cruz Biotechnology (Santa Cruz, Calif.). Normal mouse IgG and HRP-conjugated goat anti-rabbit Ig were purchased from Dako Cytomation (Carpinteria, Calif.). Monoclonal antibodies to $\alpha v \beta 3$ (LM609) and $\alpha v \beta 5$ (P1F6), as well as purified $\alpha v \beta 3$, were purchased from Chemicon (Temecula, Calif.). L-[$^{125}$I]-T4 (specific activity, 1250 µCi/µg) was obtained from Perkin Elmer Life Sciences (Boston, Mass.).

Chorioallantoic Membrane (CAM) Model of Angiogenesis:

In vivo neovascularization was examined by methods described previously. 9-12 Ten-day-old chick embryos were purchased from SPAFAS (Preston, Conn.) and incubated at 37° C. with 55% relative humidity. A hypodermic needle was used to make a small hole in the shell concealing the air sac, and a second hole was made on the broad side of the egg, directly over an avascular portion of the embryonic membrane that was identified by candling. A false air sac was created beneath the second hole by the application of negative pressure at the first hole, causing the CAM to separate from the shell. A window approximately 1.0 cm$^2$ was cut in the shell over the dropped CAM with a small-crafts grinding wheel (Dremel, division of Emerson Electric Co.), allowing direct access to the underlying CAM. FGF2 (1 µg/mL) was used as a standard proangiogenic agent to induce new blood vessel branches on the CAM of 10-day-old embryos. Sterile disks of No. 1 filter paper (Whatman International) were pretreated with 3 mg/mL cortisone acetate and 1 mmol/L PTU and air dried under sterile conditions. Thyroid hormone, hormone analogs, FGF2 or control solvents, and inhibitors were then applied to the disks and the disks allowed to dry. The disks were then suspended in PBS and placed on growing CAMs. Filters treated with T4 or FGF2 were placed on the first day of the 3-day incubation, with antibody to FGF2 added 30 minutes later to selected samples as indicated. At 24 hours, the MAPK cascade inhibitor PD 98059 was also added to CAMs topically by means of the filter disks.

Microscopic Analysis of CAM Sections:

After incubation at 37° C. with 55% relative humidity for 3 days, the CAM tissue directly beneath each filter disk was resected from control and treated CAM samples. Tissues were washed 3× with PBS, placed in 35-mm Petri dishes (Nalge Nunc), and examined under an SV6 stereomicroscope (Zeiss) at ×50 magnification. Digital images of CAM sections exposed to filters were collected using a 3-charge-coupled device color video camera system (Toshiba) and analyzed with Image-Pro software (Media Cybernetics). The number of vessel branch points contained in a circular region equal to the area of each filter disk were counted. One image was counted in each CAM preparation, and findings from 8 to 10 CAM preparations were analyzed for each treatment condition (thyroid hormone or analogs, FGF2, FGF2 antibody, PD 98059). In addition, each experiment was performed 3 times. The resulting angiogenesis index is the mean±SEM of new branch points.

FGF2 Assays.

ECV304 endothelial cells were cultured in M199 medium supplemented with 10% fetal bovine serum. ECV304 cells ($10^6$ cells) were plated on 0.2% gel-coated 24-well plates in complete medium overnight, and the cells were then washed with serum-free medium and treated with T4 or T3 as indicated. After 72 hours, the supernatants were harvested and assays for FGF performed without dilution using a commercial ELISA system (R&D Systems) (See Davis et al., Circ Res 94:1500-1506 (2004)).

MARK Activation:

ECV304 endothelial cells were cultured in M199 medium with 0.25% hormone-depleted serum 13 for 2 days. Cells were then treated with T4 ($10^{-7}$ mol/L) for 15 minutes to 6 hours. In additional experiments, cells were treated with T4 or FGF2 or with T4 in the presence of PD 98059 or CGP41251. Nuclear fractions were pre-pared from all samples by the method reported previously (see Li et al., Carcinogenesis 29:62-69 (2008)), the proteins separated by polyacrylamide gel electrophoresis, and transferred to membranes for immunoblotting with antibody to phosphorylated ERK 1/2. The appearance of nuclear phosphorylated ERK1/2 signifies activation of these MAPK isoforms by T4.

Reverse Transcription-Polymerase Chain Reaction:

Confluent ECV304 cells in 10-cm plates were treated with T4 ($10^{-7}$ mol/L) for 6 to 48 hours and total RNA extracted using guanidinium isothiocyanate (Biotecx Laboratories). RNA (1 µg) was subjected to reverse transcription-polymerase chain reaction (RT-PCR) using the Access RT-PCR system (Promega). Total RNA was reverse transcribed into cDNA at 48° C. for 45 minutes, then denatured at 94° C. for 2 minutes. Second-strand synthesis and PCR amplification were performed for 40 cycles with denaturation at 94° C. for 30 s, annealing at 60° C. for 60 s, and extension at 68° C. for 120 s, with final ex-tension for 7 minutes at 68° C. after completion of all cycles. PCR primers for FGF2 were as follows: FGF2 sense strand 5'-TGGTATGTGGCACT-GAAACG-3' (SEQ ID NO:1), antisense strand 5' CTCAAT-GACCTGGCGAAGAC-3' (SEQ ID NO:2); the length of the PCR product was 734 bp. Primers for GAPDH included the sense strand 5'-AAGGTCATCCCTGAGCTGAACG-3' (SEQ ID NO:3), and antisense strand 5'-GGGTGTCGCTGT-TGAAGTCAGA-3' (SEQ ID NO:4); the length of the PCR product was 218 bp. The products of RT-PCR were separated by electrophoresis on 1.5% agarose gels and visualized with ethidium bromide. The target bands of the gel were quantified using LabImage software (Kapelan), and the value for [FGF2/GAPDH]×10 calculated for each time point.

Statistical Analysis:

Statistical analysis was performed by 1-way analysis of variance (ANOVA) comparing experimental with respective control group and statistical significance was calculated based on $P<0.05$.

In Vivo Angiogenesis in Matrigel $FGF_2$ or Cancer Cell Lines Implanted in Mice:

In Vivo Murine Angiogenesis Model:

The murine matrigel model will be conducted according to previously described methods (see Hashimoto et al., J Biol Chem 277:36288-95 (2002)) and as implemented in other laboratories (see Mousa et al., Angiogenesis 11:183-90 (2008)). Briefly, growth factor free matrigel (Becton Dickinson, Bedford Mass.) will be thawed overnight at 4° C. and placed on ice. Aliquots of matrigel will be placed into cold polypropylene tubes and FGF2, thyroid hormone analogs or cancer cells ($1\times10^6$ cells) will be added to the matrigel. Matrigel with saline, FGF2, thyroid hormone analogs or cancer cells will be subcutaneously injected into the ventral midline of the mice. At day 14, the mice will be sacrificed and the solidified gels will be resected and analyzed for presence of new vessels. Compounds will be injected subcutaneously at different doses. Control and experimental gel implants will be placed in a micro centrifuge tube containing 0.5 ml of cell lysis solution (Sigma, St. Louis, Mo.) and crushed with a pestle. Subsequently, the tubes will be allowed to incubate overnight at 4° C. and centrifuged at 1,500×g for 15 minutes on the following day. A 200 µl aliquot of cell lysate will be added to 1.3 ml of Drabkin's reagent solution (Sigma, St. Louis, Mo.) for each sample. The solution will be analyzed on a spectrophotometer at a 540 nm. The absorption of light is proportional to the amount of hemoglobin contained in the sample.

Tumor Growth and Metastasis—Chick Chorioallantoic Membrane (CAM)

Figure 9:
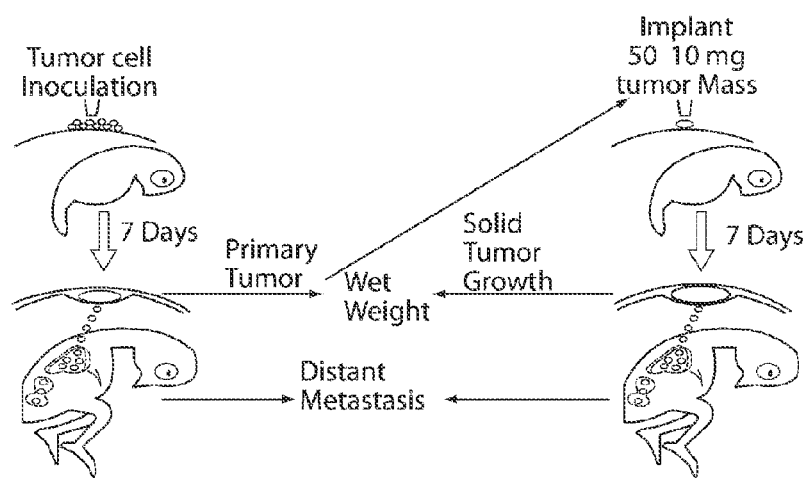
FIG. 9 shows the 7 Day Chick Embryo Tumor Growth Model. Illustration of the Chick Chorioallantoic Membrane (CAM) model of tumor implant.
Figure 11:
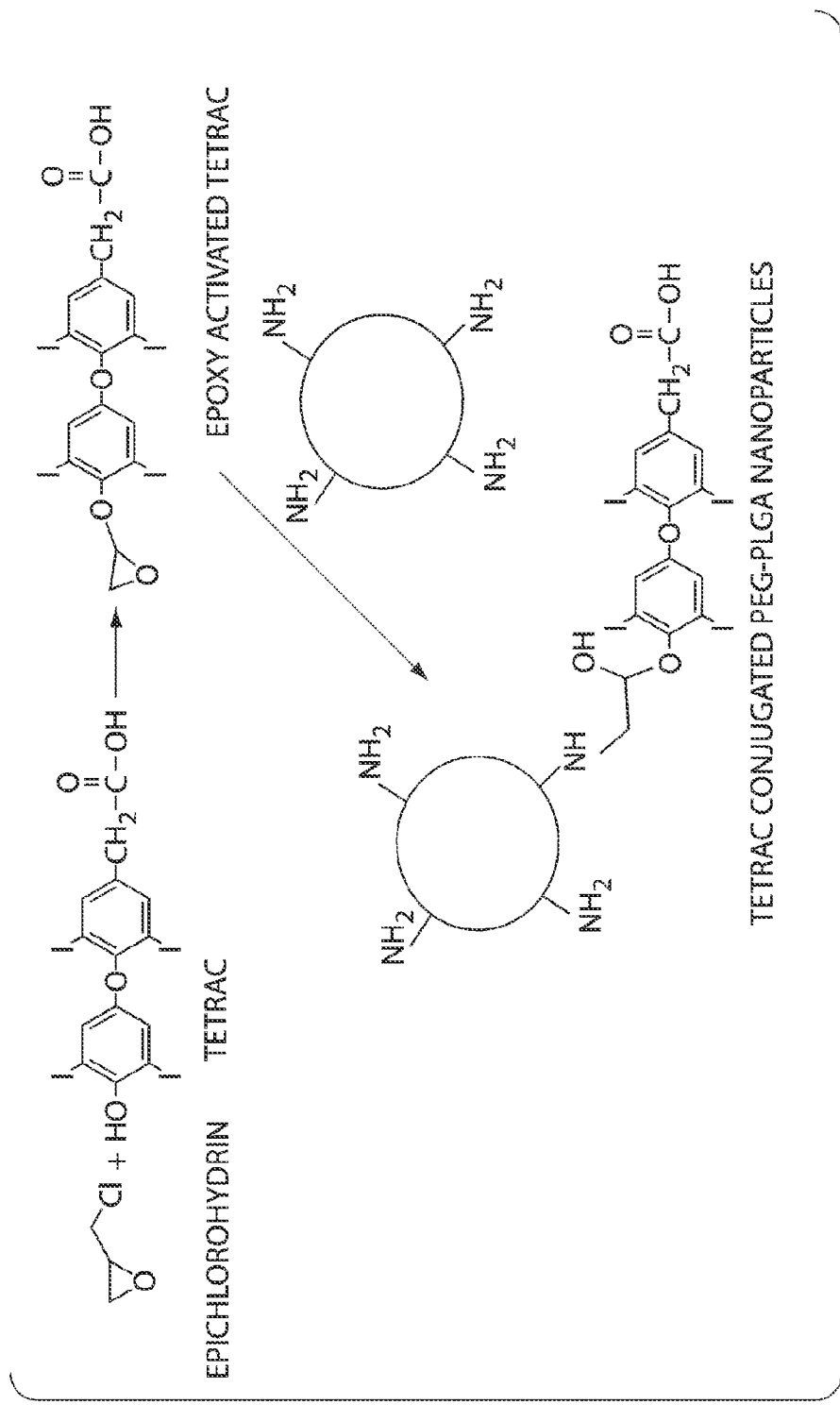
FIG. 11 shows the conjugation of Tetrac to PEG-PLGA nanoparticles using epichlorohydrin as a linker.

Model of Tumor Implant:

The protocol is as previously described. (See Kim et al., J Biol Chem 277(9):6799-805 (Epub December 2001)). Briefly, $1\times10^7$ tumor cells will be placed on the surface of each CAM (7 day old embryo) and incubated for one week. The resulting tumors will be excised and cut into 50 mg fragments. These fragments will be placed on additional 10 CAMs per group and treated topically the following day with 25 µl of compounds dissolved in PBS. Seven days later, tumors will then be excised from the egg and tumor weights will be determined for each CAM. FIG. 9 is a diagrammatic sketch showing the steps involved in the in vivo tumor growth model in the CAM.

The effects of Tetrac, Triac, and thyroid hormone antagonists on tumor growth rate, tumor angiogenesis, and tumor metastasis of cancer cell lines can be determined.

Tumor Growth and Metastasis—Tumor Xenograft Model in Mice:

The model is as described in earlier publications by Kerr et al., Anticancer Res 19:959-68 (1999); Sunwoo et al., Clin Cancer Res 7:1419-28 (2001); and Ali et al., Mol Cancer Ther 7:1708-19 (2008), each of which is incorporated herein by reference in its entirety. The anti-cancer efficacy for Tetrac, Triac, and other thyroid hormone antagonists at different doses and against different tumor types can be determined and compared.

Effect of Thyroid Hormone Analogs on Angiogenesis:

The CAM assay has been used to validate angiogenic activity of a variety of growth factors and other promoters or inhibitors of angiogenesis. $T_4$ in physiological concentrations was shown to be pro-angiogenic, with comparable activity to that of FGF2. The presence of PTU did not reduce the effect of $T_4$, indicating that de-iodination of $T_4$ to generate $T_3$ was not a prerequisite in this model. Because the appearance of new blood vessel growth in this model requires several days, it was assumed that the effect of thyroid hormone was totally dependent upon the interaction of the nuclear receptor for thyroid hormone (TR). Actions of iodothyronines that require intranuclear complexing of TR with its natural ligand, $T_3$, are by definition, genomic, and culminate in gene expression. On the other hand, the preferential response of this model system to $T_4$ rather than $T_3$, the natural ligand of TR, raised the possibility that angiogenesis might be initiated non-genomically at the plasma membrane by $T_4$ and culminate in effects that require gene transcription. Non-genomic actions of $T_4$ have been widely described, are usually initiated at the plasma membrane and may be mediated by signal transduction pathways. They do not require intranuclear ligand binding of iodothyronine and TR, but may interface with or modulate gene transcription. Non-genomic actions of steroids have also been well-described and are known to interface with genomic actions of steroids or of other compounds. Experiments carried out with $T_4$ and Tetrac or with agarose-$T_4$ indicated that the pro-angiogenic effect of $T_4$ indeed very likely was initiated at the plasma membrane. Tetrac blocks membrane-initiated effects of $T_4$, but does not, itself, activate signal transduction. Thus, it is a probe for non-genomic actions of thyroid hormone. Agarose-$T_4$ is thought not to gain entry to the cell interior and has been used by us and others to examine models for possible cell surface-initiated actions of the hormone.

These results suggest that another consequence of activation of MAPK by thyroid hormone is new blood vessel growth. The latter is initiated nongenomically, but of course requires a consequent complex gene transcription program.

The ambient concentrations of thyroid hormone are relatively stable. The CAM model, at the time tested, was thyroprival and thus may be regarded as a system, which does not reproduce the intact organism. Thus, circulating levels of $T_4$ serve, with a variety of other regulators, to modulate the sensitivity of vessels to endogenous angiogenic factors, such as VEGF and FGF2.

Example 1

Effect of Thyroid Hormone on Angiogenesis

Figure 1:
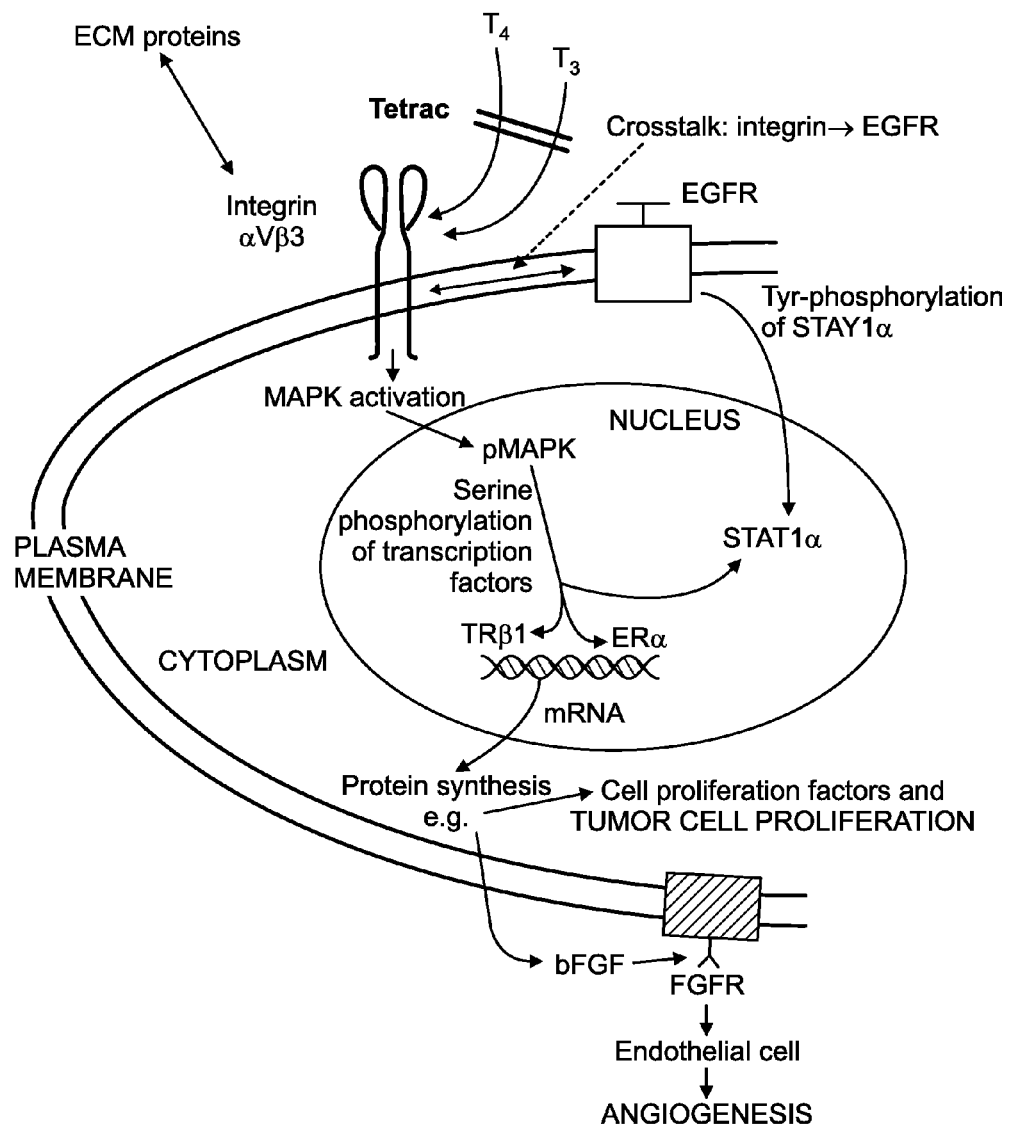
FIG. 1 is a schematic showing the ability of Tetrac to inhibit the action of T4 and T3 on integrin αvβ3.
Figures 2A, 2B:
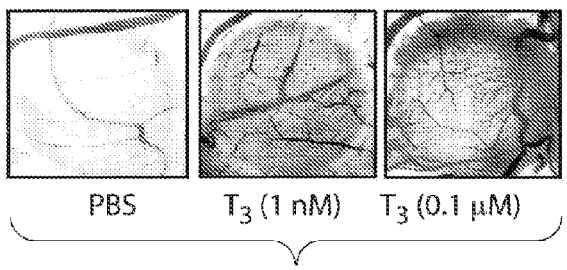
In FIG. 2A, control samples were exposed to PBS and additional samples to 1 nM T3 or 0.1 μmol/L T4 for 3 days. Both hormones caused increased blood vessel branching in these representative images from 3 experiments.
FIG. 2B shows the tabulation of mean±SEM of new branches formed from existing blood vessels during the experimental period drawn from 3 experiments, each of which included 9 CAM assays. At the concentrations shown, T3 and T4 caused similar effects (1.9-fold and 2.5-fold increases, respectively, in branch formation). **P<0.001 by 1-way ANOVA, comparing hormone-treated with PBS-treated CAM samples.

As seen in FIG. 2A and summarized in FIG. 2B, both T4 and T3 enhanced angiogenesis in the CAM assay. T4, at a physiologic total concentration in the medium of 0.1 μmol/L, increased blood vessel branch formation by 2.5-fold ($P<0.001$). T3 (1 nmol/L) also stimulated angiogenesis 2-fold.

Example 2

Effects of T4-Agarose and Tetrac

It has been shown previously that T4-agarose stimulates cellular signal transduction pathways initiated at the plasma membrane in the same manner as T4 and that the actions of T4 and T4-agarose are blocked by a deaminated iodothyronine analog, Tetrac, which is known to inhibit binding of T4 to plasma membranes. In the CAM model, the addition of Tetrac (0.1 μmol/L) inhibited the action of T4 (FIG. 3A), but Tetrac alone had no effect on angiogenesis (FIG. 3C). The action of T4-agarose, added at a hormone concentration of 0.1 μmol/L, was comparable to that of T4 in the CAM model (FIG. 3B), and the effect of T4-agarose was also inhibited by the action of Tetrac (FIG. 3B; summarized in 3C).

Example 3

Enhancement of Proangiogenic Activity of FGF2 by a Sub-Maximal Concentration of T4

Figures 4A, 4B:
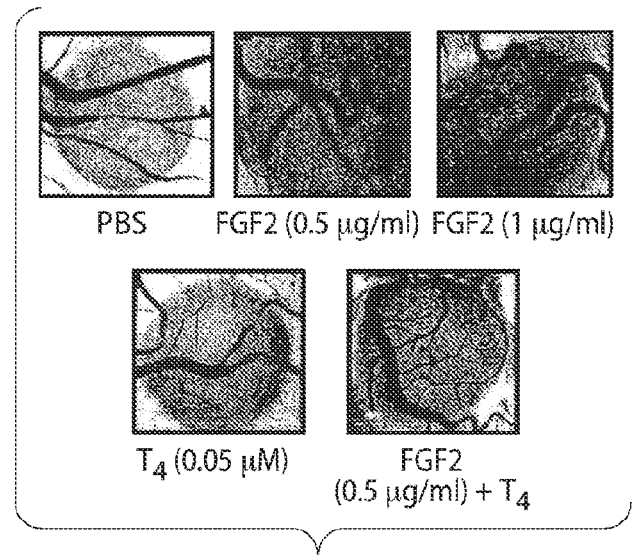
As shown in FIG. 4A, tandem effects of T4 (0.05 μmol/L) and FGF2 (0.5 μg/mL) in submaximal concentrations are additive in the CAM assay and equal the level of angiogenesis seen with FGF2 (1 μg/mL in the absence of T4).
FIG. 4B shows a summary of results from 3 experiments that examined actions of FGF2 and T4 in the CAM assay (means±SEM) as in A. *P<0.05; **P<0.001, comparing results of treated samples with those of PBS-treated control samples in 3 experiments.
Figures 5A, 5B:
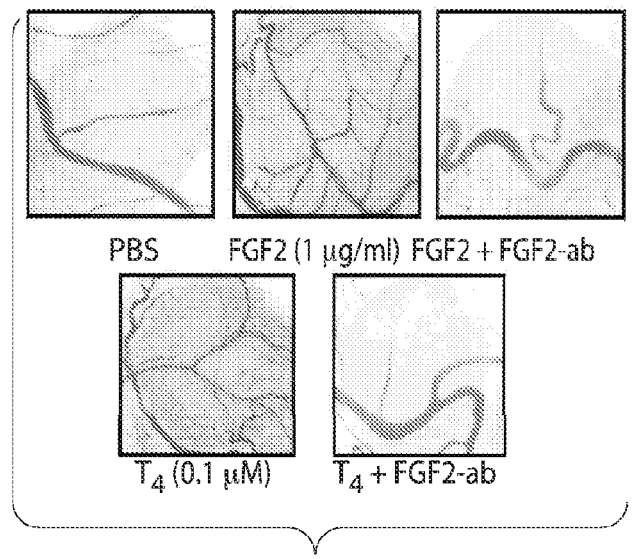
As seen in FIG. 5A, FGF2 caused a 2-fold increase in angiogenesis in the CAM model in 3 experiments, an effect inhibited by antibody (ab) to FGF2 (8 μg). T4 also stimulated angiogenesis 1.5-fold, and this effect was also blocked by FGF2 antibody, indicating that the action of thyroid hormone in the CAM model is mediated by an autocrine/paracrine effect of FGF2 because T4 and T3 cause FGF2 release from cells in the CAM model. As shown previously, a nonspecific IgG antibody has no effect on angiogenesis in the CAM assay.
FIG. 5B shows a summary of results from 3 CAM experiments that studied the action of FGF2-ab in the presence of FGF2 or T4. *P<0.01; **P<0.001, indicating significant effects in 3 experiments studying the effects of thyroid hormone and FGF2 on angiogenesis and loss of these effects in the presence of antibody to FGF2.

Angiogenesis is a complex process that usually requires the participation of polypeptide growth factors. The CAM assay requires at least 48 hours for vessel growth to be manifest; thus, the apparent plasma membrane effects of thyroid hormone in this model are likely to result in a complex transcriptional response to the hormone. Therefore, whether FGF2 was involved in the hormone response and whether the hormone might potentiate the effect of sub-physiologic levels of this growth factor was examined. T4 (0.05 μmol/L) and FGF2 (0.5 μg/mL) individually stimulated angiogenesis to a modest degree (FIGS. 4A-B). The angiogenic effect of this sub-maximal concentration of FGF2 was enhanced by a sub-physiologic concentration of T4 to the level caused by 1.0 μg FGF2 alone. Thus, the effects of sub-maximal hormone and growth factor concentrations appear to be additive. To define more precisely the role of FGF2 in thyroid hormone stimulation of angiogenesis, a polyclonal antibody to FGF2 was added to the filters treated with either FGF2 or T4, and angiogenesis was measured after 72 hours. FIGS. 5A-5B demonstrate that the FGF2 antibody inhibited angiogenesis stimulated either by FGF2 or by T4 in the absence of exogenous FGF2, suggesting that the T4 effect in the CAM assay was mediated by increased FGF2 expression. Control IgG antibody has no stimulatory or inhibitory effect in the CAM assay.

Example 4

Stimulation of FGF2 Release from Endothelial Cells by Thyroid Hormone

Levels of FGF2 were measured in the media of ECV304 endothelial cells treated with either T4 (0.1 μmol/L) or T3 (0.01 μmol/L) for 3 days. As shown below, T3 stimulated FGF2 concentration in the medium 3.6-fold, whereas T4 caused a 1.4-fold increase. These findings indicate that thyroid hormone may enhance the angiogenic effect of FGF2, at least in part, by increasing the concentration of growth factor available to endothelial cells.

Effect of T4 and T3 on Release of FGF2 from ECV304 Endothelial Cells

| Cell Treatment | FGF2 (pg/mL/$10^6$ cells) |
| --- | --- |
| Control | 27.7 ± 3.1 |
| T3 (0.01 μmol/L) | 98.8 ± 0.5* |
| T3 + PD 98059 (2 μmol/L) | 28.4 ± 3.2 |
| T3 + PD 98059 (20 μmol/L) | 21.7 ± 3.5 |
| T4 (0.1 μmol/L) | 39.2 ± 2.8† |
| T4 + PD 98059 (2 μmol/L) | 26.5 ± 4.5 |
| T4 + PD 98059 (20 μmol/L) | 23.2 ± 4.8 |

*$P < 0.001$, comparing T3-treated samples with control samples by ANOVA;
†$P < 0.05$, comparing T4-treated samples with control samples by ANOVA.

Example 5

Role of the ERK1/2 Signal Transduction Pathway in Stimulation of Angiogenesis by Thyroid Hormone and FGF2

A pathway by which T4 exerts a nongenomic effect on cells is the MAPK signal transduction cascade, specifically that of ERK1/2 activation. It has been shown that T4 enhances ERK1/2 activation by epidermal growth factor. The role of the MAPK pathway in stimulation by thyroid hormone of FGF2 expression was examined by the use of PD 98059 (2 to 20 μmol/L), an inhibitor of ERK1/2 activation by the tyrosine-threonine kinases MAPK kinase-1 (MEK1) and MEK2. The data in FIG. 6C demonstrate that PD 98059 effectively blocked the increase in FGF2 release from ECV304 endothelial cells treated with either T4 or T3. Parallel studies of ERK1/2 inhibition were performed in CAM assays, and representative results are shown in FIG. 6. A combination of T3 and T4, each in physiologic concentrations, caused a 2.4-fold increase in blood vessel branching, an effect that was completely blocked by 3 μmol/L PD 98059 (FIG. 6A). FGF2 stimulation of branch formation (2.2-fold) was also effectively blocked by this inhibitor of ERK1/2 activation (FIG. 6B). Thus, the proangiogenic effect of thyroid hormone begins at the plasma membrane and involves activation of the ERK1/2 pathway to promote FGF2 release from endothelial cells. ERK1/2 activation is again required to transduce the FGF2 signal and cause new blood vessel formation.

Example 6

Action of Thyroid Hormone and FGF2 on MAPK Activation

Figure 7A:
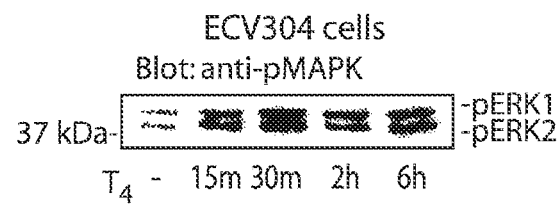
As seen in FIG. 7A, T4 causes increased phosphorylation and nuclear translocation of ERK1/2 in ECV304 cells. The effect is maximal in 30 minutes, although the effect remains for ≥6 hours.
Figure 7B:
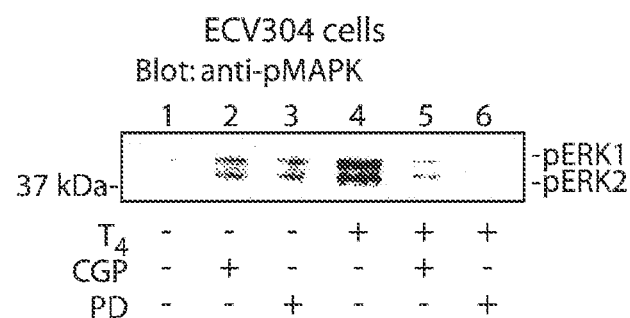
In FIG. 7B, ECV304 cells were treated with the ERK1/2 activation inhibitor PD 98059 (PD; 30 μmol/L) or the PKC inhibitor CGP41251 (CGP; 100 nmol/L) for 30 minutes, after which $10^{-7}$ M T4 was added for 15 minutes to cell samples as shown. Nuclei were harvested, and this representative experiment shows increased phosphorylation (activation) of ERK1/2 by T4 (lane 4), which is blocked by both inhibitors (lanes 5 and 6), suggesting that PKC activity is a requisite for MAPK activation by T4 in endothelial cells.
Figure 7C:
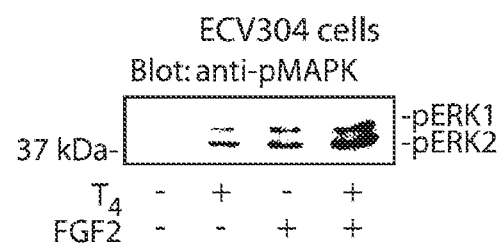
In FIG. 7C, ECV304 cells were treated with either T4 ($10^{-7}$ mol/L), FGF2 (10 ng/mL), or both agents for 15 minutes. The Figure shows pERK1/2 accumulation in nuclei with either hormone or growth factor treatment and enhanced nuclear pERK1/2 accumulation with both agents together.

Stimulation of phosphorylation and nuclear translocation of ERK1/2 MAPK proteins was studied in ECV304 cells treated with T4 ($10^{-7}$ mol/L) for 15 minutes to 6 hours. The appearance of phosphorylated ERK1/2 in cell nuclei occurred within 15 minutes of T4 treatment, reached a maximal level at 30 minutes, and was still apparent at 6 hours (FIG. 7A). This effect of the hormone was inhibited by PD 98059 (FIG. 7B), a result to be expected because this compound blocks the phosphorylation of ERK1/2 by MAPK kinase. The traditional protein kinase C (PKC)-α, PKC-β, and PKC-γ inhibitor CGP41251 also blocked the effect of the hormone on MAPK activation in these cells, as seen with T4 in other cell lines. Thyroid hormone enhances the action of several cytokines and growth factors, such as interferon-γ13 and epidermal growth factor. In ECV304 cells, T4 enhanced the MAPK activation caused by FGF2 in a 15-minute co incubation (FIG. 7C). Applying the observations made in ECV304 cells to the CAM model, it appears that the complex mechanism by which the hormone induces angiogenesis includes endothelial cell release of FGF2 and enhancement of the autocrine effect of released FGF2 on angiogenesis.

Example 7

RT-PCR in ECV304 Cells Treated with Thyroid Hormone

Figure 8:
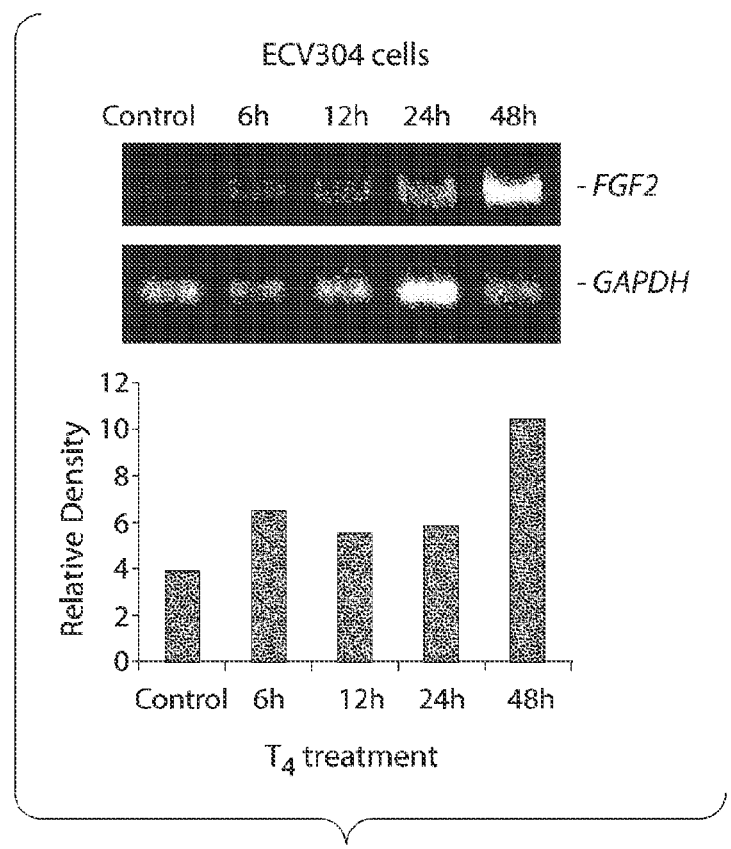
FIG. 8 shows that T4 increases accumulation of FGF2 cDNA in ECV304 endothelial cells. Cells were treated for 6 to 48 hours with T4 ($10^{-7}$ mol/L) and FGF2 and GAPDH cDNAs isolated from each cell aliquot. The levels of FGF2 cDNA, shown in the top blot, were corrected for variations in GAPDH cDNA content, shown in the bottom blot, and the corrected levels of FGF2 are illustrated below in the graph (mean±SE of mean; n=2 experiments). There was increased abundance of FGF2 transcript in RNA extracted from cells treated with T4 at all time points. *P<0.05; **P<0.01, indicating comparison by ANOVA of values at each time point to control value.

The final question addressed in studies of the mechanism of the proangiogenic action of T4 was whether the hormone may induce FGF2 gene expression. Endothelial cells were treated with T4 ($10^{-7}$ mol/L) for 6 to 48 hours, and RT-PCR-based estimates of FGF2 and GAPDH RNA (inferred from cDNA measurements; FIG. 8) were performed. An increase in abundance of FGF2 cDNA, corrected for GAPDH content, was apparent by 6 hours of hormone treatment and was further enhanced by 48 hours.

Example 8

Design of Nanoparticles Formulation for Ocular Use

Different kinds of nanoparticle formulations based on different polymers can be prepared, which allows one to vary physicochemical parameters such as surface charge, size and mucoadesiveness. Tetrac can be conjugated in all of these nanoparticles formulations, and depending on the polymers employed, will allow for different ocular kinetics. Broadly PLGA, chitosan and custom made co-polymeric nanoparticles with different ratio of N-isopropylacrylamide, N-3-aminopropylmethacrylamide hydrochloride, and acrylic acid can be utilized. (See WO2008/140507)

Figure 19:
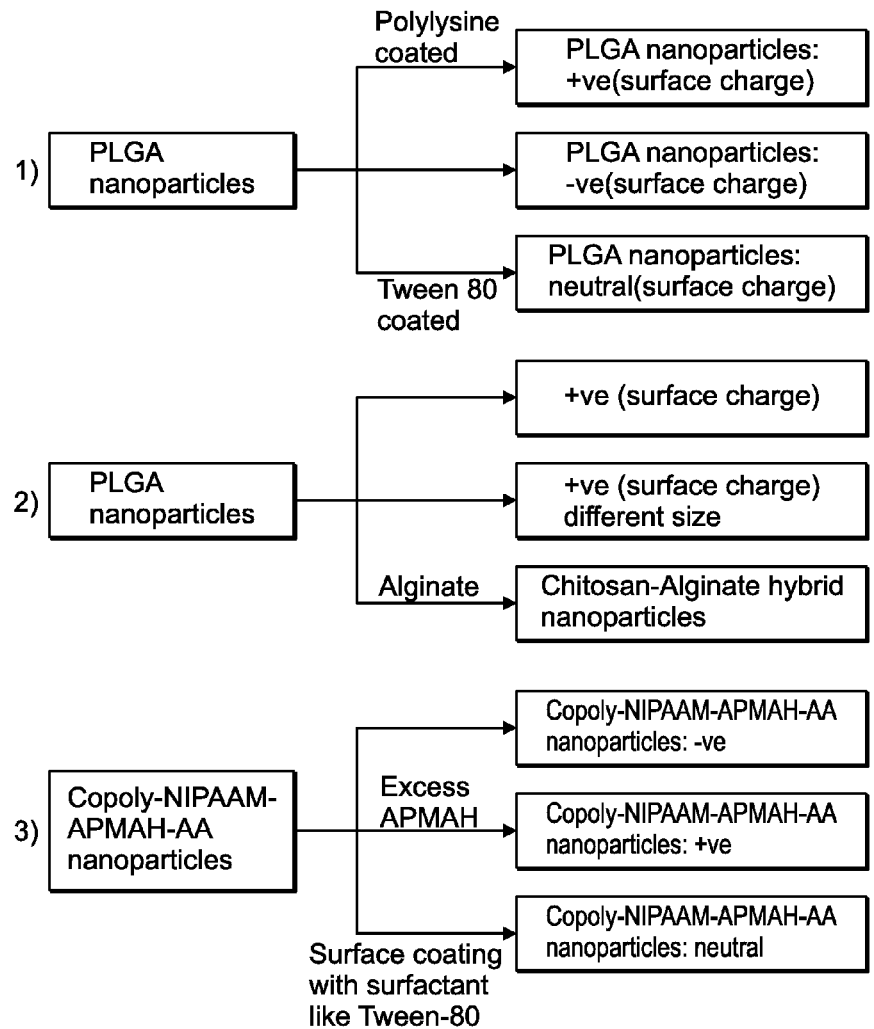
FIG. 19 is a schematic representation showing the synthesis of different kinds of Tetrac nanoparticles and their surface modification.

A schematic representation showing synthesis of different kinds of Tetrac nanoparticles and their surface modification(s) is shown in FIG. 19.

Example 9

Novel $T_4$/Polymeric Conjugates and $T_4$/Nanoparticle Conjugates

The thyroid gland is the source of two fundamentally different types of hormones. The iodothyronine hormones include thyroxine ($T_4$) and 3,5,3'-triiodothyronine ($T_3$). They are essential for normal growth and development and play an important role in energy metabolism. The thyroid hormones are aromatic amino acids ultimately derived from tyrosine. They are chemically and biosynthetically similar to L-DOPA and 5-hydroxytryptophan, the biosynthetic precursors of the neurotransmitters dopamine and serotonin (5-hydroxytryptamine), respectively. The chemical structures of $T_4$ and $T_3$ and their biosynthetic analogs are shown below.

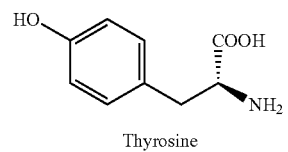

Thyrosine

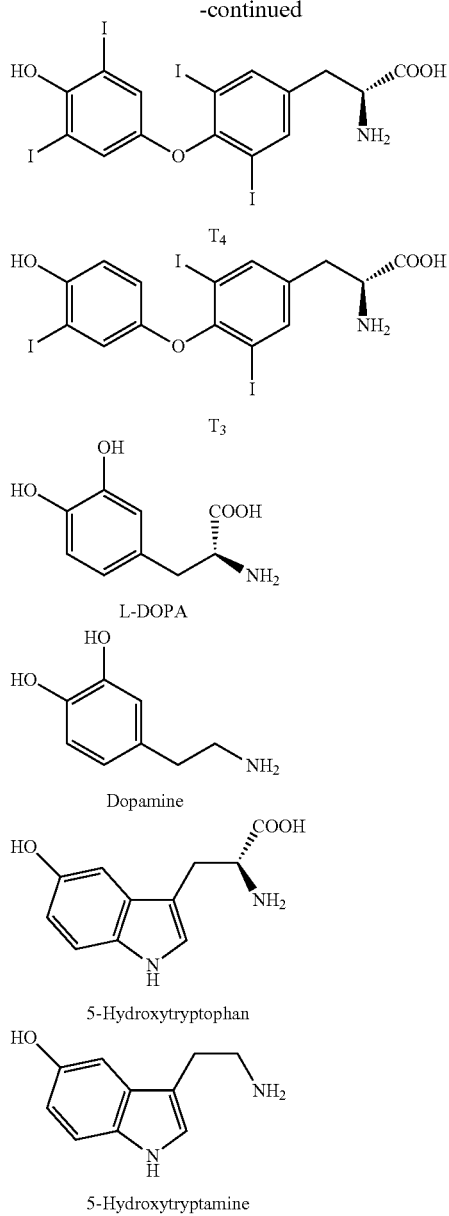

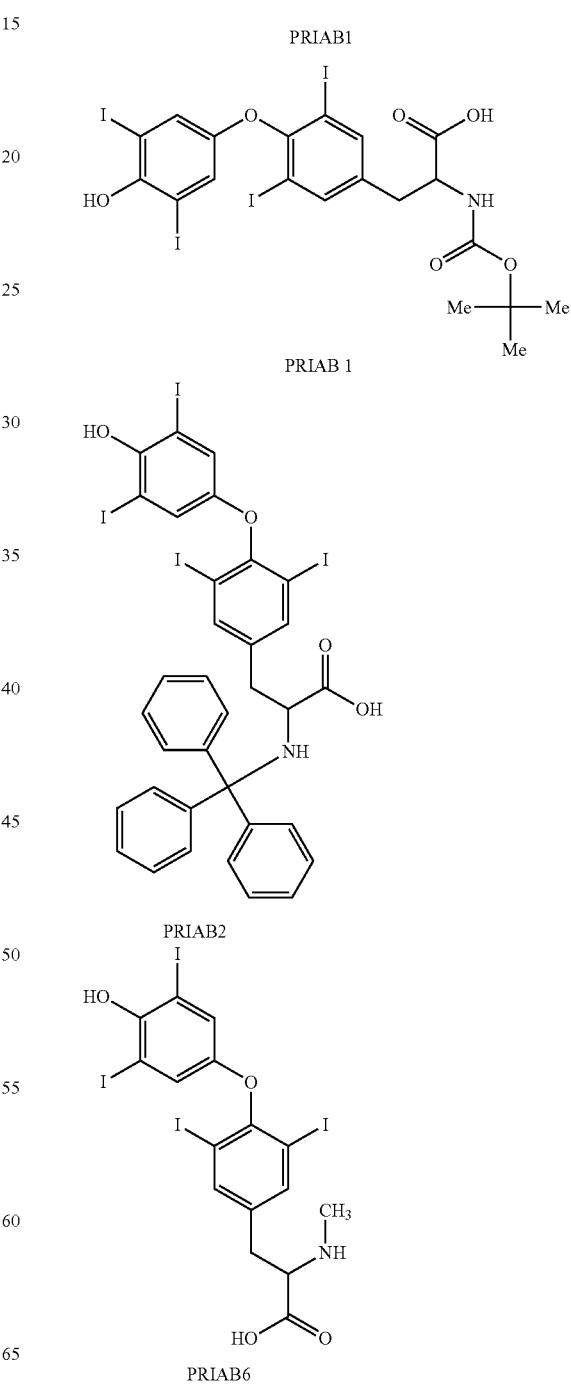

phenol and the zwiterionic form of the commercial $T_4$. This was done using an equimolar amount of products, a mineral base ($Na_2CO_3$) or an organic base (TEA) in polar solvent (DMA or DMF). Compounds (PRIAB1, PRIAB4 and PRIAB5) were synthesized under the reaction conditions shown in WO2008/140507.

The general procedure to get the analytically pure samples for testing is also set forth in WO2008/140507 using 2-[(tert-butoxycarbonyl)amino]-3-[4-(4-hydroxy-3,5-diiodophenoxy)-3,5-diiodophenyl]propanoic acid (PRIAB1) as an example. PRIAB2, PRIAB6 and PRIAB12 (each shown below) can also be synthesized, deprotected and tested for purity, in a similar manner.

The conjugation of either $T_3$ or $T_4$ with a polymer or immobilization of $T_3$ or $T_4$ with nanoparticles will result in particles with a diameter that does not allow the conjugate to cross the nucleus membrane. Thus, only the cell surface activity of $T_3$ or $T_4$ may be obtained without any undesirable genomic effects.

$T_3$ and $T_4$ both bear three functional groups which may react to form a polymer conjugate: one carboxylic acid group, one amine group, and one hydroxyl group. Those skilled in the art will recognize that, for each of the embodiments described in this Example, $T_3$ may be used instead of $T_4$.

Protection of the Amino Group of $T_4$

Protection of the amino group of L-$T_4$ can be done using acetic anhydride ($Ac_2O$), ditertbutyldicarbonate ($BOC_2O$) and butyric anhydride ($Bu_2O$) as the protecting agents, or using any suitable long aliphatic groups. (See WO2008/140507, which is herein incorporated by reference in its entirety).

$T_4$ was selectively protected taking into consideration the reactivity of the amino group compared to the one of the

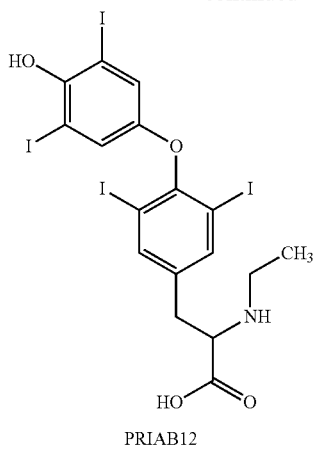 [SMILES: CCNC(Cc1cc(I)c(Oc2cc(I)c(O)c(I)c2)c(I)c1)C(=O)O]

PRIAB12

These novel N-substituted groups (N-Methyl, N-Ethyl or N-Triphenyl) showed comparable pro-angiogenesis efficacy to that of b-FGF or T4 in the CAM model, as shown below. (See also WO2008/140507).

Effect of L-T4 Analogs PRIAB2, PRIAB6, PRIAB12 in CAM Model of Angiogenesis

| Treatment | Branch pts ± SEM | % Inhibition ± SEM |
|---|---|---|
| PBS | 76.0 ± 8.5 | |
| FgF (1.25 µg/ml)) | 137.9 ± 7.5 | |
| PRIAB2 (0.1 µM) (T4 analog) | 136.0 ± 18.1 | |
| PRIAB6 (0.1 µM) (T4 analog) | 136.2 ± 12.4 | |
| PRIAB12 (0.1 µM) (T4 analog) | 121.7 ± 13.6 | |

Figure 12:
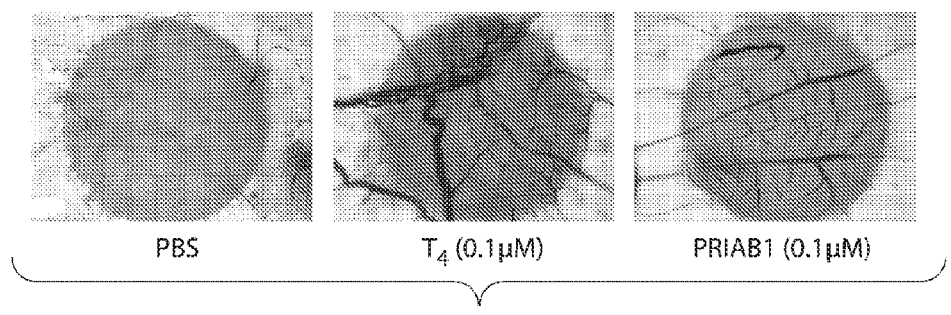
FIG. 12 are photographs showing the test results of PRIAB1 and the chick chorioallantoic membrane (CAM) assay before conjugation which results in clear pro-angiogenesis action by the protected $T_4$ analogs and the bulkiest protective group showed the merest activity.
Figure 13A:
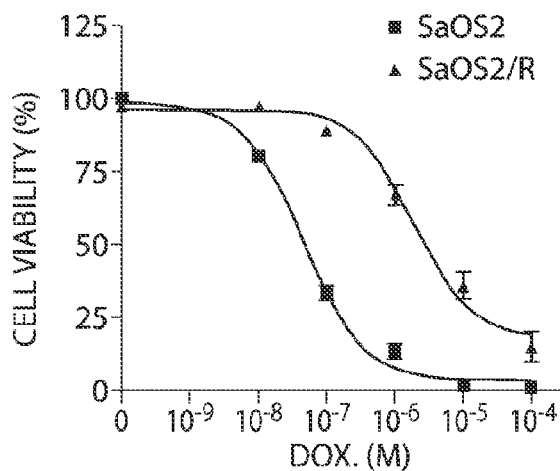
FIGS. 13A-F shows the effect of Tetrac or Doxirubicin on the proliferation of drug-sensitive versus drug-resistant cancer cells. Drug-sensitive and -resistant SKN-SH (FIGS. 13C-D), SaOS2 (FIGS. 13A-B), and MCF7 (FIGS. 13E-F) cells were subjected to treatment with increasing concentrations of Tetrac or Doxirubicin over a period of 4 days. Cell viability was then measured by MTT assay. The data represent the average of 4 determinations±SE.
Figure 13B:
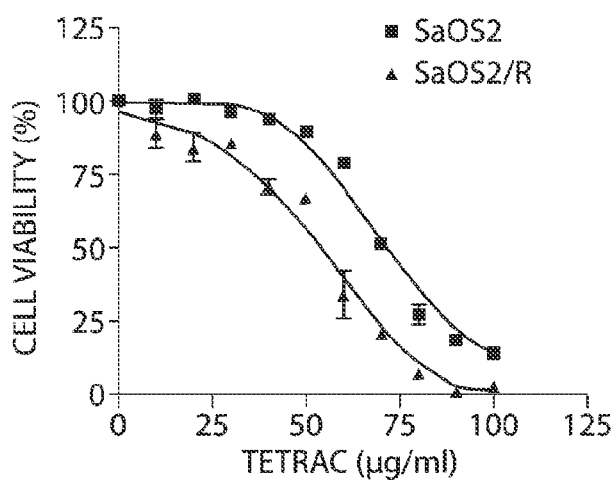
Figure 13C:
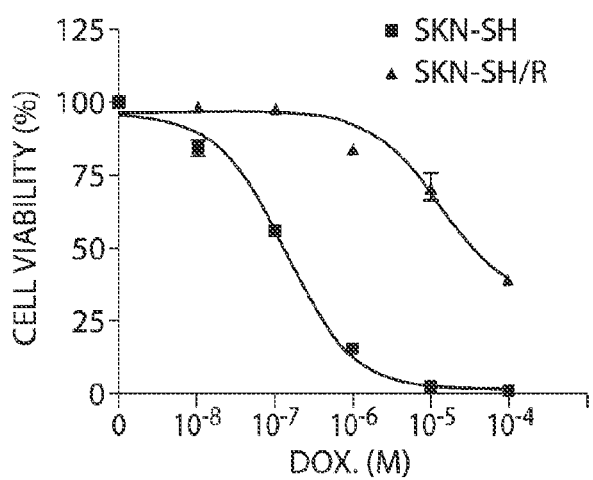
Figure 13D:
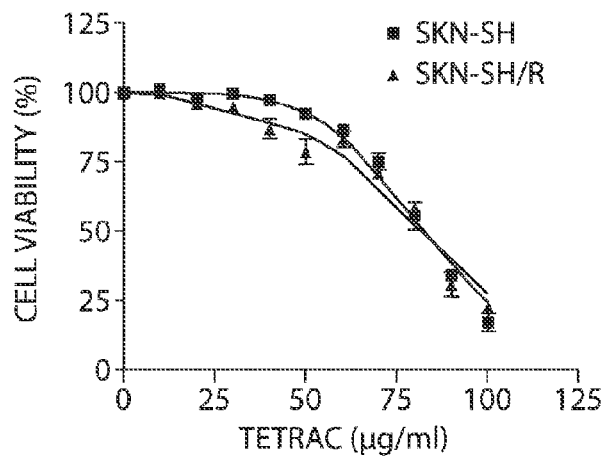
Figure 13E:
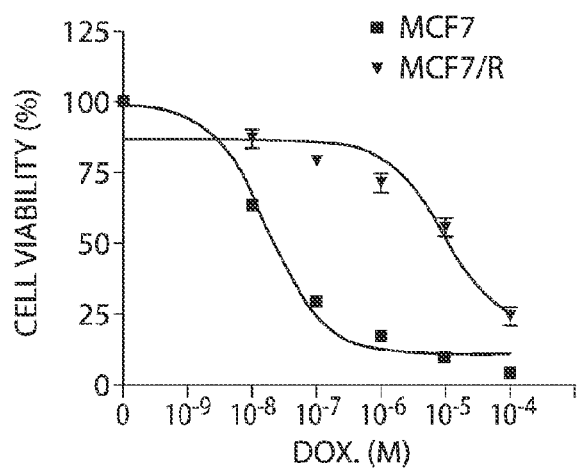
Figure 13F:
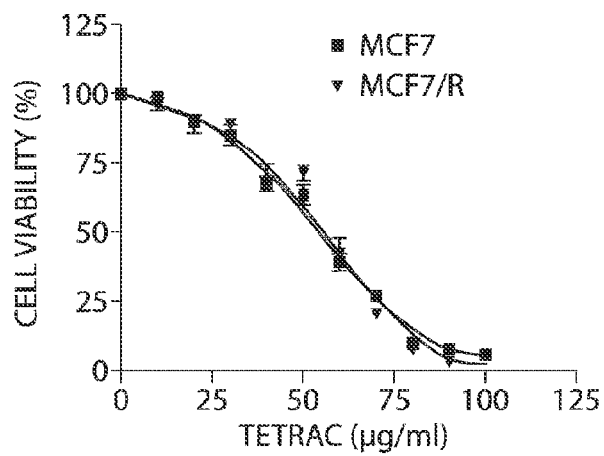

PRIAB1, as described above, was tested using the chick chorioallantoic membrane (CAM) assay before conjugation. The results are presented herein and in FIG. 12 for PRIAB1.

| Treatment | Branch pts ± SEM |
|---|---|
| PBS | 65.2 ± 14.9 |
| T4 (0.1 µM) | 137.3 ± 8.8 |
| PRIAB1 (0.1 µM) | 173 ± 9.9 |

These test results show a clear pro-angiogenesis action by the protected $T_4$ analogs and the bulkiest protective group showed the merest activity. Due to the formation of an amide bound, the free doublet of electrons carried by the secondary nitrogen of those molecules is displaced toward the carbonyl which renders the amine non-nucleophylic (deactivation of the amine by the carbonyl group is shown below). Nevertheless, it is still basic.

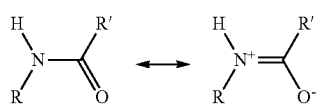

New analogs can be designed to carry a protected amino group (differing in bulkiness), which render the amine basic and nucleophilic are shown below:

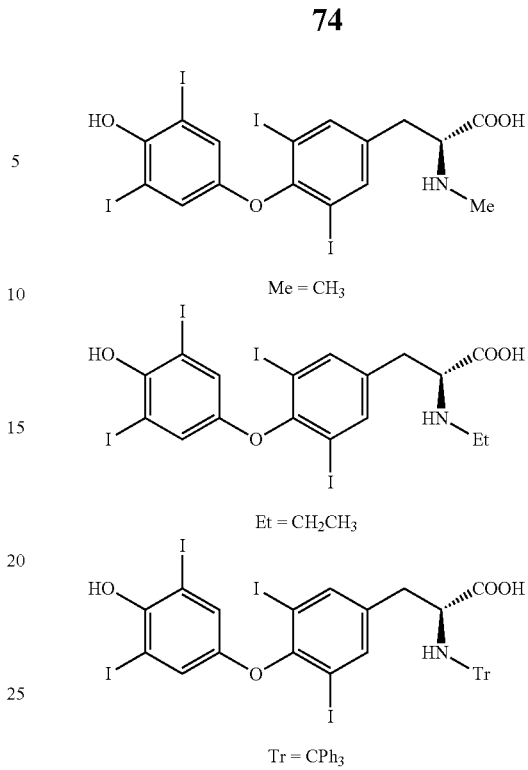

Me = $CH_3$

Et = $CH_2CH_3$

Tr = $CPh_3$

Activation of $T_4$-BOC $T_4$-BOC may be activated using epichlorohydrin, or other suitable activating agent (e.g., epibromohydrin). (See WO2008/140507).

Synthesis of Novel $T_4$/Polymeric Conjugates:

Activated $T_4$-BOC can be conjugated to different polymers, including without limitation PVA, PEG, PLGA, PolyLysine, PolyArgine, polylactide, polyglycolide, and co-polymers thereof. Conjugation of $T_4$ to a polymer through the phenolic hydroxyl group may be desirable because $T_4$ and $T_3$ are each conjugated to glucuronic acid and sulfonic acid in the liver during degradation. Synthesis schematics of the conjugation of activated $T_4$-Boc to PolyLysine and $T_4$-Boc to PolyArgnine are shown in WO2008/140507.

Likewise, a schematic showing the protection of $T_4$ using acetic anhydride ($Ac_2O$) or ditertbutyldicarbonate ($BOC_2O$), deprotection, and subsequent conjugation to PVA or PEG, is also shown in WO2008/140507.

Preparation of $T_4$ Conjugated PEG-PLGA Nanoparticles $T_4$/PEG conjugates may be used for immobilization with nanoparticles by conjugation to nanoparticles using a suitable conjugation method(s) known to one of ordinary skill in the art. As an illustrative example, the highly reactive amino group present in $T_4$ was blocked first by using either acetic anhydride ($Ac_2O$) or ditertbutyldicarbonate ($BOC_2O$), then activated with epicholorohydrin, and conjugated to nanoparticles, as detailed in WO2008/140507.

Example 10

Chemistry of Immobilized Tetrac Nanoparticles

Shown below are two approaches for immobilizing Tetrac. In one approach a linear intermediate is used and in a second approach, cyclic epichlorohydrin is used. The products were purified by column chromatography. The synthesized compounds can be conjugated to a polymer and immobilized in nanoparticles or can be attached to the surface of void nanoparticles.

Synthesis of PRIAB24

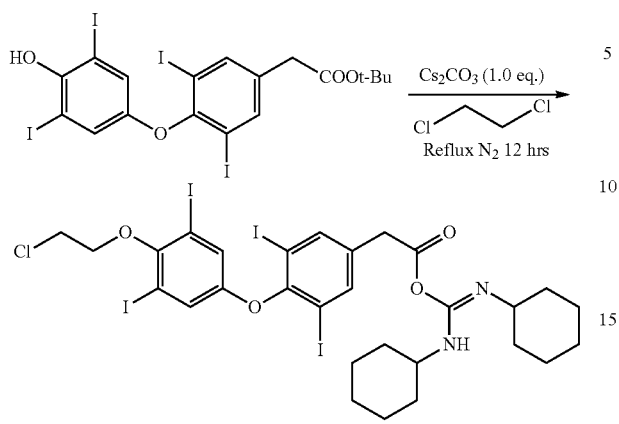

Synthesis of PRIAB19

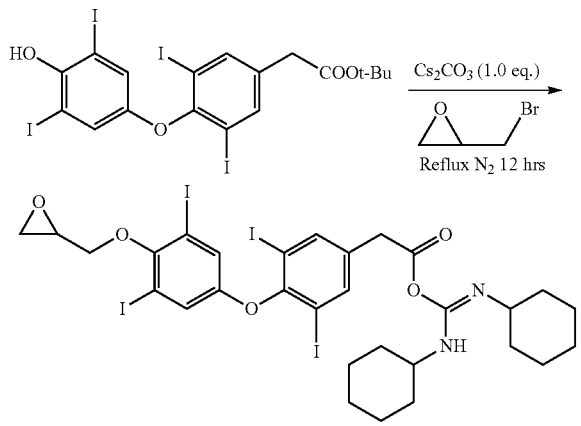

The synthesis of the analog activated using the epibromohydrin was synthesized in a 2% yield. Starting from 2 g of the starting material, approximately 60 mg of the recrystallized product were obtained as a white powder.

Example 11

Design and Synthesis Pathway of $T_4$ Conjugated Nanoparticles

The cell surface pro-angiogenesis effect of $T_4$ was thought to be achievable by conjugating the $T_4$ molecule with a nanoparticle which will have amino groups at its ends. As noted, $T_4$ has three functional groups, one amine, one carboxylic acid and a hydroxyl. After testing the effects of $T_4$ and Tetrac on the integrin active site, it was found that the hydroxyl was not potently contributing to the observed effects of those molecules. Thus, the strategy followed for the conjugation was to protect the amino group, first and then the carboxylic acid of $T_4$ in a second step, and then to activate the intermediate using an epoxide derivative as a linker. Epicyclohydrin or epibromohydrin were found best for this purpose because the highly reactive epoxide would lie unhindered after the condensation with $T_4$ and be free to react with any amino group of the nanoparticle. Thereafter, the acidolysis of both the amide and the ester (i.e., deprotection) in mild conditions would then be used to obtain the desired product.

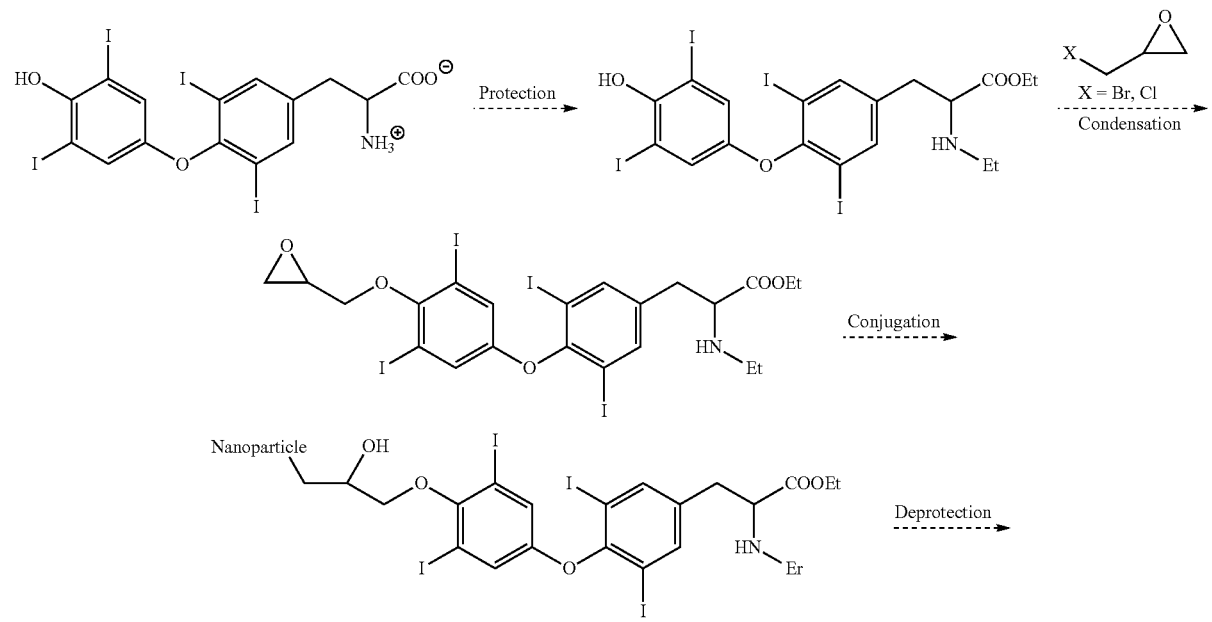

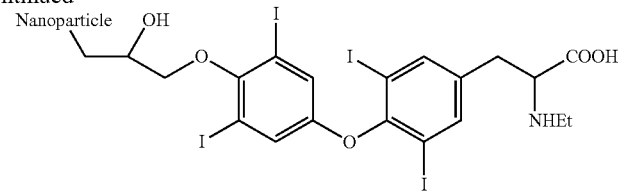

Synthesis Strategy of the Activation of T₄ Prior to Conjugation

First Step: Synthesis of ethyl-2-(ethylamino)-3-[4-(4-hydroxy-3,5-diiodophenoxy)-3,5-diiodophenyl] propanoate (PRIAB20)

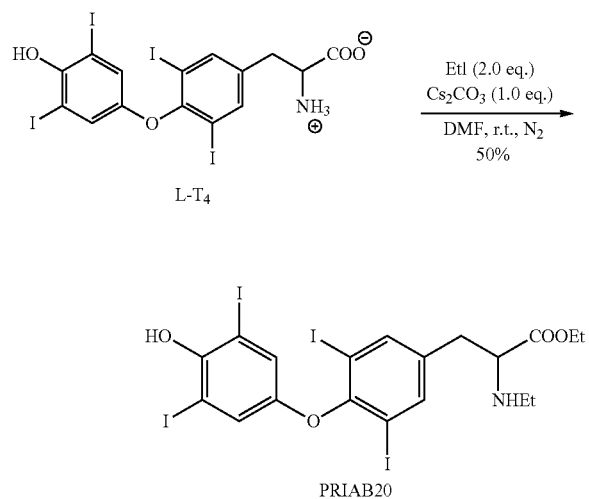

To a stirred suspension of $T_4$ (1.0 g, 1.29 mmol, 1.0 eq.) in DMF (20 mL) was added $Cs_2CO_3$ (419.4 mg, 1.29 mmol, 1.0 eq.). After stirring for 5 minutes, EtI (206 µL, 2.57 mmol 2.0 eq.) was added drop wise. After stirring for 1 hr., the solvent of the reaction was removed, the residue dissolved in a minimum of acetone and the obtained solution added drop wise to 40 mL of $H_2O$. The precipitate was then filtrated and recrystallized.

Yield: 50%; off-white solid; recrist. solvent.: EtOH; TLC: Rf=0.43 (EtOAc/EtOH 9/1); RPTLC: Rf=0.43 (AcOH/$H_2O$ 8/2); mp=136° C.; IR ($\upsilon$ cm$^{-1}$): 1730 (CO); $^1$H NMR (DMSO-d6) δ (ppm): 7.79 (s, 2H, ArH), 7.14 (s, 2H, ArH), 4.06-4.02 (m, 2H, CH₂), 3.93-3.89 (q, J=7.0 Hz, 2H, CH₂), 3.59-3.56 (t, J=7.0 Hz, 1H, CH), 2.80-2.77 (m, 2H, CH₂), 1.88 (br, 1H, NH), 1.41-1.39 (t, J=7.0 Hz, 3H, CH₃), 1.15-1.12 (t, J=7.0 Hz, 3H, CH₃); MS (ESI+) m/z 911.7 [(M+DMSO)⁺, 100], 833.7 [(M+H)+, 75]. Anal. Calcd. for $C_{19}H_{19}I_4NO_4$: C, 27.40; H, 2.30; N, 1.68. Found: C, 27.54; H, 1.94; N, 1.66. Solubility $10^{-3}$ M in water after preparing a solution at $10^{-1}$ M in DMSO. It is noteworthy that if a suspension of $T_4$ is prepared overnight, the yield can be increased.

Second Step: Synthesis of ethyl 3-(4-(3,5-diiodo-4-(oxiran-2-ylmethoxy)phenoxy)-3,5-diiodophenyl)-2-(ethylamino) propanoate (PRIAB26)

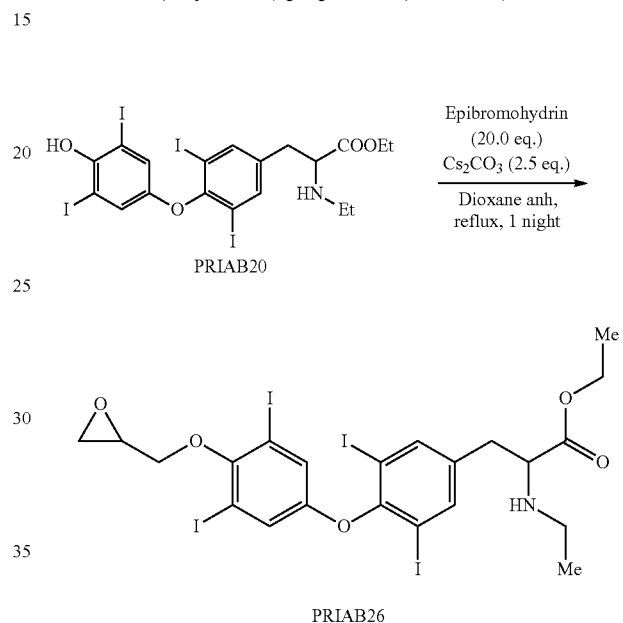

PRIAB20 (866.4 mg, 1.0 mmol, 1.0 eq.) was dissolved in anhydrous dioxane (30 mL), then $Cs_2CO_3$ (325.8 mg, 1.0 mmol, 1.0 eq.) was added and then epibromohydrin (1.78 mL, 20.8 mmol, 20.0 eq.) was added. The reaction medium was then slowly heated to reflux. The mixture was stirred overnight upon reflux then cooled to room temperature. The organic solution was then evaporated and purified by column chromatography using silica gel (eluent DCM/Ethyl Acetate, 1/9) to yield a white powder which was further recrystallized.

Third Step: Synthesis of ethyl 3-(4-(4-(2-chloroethoxy)-3,5-diiodophenoxy)-3,5-diiodophenyl)-2-(ethylamino)propanoate (PRIAB27)

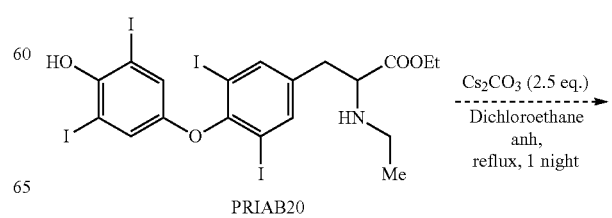

-continued

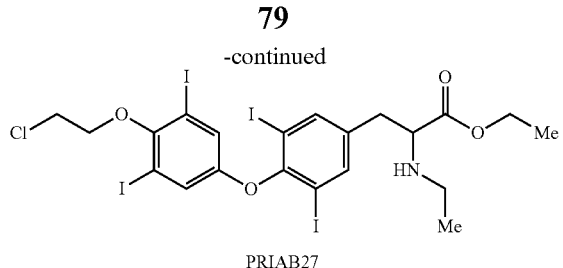

PRIAB27

PRIAB20 (1.0 eq.) was dissolved in anhydrous dichloroethane (30 mL) and then Cs$_2$CO$_3$ (2.5 eq.) was added. The reaction medium was then slowly heated to reflux. The mixture was stirred overnight upon reflux then cooled to room temperature, filtered and the solvent was removed under vacuum. The residual oil then was purified by column chromatography to yield a product which was further recrystallized.

Fourth Step: Synthesis of Nanoparticles

Step 1: A solution of PLGA (poly-lactide-co-glycolide) solution in DMSO was prepared. The concentration of the PLGA in DMSO is 40 mg/ml.

Step 2: 100 μL of this 40 mg/ml PLGA (poly-lactide-co-glycolide) solution in DMSO was added to 10 ml of a 1% PVA (polyvinyl alcohol) solution and stirred for 12 hours at room temperature to make the nanoparticles.

Step 3: The nanoparticles suspension was then dialyzed for 6 hours in a 10-12 kD membrane.

Step 4: To this 10 ml solution 1 ml of PBS buffer (pH~7.4, 10×) was added followed by the addition of 60 mg of N-(3-dimethylaminopropyl)-N'-ethylcarbodiimide hydrochloride (EDC hydrochloride) and stirred for at least 30 minutes to 1 hr.

Step 5: To the above solution again 60 mg of ethylenediamine was added and stirred overnight.

Step 6: The whole solution was then dialyzed (through 3.5 KD membrane) for around 8 hrs to eliminated un-reacted materials.

Step 7: Now to the above PLGA nanoparticles with —NH$_2$ group 100 μl of the activated T$_4$ (around 20 mg/ml DMSO) was added and stirred for 24 hours.

Step 8: The solution was then dialyzed for at least 12 hrs for purification.

After verifying the size and size distribution of the newly formulated T$_4$ nanoparticle, the tertbutanol ester was saponificated under mild acidic conditions using TFA. The particle size ranged from 200-250 nm. T4 immobilized nanoparticles were characterized by its size distribution, and surface charges. The stability of T4 nanoparticles was shown by testing the changes in size distributions over time (day 1, week 1 and 1 month) of immobilized T4 in solution kept at 4 degree centigrade. The average nanoparticles size ranged from 200-250 nm and did not show any significant changes from that range over a 1 month period and no detectable free T4 from the nanoparticles. Upon 5 mM NaOH 100% free T4 was released from the nanoparticles upon incubation overnight.

Fifth Step: Acidolysis of the Nanoparticle

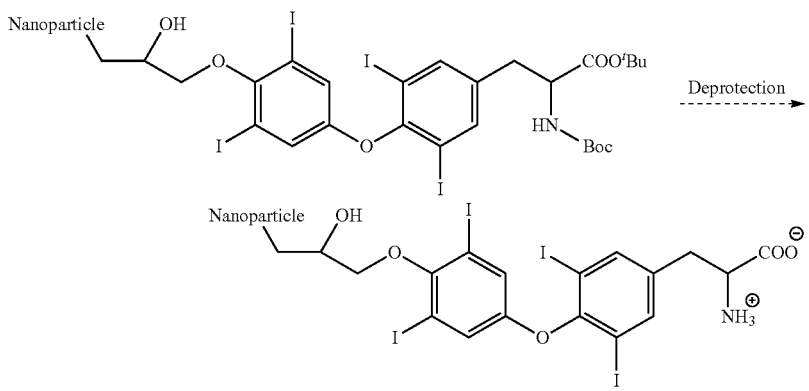

The deprotection is done on the T$_4$-nanoparticles by stirring the particles in a solution of TFA or HF diluted in water during 12 hrs and then purified.

Example 12

Design and Semisynthesis of T4 and T4 Analog Nanoparticles

The stimulation of angiogenesis activities result from an interaction of T4 with the integrin αvβ3, known to play a role in pathologic angiogenesis processes. In order to examine the relative importance of the ammonium group of T$_4$ and to probe the receptor binding site, new T$_4$ analogs variously hindered on the phenol group, the amino group, and the carboxylic acid group were designed, semisynthesized and tested in the CAM (previously described) and mouse matrigel models of angiogenesis. (See Bridoux et al., Bioorg. Med. Chem. Lett (2010), doi:10.1016/j.bmcl.2010.04.011 (in press), incorporated by reference). The relative pKa values (dissociation constants) of the functional groups have been estimated to be approximately 9.0 for the NH2 (amino) group and 2.0 for the COOH (carboxylic acid) group. The PhOH (phenol) group is a weakly basic site as determined by fluorescent quenching (pKa=6.2). (See Nilsson et al., J. Biol. Chem 246:6098 (1971)). The results described herein provide the rationale for the selection of new thyroxine nanoparticle precursor.

New T$_4$ analogs were created by the following methods:
Method A
TEA (1.0 eq.) was added to a stirred suspension of L-T$_4$ (1.0 eq.) in DMF (20 mL). After stirring for 5 minutes, the alkylating or acylating agent (1.0 eq. or 2.0 eq.) was added drop wise. After stirring for 45 minutes, the solvent of the reaction was removed, the residue dissolved in a minimum of acetone and the obtained solution added drop wise to 40 mL of H$_2$O. The precipitate was then filtrated and recrystallized.

Method B

Na$_2$CO$_3$ (1.0 eq.) or Cs$_2$CO$_3$ (1.0 eq.) was added to a stirred suspension of L-T$_4$ (1.0 eq.) in DMF (20 mL). After stirring for 5 minutes, the alkylating or acylating agent (1.0 eq.) was added drop wise. After stirring for 1 hr, the solvent of the reaction was removed, the residue dissolved in a minimum of acetone and the obtained solution added drop wise to 40 mL of H$_2$O. The precipitate was then filtrated and recrystallized or the solution was hydrolyzed overnight, extracted using EtOAc, then purified by column chromatography and then the product was recrystallized.

Method C

The alkylating or acylating agent (1.0 eq.) was added to a stirred suspension of T$_4$ (1.0 eq.) in DMF (20 mL). After stirring for 2 hrs, the solution was either added drop wise to 40 mL of H$_2$O, allowed to precipitate overnight, filtered, and recrystallized; either alkalinized using K$_2$CO$_3$ 10%, then purified by column chromatography and then the product was recrystallized.

Figure 20:
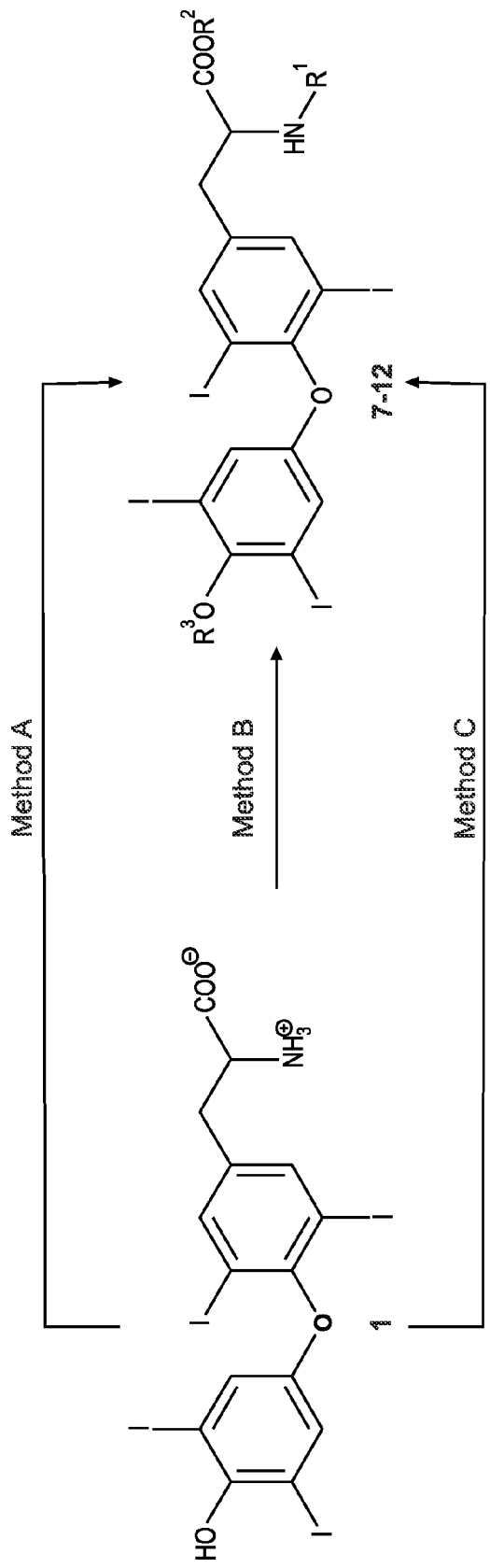
FIG. 20 is a schematic showing the synthesis of various $T_4$ analogs (compounds 7-12).
Figure 21:
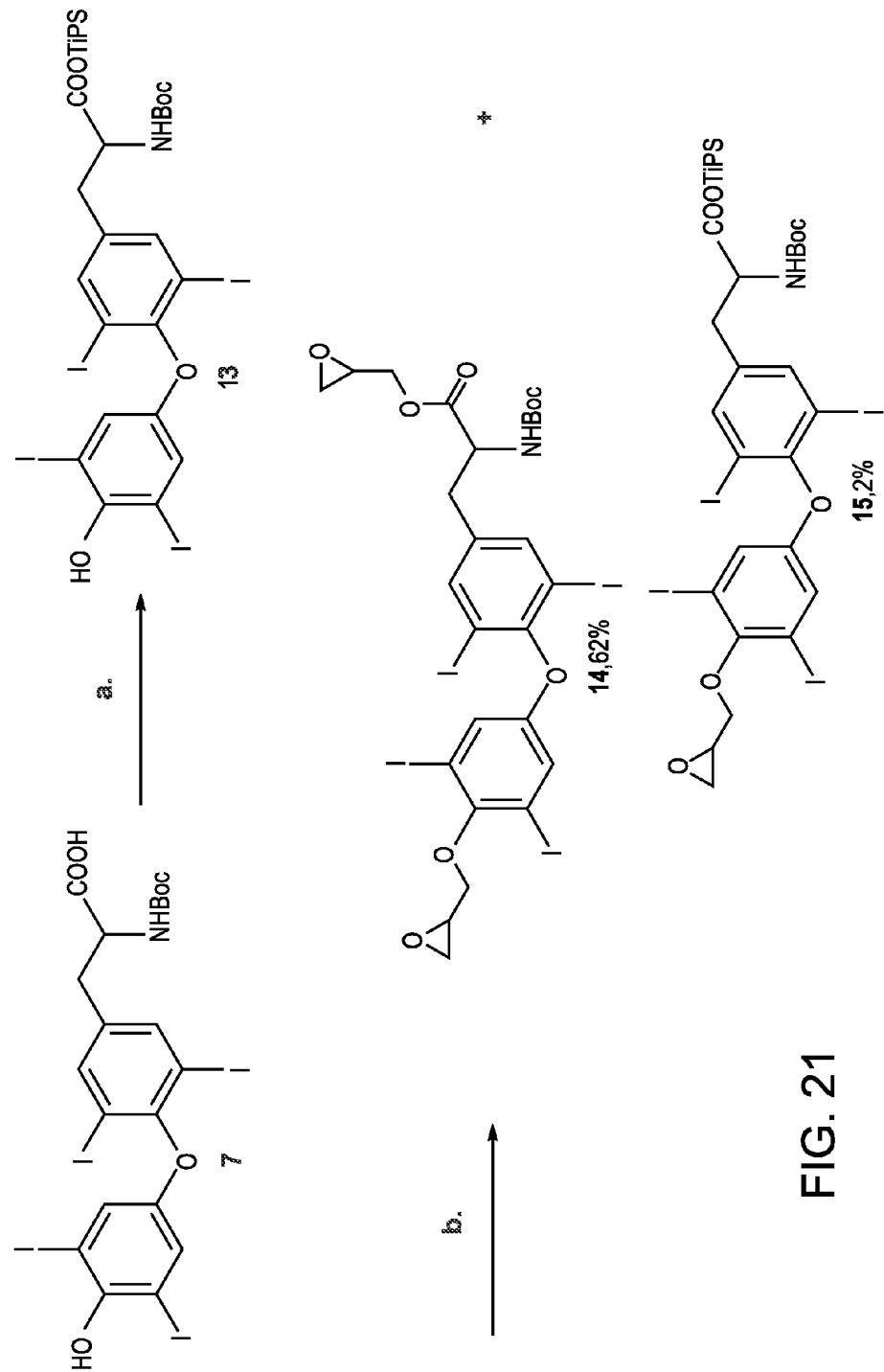
FIG. 21 is a schematic showing the synthesis of various $T_4$ analogs (compounds 13-15).
Figure 22:
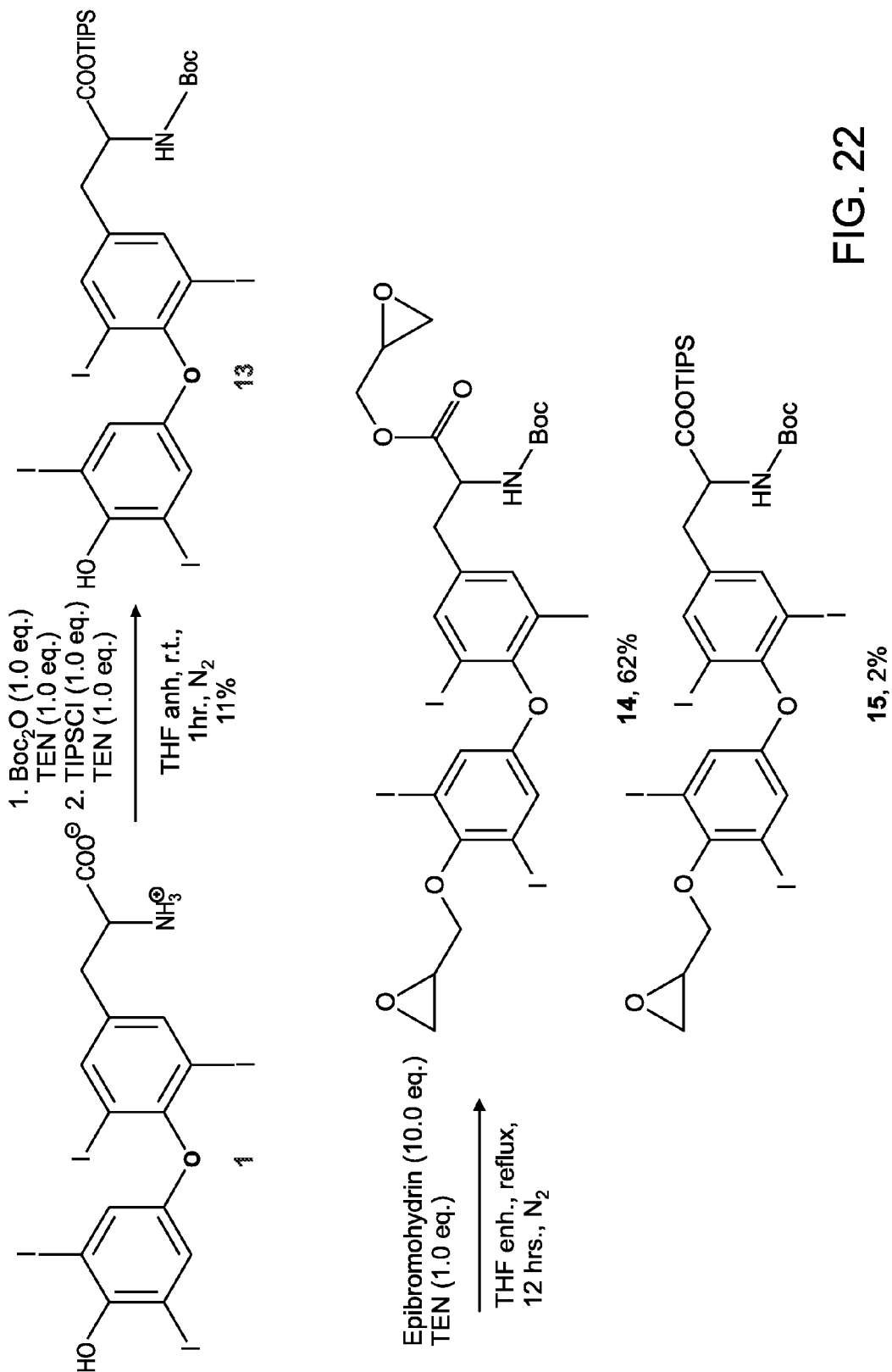
FIG. 22 shows the schematic synthesis of $T_4$ precursor triisopropylsilyl-2-(tert-butoxycarbonylamino)-3-(4-(3,5-diiodo-4-(oxiran-2-ylmethoxy)phenoxy)-3,5-diiodophenyl) propanoate (compound 15) prior to conjugation to a nanoparticle.

A schematic of the synthesis of compounds 7-12 is shown in FIG. 20 and a schematic of the synthesis of compounds 13-15 is shown in FIG. 21. The structures of T4 and the T4 analogs (compounds 7-15) are shown below.

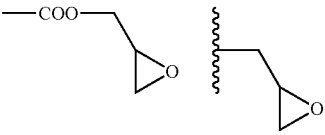

| Compounds | R$^1$ | R$^2$ | R$^3$ |
|---|---|---|---|
| Thyroxine 1 | —NH$_3^\oplus$ | —COO$^\ominus$ | —H |
| 7 | —NHBoc | —COOH | —H |
| 8 | —NHBu | —COOH | —H |
| 9 | —NHAc | —COOH | —Ac |
| 10 | —NHMe | —COOH | —H |
| 11 | —NHEt | —COOH | —H |
| 12 | —NHEt | —COOEt | —H |
| 13 | —NHBoc | —COOTiPS | —H |
| 14 | —NHBoc | 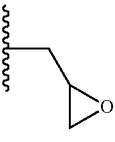 [SMILES: *CC1CO1] | |
| 15 | —NHBoc | —COOTiPS | |

Analytical Characterization

2-[(Tert-butoxycarbonyl)amino]-3-[4-(4-hydroxy-3, 5-diiodophenoxy)-3,5-diiodophenyl]propanoic acid (Compound 7)

L-T$_4$ (250 mg, 0.3 mmol); Boc$_2$O (70 mg, 0.3 mmol)

Method C: yield: 90%, white powder; recrystallization solvent: EtOAc; TLC: 0.67 (DCM/MeOH 90/10); RPTLC: 0.42 (AcOH/H$_2$O 80/20); mp=212° C.; IR (υ cm$^{-1}$): 3407 (NH), 1701 (CO), 1660 (CO); UV (DMSO): λ$_{max}$ nm=259; $^1$H NMR (DMSO-d$_6$) δ (ppm): 7.82 (s, 2H, ArH), 7.05 (s, 2H, ArH), 4.16 (br, 1H, NH), 3.04-3.08 (dd, J$_1$=2.0 Hz, J$_2$=13.6 Hz, 2H, CH$_2$), 2.71-2.79 (t, J=11.7 Hz, 1H, CH), 1.34 (s, 9H, 3 CH$_3$); HRMS (ESI+) m/z: 899.7 [(M+Na)$^+$, 100], 821.7 [(M–C$_4$H$_9$)$^+$, 90], 777.7 [(M–C$_5$H$_9$O$_2$)$^+$, 85]. Analytical (C$_{20}$H$_{19}$I$_4$NO$_6$) C, 27.49; H, 1.81; N, 1.57.

2-(Butyrylamino)-3-[4-(4-hydroxy-3,5-diiodophenoxy)-3,5-diiodophenyl]propanoic acid (Compound 8)

L-T$_4$ (250 mg, 0.3 mmol); TEA (54 μL, 0.3 mmol); Bu$_2$O (53 μL, 0.3 mmol)

Method A: yield: 45%, white powder; recrystallization solvent: EtOAc; TLC: 0.30 (DCM/MeOH 90/10); RPTLC: 0.53 (AcOH/H$_2$O 80/20); mp=218° C.; IR (υ cm$^{-1}$): 3398 (NH), 1716 (CO), 1607 (CO); UV (DMSO): λ$_{max}$ nm=258; $^1$H NMR (DMSO-d6) δ (ppm): 7.79 (s, 2H, ArH), 7.03 (s, 2H, ArH), 4.48 (br, 1H, NH), 3.05-3.10 (dd, J$_1$=2.0 Hz, J$_2$=13.6 Hz, 2H, CH$_2$), 2.71-2.79 (t, J=11.7 Hz, 1H, CH), 1.97-2.07 (m, 2H, CH$_2$), 1.38-1.46 (m, 2H, CH$_2$), 0.70-0.75 (t, J=7.3 Hz, 3H, CH$_3$); HRMS (ESI+) m/z: 869.7 [(M+Na)$^+$, 100], 847.7 [(M+H)$^+$, 90], 777.7 [(M–C$_4$H$_9$)$^+$, 5]. Analytical (C$_{19}$H$_{17}$I$_4$NO$_5$) C. calcd, 26.94. found, 27.45; H, 2.02; N, 1.65.

2-Acetamido-3-[4-(4-acetoxy-3,5-diiodophenoxy)-3, 5-diiodophenyl]propanoic acid (Compound 9)

L-T$_4$ (590 mg, 0.7 mmol); TEA (99 μL, 0.7 mmol); Ac$_2$O (71 μL, 0.7 mmol)

Method A: yield: 50%, white powder; recrystallization solvent: EtOAc; TLC: 0.63 (DCM/MeOH 90/10); RPTLC: 0.62 (AcOH/H$_2$O 80/20); mp=190° C.; IR (υ cm$^{-1}$): 3269 (NH), 1724 (CO), 1647 (CO); UV (DMSO): λ$_{max}$ nm=258; HPLC (Luna NH$_2$): rt=3.5 minutes (MeOH/H$_2$O 95/5); $^1$H NMR (DMSO-d6) δ (ppm): 7.79 (s, 2H, ArH), 7.05 (s, 2H, ArH), 4.42 (br, 1H, NH), 3.03-3.08 (m, 2H, CH$_2$), 2.76-2.81 (dd, J$_1$=2.0 Hz, J$_2$=13.5 Hz, 1H, CH), 1.97 (s, 3H, CH$_3$), 1.78 (s, 3H, CH$_3$); HRMS (ESI+) m/z: 841.6 [(M–C$_2$H$_3$O+Na)$^+$, 100], 819.7 [(M–C$_2$H$_3$O)$^+$, 80]. Analytical (C$_{17}$H$_{13}$I$_4$NO$_5$) C. calcd, 26.51. found, 27.96; H, 2.02; N, 1.80.

Potassium 3-[4-(4-hydroxy-3,5-diiodophenoxy)-3,5-diiodophenyl]-2-(methylamino)propanoate dihydrate (Compound 10)

L-T$_4$ (1.0 g, 1.29 mmol); MeI (80 μL, 1.29 mmol)

Method C: yield: 24%, brown powder; TLC: 0.68 (DCM/MeOH 90/10); RPTLC: 0.62 (AcOH/H$_2$O 80/20); mp=160° C.; IR (υ cm$^{-1}$): 3297 (NH), 1232 (NHMe); UV (DMSO): λ$_{max}$ nm=257; $^1$H NMR (CDCl$_3$) δ (ppm): 7.82 (s, 2H, ArH), 7.12 (s, 2H, ArH), 3.52-3.54 (m, 3H, CH$_3$), 3.12-3.15 (dd, J$_1$=2.0 Hz, J$_2$=13.5 Hz, 2H, CH$_2$), 2.81-2.85 (q, J=8.1 Hz, 1H, CH); HRMS (ESI+) m/z: 791.7 [(M+H)$^+$, 100]. Analytical (C$_{19}$H$_{17}$I$_4$NO$_5$) C, 22.14; H, 1.51; N, 1.72.

2-(Ethylamino)-3-[4-(4-hydroxy-3,5-diiodophenoxy)-3,5-diiodophenyl]propanoic acid (Compound 11)

L-T$_4$ (1.0 g, 1.3 mmol); EtI (103 μL, 1.3 mmol). The product was washed in hot CH$_3$CN and filtered.

Method C: yield: 62%, brown powder; TLC: 0.69 (DCM/MeOH 90/10); RPTLC: 0.67 (AcOH/H$_2$O 80/20); mp=187° C.; IR (υ cm$^{-1}$): 3347 (NH), 1720 (CO), 1232 (NHEt); UV (DMSO): λ$_{max}$ nm=256; $^1$H NMR (DMSO-d6) δ (ppm): 8.32 (s, 2H, ArH), 7.58 (s, 2H, ArH), 4.88-4.91 (br, 1H, NH), 4.55-4.63 (m, 2H, CH$_2$), 3.61-3.64 (dd, J$_1$=2.0 Hz, J$_2$=13.5 Hz, 2H, CH$_2$), 3.35-3.42 (m, 1H, CH), 1.66-1.69 (t, J=7.0 Hz, 3H, CH$_3$); HRMS (ESI+) m/z: 805.7 [(M+H)$^+$, 100]. Analytical (C$_{17}$H$_{15}$I$_4$NO$_4$) C. calcd, 25.37. found, 26.46; H, 1.62; N, 1.66.

Ethyl-2-(ethylamino)-3-[4-(4-hydroxy-3,5-diiodophenoxy)-3,5-diiodophenyl]propanoate (Compound 12)

L-T$_4$ (1.0 g, 1.3 mmol); Cs$_2$CO$_3$ (419 mg, 1.3 mmol); EtI (206 μL, 2.6 mmol)

Method B: yield 10%, off-white solid; recrystallization solvent: EtOH; TLC: 0.43 (EtOAc/EtOH 90/10); RPTLC: 0.43 (AcOH/H$_2$O 80/20); mp=136° C.; IR (υ cm$^{-1}$): 1730 (CO); UV (DMSO): λ$_{max}$ nm=257; $^1$H NMR (DMSO-d6) δ (ppm): 7.79 (s, 2H, ArH), 7.14 (s, 2H, ArH), 4.02-4.06 (m, 2H, CH$_2$), 3.89-3.93 (q, J=7.0 Hz, 2H, CH$_2$), 3.56-3.59 (t, J=7.0 Hz, 1H, CH), 2.77-2.80 (m, 2H, CH$_2$), 1.88 (br, 1H, NH), 1.39-1.41 (t, J=7.0 Hz, 3H, CH$_3$), 1.12-1.15 (t, J=7.0 Hz, 3H, CH$_3$); HRMS (ESI+) m/z: 911.7 [(M+DMSO)$^+$, 100], 833.7 [(M+H)$^+$, 75]. Analytical (C$_{19}$H$_{19}$I$_4$NO$_4$) C, 27.54; H, 1.94; N, 1.66.

Triisopropylsilyl-2-(tert-butoxycarbonylamino)-3-(4-(4-hydroxy-3,5-diiodophenoxy)-3,5-diiodophenyl)propanoate (Compound 13)

7 (1.0 g, 1.1 mmol, 1.0 equiv) was dissolved in anhydrous THF, and then TEA (159 μL, 1.1 mmol, 1.0 equiv) was added dropwise. After stirring for 5 min, TiPSCl (244 μl, 1.1 mmol, 1.0 equiv) was added dropwise. After 30 min, THF was evaporated and Et$_2$O was added. The precipitate that formed was filtered. The residue was 7 (200 mg, 0.2 mmol) which did not react. The filtrate was then purified by column chromatography (DCM) to give triisopropylsilyl-2-(tert-butoxycarbonylamino)-3-(4-(4-hydroxy-3,5-diiodophenoxy)-3,5-diiodophenyl)propanoate (130 mg, 0.1 mmol) as an oil.

Yield: 13%, brown oil; TLC: 0.63 (DCM); RPTLC: 0.52 (AcOH/H$_2$O 80/20); IR (υ cm$^{-1}$): 3426 (NH), 1695 (CO); UV (DMSO): λ$_{max}$ nm=257; HPLC (μBondapak C18): rt=1.7 minutes (MeOH/H$_2$O 80/20); $^1$H NMR (CDCl$_3$) δ (ppm): 7.69 (s, 2H, ArH), 7.11 (s, 2H, ArH), 4.56 (m, 1H, CH), 3.19-3.22 (dd, J$_1$=2.0 Hz, J$_2$=13.5 Hz, 1H, CH), 2.97-3.01 (dd, J$_1$=2.0 Hz, J$_2$=13.5 Hz, 1H, CH), 1.46 (s, 9H, 3 CH$_3$), 1.05 (m, 21H, 6 CH$_3$+3 CH); HRMS (ESI−) m/z: 1032.1 [(M−H)$^-$, 38].

Oxiran-2-ylmethyl-2-(tert-butoxycarbonylamino)-3-(4-(3,5-diiodo-4-(oxiran-2-ylmethoxy)phenoxy)-3,5-diiodophenyl)propanoate (Compound 14)

In anhydrous conditions, 13 (132 mg, 0.1 mmol, 1.0 equiv) was suspended in anhydrous THF and then TEA (18 μL, 0.1 mmol, 1.0 equiv) was added. After stirring at room temperature for 5 min, epibromohydrin (105 μL, 1.0 mmol, 10.0 equiv) was added and the reaction medium was stirred at reflux (65° C.) and monitored by TLC. After 12 hrs, the reaction medium was filtered and the organic phase was evaporated. The crude product was then separated by column chromatography (CHCl$_3$) to give oxiran-2-ylmethyl-2-(tert-butoxycarbonylamino)-3-(4-(3,5-diiodo-4-(oxiran-2-ylmethoxy)phenoxy)-3,5-diiodophenyl)propanoate (62 mg, 0.06 mmol) as a solid.

Yield: 62%, white solid; TLC: 0.78 (DCM/EtOAc 90/10); RPTLC: 0.33 (AcOH/H$_2$O 80/20); mp=105° C.; IR (υ cm$^{-1}$): 3342 (NH), 1731 (CO), 1680 (CO); UV (DMSO): λ$_{max}$ nm=257; HPLC (Luna NH$_2$): rt=3.5 minutes (MeOH/H$_2$O 95/5); (μBondapak C18): rt=3.1 minutes (MeOH/H$_2$O 75/25); $^1$H NMR (CDCl$_3$) δ (ppm): 7.65 (s, 2H, ArH), 7.17 (s, 2H, ArH), 4.55-4.58 (m, 1H, CH), 4.11-4.16 (m, 2H, CH$_2$), 4.03-4.07 (m, 2H, CH$_2$), 3.14-3.09 (m, 2H, 2 CH), 2.92-2.99 (m, 3H, CH+CH$_2$), 2.79-2.81 (m, 2H, CH$_2$), 1.59 (s, 9H, 3 CH$_3$); HRMS (APCI+) m/z: 933.7 [(M−C$_4$H$_9$)$^+$, 100]. Analytical (C$_{26}$H$_{27}$I$_4$NO$_8$) C. calcd, 31.57. found, 37.41; H. calcd, 2.75. found, 3.23; N, 1.17.

Triisopropylsilyl-2-(tert-butoxycarbonylamino)-3-(4-(3,5-diiodo-4-(oxiran-2-ylmethoxy)phenoxy)-3,5-diiodophenyl)propanoate (Compound 15)

In anhydrous conditions, 13 (132 mg, 0.1 mmol, 1.0 equiv) was suspended in anhydride THF and then TEA (18 μL, 0.1 mmol, 1.0 equiv) was added. After stirring at room temperature for 5 min, epibromohydrin (105 μL, 1.0 mmol, 10.0 equiv) was added and the reaction medium was stirred at reflux (65° C.) and monitored by TLC. After 12 hrs, the reaction medium was filtered, and the organic phase was evaporated. The crude product was then separated by column chromatography (CHCl$_3$) to give triisopropylsilyl-2-(tert-butoxycarbonylamino)-3-(4-(3,5-diiodo-4-(oxiran-2-ylmethoxy)phenoxy)-3,5-diiodophenyl)propanoate (2 mg, 0.001 mmol) as a solid.

Yield: 2%, white solid; TLC: 0.40 (CHCl$_3$/EtOAc 95/5); RPTLC: 0.24 (AcOH/H$_2$O 80/20); mp=109° C.; IR (υ cm$^{-1}$): 3348 (NH), 1698 (CO); UV (DMSO): λ$_{max}$ nm=256; HPLC (Luna NH$_2$): rt=3.7 minutes (MeOH); HPLC (μBondapak C18): rt=3.1 minutes (MeOH/H$_2$O 75/25); $^1$H NMR (CDCl$_3$) δ (ppm): 7.65 (s, 2H, ArH), 7.17 (s, 2H, ArH), 4.61 (m, 1H, CH), 4.02-4.15 (m, 2H, CH$_2$), 3.71-3.78 (m, 2H, CH$_2$), 3.50-3.52 (m, 1H, CH), 3.10-3.12 (m, 1H, CH), 2.95-2.96 (m, 1H, CH), 2.92-2.94 (m, 1H, CH), 2.78-2.80 (m, 1H, CH), 1.55 (s, 18H, 6 CH$_3$), 1.46 (s, 9H, 3 CH$_3$), 1.05 (s, 3H, 3 CH); HRMS (APCI±) m/z: 965.8 [(M−C$_9$H$_{21}$Si)$^+$, 65], 1087.9 [(M−H)$^-$, 90]. Analytical (C$_{32}$H$_{43}$I$_4$NO$_7$Si) C. calcd, 35.28. found, 38.44, H. calcd, 3.98. found, 4.12; N, 1.00.

Mouse Matrigel Model of Angiogenesis
Matrigel Study

Normal male mice (C57BL/6NCr) 6-8 weeks of age and weighing ~20 g were purchased from Taconic farm. Animals were housed 4 per cage, in controlled conditions of temperature (20-24° C.); humidity (60-70%) and 12 hrs. light/dark cycle provided with food and water ad libitum. Mice were allowed to acclimate for 5 days prior to the start of treatments. Matrigel (BD Bioscience, San Jose Calif.) was thawed overnight at 4° C. and placed on ice. Aliquots of matrigel were placed into cold polypropylene tubes to prevent the matrigel from solidifying and the angiogenesis promoter added to matrigel with or without agonist. Mice were treated daily. Matrigel was subcutaneously injected as triple injection per animal at 100 μL/animal. At day 14 post plug implant all animals were killed in $CO_2$ chamber and matrigel plugs were collected. Plug hemoglobin content was analyzed from three implants/mice (n=6 per group) to measure angiogenesis.

Hemoglobin Determination of Angiogenesis in Matrigel plugs

The matrigel plugs dissected from the mice were carefully stripped of any remaining peritoneum. The plugs were placed into 0.5 mL tube of dd$H_2$O and homogenized for 5-10 min. The samples were spun at 4,000 rpm on a centrifuge for 10 min. and the supernatants collected for hemoglobin measurement. Fifty microliters of supernatant were mixed with 50 mL Drabkin's reagent and allowed to sit at room temperature for 15-30 min. and then 100 mL of this mixture was placed in a 96-well plate. Absorbance was read with a Microplate Manager ELISA reader at 540 nm. Hemoglobin (Hb) concentration was determined by comparison with a standard curve in mg/mL. Hemoglobin concentration is a reflection of the number of blood vessels in the plugs.

Docking

Docking of ligand compound 7 (2-[(Tert-butoxycarbonyl)amino]-3-[4-(4-hydroxy-3,5-diiodophenoxy)-3,5-diiodophenyl]propanoic acid) and Tetrac analog to the structure of $\alpha_v\beta_3$ was performed with Autodock, version 2.4.

Results

Angiogenesis Assays

The results of Tetrac inhibition of FGF-stimulated angiogenesis are shown below.

Anti-Angiogenesis Efficacy of $T_4$ Analogs in the CAM Model

| Treatment | Mean Branch points[1] | Mean % of stimulation (comparing to PBS) |
|---|---|---|
| PBS | 73 ± 6 | — |
| FGF (1.25 µg/mL) | 130 ± 11 | 78.1 ± 7.5 |
| $T_4$ (0.1 µM) | 137 ± 8 | 87.7 ± 7 |
| 7 (0.1 µM) | 173 ± 9 | 137 ± 7.5 |
| 8 (0.1 µM) | 98 ± 11 | 34.2 ± 8.5 |
| 9 (0.1 µM) | 122 ± 4 | 67.1 ± 5 |
| 10 (0.1 µM) | 105 ± 7 | 43.8 ± 6.5 |
| 11 (0.1 µM) | 136 ± 12.8 | 86.3 ± 9.4 |
| FGF (1.25 µg/ml) + 12 (0.1 µM) | 46 ± 2 | −37.9 ± 4 (inhibition) |
| 13 (1 µM) | 76 ± 7 | 4.1 ± 6.5 |
| 14 (1 µM) | 114 ± 11 | 56.2 ± 7.5 |
| 15 (1 µM) | 98 ± 8 | 34.2 ± 7 |

[1]Data representing mean ± SEM, n = 8

$T_4$-Stimulated Angiogenesis in Mouse Matrigel Model

Synthesized compounds 8, 9, 10, 11, 12, 13, 14, and 15 were tested for their ability to stimulate angiogenesis, as measured by the production of hemoglobin in the matrigel assay. $T_4$ significantly induced angiogenesis. $T_4$ analog compounds 8, 9, and 10 also induced angiogenesis in a comparable fashion to $T_4$ (62, 95, and 87%, respectively).

Pro-Angiogenesis Efficacy of $T_4$ Analogs on Angiogenesis in the Mouse-Matrigel Model

| | Hemoglobin (mg/mL) ± SEM[1] | Mean stimulation of angiogenesis (%)[2] |
|---|---|---|
| Control | 0.3 ± 0.1 | — |
| $T_4$ (0.1 µM) | 0.9 ± 0.2 | 100 ± 22 |
| 7 | 0.25 ± 0.1 | 0 ± 8 |
| 8 | 0.7 ± 0.2 | 62 ± 38 |
| 9 | 0.9 ± 0.2 | 95 ± 33 |
| 10 | 0.8 ± 0.2 | 87 ± 33 |
| 11 | 0.6 ± 0.2 | 45 ± 33 |
| 13 | 0.3 ± 0.1 | 0 ± 17 |
| 14 | 0.3 ± 0.1 | 0 ± 17 |
| 15 | 0.3 ± 0.1 | 0 ± 17 |

[1]Hemoglobin data represent mean ± SEM, n = 6-7
[2]All thyroid analogs were tested at a concentration of 10 µg/matrigel plug $T_4$ analog 12 appeared to inhibit T4-induced angiogenesis, as shown below.

Anti-Angiogenesis Efficacy of $T_4$ Analog 12 on Angiogenesis in the Mouse-Matrigel Model

| | Hemoglobin (mg/mL) ± SEM[1] | Mean inhibition of angiogenesis (%) |
|---|---|---|
| Control | 0.3 ± 0.1 | — |
| $T_4$ | 1.2 ± 0.4 | — |
| $T_4$ + Tetrac | 0.4 ± 0.1 | 89 ± 11 |
| $T_4$ + 12 | 0.4 ± 0.1 | 89 ± 11 |

Figure 23:
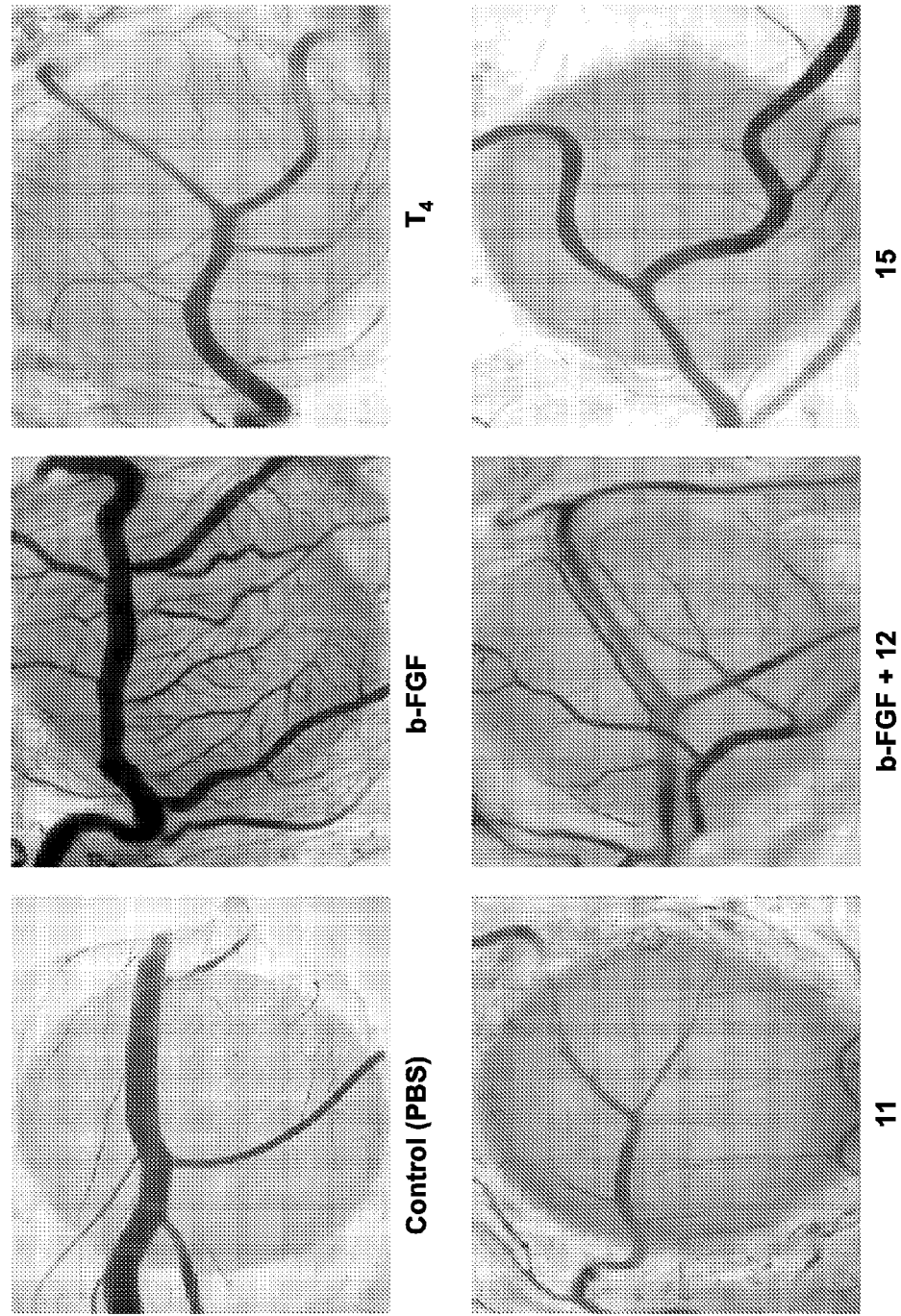
FIG. 23 shows representative illustrations for the proangiogenesis effects of b-FGF; $T_4$; and compound 11. Also shown are the effects of compound 12 (anti-angiogenic) and compound 15 (no effect).

[1]Hemoglobin data represent mean ± SEM, n = 25
[2]$T_4$, 12, and Tetrac were tested at a concentration of 10 µg/matrigel plug FIG. 23 depicts representative images showing the effect on angiogenesis of b-FGF, $T_4$, and compounds 11, 12, and 15.

From the results of both the CAM and matrigel assays, the nucleophilicity of the amino group has only little influence on the activity because the amine was prevented to react via any covalent bonding. These results indicated that the greater the extent of hindrance of the $NH_2$ group, the greater the inhibition of $T_4$ pro-angiogenic activity. That is, all mono-acylated and monoalkylated analogs demonstrated clearly diminished stimulation. A second substitution on the PhOH end (9) did not significantly reduce the potency of the drug, which suggested that this part of the molecule did not participate in binding. A second substitution at the COOH end, on the other end, prevented stimulation completely. One analog, compound 12, had the surprising effect of entirely inhibiting FGF and $T_4$ activity. Compared to analog 11, the presence of an Et group at the acid end of 12 appeared to disable the molecule in terms of stimulating the production of new blood vessels and antagonized the effects of $T_4$ to the same extent as Tetrac.

Figure 24:
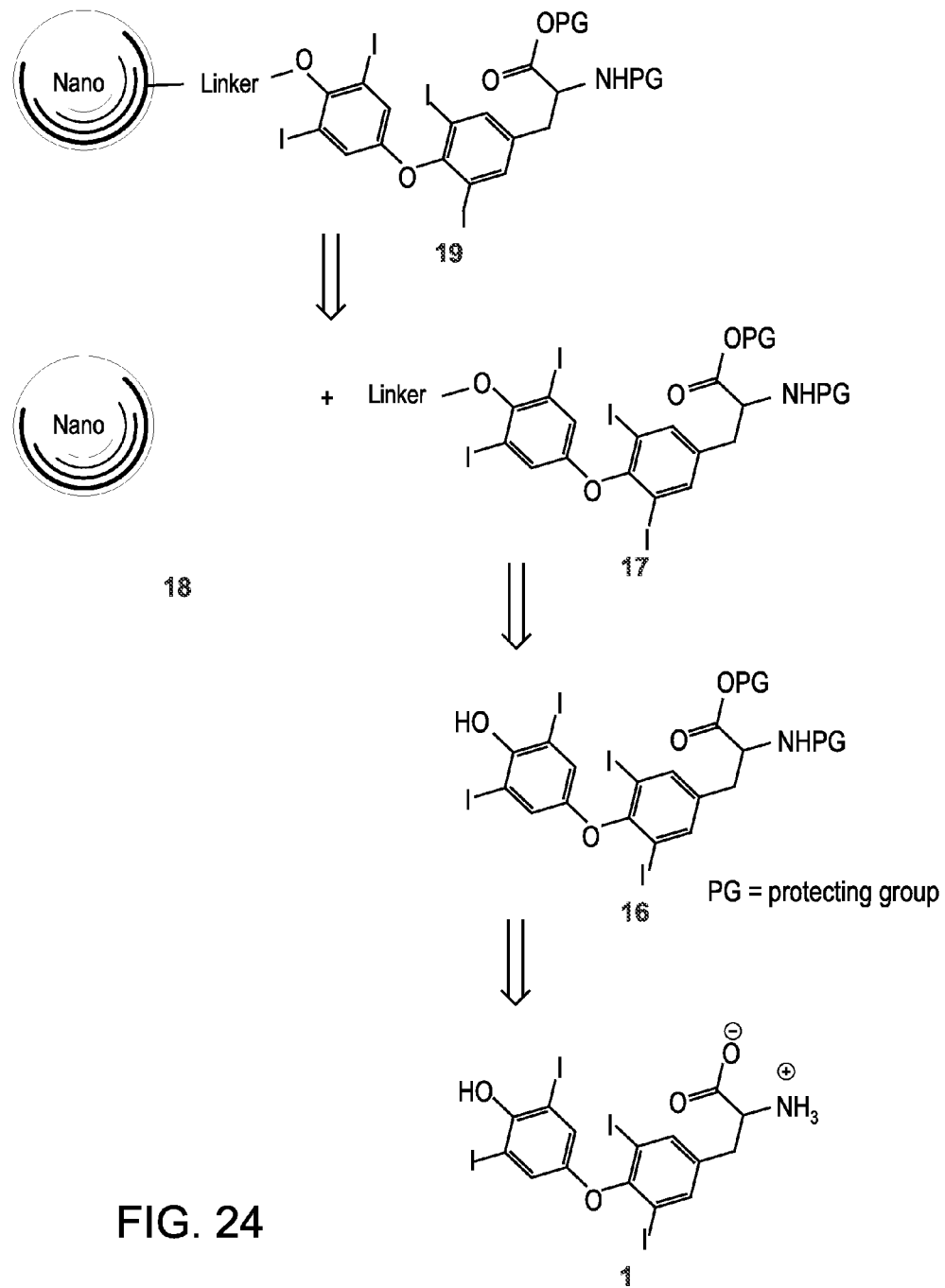
FIG. 24 shows a retrosynthetic scheme for T4-conjugated nanoparticle (19) with synthons PLGA-PVA based nanoparticle (18); activated T4 analog (17); protected T4 analog (16); and T4 (compound 1).

In summary, synthetic modifications of thyroid hormone led to a significantly improved understanding of the functional importance of the COOH and NH2 groups of the molecule for pro-angiogenic activity. A useful compound has been validated as a precursor for a water-soluble nanoparticle formulation of the hormone. The results suggested the OH and PhOH group as the best site for condensation with a nanoparticle. FIG. 24 shows a retrosynthetic scheme for $T_4$-conjugated nanoparticles.

Example 13

Design and Semisynthesis of Tetrac Nanoparticles

Tetrac, a derivative of thyroid hormone, has been shown to significantly reduce the sprouting of vasculature from existing cells and to regulate angiogenesis mediated by thyroid or other growth factors. In order to retain only its anti-angiogenesis effect, Tetrac was immobilized on nanoparticles to prevent intracellular actions of this thyroid hormone analog. Before immobilization, semisynthetic precursors were probed to find the best candidate for further evaluation. (See Bridoux et al., Bioorganic & Medicinal Chemistry Letters 19:3259-63 (2009), incorporated herein by reference). During the course of the planned semisynthesis of Tetrac nanoparticles, a suitable protecting group at the phenylacetic acid end of the Tetrac was required as a first step in the synthesis of the nanoparticle precursors. Since the association to the nanoparticles was conceived to occur at the phenol's OH, it was alkylated after the formation of the carbon and silicon based esters. Representative analog compounds in accordance with this Example are shown below.

Structure of Tetrac Analogs 2-9

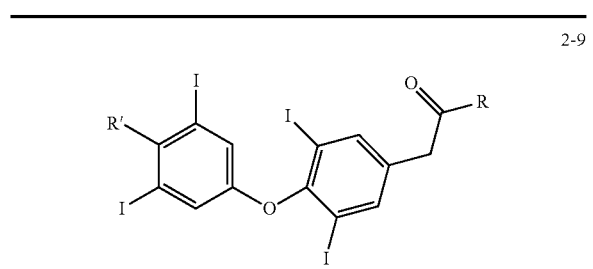

| Compounds | R | R' |
|---|---|---|
| 2 | OMe | H |
| 3 | O$^t$Bu | H |
| 4 | ⁝—N⟨cyclohexyl⟩ | H |
| 5 | OTiPS | H |
| 6 | ⁝—N⟨cyclohexyl⟩ | ⁝—O—CH₂—epoxide |
| 7 | OTiPS | ⁝—O—CH₂—epoxide |
| 8 | ⁝—O—CH₂—epoxide | ⁝—O—CH₂—epoxide |
| 9 | H | ⁝—O—CH₂—epoxide |

Structure of 10-14

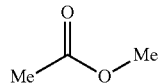

10

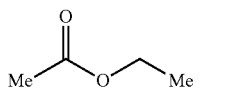

11

[structures 12, 13, 14 continued]

Structure of 10-14

Chain ramification design at the acetic acid end of Tetrac allowed for the consideration of several modulated analogs towards the discovery of a linear synthesis strategy of the nanoparticles' precursors. Anti-angiogenesis efficacy was carried out using the Chick Chorioallantoic Membrane (CAM) model and the mouse matrigel model of angiogenesis.

These compounds were prepared following literature methods. A schematic showing the synthesis of various Tetrac analogs is shown in FIG. 25. The methyl ester (compound 2) was prepared following the method described in Wilkinson, Biochem. J. 63:601 (1956) and published PCT application WO/805761 (1958). Compounds 3 and 4 (see Neises et al., Org. Synth 7:93 (1990)) were new products of the same reaction. Unexpectedly, the main product of the reaction was compound 4. Compound 5 was new and synthesized by deprotonation of Tetrac with TEA or $Cs_2CO_3$ in anhydride DCM and then by addition of TiPSCl. All compounds were submitted to a general method, which consisted of adding a series of several carbon based and silicon based protecting groups to the starting material activated by $Cs_2CO_3$ towards the formation of the esters (compounds 5 and 10-14).

Briefly, compound 6 was obtained by refluxing epibromohydrin with compound 4 in anhydride dioxane. While optimizing the reaction conditions of compound 5 with epibromohydrin, compound 8 was found to be the major side product. During the first attempt, compound 8 was formed equivalently as compound 7. Following attempts to minimize the formation of compound 8, the two step synthesis that was developed to obtain compounds 5 and 7 were condensed via a one-pot semisynthetic process to obtain compound 7. Product 9 was then easily recrystallized in EtOH.

Synthesis and Analytical Characterization

Methyl-2-(4-(4-hydroxy-3,5-diiodophenoxy)-3,5-diiodophenyl)acetate (Compound 2)

Method A: In anhydrous conditions, Tetrac (5.0 g, 6.7 mmol, 1.0 eq.) was dissolved in anhydrous methanol (200 mL). To the solution was then added dropwise $SOCl_2$ (485 μL, 6.7 mmol, 1.0 eq.). The reaction was set to reflux for 2 days. Water was then added to the reaction medium (200 mL)

and then the solution was concentrated to yield a precipitate. The precipitate was then collected by vacuum filtration and then recrystallized to give orange crystals (3.10 g, 4.0 mmol) of methyl-2-(4-(4-hydroxy-3,5-diiodophenoxy)-3,5-diiodophenyl)acetate in 61% yield.

Method B: In anhydrous conditions, Tetrac (1.0 g, 1.3 mmol, 1.0 eq.) was suspended in MeOH (20 mL). TEA (181.4 µL, 1.3 mmol, 1.0 eq.) was then added dropwise followed by benzylchloroformate 184.8 µL, 1.3 mmol, 1.0 eq.). After stirring for 30 minutes, the solution was filtered, the solvent was removed from the residue and the product was separated by silica gel chromatography (eluent=DCM). The collected fractions were then evaporated to give a white powder which was recrystallized to give orange crystals (990 mg, 1.3 mmol) of methyl-2-(4-(4-hydroxy-3,5-diiodophenoxy)-3,5-diiodophenyl)acetate in a quantitative yield.

Orange crystals; recrystallization solvent: EtOH; TLC: 0.81 (DCM); RPTLC: 0.49 (AcOH/H$_2$O, 9/1); IR (υ cm$^{-1}$): 1719 cm$^{-1}$ (CO); HPLC (µBondapak C18): rt=3.2 min (MeOH/H$_2$O 65/35); $^1$H NMR (CDCl$_3$) δ (ppm): 7.78 (s, 2H, ArH), 7.12 (s, 2H, ArH), 5.53 (br, 1H, OH), 3.75 (s, 3H, CH$_3$), 3.58 (s, 2H, CH$_2$); $^{13}$C NMR (CDCl$_3$) δ (ppm): 171.0, 152.8, 150.2, 149.6, 141.3, 135.2, 126.1, 90.9, 81.8, 52.7, 39.8; MS (ESI$^+$) m/z: 785 [M+Na]$^+$; (ESI$^-$) m/z: 761 [M−H]$^-$. Analytically Calculated for C$_{15}$H$_{10}$I$_4$O$_4$: C, 23.55; H, 1.32. Found: C, 24.97; H, 1.33.

tert-Butyl-2-(4-(4-hydroxy-3,5-diiodophenoxy)-3,5-diiodophenyl)acetate (Compound 3)

In anhydrous conditions, Tetrac (30.0 g, 40.1 mmol, 1.0 eq.) was dissolved in anhydrous dioxane (200 mL). Tert-butyl alcohol (11.4 mL, 120.3 mmol, 3.0 eq.) and 4-dimethylaminopyridine (3.9 g, 32.1 mmol, 0.8 eq.) were then added. The solution was stirred and dicyclohexylcarbodiimide (9.1 g, 44.1 mmol, 1.1 eq.) was added over a 5 minutes period. The mixture was stirred for 3 hours at room temperature. The cyclohexylurea that has precipitated was removed by filtration through a fritted Büchner funnel, and the filtrate was washed with 10% potassium bicarbonate solution (2×100 mL). During this procedure, some additional cyclohexylurea precipitated and was removed by filtration of both layers to facilitate their separation. The organic solution was then dried over magnesium sulfate, filtered and then evaporated with a rotary evaporator to obtain the crude product as a yellow powder which was purified by column chromatography (DCM/cyclohexane 90/10) to yield tert-butyl-2-(4-(4-hydroxy-3,5-diiodophenoxy)-3,5-diiodophenyl)acetate (3.2 g, 4.0 mmol) as a solid.

Yield: 10%; white powder; recrystallization solvent: EtOH; TLC: 0.86 (DCM); IR (υ cm$^{-1}$): 1726 (CO); UV-vis (DMSO): λ$_{max}$ nm=257; HPLC (µBondapak C18): rt=4.4 minutes (MeOH/H$_2$O 95/5); HPLC (Luna NH$_2$): rt=3.5 minutes (MeOH/H$_2$O 95/5); $^1$H NMR (CDCl$_3$) δ (ppm): 7.97 (s, 2H, ArH), 7.20 (s, 2H, ArH), 3.71 (s, 2H, CH$_2$), 1.58 (s, 9H, 3 CH$_3$); MS (ESI+) m/z: 804.5 [(M+H)$^+$, 50].

N-cyclohexyl-2-(4-(4-hydroxy-3,5-diiodophenoxy)-3,5-diiodophenyl)acetamide (Compound 4)

In anhydrous conditions, Tetrac (30.0 g, 40.1 mmol, 1.0 eq.) was dissolved in anhydrous dioxane (200 mL). Tert-butyl alcohol (11.4 mL, 120.3 mmol, 3.0 eq.) and 4-dimethylaminopyridine (3.9 g, 32.1 mmol, 0.8 eq.) were then added. The solution was stirred and dicyclohexylcarbodiimide (9.1 g, 44.1 mmol, 1.1 eq.) was added over a 5 minutes period. The mixture was stirred for 3 hours at room temperature. The cyclohexylisocyanate that has precipitated was removed by filtration through a fritted Büchner funnel, and the filtrate was washed with 10% potassium bicarbonate solution (2×100 mL). During this procedure, some additional cyclohexylisocyanate precipitated, which was removed by filtration of both layers to facilitate their separation. The organic solution was then dried over magnesium sulfate, filtered and then evaporated with a rotary evaporator to obtain the crude product as a yellow powder which was purified by column chromatography (DCM/cyclohexane 90/10) to yield N-cyclohexyl-2-(4-(4-hydroxy-3,5-diiodophenoxy)-3,5-diiodophenyl)acetamide (11.2 g, 12.0 mmol) as a solid.

Yield: 30%; white powder; recrystallization solvent: EtOH; TLC: 0.88 (DCM/EtOAc 80/20); IR (υ cm$^{-1}$): 1724 (CO); UV-vis (DMSO): λ$_{max}$ nm=257; MS (ESI+) m/z 829.7 [(M+H)$^+$, 100].

Triisopropylsilyl-2-(4-(4-hydroxy-3,5-diiodophenoxy)-3,5-diiodophenyl)acetate (Compound 5)

In anhydrous conditions, Tetrac (2.1 g, 2.9 mmol, 1.0 eq.) was suspended in THF. TEA (402 µL, 2.9 mmol, 1.0 eq.) was added. After stirring at room temperature for 5 minutes, TiPSCl (618 µL, 2.9 mmol, 1.0 eq.) was added drop by drop. After stirring for 20 minutes, the solvent was evaporated and the crude product was precipitated with diethylether, filtered, and then recrystallized to give triisopropylsilyl-2-(4-(4-hydroxy-3,5-diiodophenoxy)-3,5-diiodophenyl)acetate (2.1 g, 2.3 mmol) as a powder.

Yield: 80%; white powder; recrystallization solvent: EtOH; TLC: 0.77 (DCM); mp=146° C.; IR (υ cm$^{-1}$): 1701 (CO); UV-vis (DMSO): λ$_{max}$ nm=228; HPLC (µBondapak C18): rt=1.5 minutes (CH$_3$CN/buffer pH=4.0 70/30); $^1$H NMR (DMSO-d6) δ (ppm): 7.81 (s, 2H, ArH), 7.11 (s, 2H, ArH), 5.56 (br, 1H, OH), 3.61 (s, 2H, CH$_2$), 1.27-1.33 (m, 3H, 3 CH), 1.05-1.17 (m, 18H, 6 CH$_3$); MS (ESI−) m/z: 903.3 [(M−H)$^-$, 100]. Analytically Calculated for C$_{23}$H$_{28}$I$_4$O$_4$Si: C, 30.55; H, 3.12. Found: C, 30.47; H, 2.83.

N-cyclohexyl-2-(4-(3,5-diiodo-4-(oxiran-2-ylmethoxy)phenoxy)-3,5-diiodophenyl)acetamide (Compound 6)

Compound 4 (2.0 g, 2.1 mmol, 1.0 eq.) was dissolved in anhydrous dioxane (30 mL), then anhydrous Cs$_2$CO$_3$ (684 mg, 2.1 mmol, 1.0 eq.) was added and then epibromohydrin (1.8 mL, 21.0 mmol, 10.0 eq.) was added dropwise. The reaction medium was then slowly heated to reflux. The mixture was stirred during 12 hours upon reflux then cooled to room temperature. EtOAc (10 mL) was then poured and the precipitate was filtered. EtOH (20 mL) was then added to the solution and the precipitate was filtered off. The remaining solution was analyzed by TLC. The first precipitate was washed thoroughly with EtOAc (30 mL). The organic solution was then evaporated and purified by column chromatography using silica gel (DCM/hexanes 80/20). The product was further recrystallized to give N-cyclohexyl-2-(4-(3,5-diiodo-4-(oxiran-2-ylmethoxy)phenoxy)-3,5-diiodophenyl)acetamide (93 mg, 0.1 mmol) as a powder. The second filtrate and the remaining solution were revealed by TLC to be the starting material which did not react.

Yield: 5%; white powder; recrystallization solvent: EtOAc; TLC: 0.37 (DCM); mp=242° C.; IR (υ cm$^{-1}$): 3280 (NH), 1625 (CO); UV-vis (DMSO): λ$_{max}$ nm=255; HPLC (µBondapak C18): rt=6.9 minutes (CH$_3$CN/H$_2$O 90/10); $^1$H NMR (DMSO-d6) δ (ppm): 7.99-8.01 (d, J=7.5 Hz, 1H, NH), 7.81 (s, 2H, ArH), 7.15 (s, 2H, ArH), 4.09-4.12 (dd, J$_1$=3.0

Hz, $J_2$=12.0 Hz, 1H, CH), 3.80-3.83 (dd, $J_1$=3.0 Hz, $J_2$=11.0 Hz, 1H, CH), 3.45-3.55 (m, 2H, 2 CH), 3.39 (s, 2H, $CH_2$), 2.84-2.86 (m, 1H, CH), 2.68-2.69 (m, 1H, CH), 1.40-1.72 (m, 10H, 5 $CH_2$); MS (ESI+) m/z: 907.8 [(M+Na)$^+$, 100]. Analytically Calculated for $C_{23}H_{23}I_4NO_4$: C, 31.21; H, 2.62; N, 1.58. Found: C, 31.60; H, 2.49; N, 1.46.

Triisopropylsilyl-2-(4-(3,5-diiodo-4-(oxiran-2-ylmethoxy)phenoxy)-3,5-diiodophenyl)acetate (Compound 7)

In anhydrous conditions, Tetrac (3.0 g, 4.0 mmol, 1.0 eq.) was suspended in anhydrous THF. TEA (559 µl, 4.0 mmol, 1.0 eq.) was then added. After stirring at room temperature for 5 minutes, TiPSCl (858 µL, 4.0 mmol, 1.0 eq.) was added drop by drop. After stirring for 20 minutes, TEA (559 µL, 4.0 mmol, 1.0 eq.) was added and then epibromohydrin (3.3 mL, 40.0 mmol, 10.0 eq.) was added and the reaction medium was stirred at reflux (55 Celsius degrees) and monitored by TLC. After 12 hours, the reaction medium was cooled, filtered and the organic phase was evaporated. The crude product was then separated by column chromatography (DCM/cyclohexane 90/10) to give triisopropylsilyl-2-(4-(3,5-diiodo-4-(oxiran-2-ylmethoxy)phenoxy)-3,5-diiodophenyl)acetate (1.5 g, 1.6 mmol) as a solid.

Yield: 40%; white powder; recrystallization solvent: EtOAc; TLC: 0.24 (DCM); mp=120° C.; IR (υ cm$^{-1}$): 1711 (CO); UV-vis (DMSO): $\lambda_{max}$ nm=256; HPLC (µBondapak C18): rt=10.6 minutes ($CH_3CN/H_2O$ 90/10); $^1$H NMR (DMSO-d6) δ (ppm): 7.80 (s, 2H, ArH), 7.16 (s, 2H, ArH), 4.10-4.15 (dd, $J_1$=4.0 Hz, $J_2$=10.0 Hz, 1H, CH), 3.99-4.06 (dd, $J_1$=4.0 Hz, $J_2$=10.0 Hz, 1H, CH), 3.61 (s, 2H, $CH_2$), 2.92-2.93 (t, J=4.0 Hz, 1H, CH), 2.78-2.79 (dd, $J_1$=4.0 Hz, $J_2$=10.0 Hz, 1H, CH), 1.28-1.33 (m, 3H, 3 CH), 1.05 (s, 18H, 6 $CH_3$); MS (ESI+) m/z: 804.3 [(M–$C_9H_{21}$Si+H)$^+$, 87], 826.9 [(M–$C_9H_{21}$Si+Na)$^+$, 100]; MS (APCI+) m/z: 961.8 [(M+H)$^+$, 20]. Analytically Calculated for $C_{26}H_{32}I_4O_5Si$: C, 32.52; H, 3.36. Found: C, 32.70; H, 3.13.

Oxiran-2-ylmethyl-2-(4-(3,5-diiodo-4-(oxiran-2-ylmethoxy)phenoxy)-3,5-diiodophenyl)acetate (Compound 8)

In anhydrous conditions, compound 5 (1.0 g, 1.1 mmol, 1.0 eq.) was suspended in anhydrous THF. TEA (154 µL, 1.1 mmol, 1.0 eq.) was then added. After stirring at room temperature for 5 minutes, epibromohydrin (902 µL, 11.0 mmol, 10.0 eq.) was added and the reaction medium was stirred at reflux (55 Celsius degrees) and monitored by TLC. After 12 hours, the reaction medium was filtered and the organic phase was evaporated. The crude product was then separated by column chromatography (DCM/cyclohexane 90/10) to give oxiran-2-ylmethyl-2-(4-(3,5-diiodo-4-(oxiran-2-ylmethoxy)phenoxy)-3,5-diiodophenyl)acetate (236 mg, 0.3 mmol) as a solid.

Yield: 25.5%; white powder; recrystallization solvent: EtOH; TLC: 0.29 (DCM); mp=116° C.; IR (υ cm$^{-1}$): 1732 (CO); UV-vis (DMSO): $\lambda_{max}$ nm=280; HPLC (Luna $NH_2$): rt=4.1 minutes (MeOH); $^1$H NMR (DMSO-d6) δ (ppm): 7.80 (s, 2H, ArH), 7.19 (s, 2H, ArH), 4.11-4.14 (m, 1H, CH), 4.03-4.06 (m, 1H, CH), 3.98-4.00 (m, 2H, 2 CH), 3.64 (s, 2H, $CH_2$), 3.52-3.54 (br, 1H, CH), 3.26 (br, 1H, CH), 2.93-2.94 (t, J=4.5 Hz, 1H, CH), 2.88-2.89 (t, J=4.5 Hz, 1H, CH), 2.79-2.80 (br, 1H, CH), 2.65-2.66 (m, 1H, CH); MS (APCI+) m/z: 860.7 [(M+H)$^+$, 100]. Analytically Calculated for $C_{20}H_{16}I_4O_6$: C, 27.93; H, 1.88. Found: C, 28.20; H, 1.66.

{4-[3,5-diiodo-4-(oxiran-2-ylmethoxy)phenoxy]-3,5-diiodophenyl}acetic acid (Compound 9)

Compound 7 (1.0 g, 1.0 mmol) was left exposed at ambient temperature during 2 weeks and then recrystallized to give {4-[3,5-diiodo-4-(oxiran-2-ylmethoxy)phenoxy]-3,5-diiodophenyl}acetic acid (700 mg, 0.9 mmol) as a powder.

Yield: 84%; white powder; recrystallization solvent: EtOH; TLC: 0.33 (EtOH/EtOAc 90/10); mp=176° C.; IR (υ cm$^{-1}$): 1705 (CO); UV-vis (DMSO): $\lambda_{max}$ nm=256; HPLC (µBondapak C18): rt=4.4 minutes (MeOH/$H_2O$ 95/5); HPLC (Luna $NH_2$): rt=3.5 minutes (MeOH/$H_2O$ 95/5); $^1$H NMR (DMSO-d6) δ (ppm): 7.86 (s, 2H, ArH), 7.16 (s, 2H, ArH), 4.09-4.12 (dd, $J_1$=3.0 Hz, $J_2$=11.0 Hz, 1H, CH), 3.76-3.84 (dd, $J_1$=6.5 Hz, $J_2$=11.0 Hz, 1H, CH), 3.63 (s, 2H, $CH_2$), 3.16-3.17 (t, J=2.5 Hz, 1H, CH), 2.85-2.86 (t, J=5.0 Hz, 1H, CH), 2.69-2.70 (d, J=2.5 Hz, 1H, CH); MS (ESI±) m/z: 827.0 [(M+Na)$^+$, 75], 759.2 [(M–$CHO_2$)$^-$, 100], 803.5 [(M–H)$^-$, 19]. Analytically Calculated for $C_{17}H_{12}I_4O_5$: C, 25.40; H, 1.50. Found: C, 26.01; H, 1.22.

2-(4-(4-(2-chloroethoxy)-3,5-diiodophenoxy)-3,5-diiodophenyl)-N-cyclohexylacetamide (Compound 15)

Compound 4 (2.0 g, 2.1 mmol, 1.0 eq.) was dissolved in anhydrous dichloroethane (30 mL) and then $Cs_2CO_3$ (1.7 g, 5.2 mmol, 2.5 eq.) was added. The reaction medium was then slowly heated to reflux. The mixture was stirred for 12 hrs. upon reflux then cooled to room temperature, filtered and the solvent was removed under vacuum. The residual oil then was purified by column chromatography (DCM/hexanes 80/20). The product was further recrystallized to give 2-(4-(4-(2-chloroethoxy)-3,5-diiodophenoxy)-3,5-diiodophenyl)-N-cyclohexylacetamide, compound 15, (94 mg, 0.1 mmol) as a powder.

Yield: 5%; white powder; recrist. solvt.: EtOAc; TLC: 0.24 (DCM); mp=263° C.; IR (υ cm$^{-1}$): 3270 (NH), 1643 (CO); UV-vis (DMSO): $\lambda_{max}$ nm=257; HPLC (µBondapak C18): rt=10.6 min $CH_3CN/H_2O$ 90/10); $^1$H NMR (DMSO-d6) δ (ppm): 7.99-8.01 (d, J=7.5 Hz, 1H, NH), 7.81 (s, 2H, ArH), 7.16 (s, 2H, ArH), 4.13-4.15 (t, J=4.5 Hz, 2H, $CH_2$), 3.99-4.01 (t, J=5.0 Hz, 2H, $CH_2$), 3.45-3.50 (m, 2H, 2 CH), 3.39 (s, 2H, $CH_2$), 1.14-1.73 (m, 10H, 5 $CH_2$); MS (ESI+) m/z 913.6 [(M+Na)$^+$, 100]. Anal. Calcd. for $C_{22}H_{22}Cl_{14}NO_3$: C, 29.64; H, 2.49; N, 1.57. Found: C, 30.62; H, 2.38; N, 1.44.

Results

Synthesis of Tetrac Analogs

As noted above, the first Tetrac analogs were prepared following literature methods. The methyl ester compound 2 was prepared following a described method in 80% yield. Compounds 3 and 4 were new products of the same reaction and were prepared following another described method for the synthesis of tert-butyl esters. The main product of the reaction was compound 4 (30% yield) and was obtained after activation of Tetrac with dicyclohexylcarbodiimide (DCC) in presence of 4-dimethylaminopyridine (DMAP) in a catalytic quantity, at room temperature and in anhydrous dioxane. Compound 5 was new and synthesized as shown in FIG. 25.

Moreover, a yet undetermined product of decomposition was obtained when stirred with benzylchloroformate in the same reaction conditions. Investigations of the syntheses of other analogs were done still using an aprotic solvent and revealed to be unsuccessful as Tetrac reacted hardly with any other substances towards the formation of the esters (Compounds 2-8) (FIGS. 25-26).

Esterification of Tetrac

Only few examples of experiments devoted to the synthesis of Tetrac analogs have appeared in the literature. As the esterification of Tetrac mainly involved the reaction of the carboxylic acid with an alcohol and an acid catalyst, the first compound 2 (FIG. 25) was prepared in this way using dimethoxypropane as a dehydrating agent and camphor sulfonic acid as the catalyst. The alkaline hydrolysis method used for this type of ester had no synthetic value in deprotecting Tetrac when linked to a nanoparticle. Thus, the tert-butyl esterification of Tetrac was a preferred pathway to follow and also because of its well characterized acidolysis deprotection. When looking at the literature, precursor studies that allowed the obtaining of tert-butyl esters of carboxylic acids in excellent yield were reported and were taken in consideration to produce the selectively modified Tetrac ester compound 3. Here, it was determined that when treating Tetrac with DMAP in anhydrous dioxane, on a catalyst-to-acid ratio of 0.8, the tert-butyl ester compound 3 was obtained in a low 10% yield as the minor product of the reaction. Surprisingly, the major product was the compound 4 (FIG. 25). It is also noteworthy that even after repetitive filtration, those products were both still found to be highly contaminated by a compound which showed clear multiple displacements in the cycloalkane region by $^1$H NMR spectroscopic analysis. This impurity was then found to be similar to the cyclohexylurea spectra by IR spectrometry and NMR spectroscopy.

Figure 26:
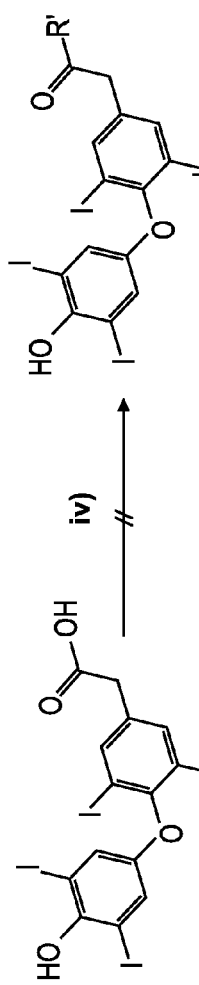
FIG. 26 is a schematic showing the synthesis attempts of Tetrac analogs following $SN_2$ type reaction conditions.

Tetrac was later mixed in anhydrous conditions with several substances of varied strength to probe its nucleophilicity in $SN_2$ type esterification (FIG. 26). These involved alkylating the carboxylic acid using a base to obtain the carboxylate and preferably a haloalkane containing an iodide such as iodomethane or iodoethane. For those products (compounds 2 and 6), the yield of the reactions were very low and chromatography of the detected products did not afford a sufficient amount for further structure characterizations and method developments. In these reactions, the aprotic solvent was used to complex the cation formed after deprotonation and to enhance the reactivity of the nucleophile. In these conditions, the less hindered alkane substrates should have reacted better. Attempts to obtain aromatic esters have also been made by treating the acid with benzylbromide (BnBr) but, despite a good leaving group, no reactivity was detected toward the reagent. Moreover, only an unexpected product was obtained when Tetrac was mixed with benzylchloroformate in THF. The proton NMR spectrum indicated the presence of an additional methyl group revealed to be linked to the phenol by carbon NMR spectroscopy. Positive and then negative mass spectrometry scans revealed a molecular ion of 1 unit above the expected m/z if the diiodophenol was only methylated.

Semisynthetic Pathways to the Nanoparticle Precursors

Figure 30:
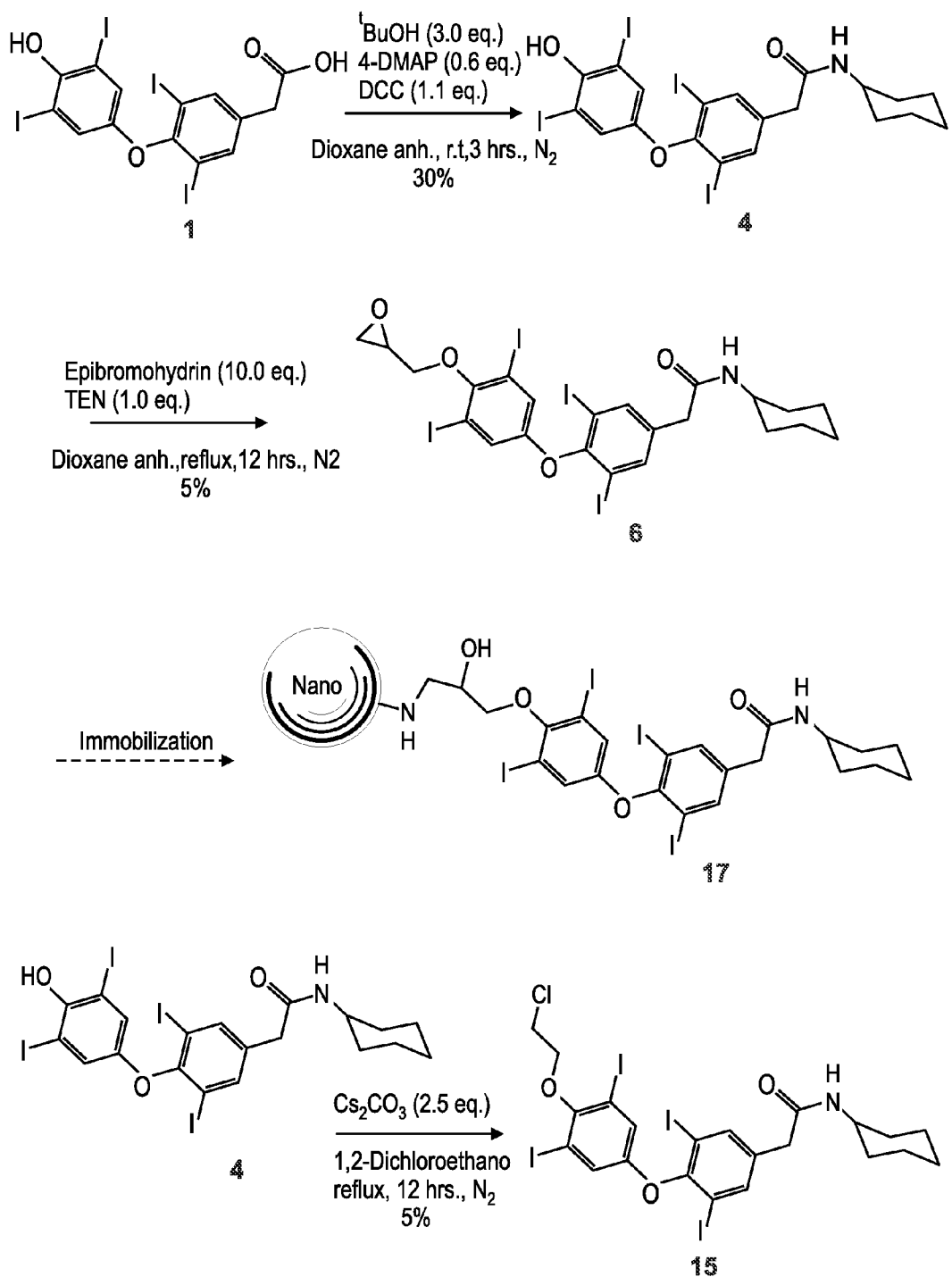
FIG. 30 is a schematic of the syntheses of precursors N-cyclohexyl-2-(4-(3,5-diiodo-4-(oxiran-2-ylmethoxy)phenoxy)-3,5-diiodophenyl)acetamide (compound 6) and 2-(4-(4-(2-chloroethoxy)-3,5-diiodophenoxy)-3,5-diiodophenyl)-N-cyclohexylacetamide (compound 15).

In parallel to the experiments testing the nucleophilicity of Tetrac, compound 4 originally served to probe the strategy of experiments devoted to the immobilization of the free molecule. Without further purification of the urea, compound 4 was used for the preparation of compound 6 and compound 17 (FIG. 30). Compound 4 was dissolved in anhydrous dioxane and then an inorganic base and epibromohydrin were added. The reaction was heated at reflux and then, after a chromatography, compound 6 was obtained in 5%. Following the same pathway, the chloroethyl-substituted cyclohexylcarboxamido analog compound 15 was obtained in 5%.

Figure 31:
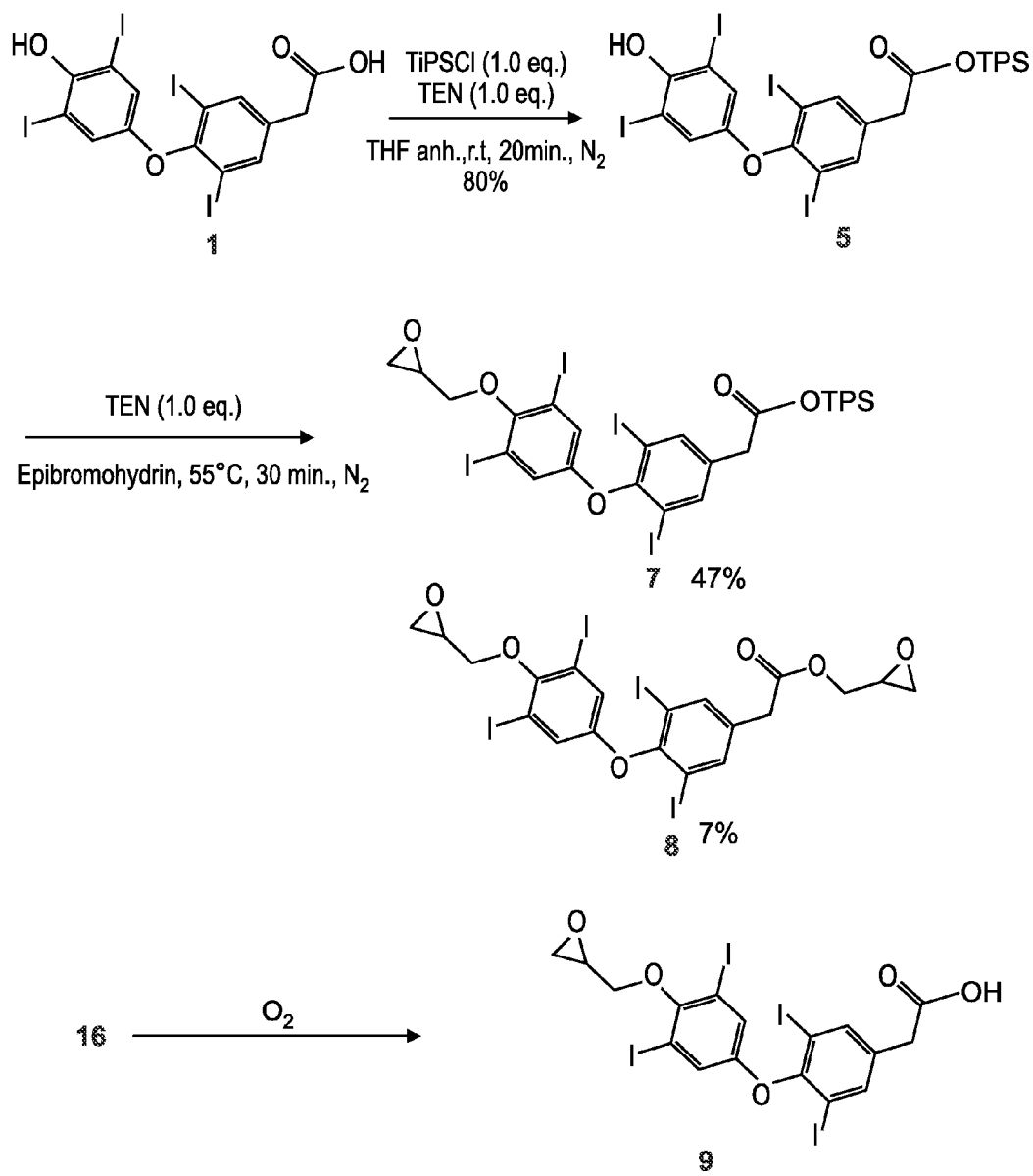
FIG. 31 is a schematic of the syntheses of precursors triisopropylsilyl-2-(4-(3,5-diiodo-4-(oxiran-2-ylmethoxy)phenoxy)-3,5-diiodophenyl)acetate (compound 7) and {4-[3,5-diiodo-4-(oxiran-2-ylmethoxy)phenoxy]-3,5-diiodophenyl}acetic acid (compound 9).

Nevertheless, these two candidates to immobilization were considered to be the best suitable and reachable forms of the activated and protected Tetrac nanoparticles precursors. For practical reasons, as the association to the nanoparticle is done in water, only compound 6 was chosen for a future immobilization in compound 17. As Tetrac was then found to be protected by the TiPSC1 in high yield, this pathway seemed the best to follow to reach the immobilized formulation compound. TiPSC1 (1.0 eq.) was stirred with the carboxylate form of Tetrac during 2 hrs. in anhydrous DCM, acetone and THF to afford compound 5 within the same range of yield (FIG. 31). Moreover, this group was deprotected quantitatively with an aqueous tetrabutylammonium fluoride (TBAF) solution from compound 5 to reversely give Tetrac.

Figure 27:
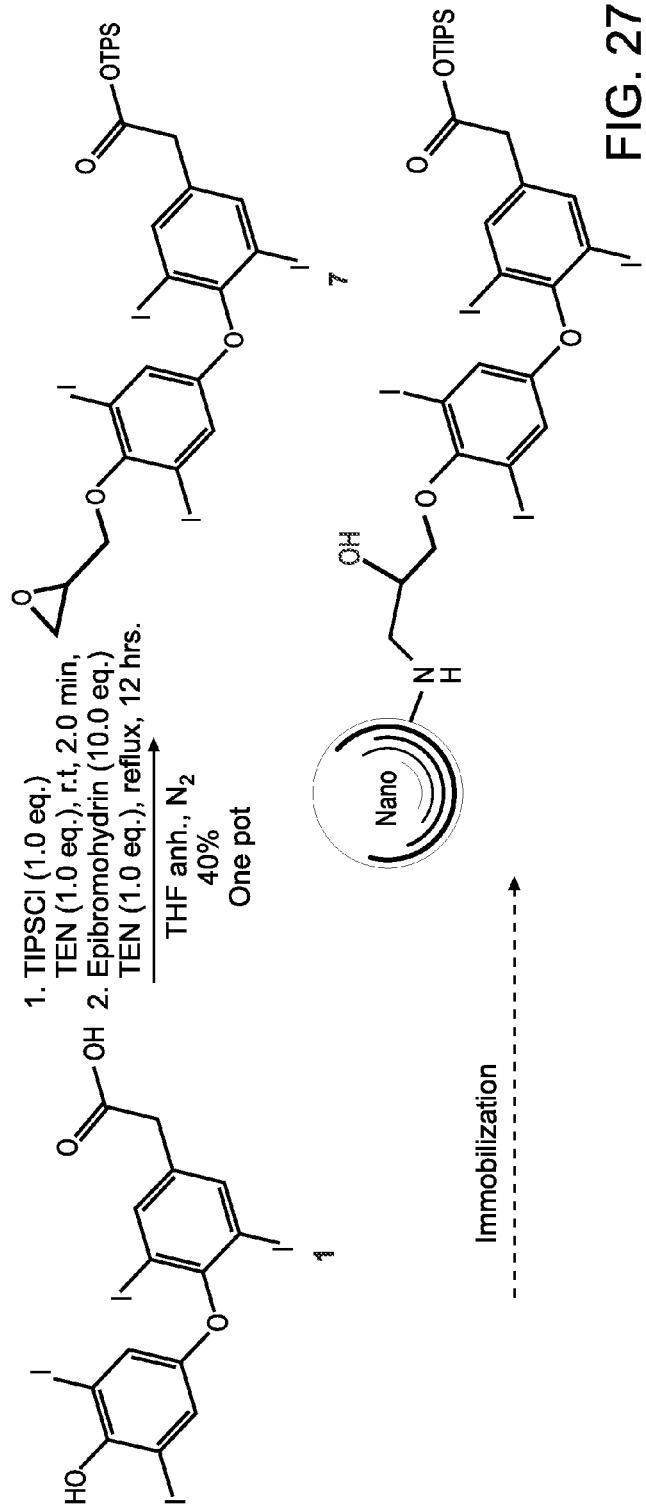
FIG. 27 is a schematic of the one pot synthesis of triisopropylsilyl-2-(4-(3,5-diiodo-4-(oxiran-2-ylmethoxy)phenoxy)-3,5-diiodophenyl)acetate (compound 7) and subsequent conjugation to a nanoparticle.
Figure 29:
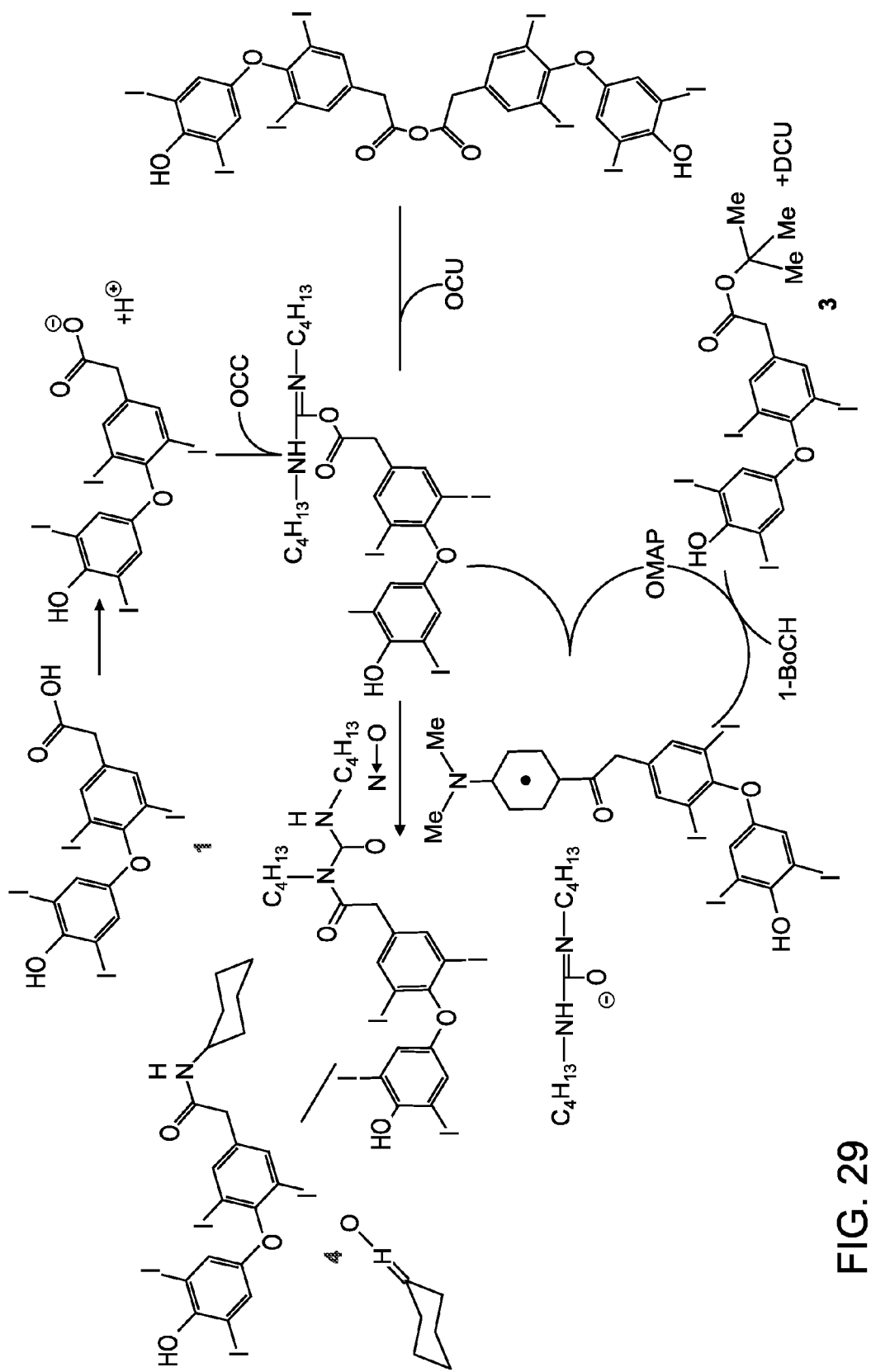
FIG. 29 is a schematic of the reaction mechanism for the formation of tert-butyl-2-(4-(4-hydroxy-3,5-diiodophenoxy)-3,5-diiodophenyl)acetate (compound 3) and N-cyclohexyl-2-(4-(4-hydroxy-3,5-diiodophenoxy)-3,5-diiodophenyl)acetamide (compound 4).
Figure 32A:
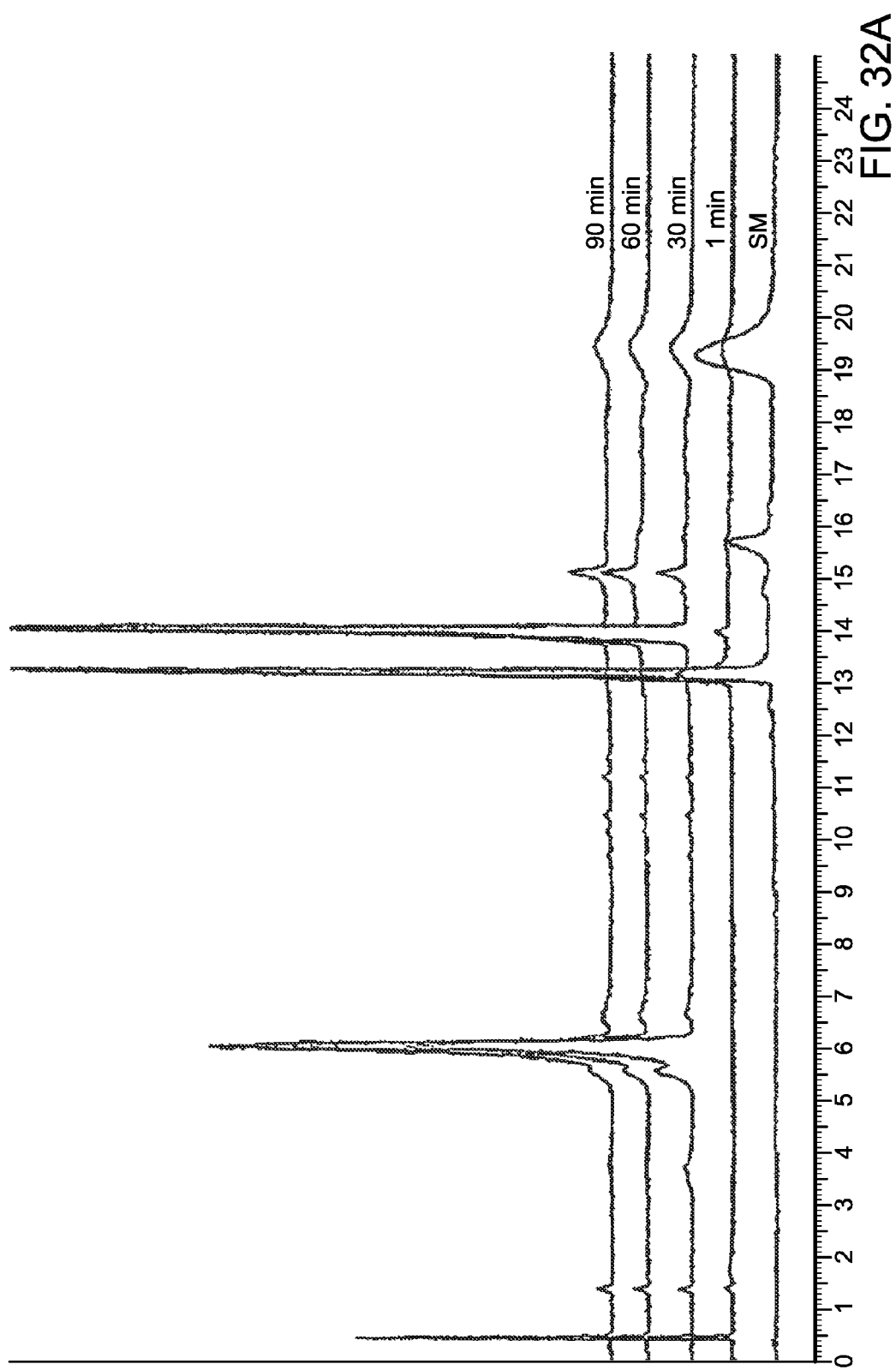
FIGS. 32A-E show HPLC chromatograms of the optimization study of the synthesis of Triisopropylsilyl-2-(4-(3,5-diiodo-4-(oxiran-2-ylmethoxy)phenoxy)-3,5-diiodophenyl) acetate (compound 7).
Figure 32B:
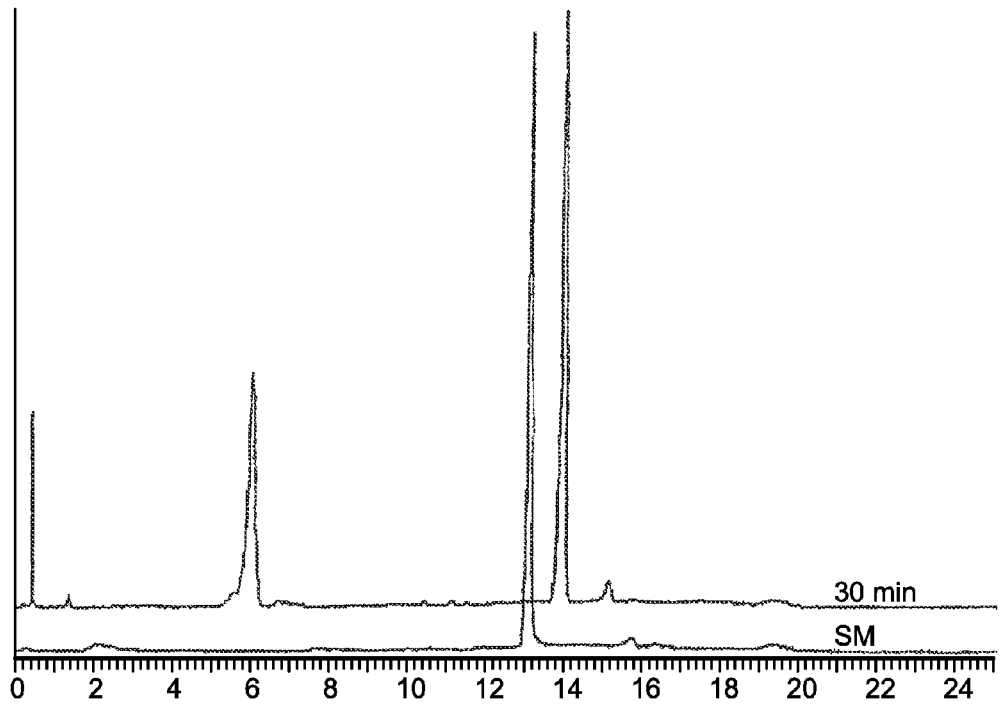
Figure 32C:
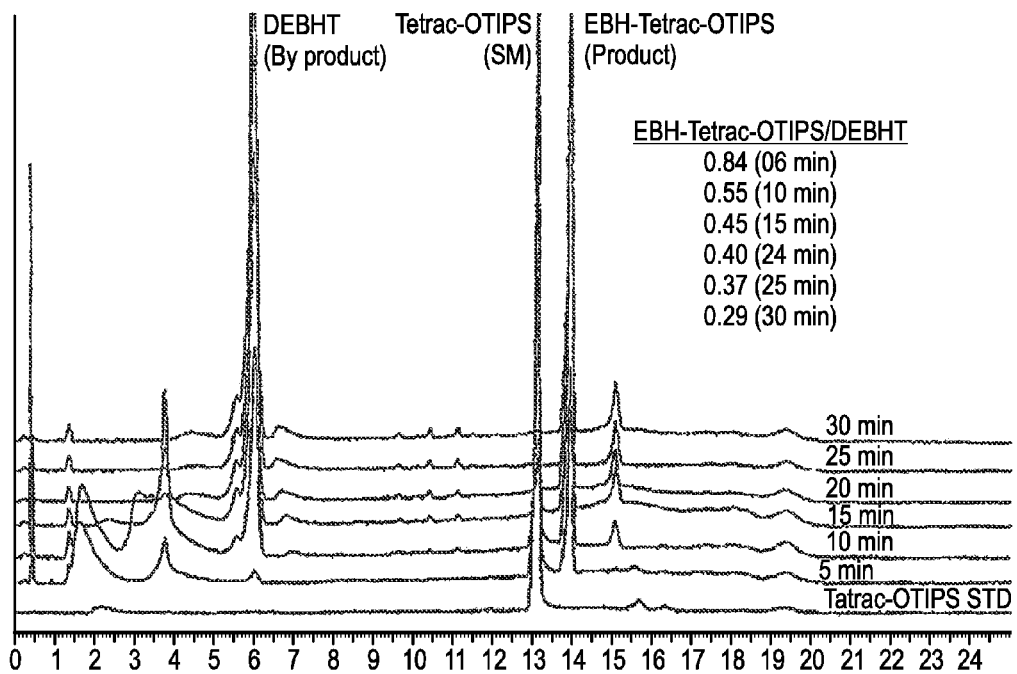
Figure 32D:
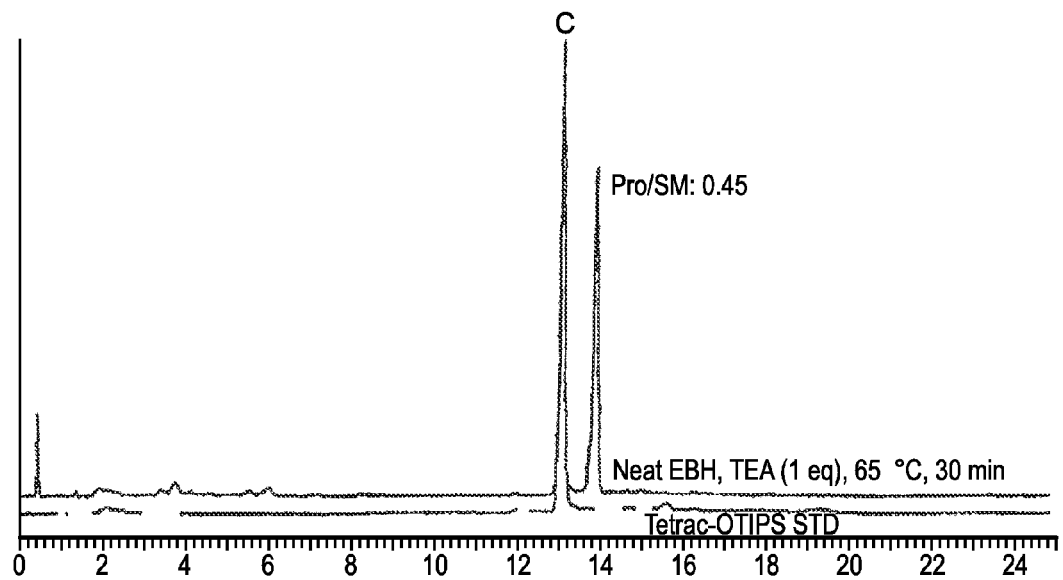
Figure 32E:
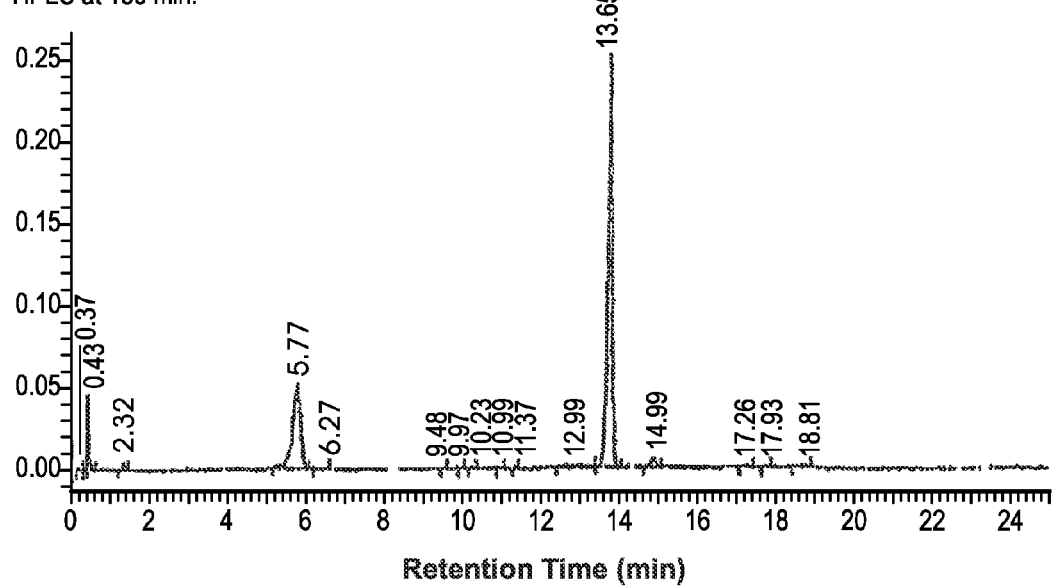

While optimizing the reaction conditions of the condensation of compound 5 (Tetrac-OTiPS) with epibromohydrin (EBH), compound 8 (DEBHT) was found to be the major side product (FIG. 31). During the first attempt, compound 8 was formed equivalently as compound 7 (EBH-Tetrac-OTiPS). In order to minimize the formation of compound 8, five experiments were subsequently done and were monitored by HPLC (FIG. 32). At first, the reaction conditions were modulated to minimize the formation of compound 8 by temperature/time control. The starting material was completely transformed at 30 min. and no evolution in the compound 7/8 ratio was detected over 90 min. (FIG. 32A). The second experiment analyzed the effect of using an excess of the base (FIG. 32B). A larger amount was found to have minor effect on the course of the reaction as the compound 7/8 ratio was just slightly higher at 30 min. In the third experiment, the reaction kinetics were monitored at 5 min. intervals from 0 to 30 min. (FIG. 32C). The starting material was nearly consumed at 20 min. and the compound 7/8 ratio changed from 0.94 to 0.29 from 5 to 30 minutes. Interestingly, when using 1.0 eq. of TEN, no deprotection of compound 5 was detected over a period of 30 min. (FIG. 32D) as only one additional peak corresponding to the retention time of compound 7 was detected on the chromatogram by lowering the heating temperature to 55° C. using 1.0 eq. of base and a large excess of epibromohydrin at a reaction time of 150 min. Also, the reaction was found to be neater, in those conditions at a reaction time of 30 min. Thereafter, the reaction was performed on a larger scale (300 mg) with 1.0 eq. of base and monitored over a 150 min. period (FIG. 32E). From 30 min. to 150 min. and longer, the compound 7/8 ratio was found staggering to 0.73 together with a total consumption of the starting material in 47% yield (FIG. 31). Using the optimized conditions, the two steps synthesis developed to obtain compounds 5 and 7 were then reproduced via a one pot semisynthetic process to obtain compound 7 in an overall 40% yield in which Tetrac was first quantitatively esterified and the intermediate directly condensated with large excess of epibromohydrin at reflux (FIG. 27).

Figure 33:
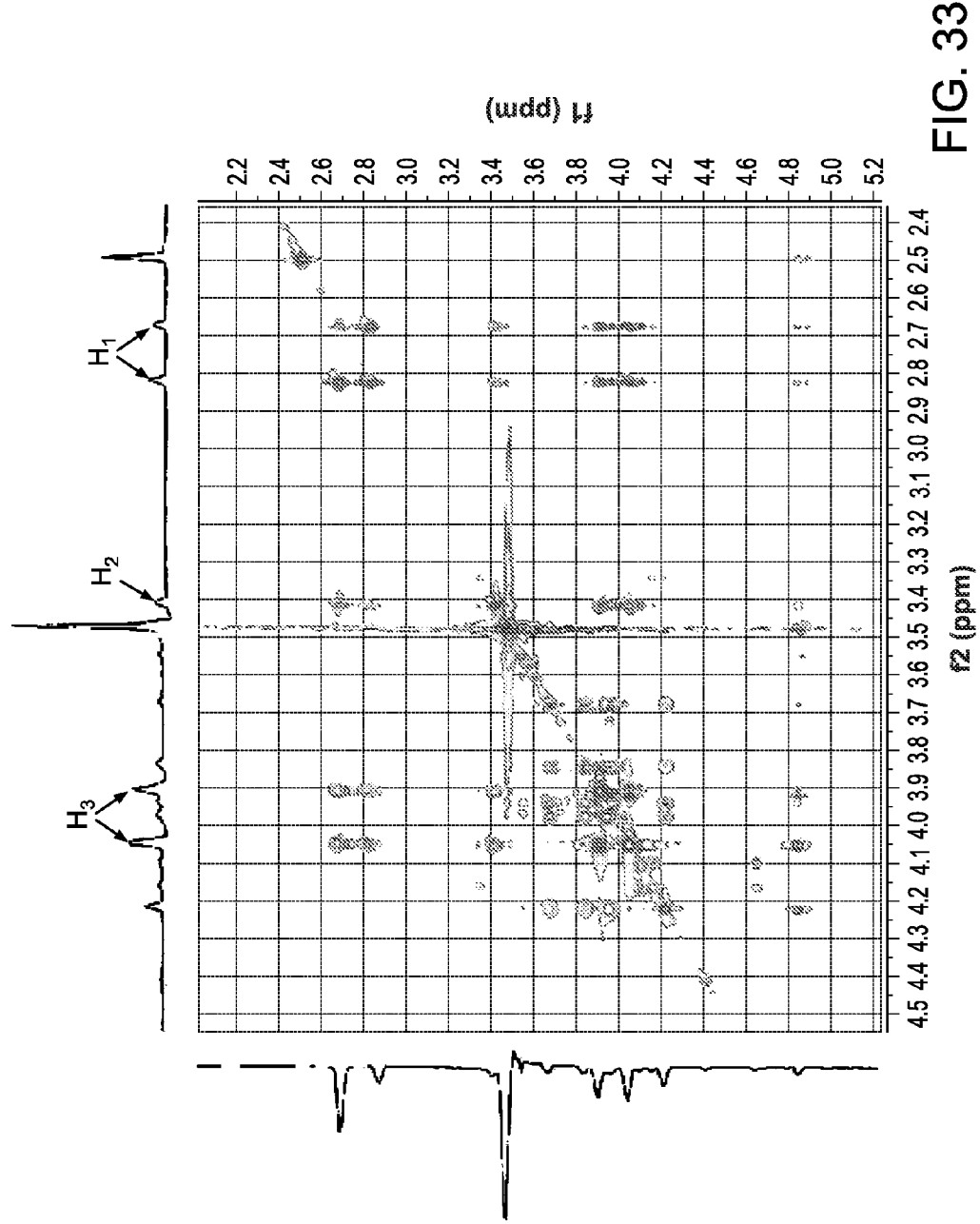
FIG. 33 is a graph of the TOCSY 2D NMR spectrum of {4-[3,5-diiodo-4-(oxiran-2-ylmethoxy)phenoxyl]-3,5-diiodophenyl}acetic acid (compound 9). A zoom in of the aliphatic region is shown.

Interestingly, the product, compound 9 was then isolated after exposure of compound 7 to ambient air and then recrystallized in EtOH (FIG. 31). Compound 9 showed the expected aliphatic displacements by $^1$H NMR and further TOCSY 2D NMR (FIG. 33) spectroscopic analysis showed the expected NOE resonances couplings between all neighbor protons on the epoxide aliphatic chain (long vertical lines of five dots at $\delta_{ppm}$=4.09-4.12 ($H_3$), 3.76-3.84 ($H_3$), 3.17-3.16 ($H_2$), 2.86-2.85 ($H_1$), and 2.70-2.69 ($H_1$)). This fully characterized compound clearly could be used as a nanoparticle precursor too and was thus analyzed for its anti-angiogenic activity with the other analogs.

Figure 34:
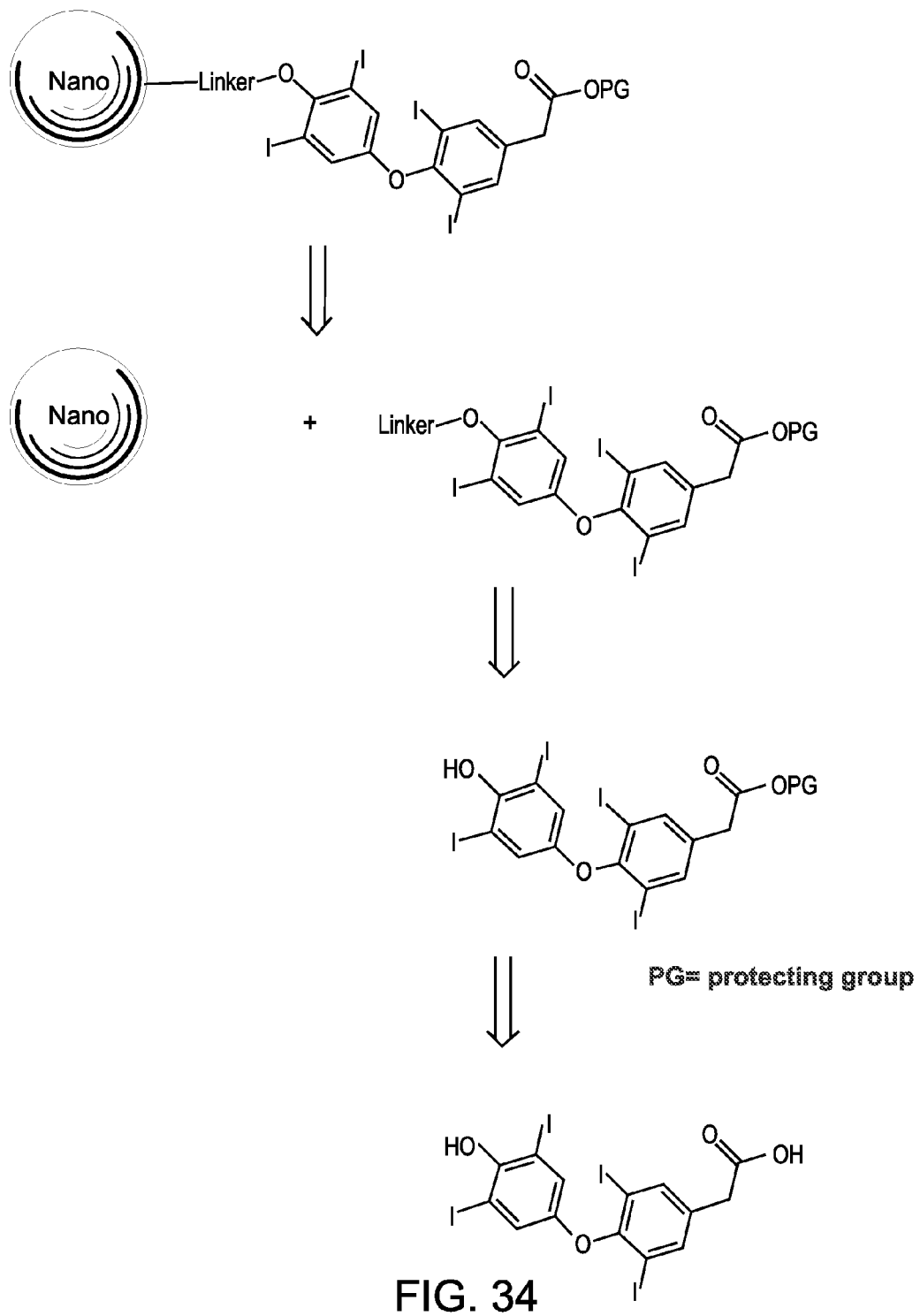
FIG. 34 is a schematic showing the retrosynthetic analysis of a Tetrac nanoparticle.

FIG. 34 shows a retrosynthetic analysis of nanoparticulate Tetrac.

Tetrac Inhibition of FGF-Stimulated Angiogenesis

In the experiments, compounds were considered to be strong inhibitors if they achieved more than 50% inhibition as compared to the control. In the CAM experiments, Tetrac analog compounds showed a strong inhibitory effect on new blood vessel formation within the range from 75% to 97%, as shown below, comparable to 85% of Tetrac.

Anti-Angiogenesis Efficacy of Tetrac Analogs in the CAM Model

| Treatment | Mean Branch points[1] | Mean % Inhibition[2] |
|---|---|---|
| PBS | 73 ± 6 | — |
| FGF (1.25 µg/ml) | 130 ± 11 | — |
| FGF + Tetrac | 81 ± 8 | 85 ± 14 |
| FGF + 3 | 79 ± 7 | 88 ± 13 |
| FGF + 4 | 121 ± 4 | 15 ± 8 |
| FGF + 5 | 87 ± 11 | 75 ± 19 |
| FGF + 13 | 105 ± 7 | 44 ± 13 |
| FGF + 16 | 75 ± 11 | 96 ± 21 |
| FGF + 17 | 112 ± 10 | 31 ± 18 |
| FGF + 18 | 94 ± 10 | 62 ± 18 |

[1]Data representing mean ± SEM, n = 8
[2]Tetrac and analogs were tested at 10 µg/plug Tetrac Inhibition of FGF-Stimulated Angiogenesis in Mouse Matrigel Model Different doses of Tetrac (10 or 30 µg) significantly inhibited FGF induced angiogenesis (85-91% inhibition, respectively) in the mouse matrigel model. Tetrac analog compounds also blocked the FGF induced angiogenesis in a comparable fashion to Tetrac (+10%) (see below).

Anti-angiogenesis Efficacy of Tetrac Analogs on FGF-Induced Angiogenesis in the Mouse-Matrigel Model

| | Hemoglobin (mg/mL) ± SEM[1] | Mean inhibition of angiogenesis (%)[2] |
|---|---|---|
| Control | 0.3 ± 0.1 | — |
| FGF 100 ng | 2.4 ± 0.4 | — |
| FGF + Tetrac 10 µg | 0.5 ± 0.1 | 90 ± 13 |
| FGF + 3 | 0.4 ± 0.1 | 95 ± 14 |
| FGF + 4 | 0.2 ± 0.1 | 104 ± 12 |
| FGF + 5 | 0.2 ± 0.1 | 104 ± 14 |
| FGF + 6 | 0.7 ± 0.1 | 80 ± 16 |
| FGF + 7 | 0.3 ± 0.1 | 100 ± 9 |
| FGF + 8 | 0.3 ± 0.1 | 100 ± 14 |
| FGF + 9 | 0.3 ± 0.1 | 100 ± 12 |

[1]Hemoglobin data represent mean ± SEM, n = 7-14
[2]Tetrac and analogs were tested at 10 µg/plug Inhibition with compounds 3, 4, 5, 6, 7, 8, and 9 was observed to be strong. Any modulations on either or both sides of Tetrac did not affect greatly the antagonist effect of the parent compound. Though the inhibition of angiogenesis in the CAM assay by compounds 4, 6, and 8 was not as strong as compounds 3, 5, 7, and 9, their activities were better in the matrigel assay.

As the highly stable tertbutyl-Tetrac ester (compound 3), which can only be deprotected in acidic conditions and the compound 7, which was protected at both ends showed the same activity at inhibiting FGF-induced angiogenesis, the phenol and carboxylic acid were proven not to be mandatory for the activity of the molecule. These results support the hypothesis of a specific binding site on the integrin designed to interact with the tetraiodophenoxyphenol core of the thyroid hormones.

Solutions to the Low Solubility of Tetrac and Structure Activity Relationship Analysis of the Tetrac Analogs Tetrac was a compound difficult to solubilize in water and required a high volume of cosolvent (DMSO). When looking at the amorphous state, the solid was not stable and quickly returned to the crystal state. Thus, Tetrac was used as a salt with Na$^+$ as the counterion which reduced the use of DMSO to 10%. Then all analogs were solubilized with 10% DMSO in water for the TiPS protected analogs and in PBS for the others.

Any modulations on either or both sides of Tetrac did not affect greatly the antagonist effect of the parent compound. A minor difference was detected between the compounds permanently protected compounds 4, 6, and 8 and the temporarily protected analogs compounds 5 and 7. The TiPS protected analogs were equal to or better antagonist than Tetrac. Those results tend to indicate that Tetrac and its analogs act as competitive binders as the highly stable cyclohexylcarboxamido-Tetrac compound 4, which can only be deprotected in strong acidic conditions, and Tetrac-OTiPS compound 5 solely could have interacted by Van der Waals forces at the site of action, moreover, the analog compound 8, which possess two potent sites of interactions by covalent bonding, showed the same activity. In addition, these observations considered with previously reported results tend to implicate utterly the tetraiodophenoxyphenol core for site recognition independently of the substitution.

Example 14

Preparation of a PLGA-Tetrac Conjugate Containing a Linking Moiety, and Preparation of Tetrac Nanoparticles PLGA-amino-Tetrac conjugate (7) was prepared in 6 steps as shown in Sketch 14-1 and as described below. Tetrac nanoparticles were prepared from PLGA-amino-Tetrac (7) as described below.

Step 1. Dichloro-Tetrac derivative (2) was prepared according to the following procedure. Potassium carbonate (76 g, 0.55 moles, 325 mesh) was added in portions (20 g size) to a mixture of Tetrac (1) (119.5 g, 0.16 moles), and 1-bromo-3-chloropropane (252 g, 1.60 moles) in acetone (1.25 L). The suspension was slowly (30 min) heated to a gentle reflux (58-59° C.). After 5.5 h the reaction mixture was cooled to ~45° C. and filtered. The cake was washed with dichloromethane (3×500 mL) and the filtrate was evaporated to an oil. n-Heptane (1.5 L) was added to the oil and evaporated to a volume of approximately 1 L. The white solids of the dichloro-Tetrac derivative (2) were allowed to stand overnight at room temperature and filtered. The solids were washed with n-Heptane (2×200 mL) and dried under vacuum (room temperature) to give 137.9 g (Yield=95%).

Step 2. Dichloro-Tetrac derivative (2) was converted to chloro-Tetrac derivative (3) according to the following procedure. A solution of potassium hydroxide (50 g, 88%, 0.78 moles) in ethanol (1.0 L, 190 proof) was added to a mixture of (2) (135 g, 0.15 moles) in ethanol (1.0 L, 190 proof). The resulting mixture was stirred at room temperature for 5 h and then cooled to 12° C. The reaction mixture was acidified with hydrochloric acid (~70 mL, 0.86 moles) in ethanol (100 mL, 190 proof) to a pH of approximately 1. The suspension was evaporated to ~1 L volume and deionized (DI) water (1.5 L) was added. The mixture was allowed to cool to room temperature and filtered. The precipitate was washed with DI water (4×300 mL). The precipitate was dried at 45° C. under vacuum for three days to give 124.3 g of Chloro-Tetrac derivative (3) (yield=100%).

Step 3. Chloro-Tetrac derivative (3) was converted to iodo-Tetrac derivative (4) using the following procedure. A solution of (3) (138 g, 0.165 moles) in acetone (1.0 L) was added to a solution of sodium iodide (700 g, 4.65 moles) in acetone (800 mL) and the reaction mixture was heated to a gentle reflux (59-60° C.) for 26 h. The reaction mixture was evaporated to remove most of the acetone (residual weight ~1 kg) and the resulting solid was stirred with DI water (2 L) for 1 h. The solids were filtered and washed with DI water (4×500 mL). The solid was dried at 45-50° C. under vacuum for four days to give the iodo-Tetrac derivative (4) as a pale yellow solid (151.9 g, yield=100%).

Step 4. Iodo-Tetrac derivative (4) was converted to diamino-Tetrac derivative (5) using the following procedure. Iodo-Tetrac derivative (4) (50 g, 0.05 moles) was added to 1,3-diaminopropane (500 mL, 5.9 moles) slowly while maintaining temperature below 28° C. The clear reaction mixture was stirred at room temperature for 2 h. A solution of sodium hydroxide (1 N, 50 mL) was added and the solvent was evaporated at 50-55° C. using a high vacuum pump until a weight of 77.5 g was reached. The crude diamino-Tetrac derivative (5) was purified over silica gel 500 g (70-230 mesh) eluting with a mixture of $CH_2Cl_2$:MeOH:7N $NH_3$ (60:40:6). Pure fractions (TLC, silica plates) were collected and evaporated. The resulting mixture was stirred with a mixture of ethanol (200 mL) and $CH_2Cl_2$ (300 mL). After two hours of stirring the solids were filtered and washed with a mixture of ethanol:$CH_2Cl_2$ (50 mL, 1:1 mixture). The product was dried at 45° C. overnight to give diamino-Tetrac derivative (5) (24.1 g, yield=56%).

Step 5. PLGA-NHS (6) was prepared separately according to the following procedure. Polylactide-co-glycolide (PLGA, average MW=8,300, having hydroxide and carboxylic acid end groups) was dissolved in $CHCl_3$ (5 mL/g) containing 10 equivalents each of N-hydroxysuccinimide and EDC HCl (1-ethyl-3-(3-dimethylaminopropyl)carbodiimide). The resulting solution was stirred overnight at ambient temperature followed by concentration under vacuum at ambient temperature. Concentration of the mixture afforded a viscous solution to which was added to ca. 15 volumes of methanol. Upon addition of methanol, a white precipitate immediately formed. The mixture was allowed to stir for 3 h at ambient temperature, the supernatant decanted and fresh methanol (ca. 3 volumes) added. The suspension was stirred overnight and the methanol decanted. The PLGA-NHS was dried under vacuum at ca. 55° C. for several hours.

Step 6. PLGA-amino-Tetrac conjugate (7) was prepared according to the following procedure. One equivalent of PLGA-NHS (6) was dissolved in DMSO (10.5 mL/g) and stirred until homogenous. To this was added Diamino-Tetrac derivative (5) (1.5 equivalents) in one portion providing a heterogeneous mixture. The mixture was stirred overnight. The mixture was slowly poured into methanol (15 volumes relative to DMSO) producing a white precipitate. The mixture was stirred for several hours and the methanol decanted from the solid. Fresh methanol (60 mL) was added to the product, the methanol decanted from the solid product and the desired PLGA-amino-Tetrac conjugate (7) (see FIG. 51) dried in vacuo.

Preparation of Tetrac Nanoparticles.

Tetrac nanoparticles were prepared by dissolving the PLGA-amino-Tetrac conjugate (7) in an organic solvent (methylene chloride) and subsequently dispersing in an aqueous phase containing 1-2% polyvinyl alcohol using a homogenizer. This primary emulsion was then passed through a secondary homogenizer to produce a nanoemulsion. The nanoemulsion was then transferred to larger volume of water to extract the organic solvent and precipitate the nanoparticles. The nanoparticles were then concentrated by tangential flow filtration, and reduced to dryness by lyophilization.

Sketch 14-1. Preparation of a PLGA-Tetrac Nanoparticle Conjugate Containing a Linking Moiety:

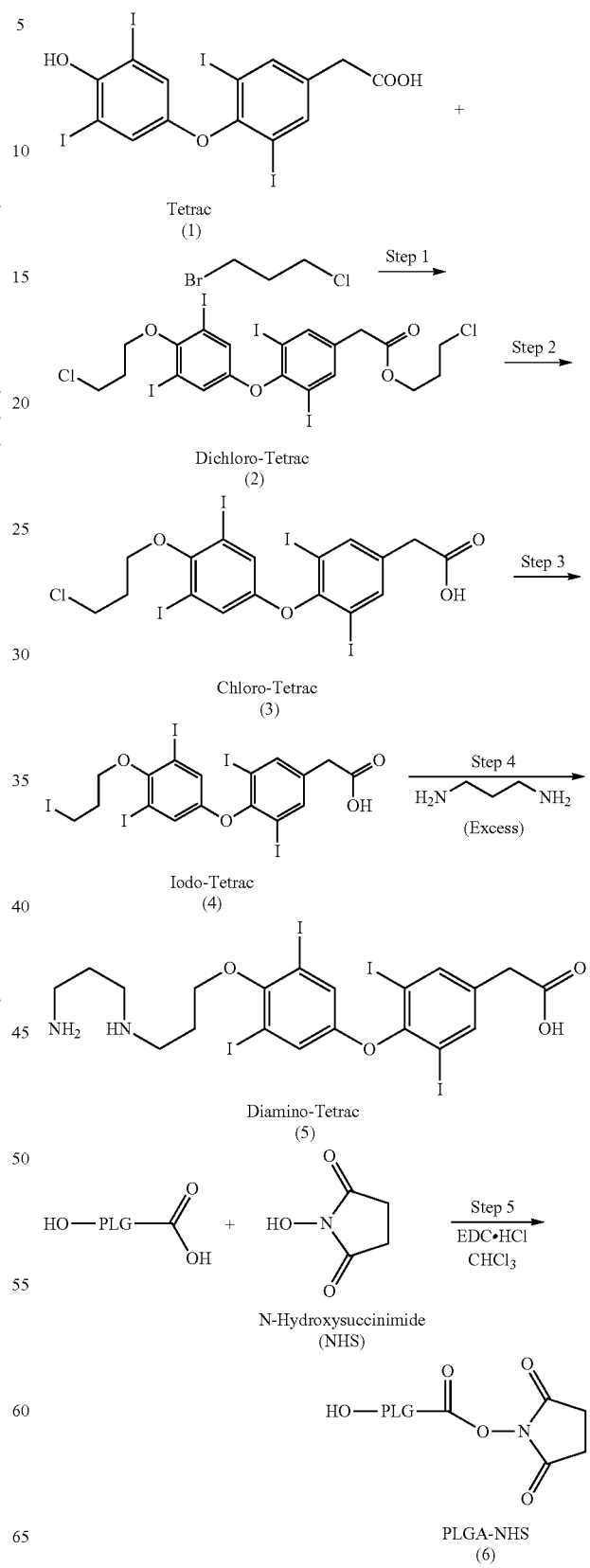

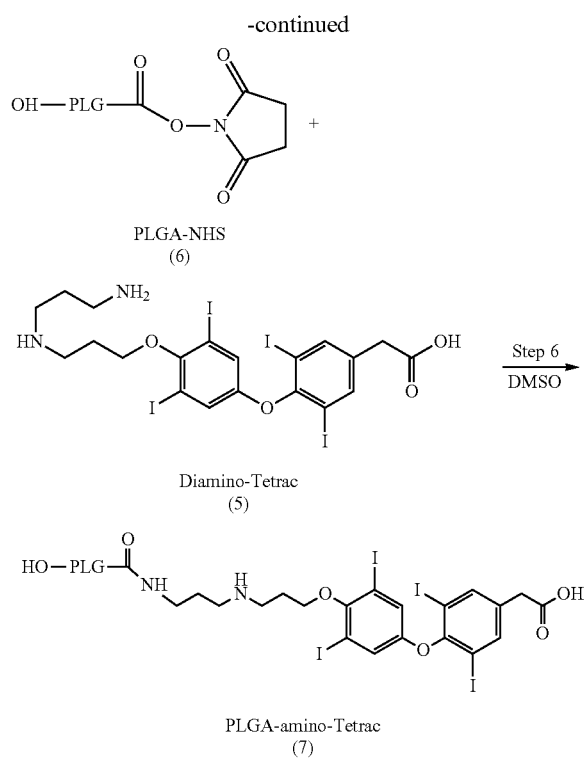

PLGA-NHS
(6)

Diamino-Tetrac
(5)

PLGA-amino-Tetrac
(7)

A non-limiting example of a suitable linker that can be used in accordance with these methods is shown in FIG. 35.

Preparation of Tetrac-PLGA Nanoparticles

Another method for the Tetrac-PLGA is shown in FIG. 66A-C. FIG. 66A shows the production of aminopropyl-tetrac. The preparation of activated PLGA is shown in FIG. 66B. The preparation of PLGA-Tetrac was scaled up from 30 mg scale. The product was precipitated three times from methylene chloride/ether to purify. (See FIG. 66C).

The DMSO solutions containing Tetrac-PLGA conjugate were introduced into a 05% aqueous solution of PVA (250 mL0 using 30-mL syringe through the think needle. The table below shows the mode of addition and stirring parameters. The needle tip was over the PVA solution surface in both cases. Addition was performed drop-wise (2-3 drops per second over 14 minutes) for Batch Z1-05-96, and as a stream (over 2.5 minutes) in Batch Z-05-97.

Mode of Addition and Stirring Parameters for Nanoparticles Fabrication

| Batch # | Batch ID # | Mode of AT-PLGA Solution Addition and Time | Stirring Parameters (RPM; Size of Magnetic Stirring Bar) |
|---|---|---|---|
| 1 | ZI-05-96 | Drop-wise, 14.0 min | ~600; 40 × 16 mm |
| 2 | ZI-05-97 | Stream-wise, 2,5 | !150; 25 × 8 mm |

Stirring was continued for one hour and the Tetrac-PLGA/PVA suspensions were filtered through a 3.1 um glass fiber filter: six filters—for ZI-05-96 batch and four filters for ZI-05-97 batch.

Both fresh nanoparticles suspensions were analyzed by Malvern Analyzer (size and size distribution patterns shown in table below).

Malvern Analysis of Fresh Nanoparticles Suspension

| Batch # | Batch ID # | Size (nm, Vol. Weighted Mean) | Uniformity |
|---|---|---|---|
| 1 | ZI-05-96 | 152 | 0.167 |
| 2 | ZI-05-97 | 156 | 0.264 |

Both batches of nanoparticles were dialyzed (Regenerated Cellulose Tubes, MWCO 3500) for over 27.5 hours against 12 liters of DI Water; the media was replaced twice. Dialyzed material was filtered through the 3.1 um glass fiber filter (one filter per batch) and was re-analyzed with Malvern Analyzer (see table below for parameters) for the lyophilization.

Malvern Analysis of Fresh Nanoparticles Suspension

| Batch # | Batch ID # | Size (nm, Vol. Weighted Mean) | Uniformity |
|---|---|---|---|
| 1 | ZI-05-97-1 | 147 | 0.323 |
| 2 | ZI-05-97-2 | 161 | 0.266 |
| — | ZI-05-98 | 157 | 0.285 |

Combined nanoparticles suspension was transferred into five 500-mL shallow plastic containers and lyophilized following the parameters below:

General Lyophilization Parameters

| Step | Temperature | Vacuum | Time |
|---|---|---|---|
| 1 | Room Temp → 20 C. | Ambient | N/A |
| 2 | Hold at −20 C. | Ambient → 50 mTorr | 0.5 h |
| 3 | −20 C. → 20 C. | Hold at 50 mTorr | 2.5 h |
| 4 | Hold at 20 C. | Hold at 50 mTorr | 72 h |
| 5 | Hold at 20 C. | 50 mTorr → Ambient | N/A |

Example 15

Tetraiodothyroacetic Acid (Tetrac) and Nanoparticulate Tetrac Arrest Growth of Human Medullary Carcinoma of the Thyroid Human medullary carcinoma of the thyroid (MTC) cells were implanted in the chick chorioallantoic membrane (CAM) model (n=8 per group) and the effects of Tetrac and nanoparticulate Tetrac (Tetrac NP) at 1 μg/CAM were determined on tumor-angiogenesis and tumor growth after 8 d. Additionally, MTC cells were implanted subcutaneously in nude mice (two implants per animal on the right and left flanks) (n=6 animals per group) and the actions on established tumor growth of unmodified Tetrac (10 mg/kg, i.p. daily for 3 weeks) and Tetrac NP (1 mg/kg, i.p. of Tetrac equivalent daily for 3 weeks) were determined. Tetrac gains access to the cell interior, whereas nanoparticulate Tetrac (poly[lactide-co-glycolide], PLGA, covalently bound to the outer ring phenolic hydroxyl site) is excluded from the cell and binds only to the integrin receptor. In the CAM tumor implant model, Tetrac and Tetrac NP resulted in effective inhibition of tumor-mediated angiogenesis and tumor growth. In the nude mouse xenograft model, the tumors grew progressively over 21 d to 450-500 mm$^3$. Within 2 days of initiation of Tetrac or Tetrac NP treatment, reductions in tumor size were detected in the treated animals and reductions in tumor size to less than the initial cell mass (<100 mm$^3$) occurred over 21 days. Tumor tissue hemoglobin content, an index of vascularity, decreased by 66% over the course of Tetrac and Tetrac NP administration. RNA microarray analysis of tumor cells revealed that both Tetrac formulations significantly induced anti-angiogenic thrombospondin gene expression and decreased VEGF gene expression. Expression of apoptosis activator genes was also induced by the agents. Acting via a cell surface receptor, Tetrac and Tetrac NP inhibit growth of human MTC cells and associated angiogenesis in CAM and mouse xenograft models.

Materials and Methods
Materials:

Polyvinyl alcohol (PVA), N-(3-Dimethylaminopropyl-N' ethylcarbodiimide-hydrochloride (EDC) and the dialysis tubing cellulose membrane were purchased from Sigma Aldrich, St. Louis, Mo. Poly(d-lactide-co-glycolide [70:30]), (PLGA) were purchased from Polysciences Inc. (Warrington, Pa.). Ethylenediamine dihydrochloride was purchased from Pierce Biotechnology, Rockford, Ill. Expoxy-Tetrac intermediates were custom-synthesized.

Obtained from Biocare Medical (Concord, Calif.) were Diva Pretreatment Solution (DV2004), aqua DePar (ADP1002), Mach 4 detection kit (M4U534), Background Sniper (BS966), rat anti-mouse CD31 detection kit (Predilute, RT517), Factor VIII (CP039, used at 1:100), Wash Buffer (TWB945) and DAB (BDB 2004). Hemoglobin standard, Drabkin's reagent and other common reagents were purchased from Sigma (St. Louis, Mo.).

PLGA Nanoparticle.

Nanoparticles were synthesized by modification of a method (single emulsion solvent diffusion) originally described by Jeffrey et al., Int J Pharm 77(2-3):169-75 (1991) and Song et al., J Controlled Release 43(2-3):197-212 (1997). Amino-functionalized PLGA nanoparticles were obtained by conjugating these PLGA nanoparticles with ethylenediamine, using carbadiimide chemistry. Finally, amino functionalized PLGA nanoparticles were reacted with eposxy Tetrac derivative to obtain the final product (Tetrac conjugated PLGA nanoparticles). The custom made expoxy Tetrac intermediate was composed of Tetrac conjugated to epibromohydrin through the phenolic —OH group present on it. This epoxy group reacts with the amino group (see Hermanson, Bioconjugate Technique. Academic Press, San Diego, Calif., pp. 617-618 (1996) and Bergstrom et al., Biomed Matter Res 26:779-90 (1992)) present in the modified PLGA nanoparticles in aqueous condition.

In a typical experiment, PLGA nanoparticles were synthesized by adding 200 µl of PLGA (poly-lactide-co-glycolide) (40 mg/ml in DMSO) to 20 mL of a 1% aqueous solution of polyvinyl alcohol (PVA). This mixture was constantly stirred for about 12 h at room temperature to form the nanoparticles. The nanoparticle suspension was then dialyzed for 6 h (membrane cut off, 10-12 kD) to remove the impurities as well as the organic solvent. To 18 mL of this void PLGA nanoparticulate solution were added 2 mL of PBS buffer (10×) and 500 µL of N-(3 dimethylaminopropyl)-N'-ethylcarbodiimide hydrochloride (EDC) (180 mg/mL in 10×PBS). The mixture was magnetically stirred for about 1 h, followed by another addition of 500 µL, of ethylenediamine (280 mg/mL in 10×PBS) and stirring continued for at least 24 h. The whole solution was then dialyzed (10-12 KD cut-off membrane) for 10-12 h to eliminated unreacted materials. A stock solution of the custom-made expoxy-activated Tetrac in anhydrous DMSO (5 mg/mL) was prepared, and 100 µL of this activated Tetrac solution was added to 10 ml of the above amino functionalized PLGA nanoparticles and stirred for at least 24 h. The solution was then dialyzed for at least 12 h for purification (12 kD cut-off membrane) and lyophilized. These lyophilized Tetrac-conjugated PLGA nanoparticles were reconstituted in deionized water/PBS and used for the experiments described below.

Cells and Cell Culture.

Human medullary carcinoma cells (TT, Catalog No. CRL-1803) were purchased from American Type Culture Collection (Manassas, Va.) and cultured as instructed by the supplier, using a complete growth medium consisting of F-12K medium with 10% FBS. Cells were cultured in 5% $CO_2$/air atmosphere at 37 C to sub-confluence and then treated with 0.25% (w/v) trypsin/EDTA to affect cell release from the culture vessel. After washing with culture medium, the cells were suspended in DMEM (free of phenol red and FBS) and counted.

Tetrac Versus Tetrac NP Distribution in h-MTC.

Human medullary thyroid carcinoma cells were grown in F-12K media (Invitrogen, Grand Island, N.Y.) supplemented with 10% fetal calf serum (Atlanta Biologicals, Lawrenceville, Ga., USA). Penicillin streptomycin (1%) was present in both culture media. The cells were trypsinized, centrifuged, and the cell pellet was re-suspended in the corresponding media. Then, 500 uL of the suspension (~50,000 cells) was transferred to each well of a 4-well glass slide, Chamber slide System (Nalge Nunc International, Naperville, Ill.) and incubated for 24 h at 37° C. with 5% $CO_2$ (Thermo Electron Corp., Form a Series II). The cells were treated with 20 µL of each free Tetrac tagged with Cy3 dye or PLGA-Tetrac tagged with Cy3 and separately incubated (37° C., 5% $CO_2$) for around 2 h. After incubation, the plates were washed several times with PBS and then fixed in 1% formaldehyde (Sigma, St. Louis Mo., USA), and mounted with the help of Vectashield (Vector Laboratories Inc, Burlingame, Calif. Confocal images were taken using a Leica TCS SP5 Confocal with a 63×(NA=1.3 glycerol immersion) objective. A 405 nm laser was used for excitation, and emission was detected between 565 nm and 688 nm.

Tumor Growth in the CAM Cancer Implant Model.

The effect of Tetrac versus nanoparticulate Tetrac at 1.0 µg/CAM on tumor angiogenesis and tumor growth of 1×10$^6$ medullary thyroid carcinoma cells implanted in Matrigel in 7 day-old CAM's was determined 8 days after implantation. (See Mousa et al., J Cell Biochem 97:1370-78 (2006)). Data represent mean tumor weight (mg) and tumor hemoglobin (mg/dL)±SEM per treatment group, n=8 per group.

Cell Implantation in Nude Mice.

Female NCr nude homozygous mice aged 5-6 weeks and body weights of 20 g were purchased form Taconic Farms (Hudson N.Y.). Animals were maintained under specific pathogen-free conditions and housed 4 animals per cage, under controlled conditions of temperature (20-24° C.) and humidity (60-70%) and a 12 h light/dark cycle. Water and food were provided ad libitum. Xenograft experiments were carried out in the animal research facility of the Veterans Affairs (VA) Medical Center, Albany, N.Y. and the experimental protocol was approved by the VA IACUC. Mice were allowed to acclimate for 5 days prior to the start of treatments.

Matrigel (BD Bioscience, San Jose Calif.) was thawed overnight at 44° C. and placed on ice. The tumor cells in exponential growth phase were harvested using 0.25% trypsin-EDTA washed and suspended in medium. Only suspensions of single cells with a viability exceeding 95% were used. Approximately $2\times10^6$ cells in 100 µL of medium mixed with same volume (100 µL) of Matrigel was injected subcutaneously into the left and right flank regions of each mouse.

Treatment of Animals with Unmodified or Nanoparticulate Tetrac.

Tumors were measured daily by calipers and tumor volume was calculated according to a standard formula ($W\times L^2/2$), where W=width and L=length. Tumor volume measurements were made every other day after implantation for the first 5 weeks after inoculation and tumor volumes were measurable by 33 days after implant, at which time treatment was started. Mice with tumors of 225-275 mm$^3$ in volume proximal to the injection site were randomized into 3 groups (n=6): control, Tetrac (10 mg/kg) group and Tetrac NP (1 mg/kg) group. Drugs were administered intraperitoneally (i.p.) daily for 21 days. Mice were weighed daily and tumor size was measured daily, starting on day 1 until the end of the experiment.

Estimation of Tumor Response to Tetrac or Nanoparticulate Tetrac.

At the conclusion of experiments, all animals were sacrificed in a $CO_2$ chamber and tumor masses were collected and weighed. Tumor mass hemoglobin content was measured to index vascularity of tumor. For this purpose, each tumor mass was placed into a 0.5-mL tube of double-distilled $H_2O$ and homogenized for 5-10 min. The samples were then centrifuged at 4,000 rpm for 10 min and the supernatants collected for hemoglobin measurement. Fifty µL of supernatant was mixed with 50 µL Drabkin's reagent and allowed to sit at room temperature for 15-30 min; 100 µL of this mixture was placed in a 96-well plate and absorbance measured at 540 nm with a Microplate Manager ELISA reader. Hemoglobin concentration was determined by comparison with a standard curve in mg/mL.

Statistical Analysis for CAM and Xenograft Studies.

Statistical analysis was performed by one-way ANOVA, using Statview software (Adept Scientific, Acton, Mass.) and comparing the mean±SD from each experimental group with its respective control group. Statistical significance was defined as $P<0.05$.

RNA Microarray Analysis.

Technical aspects of microarray studies, stringent quality control of microarray studies and statistic analysis of gene expression were as described previously. (See Glinsky et al., J Clin Invest 115:1503-21 (2005); Glinsky et al., Clin Cancer Res 10:2272-83 (2004); Glinsky et al., J Clin Invest 113:913-23 (2004); Glinsky et al., Mol Carcinog 37:209-21 (2003)). In brief, the array hybridization and processing, data retrieval and the analysis were carried out with standard sets of Affymetrix (Santa Clara, Calif.) equipment, software and protocols in an Affymetrix microarray core facility. RNA was extracted from cell cultures of two independent biological replicates of each experimental condition and analyzed for sample purity and integrity, using BioAnalyzer instrumentation (Agilent, Santa Clara, Calif.). Expression analysis of 54,675 transcripts was conducted for each sample, using Affymetrix HG-U133A Plus 2.0 arrays. Data retrieval and analysis was completed by MAS5.0 software. Concordant changes of gene expression for each experimental condition were determined at the statistical threshold P value, $<0.01$ (two-tailed t test).

Results

Tetrac Vs. Tetrac NP Distribution within h-MTC Cells.

Confocal imaging revealed that unmodified Tetrac was distributed in the cytoplasm of MTC cells, whereas Tetrac NP was restricted to the plasma membrane (FIG. 36).

Effect of Tetrac and Tetrac NP on Tumor Angiogenesis and Tumor Growth in the CAM Model.

Figure 37B:
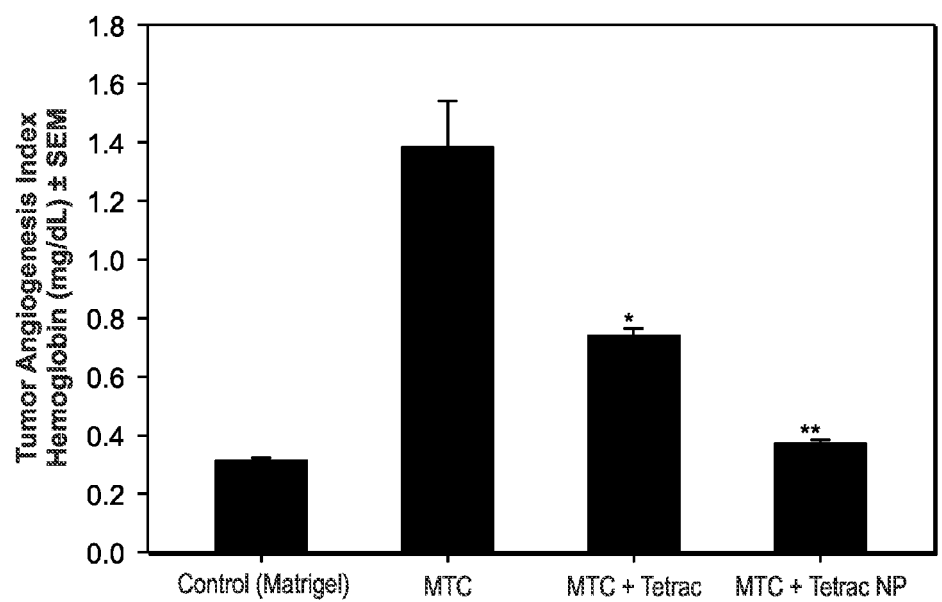
FIG. 37 shows the effect of Tetrac and Tetrac nanoparticle (Tetrac NP) at 1 μg/CAM on medullary thyroid carcinoma tumor growth (A) and tumor angiogenesis (B) in the CAM cancer cell implant model. *P<0.01, **P<0.001.

MTC cells were implanted in $1\times10^6$ aliquots in the CAM model (7 day-old chick eggs, n=8 eggs per group), and the effect of Tetrac and Tetrac NP at 1 µg/CAM was determined on tumor-related angiogenesis and tumor growth after implantation. Tetrac and Tetrac NP treatment resulted in significant inhibition ($P<0.01$) of tumor-mediated angiogenesis (FIG. 37A). Additionally, Tetrac and Tetrac NP exposure both resulted in effective inhibition ($P<0.01$) of tumor growth (FIG. 37B).

Response of Human Tumor Xenografts to Tetrac and Tetrac Nanoparticle Administration.

Figure 38A:
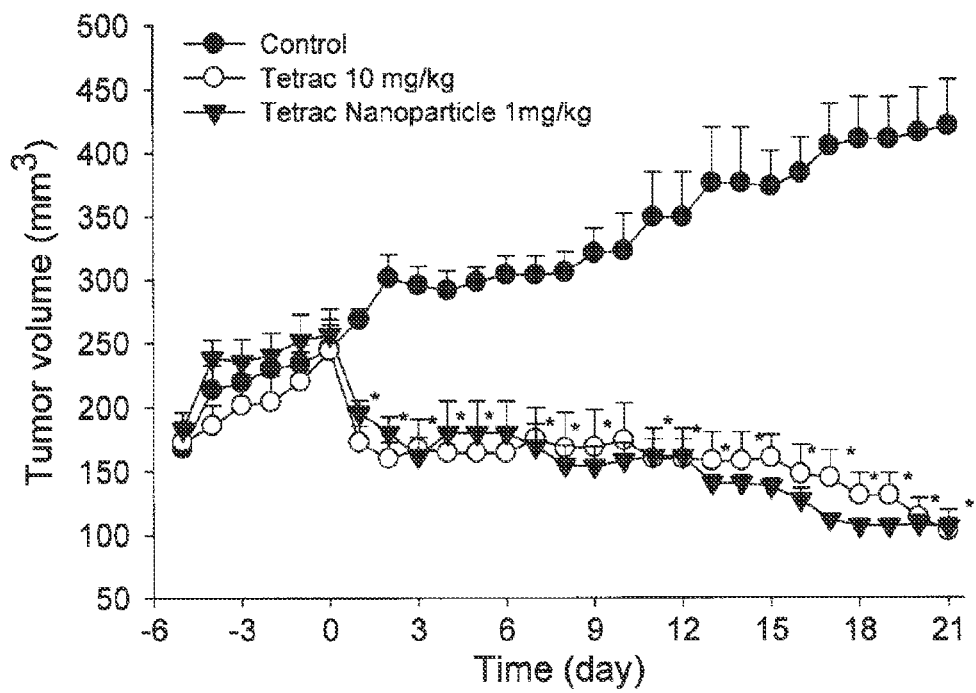
FIGS. 38A-B show the effect of Tetrac and Tetrac nanoparticle treatment on MTC (medullary thyroid carcinoma)
Figure 38B:
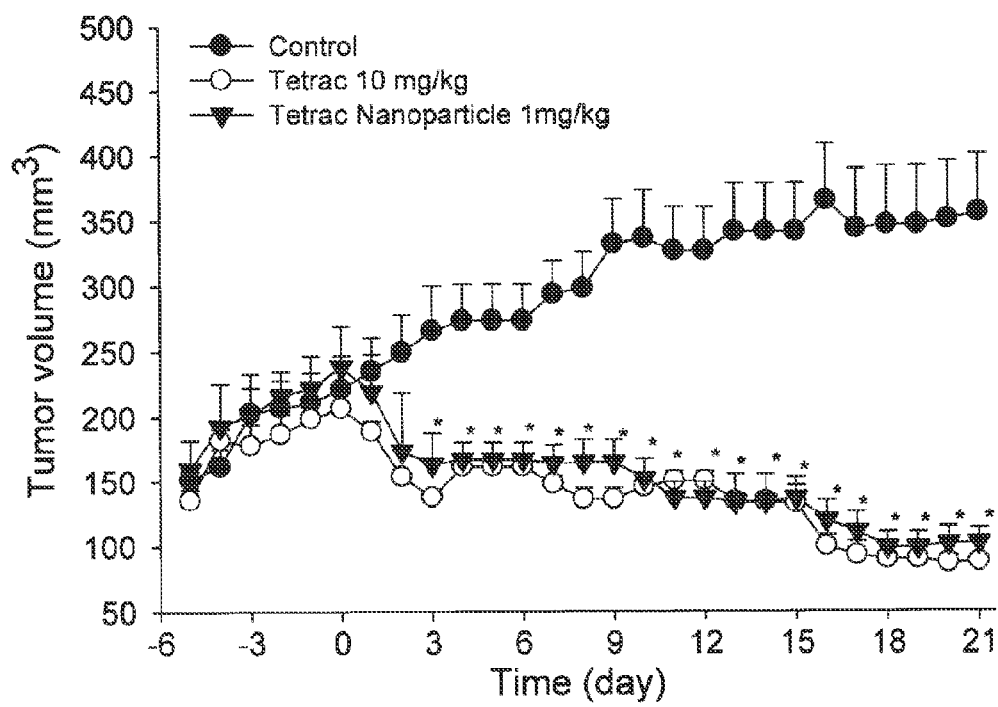

Daily treatment of xenografted animals with Tetrac (10 mg/kg; i.p.) or Tetrac NP (1 mg/kg i.p.) resulted in immediate suppression in tumor volume by day 2 (FIGS. 38A-B); inhibition was sustained with daily administration of the formulations of Tetrac for up to 21 days (FIGS. 38A-B) ($P<0.01$). At the end of the study, tumor weight was directly measured in the untreated, Tetrac-, and Tetrac NP-treated groups. Treatment with both Tetrac (10 mg/kg i.p.) and nanoparticulate Tetrac (1 mg/kg i.p.) resulted in 65-80% reduction of tumor mass compared to controls ($P<0.01$) (FIG. 39).

Effect of Tetrac and Tetrac Nanoparticl on Tumor Angiogenesis.

Treatment with either Tetrac (10 mg/kg i.p.) or Tetrac NP (1 mg/kg i.p.) daily for 21 days resulted in reduction of 70-80% in tumor-associated neovascularization ($P<0.01$), as evidenced by the hemoglobin levels in tumor tissue (FIG. 40).

Effect of Tetrac and Tetrac Nanoparticle on Body Weight.

Daily treatment with Tetrac (10 mg/kg i.p.) or Tetrac NP (1 mg/kg i.p.) for 21 days did not result in a significant effect on incremental body weight growth in these groups, compared to the untreated group (FIG. 41)

Microarray Analysis of h-MTC Cells Treated with Tetrac or Tetrac NP.

There was concordance in global gene expression between Tetrac- and tetra NP-treated cells. Tetrac and Tetrac NP (Pearson correlation 0.89, $P<0.0001$), indicating that the agents have a common spectrum of molecular targets at the gene expression level. Because Tetrac NP does not gain access to the cell interior, the results indicate that both formulations of Tetrac expressed their effects via the cell surface receptor. (See Bergh et al., Endocrinology 146:2864-71 (2005)). Exposure of cells to Tetrac and to Tetrac NP resulted in significantly decreased expression of VEGFA, whose gene product is a potent angiogenesis activator, and a concomitant increase in the gene coding for the angiogenesis inhibitor protein, thrombospondin (THBS1). The mRNA expression ratio for THBS1/VEGFA was comparable for both formulations. This combination of findings is a basis for a strong anti-angiogenic effect of Tetrac and Tetrac NP in MTC cells. (FIG. 42), Tetrac and Tetrac NP also caused expression of genes associated with induction of apoptosis, including caspase-2 (CASP2), DFFA, FAF1 and CASP8AP2. CASP2 may be pro-apoptotic or function as a tumor suppressor. (FIG. 43; see Kitevska et al., Apoptosis 14(7):829-48 (2009)). These microarray observations suggest that Tetrac, itself, has pro-apoptotic activity (see Rebbaa et al., Angiogenesis 11(3):269-76 (2008)) beyond its inhibition of at the integrin receptor of expression of the anti-apoptotic actions of agonist thyroid hormone analogs (see Lin et al., Steriods 72:180-87 (2007); Lin et al., Carcinogenesis 29:62-69 (2008)).

Discussion

Medullary carcinoma of the human thyroid gland is a tumor that responds unsatisfactorily to conventional chemotherapy (see Schlumberger et al., Nat Clin Prac Endocrinol Metab 1:22-32 (2008)) and to radiation (see Hoff et al., Hematol Oncol Clin North Am 1(3):475-488 (2007)). As shown here, unmodified tetraiodothyroacetic acid (Tetrac) and nanoparticulate Tetrac are effective inhibitors of growth of human medullary carcinoma xenograft in the nude mouse. Administered parenterally, the agents promptly decreased tumor volume and over the course of 3 weeks of treatment reduced tumor size below that of the initial volume of implanted cells.

In these studies, nanoparticulate Tetrac was ten times more effective than unmodified Tetrac as an anti-proliferative agent. The nanoparticle does not gain access to the cell interior and thus the Tetrac ether-bonded to the PLGA particle via the outer ring hydroxyl can act only at the integrin receptor—where it is exclusively an antagonist—and not at the nuclear receptor for thyroid hormone (TR). Unmodified Tetrac does gain access to the cell and can interact with TR where it is a low potency agonist (thyromimetic). (See Moreno et al., Thyroid 18(2):239-53 (2008)). The increased potency of Tetrac NP (vs. unmodified Tetrac) as an anti-proliferative agent may reflect 1) the presentation of the ligand (Tetrac) to the receptor site when it is attached to the nanoparticle or 2) action(s) of unmodified Tetrac inside the cell that support cell proliferation, combined with anti-proliferative effects of Tetrac at the integrin.

These studies also reveal that the anti-angiogenic activity of Tetrac that has been shown in the chick chorioallantoic membrane (CAM) model (see Davis et al., Circ Res 94:1500-06 (2004)) and the microvascular endothelial cell-Matrigel assay (see Mousa et al., J Cardiovasc Pharmacol 46:356-60 (2005); Mousa et al., Int Angiol 25:407-13 (2006)) is also apparent in the xenograft-bearing intact nude mouse. Both unmodified Tetrac and nanoparticulate Tetrac reduced the vascularity of medullary carcinoma tumors. Anti-angiogenic agents clinically directed at a specific vascular growth factor have come to be regarded as adjuncts to standard chemotherapy, rather than as primary anti-cancer modalities. (See Bergers et al., Nat Rev Cancer 8:592-603 (2008)). The effectiveness of Tetrac against medullary carcinoma of the thyroid secondarily involves anti-angiogenesis. On the other hand, Tetrac blocks the effects of more than one vascular growth factor, e.g., VEGF and bFGF. Thus, the observed anti-angiogenesis actions of Tetrac may be more important than the adjunctive effect obtained clinically with agents that target a single specific vascular growth factor or vascular growth factor receptor.

Moreover, microarray studies provided additional insight into the anti-angiogenic activity of Tetrac, which, whether unmodified or conjugated to a nanoparticle, was shown to downregulate the proangiogenic VEGFA gene and to induce significantly the expression of thrombospondin (THSP1) (whose gene product is an endogenous anti-angiogenic protein that is usually suppressed in tumor cells. (See Almog et al., Cancer Res 69:836-44 (2009)).

The action of Tetrac on medullary carcinoma tumor volume had two components: a relatively acute effect that was apparent within 1-to-3 days of the initiation of Tetrac treatment (FIG. 38) and a progressive effect. The conventional pro-apoptotic activity ascribed to Tetrac (see Rebbaa et al., Angiogenesis 11(3):269-76 (2008)) would account for the progressive decrease in tumor volume that occurred over three weeks of treatment. Likewise, the microarray results presented here show that Tetrac induces the expression of a number of apoptosis-associated genes. Thus, the mechanisms of action of Tetrac in the tumor cell setting include 1) inhibition at the integrin receptor for thyroid hormone of the proliferative effects of the important circulating thyroid hormones (see Davis et al., Cancer Res 66:7270-75 (2006); Lin et al., Steroids 72:180-87 (2007); and Bergers et al., Nat Rev Cancer 8:592-603 (2008)) as well as 2) support of apoptosis.

Thus, targeting an integrin with Tetrac may induce loss of cell anchorage and the form of apoptosis termed anoikis (see Chiarugi et al., Biochem Pharmacol 76:1352-64 (2008)) or separation of cells from the tumor mass into the circulation. Finally, Tetrac in the xenograft setting may induce necrosis in the grafted cells, which was not seen in in vitro studies of the action of this thyroid hormone antagonist.

While the present experiments were not designed to assess toxicology of systemically administered unmodified Tetrac and Tetrac NP, at the dosage used, there was no mortality in the control animals or those that were treated with Tetrac or Tetrac Nanoparticle for 3 weeks. Moreover, as shown in FIG. 41, weight gain in the treated and untreated animals was identical, indicating no specific adverse effect of Tetrac or nanoparticulate Tetrac on appetite or metabolism. An effect on the latter was a possibility in the case of unmodified Tetrac because of the access of this agent to the cell interior and the possibility of induction of low-grade hyperthyroidism.

Example 16

Modification of Survival Pathway Gene Expression in Human Breast Cancer (MDA-MB-231) Cells By Tetraiodothyroacetic Acid (Tetrac) and Tetrac Nanoparticle MDA-MB-231 cells are estrogen receptor-negative human breast cancer cells shown to be responsive to Tetrac in terms of decreased cell proliferation. The actions initiated at the cell surface receptor by unmodified Tetrac and nanoparticulate Tetrac on a panel of survival pathway genes in estrogen receptor-negative human breast cancer (MDA-MB-231) cells are described herein.

Thyroid hormone is a growth factor for the human estrogen receptor (ER)-positive breast cancer (MCF-7) cell line. (See Tang et al., Endocrinology 145:3265-3271 (2004)). This proliferative effect of thyroid hormone is initiated at the cell surface and mimics the action of 17-β-estradiol (E2), in that it involves Ser-118 phosphorylation of tumor cell ERα and is blocked by ER antagonist ICI 182,780. (See Tang et al., Endocrinology 145:3265-3271 (2004)).

ERα-negative human breast cancer cell line, MDA-MB-231 was surveyed by RNA microarray for actions of Tetrac on tumor cell survival pathways. These results were compared with those obtained with nanoparticulate Tetrac, a proprietary reformulation of the agent in which it is covalently bound to a poly(lactide-co-glycolide) (PLGA) nanoparticle (see Yalcin et al., Anti-Cancer Res, 10:3825-31 (2009)) that prevents access of Tetrac to the cell interior. Nanoparticulate Tetrac acts exclusively at the cell surface receptor for thyroid hormone and its use permitted us to distinguish between Tetrac effects that are nongenomically initiated at the plasma membrane and directly genomic effects initiated by Tetrac within the cell nucleus. From this limited survey, it is clear that Tetrac/nanoparticulate Tetrac can act at the plasma membrane to inhibit several cancer cell survival pathways. These molecules also have actions on pro-apoptotic genes and enhance expression of the thrombospondin (THBS1) gene, whose gene product is anti-angiogenic. Moreover, MDA-MB-231 cell proliferation is fully suppressed by nanoparticulate Tetrac.

Materials and Methods

Tetrac and Nanoparticulate Tetrac.

Tetrac was custom-synthesized by Peptido GMBH (Bembach, Germany). The proprietary Tetrac nanoparticle was custom-synthesized by covalently-bonding of the outer ring hydroxyl of Tetrac to PLGA via an intervening linker. Nanoparticle size averaged 200 nM and the particles have been shown to be excluded from the cell interior.

Cell Culture for Definition of Effects of Tetrac Formulations on Tumor Cell Proliferation.

MDA-MB-231 cells were purchased from ATCC (Manassas, Va.). Cells were maintained until use in DMEM that contained 10% FBS. The incubator conditions were 5% $CO_2$/95% $O_2$ and 37° C. The action of unmodified Tetrac and nanoparticulate on MDA-MB-231 cells was determined in a perfusion bellows cell culture system we have recently described for quantitating pharmaceutical agent pharmacodynamics in vitro. (See Lin et al., J Steroid Biochem Mol Biol 113: 182-188 (2009)). In brief, the cell culture system is a disposable bioreactor capable of high density cell culture for studies of anti-cancer drugs. Bellows-induced alternate flow of culture medium and air through porous matrices where cells are grown provides a relatively low shear, high aeration, foam-free culture environment. Medium level is raised and lowered to submerge and expose matrices to create a dynamic interface between air and media on the cell surface. Anchorage-dependent cells are grown on plastic flakes in the system. The flakes facilitate harvesting of whole cells for analysis. In the present studies, $5 \times 10^7$ cells were seeded in each perfusion flask and incubated at 37 C overnight. Flakes thereafter were sampled at regular intervals (FIG. 44), subjected to trypsinization and the harvested cells counted. When Tetrac or nanoparticulate Tetrac were initially added to the system, flasks contained $20\text{-}50 \times 10^6$ cells. Cell cultures were re-fed with 1% FBS-containing medium. Studies were carried out in duplicate flasks and replicated once.

Cell Culture for Harvesting of RNA.

MDA-MB-231 cells were maintained in DMEM that was supplemented with 10% FBS in a 5% $CO_2$/95% $O_2$ air incubator at 37° C. For two days prior to exposure to Tetrac and nanoparticulate Tetrac, cells were maintained in 0.25% FBS that was stripped of estrogen and thyroid hormone. (See Lin et al., Biochemistry 42: 7571-7579 (2003)).

RNA Microarray and Analysis.

Microarray analysis experiments were conducted as described previously. (See Glinsky et al., J Clin Invest 115: 1503-1521 (2005); Glinsky et al., J Clin Invest 113: 913-923 (2004); Glinsky et al., Clin Cancer Res 10: 2272-2283 (2004); and Glinsky et al., Mol Carcinog 37: 209-221 (2003)). In brief, the array hybridization and processing, retrieval of data and analysis utilized standard sets of Affymetrix (Santa Clara, Calif.) equipment, software and protocols in the microarray core facility of Ordway Research Institute. RNA was extracted from MDA-MB-231 cell cultures of two independent biological replicates of each experimental condition. Sample purity and integrity were verified with an Agilent BioAnalyzer (Santa Clara, Calif.). Expression analysis of 54,675 transcripts for each sample was by Affymetrix HG-U133A Plus 2.0 arrays. MAS5.0 software was used for data retrieval and analysis and concordant changes of gene expression in response to unmodified Tetrac and nanoparticulate Tetrac were defined by two-tailed t test at a threshold p value<0.01.

Results

Effects of Tetrac and Nanoparticulate Tetrac on MDA-MB-231 Cell Proliferation.

As shown in FIG. 44, control cells proliferated from day 0 to day 9 in the perfusion cell culture system. Unmodified Tetrac at $10^{-6}$ M, introduced at day 0, inhibited cell proliferation by more than 30% by day 9. A concentration of $10^{-6}$ M of Nanoparticulate Tetrac (lot ZI-04-30NP (Tetrac equivalent) completely suppressed cell proliferation.

RNA Microarray.

Treatment of tumor cells with Tetrac or nanoparticulate Tetrac resulted in effects on genes of several differentially-regulated cell survival pathways. As shown in FIGS. 45A and B, expression of XIAP and MCL1 was significantly inhibited by nanoparticulate Tetrac. Unmodified Tetrac also acted on XIAP, but did not significantly affect MCL1 gene expression. Both genes are associated with inhibition of apoptosis. CASP2 and BCL2L14 (FIGS. 46A and B) are associated with promotion of apoptosis and both were significantly upregulated by Tetrac nanoparticles. There was not a significant stimulatory action of unmodified Tetrac on either CASP2 or BCL2L14 expression. Actions shown here of nanoparticulate Tetrac on these pairs of genes are antithetic to tumor cell survival. These results are consistent with the previously reported pro-apoptotic effects of Tetrac on cancer cells. A third pathway affected by the agents was that of the catenins. (See Takemaru et al., Nature 422: 905-909 (2003)). CBY1 is a potent inhibitor of β-catenin and the Wnt/β-catenin system, which are major survival pathways in cancer cells. CBY1 expression was induced by Tetrac and Tetrac NP. CBY1 expression was significantly increased by both Tetrac and nanoparticulate Tetrac (FIG. 47).

Thrombospondin 1 is a potent anti-angiogenic protein that is often underexpressed in human cancers and MDA-MB-231 cells. Expression of the THBSI gene is basally inhibited in cancer cells. THBS1 expression was stimulated by both Tetrac formulations (FIG. 48) and such activity in this fourth pathway studied here is antithetic to tumor cell survival.

The family of Ras-oncogenes was differentially affected by Tetrac nanoparticles, with the majority of genes (8 of 13) downregulated (FIG. 49). There appeared to be coherence, however, in the differential effects of Tetrac. For example, the principal gene upregulated by Tetrac (RAB7B) codes for a differentiating factor in monocytes of promyelocytic leukemia.

There was concordance among the actions of unmodified Tetrac and nanoparticulate Tetrac on several cancer survival pathway genes, but it is clear that the nanoparticulate formulation has a broader spectrum of actions than unmodified Tetrac. The nanoparticulate, alone, was shown to affect expression in MDA-MB-231 cells of MCL1, CASP2, BCL2L14 and EGFR. XIAP, CBY1 and THBS1 were similarly affected by both forms of Tetrac.

Discussion

That thyroid hormone can modulate gene expression from a cell surface hormone receptor was initially disclosed in studies of iodothyronine-induced angiogenesis in which the receptor on integrin αvβ3 was disclosed. (See Bergh et al., Endocrinology 146: 2864-2871 (2005)). Subsequent studies focused on several genes associated with angiogenesis or tumor cell proliferation established that via the integrin receptor, thyroid hormone analogs affected these processes. (See Lin et al, Carcinogenesis 29: 62-69 (2008); Rebbaa et al., Angiogenesis 11: 269-276 (2008); Mousa et al., J Cardiovasc Pharmacol 46: 356-360 (2005)). That plasma membrane integrin αvβ3 regulates expression of a spectrum of genes, including several that are cell cycle-relevant, was shown by Mangale et al. (Reprod Fertil Dev 20: 311-319 (2008) in studies of the interaction of the integrin with a natural extracellular matrix protein ligand, vitronectin. Thus, both protein ligands and small molecule ligands of the integrin may affect the latter's ability to regulate gene expression.

The genomic actions of thyroid hormone initiated at its cell surface αvβ3 receptor in a well-studied human cancer cell line were examined by RNA microarray analysis. Previous reports have documented the proliferative effect of agonist thyroid hormone analogs on human breast cancer cells (see Tang et al., Endocrinology 145:3265-3271 (2004)) and the ability of Tetrac to inhibit proliferation of such cells. MDA-MB-231 human breast cancer cells are nuclear ERα- and progesterone receptor-negative and have been examined in other experimental contexts (see Lin et al., J Steroid Biochem Mol Biol 113: 182-188 (2009)). The present studies concentrated on several panels of genes associated with cancer cell survival. Because thyroid hormone is anti-apoptotic (see Lin et al, Carcinogenesis 29: 62-69 (2008); Lin et al., Cell Cycle 8: 1877-1882 (2009); Lin et al., Steroids 72: 180-187 (2007)) and Tetrac is pro-apoptotic (see Lin et al., Cell Cycle 8: 1877-1882 (2009)), Tetrac-treated tumor cells were searched for expression of differentially-regulated, apoptosis-relevant genes.

Unmodified Tetrac and Tetrac covalently bound to a nanoparticle that prohibits entry into the cell both were effective in killing MDA-MB-231 cells. Then, the activity of unmodified Tetrac, which acts genomically within the cell and at the integrin receptor, was compared with that of nanoparticulate Tetrac.

Expression of apoptosis-promoting CASP2 and BCL2L14 was enhanced, whereas the expression of anti-apoptotic XIAP and MCL1 was decreased by exposure of cells to nanoparticulate Tetrac. Among the caspases, the effect of Tetrac on CASP2 in MDA-MB-231 cells may be quite specific, since prior immunoblotting studies in MCF-7 breast cancer cells revealed no effect of Tetrac on abundance of caspase-3 protein. (See Rebbaa et al., Angiogenesis 11: 269-276 (2008)). Of these four genes, only the expression of XIAP was also affected by unmodified Tetrac.

Interference with β-catenin transcriptional activity in MDA-MB-231 cells may lead to decreased cell proliferation and to apoptosis. (See Schlange et al., Breast Cancer Res 9: R63 (2007)). CBYI protein is an inhibitor of the catenin oncoprotein and CBYI gene expression has not been previously studied in MDA-MB-231 cells. Tetrac and nanoparticulate Tetrac both upregulated CBYI expression in the present studies. A novel relationship between β-catenin, the agonist thyroid hormone analogs, $T_3$, and mutation of the nuclear thyroid hormone receptor, TRβ1, has recently been described in carcinogenesis in thyroid cells. (See Guigon et al., Mol Cell Biol 28: 4598-4608 (2008)). Interestingly, $T_3$ was shown in these studies to increase turnover of the β-catenin in the presence of wild-type TRβ1. The relationship between 13-catenin and thyroid hormone analogs is thus complex, involving CBYI in the case of Tetrac and a nuclear thyroid hormone receptor in the case of $T_3$.

Differential regulation by nanoparticulate Tetrac of members of the Ras oncogene family was also shown in the current studies, with the majority of genes downregulated. Among the several genes strongly affected by Tetrac nanoparticles were Rab18, a proto-oncogene that was downregulated, and Rab7B. The latter was upregulated. Expression of Rab7B is implicated in the differentiation of malignant cells, such as monocytes in promyelocytic leukemia. (See Yang et al., Biochem Biophys Res Commun 318:792-799 (2004)).

Tetrac is anti-angiogenic, and, in part, this activity has been seen to reflect blocking of the pro-angiogenic actions of agonist thyroid hormone analogs (see Davis et al., Circ Res 145: 3265-3271 (2004)) and the ability to inhibit—in the absence of thyroid hormone—neovascularization induced by VEGF and bFGF (see Mousa et al., Angiogenesis 11: 183-190 (2008)). These microarray results present another mechanism by which Tetrac may act to block angiogenesis, namely, upregulation of expression of THBSI. Because thrombospondin protein is anti-angiogenic, the state of expression of THBSI in tumor cells is usually one of repression. (See Ren et al., Biochim Biophys Acta 1765: 178-188 (2006)). Thus, stimulation of THBSI expression by unmodified Tetrac and the nanoparticulate formulation reflects action on another biologic pathway that is antithetic to tumor cell survival.

There is also concordance described here between the actions of Tetrac and nanoparticulate Tetrac on the expression of the XIAP, THBSI and CBYI genes. However, nanoparticulate Tetrac has a broader spectrum of coherent actions of MDA-MB-231 cell genes that are relevant to cell survival, which suggests that the ways in which unmodified Tetrac and nanoparticulate Tetrac fit into the binding domain on the integrin are slightly different. Those skilled in the art will recognize that the thyroid hormone receptor domain on the integrin is complex. For example, it includes two closely-related receptor sites (see Lin et al., Am J Physiol Cell Physiol 296: C980-C991 (2009)), each of which has its own discrete downstream transduction mechanisms and cellular consequences. Thus, that the receptor domain can distinguish between unmodified and nanoparticulate Tetrac is not so surprising. It is also possible that the access of unmodified Tetrac and the cell nucleus may have effects that offset actions initiated at the integrin αvβ3 receptor site.

The EGFR observations made here have another implication. If nanoparticulate Tetrac is to be tested in in vitro or in vivo models as an adjunct to other cancer chemotherapeutic agents, it may not be useful to include among the latter the compounds that act at the EGF receptor (e.g., cetuximab). (See U.S. Ser. No. 12/751,375, which is herein incorporated by reference in its entirety).

Example 17

Tetrac and Nanoparticulate Tetrac Induce Expression of CASPASE2, CBY1, and THROMBOSPONDIN in Human Breast Cancer (MBA-MB-231) Cells and are Anti-Proliferative In additional microarray studies, the effect of Tetrac and nanoparticulate Tetrac (Tetrac NP), in the absence of $T_4$ and $T_3$, on gene expression in cancer cells was explored according to an anti-proliferative, anti-angiogenic formula. ERα-negative, highly metastatic MDA-MB-231 human breast cancer cells, in which Tetrac has been shown to be anti-proliferative, were exposed to Tetrac ($10^{-7}$ M) and Tetrac NP ($10^{-7}$ M Tetrac equivalent) in hormone-stripped serum for 24 h. Expression of ~54,000 transcripts was analyzed in control and drug-treated cultures, using Affymetrix Human Genome U133 plus 2.0 microarrays. Subsequent analysis was focused on genes affected by treatment at p<0.01. There was 93% concordance between Tetrac and Tetrac NP in terms of genes affected; notable disparities included downregulation of epidermal growth factor receptor (EGFR) by Tetrac NP and no affect of unmodified Tetrac on this gene. Where there was coherence, Tetrac NP was more potent that Tetrac.

Notable disparities included downregulation of epidermal growth factor receptor (EGFR) by Tetrac NP, whereas there was no affect of unmodified Tetrac on this gene. Thrombospondin is a potent anti-angiogenic protein that is often underexpressed in human cancers. Underexpressed in MDA-MB-231 cells, the thrombospondin gene was strongly induced by both Tetrac NP and Tetrac. Moreover, there is mechanistic coherence between these findings and the anti-vascular endothelial growth factor and anti-basic fibroblast growth factor activities of Tetrac that has previously been reported in endothelial cells in the absence of $T_4$ and $T_3$. (See Mousa et al., Angiogenesis 11:183-190 (2008)).

Expression of apoptosis effector caspase 2 was induced, whereas expression of apoptosis inhibitor XIAP was repressed by both Tetrac formulations, which is consistent with the previously reported pro-apoptotic effect of Tetrac on cancer cells. CBY1 is a potent inhibitor of β-catenin and the Wnt/β-catenin system is a major survival pathway in cancer cells. CBY1 expression was induced by Tetrac and Tetrac NP.

Nanoparticulate Tetrac targeting so-called "triple-negative" breast cancer" which constitutes ~80% of the "basal type" breast cancer: the most malignant, therapy-resistant sub-type of the disease defined by pioneering gene expression profiling experiments of the Stanford Genomics group. The therapeutic effect of this drug was documented using the best available xenograft model of human metastatic breast cancer in nude mice.

The anti-proliferative activity of the drug appears associated with the predominantly inhibitory effect on many known proto-oncogenes (21 of 23 differentially-regulated transcripts of this class are down-regulated) and cyclins (8 of 9 differentially-regulated Cyclins are down-regulated). Notably, the differentially-regulated CDK inhibitor CDKN2C is up-regulated. Moreover, the apoptosis-promoting activity of the drug appears associated with the concomitant differential effect on expression well-known apoptosis inhibitors (XIAP and MCL1 are down-regulated) and apoptosis-promoting genes (BCL2L14 and CASP2 are up-regulated).

Likewise, the inhibition of angiogenesis appears to be mediated by the concomitant differential regulation of potent angiogenesis inhibitors (expression of THBS1 and CXCL10 are up-regulated) and down-regulation of the CTSL1 gene, whose expression is essential for recruitment of endothelial progenitor cells to the ischemic sites and required for subsequent neovascularization. Moreover, the notable effect on vasculature homeostasis may be associated with increased expression of the potent vasoconstrictor, EDN1.

The observed anti-inflammatory effect(s) appear associated with the marked inhibition of expression of the interleukin genes (5 of 6 differentially-regulated interleukin transcripts are down-regulated), interferon-pathway genes (10 of 11 differentially-regulated interferon-pathway genes are down-regulated), down-regulation of the NFKB2 gene and up-regulation of the suppressor of cytokine signaling gene, SOCS4.

Inhibition of the Wnt signaling pathway which is one of the major oncogenic/stemness pathway activated in many human cancers appears associated with coordinate down-regulation of expression of the catenin genes, CTNNAI and CTNNA2, and the concomitant up-regulation of the potent nuclear inhibitor of the catenin activity, CBY1 gene.

Notably, there are 13 differentially-regulated Ras-oncogene family members of the signaling molecules, 8 of which are down-regulated after drug exposure. Thus, interference with the oncogenic signaling pathways may emerge as a significant determinant of the drug activity.

The effect on the thyroid signaling pathway also appears associated with the coordinate down-regulation of expression of the thyroid hormone receptor NR1D1/THRA and nuclear receptor coactivator 3 (NCOA3) genes.

Notable determinants of drug activity include genes encoding multiple families of cell surface receptors and nuclear receptors as well as proteins mediating chromatin remodeling and facilitating or inhibiting gene expression, thereby suggesting that, in addition to short-term biological effects, drug exposure may induce genetic and molecular reprogramming of target cells with extended long-term changes of cellular responses and behavior.

A summary of genes regulated by nanoparticulate Tetrac and Tetrac in MDA-MB-231 cells is shown below.

Genes Regulated by Nanoparticulate Tetrac and Tetrac in MDA-MB-231 Cells

| | | Change |
|---|---|---|
| CDKN2C | Cyclin-dependent kinase inhibitor | ↑ |
| Cyclins | Cell cycle regulators | ↓ |
| XIAP | X-linked inhibitor of apoptosis protein [Danson et al., Curr Cancer Drug Targets 7(8): 785-94 (2007)] | ↓ |
| MCL1 | Myeloid cell leukemia-1 (factor), prevents MOMP [Craig, Leukemia 16(4): 444-54 (2002); [Gupta et al., J Cell Mol Med 13: 1004-33 (2009)] | ↓ |
| CASP2 | Caspase 2, promotes apoptosis | ↑ |
| BCL2L14 | B cell lymphoma-2, promotes apoptosis [Gupta et al., J Cell Mol Med 13: 1004-33 (2009)] | ↑ |
| THBS1 | Thrombospondin, inhibits angiogenesis | ↑ |
| CXCL10 | Anti-endothelial cell chemokine | ↑ |
| CTSL1 | Cathepsin 1, recruits endothelial cells | ↓ |
| EDN1 | Endothelin-1 [Grant et al., Br J Cancer 88(2): 163-66 (2003); Takai et al., Oncogene 20(51): 7505-13 (2001); Panoulas et al., Endothelium 15(4): 203-12 (2008); Kitsios et al., J Epidemiol 166(6): 619-33 (2007)] | ↑ |
| Interleukins | Inflammatory cytokines | ↓ |
| CTNNA1 | Catenin (Wnt oncogene pathway) | ↓ |
| CTNNA2 | Catenin (Wnt oncogene pathway) | ↓ |
| CBY1 | Catenin inhibitor | ↑ |
| NR1D1 | Nuclear receptor Rev-erbα, orphan nuclear receptor, regulator of circadian rhythm [Kishi et al., Neurosci Res 62(4): 211-15 (2008); Duez et al., FEBS Lett. 582(1): 19-25 (2008); Fontaine et al., Curr Opin Lipidol 18(2): 141-46 (2007); Chaturvedi et al., Arthritis Rheum 54(11): 3513-22 (2006); Chin et al., Cancer Cell 10(6): 529-41 (2006)] | ↓ |

-continued

| | Change |
|---|---|
| MOMP | Mitochondrial outer membrane permeabilazation [Gupta et al., J Cell Mol Med 13: 1004-33 (2009)] |

Thus, a remarkable feature of nanoparticulate Tetrac appears to be the pleiotropic biological synergy of the multitude of biological effects on multiple therapeutically-relevant genetic and molecular pathways, which collapses this multi-dimensional bioactivity vector of concordant multitarget actions within each pathway into concomitantly altered targeted features of a physiologically and therapeutically synergistic response. Accordingly, the action of this single drug may serve as a design blueprint for targeted biological combination therapy protocols for a variety of human cancers.

Example 18

Radiosensitization of TETRAC

Cells

GL261 murine brain tumor cells were obtained from Dr. M. Ciesielski of the Roswell Park Cancer Institute, Buffalo, N.Y. Cells were grown at the Rhode Island Nuclear Science Center in DMEM/F12 medium (1:1) that contained 1% penicillin-streptomycin, L-glutamine with HEPES buffer (0.5 ml of a 1M mixture per 100 ml), streptomycin sulfate (0.04 g/l), gentamycin (0.09 g/l), Fungizone (0.002 g/l) and 7.5% fetal calf serum (FCS). All reagents were obtained from GIBCO (Grand Island Biological Co., Grand Island, N.Y.).

Tetrac Preparation

Tetrac powder (3,3',5,5'-tetraiodothyroacetic acid; $C_{14}H_8O_4I_4$: molecular weight 747.83; Sigma Chemical Co., St. Louis, Mo.) was prepared as a 100 µM stock solution in 0.04 M KOH and 4.0% propylene glycol (PG). This solution was aliquoted and stored at –20° C. Tetrac was added to cells for x-ray experiments at a concentration of 2 µM requiring 20.0 µl tetrac stock solution/L of medium. As tetrac was made up in KOH and PG, we checked the medium pH (with tetrac) to insure that there were no significant pH changes Growth of GL261 Cells: Determination of the Times of X-Ray Treatment $1\times10^5$ cells per 25 cm² flask at time zero (density 40 cells/mm²). Three flasks were utilized at each time period. The medium in the flasks was not changed over the duration of the growth curve (unfed cultures). Data were taken daily from day zero to day 11.5 post-seeding and cell numbers, age distributions, and apoptotic percentages were determined. After growth curve shapes (without and with 2 µM tetrac) were determined, irradiation times at 70 and 270 hour post-seeding were chosen.

To obtain exponential and plateau phase cell numbers, we trypsinized (0.54 M trypsin-EDTA) cells for 5 min at 37° C. Trypsinized cells then had an equal amount of medium (+FBS) added, and they were then centrifuged and resuspended in medium (without FBS, without tetrac), counted by hemacytometer, and appropriate seeding numbers for seeding were prepared Cellular Multiplicity (CM) Correction Cell multiplicity (CM) was determined from Giemsa stained slides by counting the number of cells per microcolony under 20× magnification. At least 400 microcolonies were counted.

The survival data after irradiation were corrected for the average CM. Both the extrapolation number (n) obtained from SHMT analysis and the α parameter derived from LQ analysis were divided by m to obtain corrected n and α values. (See Elkind et al., Radiat. Res. 1960. 13: 343-352). This correction also effects the derived Dq values, which were obtained using the relationship Dq (Gy)=ln n×$D_0$ (Gy) in the single-hit, multitarget (SHMT) analysis, but has no effect on the value of $D_0$ in the SHMT formalism or β in the linear-quadratic (LQ) analysis.

Cellular Multiplicity Correction for Estimation of the Turnover Time of Tetrac

The length of time that Tetrac biologically affected GL261 cells was also determined. To do this, the multiplicity relationship defined above was utilized. Tetrac was added to cells one hour prior to the determination of the multiplicity. After the exposure of exponentially growing GL261 cells to Tetrac, the Tetrac containing medium was removed from GL261 cells, which contained an unknown residual and fresh medium (without Tetrac) was added. As a function of time (i.e., 0, 1, 2, 3, 4, 6, 8, and 10 hours, and 1-6 days), the cells, containing an unknown residual amount of remaining Tetrac, were then processed for determination of the multiplicity index (i.e. the number of cells per microcolony).

Irradiation of Control Flasks for Estimation of Single Dose Survival, SLDR and PLDR (Sublethal and Potentially Lethal Damage Repair)

To irradiate 25 cm² flasks, an x-ray machine was used and (Philips 250 kVp Therapeutic X-ray Machine, Einhoven, Germany) operated at 250 kVp and 15 mA with added filtration of 0.4 mm Thoreaus filter. The target to source distance was approximately 30 cm. Dose rates were measured using an R-meter (Victoreen R-meter, Cleveland, Ohio), and converted to absorbed (Gy) doses using appropriate temperature, pressure, and R to Gy conversion factors. The dose rate was 1 Gy per min. Flasks were irradiated at ambient temperature.

SLDR was measured at 10% immediate survival level as determined from the acute single dose curve for both control and Tetrac-treated cells in both growth states (i.e. exponentially growing and plateau phase cells. Flasks were irradiated with one-half of the total dose and returned to the 37° C. incubator. At increasing periods of time, flasks were removed, and given the second half of the immediate 10% survival dose. Survival was measured at 0, 0.5, 1.0, 1.5, 2.0, 3.0, 4.0, 6.0, 8.0, and 10.0 hours after the initial dose.

PLDR was also measured using the 10% survival level in both control and Tetrac treated-cells, and was also done for both exponentially growing and plateau phase cells. The total 10% survival dose was given, and then cells were placed back into the 37° C. incubator for various periods of time. At 0, 0.5, 1.0, 1.5, 2.0, 3.0, 4.0, 6.0, 8.0, and 10.0 hours, flasks were removed, and processed for survival assessment.

Addition of Tetrac to GL261 Cell Cultures and Estimation of SLDR and PLDR

To investigate the effects of tetrac on SLDR and PLDR, cells were chosen that had been given a one-hour treatment with tetrac at two different times, i.e., at 70 and 270 hours post-seeding).

Addition of Feeder Cells (FCs) to Experimental Flasks

FCs were produced by irradiating flasks of exponentially growing GL261 cells with 30 Gy of photons from a $^{137}$Cs source (J. L. Shepard γ-irradiator, 10,000 Ci, Glendale, Calif.). The dose rate was 10 Gy per min and the dose was determined using an R-meter (Victoreen R-meter, Victoreen Co., Cleveland, Ohio) calibrated against 250 kVp x-rays, 2 and 6 MV photons. Use of these different sources allowed the correct conversion factor to be obtained in order to calibrate the R-meter for production of FCs in the $^{137}$Cs source ($^{137}$Cs photon energy 0.662 MeV) (See Chase et al., In: Principles of Radioisotope Methodology. Minneapolis, Minn. Burgess Publ. Co., 1962. p. 68, 87-90).

Experimental cells and FCs were added to treatment flasks before irradiation, and were then allowed to attach to the surfaces of the flask and incubated at 37° C. for 1 hour. After incubation the flasks were irradiated using the 250 kVp x-ray source.

Determination of Steady-State Apoptotic Percentages: TUNEL Staining Technique

Apoptotic cells were identified using TUNEL staining (Terminal deoxynucleotidyl transferase dUTP nick end labeling (TUNEL)) (staining kit obtained from Oncor, Gaithersberg, Md.; ApoTag) (See Gavrieli et al., *J. Cell. Biol.* 1992. 119:493-501). The staining procedures were carried out as instructed by the manufacturer. Gill's hematoxylin was used as a counterstain to discriminate negative cells (purple) from positive cells (brown). Negative controls were performed by omitting the terminal deoxynucleotidyl transferase enzyme. Positive controls were performed by incubating cells with Dnase I (3000 U/ml) in 50 mM Tris-HCl, pH 7.5, in 1 mg/ml bovine serum albumin (BSA) for 10 min at ambient temperature.

The percentage of cells exhibiting TUNEL-positive nuclei in control or Tetrac treated cultures was measured and were expressed as an apoptotic index (number apoptotic cells/number apoptotic plus normal cells).

Determination of Steady-State Apoptotic Percentages: Flow Cytometric (FCM) Techniques To perform FCM, a total of $10^6$ adherent cells were trypsinized and washed once in ambient temperature PBS. They were then fixed in 70% ethanol, and stored overnight, at 4° C. Cells were prepared for cell cycle analysis by first pelleting the cells, and then resuspending the pellet in 1 ml of PBS containing 0.2 mg/ml propidium bromide (Sigma Chemical Co., St. Louis, Mo.) and 0.15 µg/ml RNase (Boehringer Mannheim, Indianapolis, Ind.) The cells were then incubated for 30 minutes in dark conditions. Cells were left overnight at 4° C. in the dark and were then analyzed on a Coulter fluorescence-activated cell sorter (Coulter Electronics, Hialeah, Fla.). Cells were excited with a single 488 nm argon laser and the resulting fluorescence was detected using a 585 nm filter. Linear red-orange fluorescence (FL3) data were collected in list format and 10,000 events were collected. The distribution of cells within the cell cycle (sub-$G_1$, $G_1$, S, and $G_2$+M phases) was determined using a Coulter software program.

Use of these two procedures (TUNEL staining, flow cytometry) allowed for the determination of the fractions of apoptotic and normal cells under normal growth and after Tetrac treatment. It is noted that the steady-state levels in control GL261 cells and in GL261 cells after a 1 hour treatment with 2 µM Tetrac were determined.

Statistics: Raw Data Analysis

The raw survival data at each dose and at each time post-irradiation were first analyzed using Chauvenet's criterion (see Chase, et al., In: Principles of Radioisotope Methodology. Minneapolis, Minn. Burgess Publ. Co., 1962, p. 68, 87-90) to exclude potential "outliers" (i.e. where a measurement (N) or measurements are at considerable variance with the mean using Poisson probability statistics). This is particularly important where the number of observations per dose or time point is "small". As the experiment was replicated 4 times, there are 4 data points per dose or time point: i.e. the number of observations is small. The value for Chauvenet' criterion (ChC) obtained from the survival data at a given dose or time was examined using the relationship:

$$ChC \leq N - N\text{-bar}/SD$$

Where N-bar is the mean, and SD is the standard deviation. For an N of 4 for example, ChC must be equal to or less than 1.54 (see Chase, et al., In: Principles of Radioisotope Methodology. Minneapolis, Minn. Burgess Publ. Co., 1962, p. 68, 87-90) for a datum to be accepted. If the value obtained is equal to or greater than 1.54 (for N=4), then the value is deleted and the resulting mean is recalculated. The remaining data are then once again investigated using the Chauvenet criterion. Once all remaining data were to be retained was determined, the next step was to analyze the data.

Statistics: Cell Counts

The hemacytometer cell counts used for preparation of cell dilutions for clonogenic assay estimations has a counting error or 5% or less, as at least 400 cells were counted. (See Goldstein, A. In: Biostatistics, New York, The MacMillan Co., 1964, p. 140-146).

Statistics: Cell Culture Doubling Times (CCDTs)

For determination of CCDTs, the cell numbers per flask were determined on a daily basis. A four-day interval in the exponential region of growth to obtain the CCDTs, yielding a total of 12 estimations for analysis was utilized. A regression analysis was performed using the (log) of the cell number versus the linear time in days (SigmaPlot, V. 10, Systat Software, Inc., Point Richmond, Calif.). The log slope value and its standard error (SE) were determined, and the SE was converted to the 95% confidence limits using a two-tailed t-table at N-1 degrees of freedom where N is the number of samples. (See Goldstein, A. In: Biostatistics, New York, The MacMillan Co., 1964, p. 140-146).

Statistics: SHMT Analysis

For serine hydroxymethyltransferase (SHMT) analyses, survival data lying at or below 36.8% survival were analyzed by using the log fractional survival (log F×S) versus dose (D). Data were fit using linear regression analysis (SigmaPlot, V. 10, Systat Corp., Point Richmond, Calif.) to obtain the Y-intercept (or n, the extrapolation number) and the slope ($1/D_0$), and their 95% confidence limits. (See Goldstein, A. In: Biostatistics, New York, The MacMillan Co., 1964, p. 140-146). The $D_0$ value (Gy) is defined as the inverse of the slope, and the corrected Dq value (Gy) was then defined using the relationship:

$$Dq(Gy) = \ln n \times D_0(Gy)$$

The 95% confidence limits on Dq were defined using error propagation. (See Chase, et al., In: Principles of Radioisotope Methodology. Minneapolis, Minn. Burgess Publ. Co., 1962, p. 68, 87-90).

Statistics: LQ Analysis

For LQ analyses, data lying between a fractional survival of 1.00 and 0.05 were used. The fractional survival data at each dose were transformed using the relationship (−ln F×S/D) and plotted against dose (D). A regression analysis was performed to yield the LQ equation along with their 95% confidence limit values using a t-table with the appropriate (N−1) degrees of freedom. (See Goldstein, A. In: Biostatistics, New York, The MacMillan Co., 1964, p. 140-146). To determine the tetrac modification factor (TMF), the survival at 2 Gy obtained for control cells was divided by the survival at 2 Gy for tetrac treated cells. The 95% confidence limits on the ratio were determined using error propagation techniques. (See Chase, et al. In: Princiiples of Radioisotope Methodology, Minneapolis, Minn., Burgress Publ. Co., 1962, p. 68, 87-90).

Results

Influence of Addition of Tetrac to Medium on Medium pH

The addition of the 20.d of Tetrac in the KOH/propylene glycol solution to medium, (20 µl to 1 liter of medium) did not alter the medium pH.

GL261 Growth Curve

In FIG. 52, the growth rates of control and Tetrac-treated GL261 cells are shown. Tetrac treatment delays the onset of exponential growth from 20 hours in control cells to about 40 hours in tetrac-treated cells. The doubling time of control cells is 43.6 h (95% confidence limits 39.2 to 48.5 hours), while in tetrac treated cells, the doubling time is 43.8 hours (95% confidence limits 40.3 to 47.6 hours). Cells begin to plateau at about 10 days after seeding. However, the saturation density (SD) differs between control and GL261 tetrac-treated cells with the SD of control GL261 cells being approximately 2.4 times that of tetrac-treated cells.

GL261 Colony Forming Efficiencies (CFEs).

From the exponential to the plateau phase, the CFE decreased in control GL261 cells from 30.6% to 19.8% (see Table below). The CFE of exponentially growing GL261 cells without FCs was approximately 21%. Therefore, addition of FCs increases the CFE by approximately 50% in control GL261 cells. In tetrac-treated cells, the CFE was not significantly decreased in exponentially growing cells. In the plateau phase of growth the CFE was however, significantly reduced (P=0.05) from 19.8% in control GL261 cells to 8.8% in tetrac-treated cells.

GL261 Median Cell Volumes, Cell/Nuclear Areas, and Colony Forming Efficiencies (CFEs)

| | Median Volume ($\mu m^3$) | Median cell area ($\mu m^2$) | Mean nuclear area ($\mu m^2$) | nuclear/cell area (%) | CFE[a] (%) |
|---|---|---|---|---|---|
| Exponential (Control) Cells | 2800 | 785 | 276 | 35 | 30.6 (±6.4)[b] |
| Exponential Cells (+Tetrac)[c] | 3850 | 2814 | 1180 | 42 | 24.2 (±6.0) |
| Plateau phase (Control) Cells | 1470 | 495 | 165 | 33 | 19.8 (±5.6) |
| Plateau phase Cells (+Tetrac) | 2780 | 700 | 310 | 44 | 8.8 (±4.0) |

[a]The CFE data were determined by trypsinizing cells from the flasks, and reseeding 500 experimental cells with $10^4$ heavily irradiated feeder cells.
[b]Values in parentheses are the 95% confidence limits from 4 experiments.
[c]Tetrac was present in the (+Tetrac) flasks from times zero to 11.5 days post-seeding.

GL261 Single X-Ray Dose Survival Characteristics

The time of cell irradiations of exponential and plateau phase cells (with and without 2 µM Tetrac) is shown in FIG. 53 (i.e. 70 and 270 hours). The survival curves are shown for control and Tetrac-treated GL261 cells. The survival parameters (LQ and SHMT) are listed in the table below. Single-Hit, Multitarget (SHMT) and Linear-Quadratic (LQ) Parameters, and Fractional Survival at 2 Gy ($SF_2$) for GL261 Cells Assayed Immediately after Irradiation

| SHMT parameters | | | |
|---|---|---|---|
| | $n^a$ | $D_q^a$ (Gy) | $D_0$ (Gy) |
| Exponential phase (control) (without Tetrac) | 2.28 ()[b] | 0.88 | 0.94 |
| Exponential phase (with Tetrac) | 1.06 (−0.19−−0.15), | −0.17 | 1.08 (0.09). |
| Unfed plateau (control) Phase (without Tetrac) | 1.69 | 0.51 | 0.80 |
| Unfed plateau Phase (with Tetrac) | 1.04 | 0.00 | 0.75 |

| LQ parameters | | | | |
|---|---|---|---|---|
| | $\alpha^a$ ($Gy^{-1}$) | $\beta$ ($Gy^{-2}$) | $SF_2$ | $TMF^b$ |
| Exponential (control) Phase (without Tetrac) | 0.360 | 0.094 | 32.7 (26.6-40.2)[c] | — |
| Exponential Phase (with Tetrac) | 0.930 | 0.003 | 14.2 (10.8-18.8) | 2.3 (0.3) |
| Unfed plateau (control) Phase (without Tetrac) | 0.568 | 0.106 | 20.6 (18.7-22.7) | — |
| Unfed plateau Phase (with Tetrac) | 1.157 | 0.066 | 7.62 (6.82-8.51) | 2.7 (0.4) |

[a]n, Dq, and α were corrected for multiplicity.
[b]Tetrac modifying factor (TMF) ± propagated error derived from the 95% confidence limits on the survival at 2 Gy (SF2).
[c]Values in parentheses are the 95% confidence limits.

The SHMT values for the exponential and the plateau phases (without tetrac) are respectively n=2.28, $D_q$ (Gy) =0.88, and $D_0$ (Gy)=0.94; and 1.69 Gy, 0.51, and 0.80 Gy (see Table above). For plateau phase control cells as compared to control exponential cells, n, $D_q$ and the $D_o$ (Gy) values were reduced respectively by approximately 36, 42 and 15%.

Tetrac radiosensitizes both exponentially growing and plateau phase cells. The SHMT values for the exponential and the plateau phases (with tetrac) are respectively n=1.06, $D_q$ (Gy)=0.00, and $D_0$=1.08; and 1.04, 0.00 Gy, and 0.75 Gy. The changes in exponentially growing cells involve a decrease in n and $D_q$ values after addition of tetrac. The extrapolation number is reduced by 93%, and the Dq value is reduced by 100%. The $D_0$ value is increased by 15%. For plateau phase cells, n is again reduced by 93%, the Dq is again reduced by 100%, and the $D_0$ is reduced by 6%.

The LQ parameters for the control exponentially growing control GL261 cells were α=0.360 $Gy^{-1}$ and β=0.094 $Gy^{-2}$. The correlation coefficient was 0.962, which is significant at P<0.001. The decrease in survival induced by Tetrac treatment in exponential cells is produced by a statistically significant increase in the α parameter of the LQ equation (α=0.930, β=0.003). For control plateau phase cells, α is 0.568 while β=0.106. These α and β values in tetrac-treated plateau phase cells are respectively 1.157 and 0.066.

The survival at 2 Gy for control exponentially GL261 cells is 32.7% and the survival at 2 Gy for Tetrac-treated cells is 14.2%. For plateau phase cells, these respective control and Tetrac treated survival values were 20.7 and 7.6%. Taking the ratio of these two survivals and propagating their respective 95% confidence limits (see Goldstein, In: Biostatistics, New York, MacMillan Co., 1964. pp 140-46) (and their propagated error; indicates yields a Tetrac modification factor (TMF) value of that the obtained Tetrac modification factor value is 2.3±0.3 for exponentially-growing cells and 2.7±0.4 for plateau phase cells.

A prediction from these data, noted specifically by the decrease in the quasi-threshold dose (Dq) value, is that Tetrac affects the repair of radiation damage.

X-Ray Time-Dependent Split Dose Recovery of Exponentially Growing GL261 Cells (SLDR)

Control GL261 cells were irradiated with the first of two doses (i.e., 2.75+Δt+2.75 Gy for control cells) of 250 kVp x-rays, sufficient to reduce survival to approximately 10% (with no time between doses), and then placed back into the 37° C. incubator. As a function of time (Δt), flasks were removed and were given a second dose of 2.75 Gy. Cells were then enzymatically removed from flasks, and assayed for survival. The time-dependent data are shown in FIG. 54, where it may be seen that control GL261 cells reach a relative survival of approximately 2.5 by 2 hours after the first dose, ultimately reaching a recovery factor of approximately 4 to 5 by 10 hours post-irradiation.

Tetrac treated GL261 cells were also assayed for SLDR at the 10% survival level, which involved use of two 2.50 Gy split doses. The data are also shown in FIG. 54, which demonstrates that Tetrac treated GL261 cells do not reach the level of SLDR seen in control GL261 cells. Indeed, the recovery ratio is approximately 2.2 (at 10 hours post-irradiation). At 2 hours after the first dose, the recovery ratio is 1.8.

X-Ray Time-Dependent Split Dose Recovery in Plateau Phase GL261 Cells (SLDR)

Control GL261 cells were irradiated with the first of two doses (1.05+Δt+1.05 Gy) of 250 kVp x-rays, again sufficient to reduce survival to approximately 10% (with no time between doses), and then placed back into the 37° C. incubator. As a function of time (Δt), flasks were removed and were given a second dose of 1.05 Gy. The irradiated flasks were then returned to the incubator without medium change. From 0 to 10 hours later, cells were subcultured from flasks and assayed for survival. As shown in FIG. 54, survival increased by a factor of 1.2 fold over the assay period. The recovery of SLD in GL261 cells in the plateau phase of growth is approximately 6% of that seen in exponential cells. Therefore, plateau phase cells do exhibit SLDR, but significantly less than that seen in exponentially growing cells.

The Tetrac effect on SLDR of plateau phase cells is however, different from the SLDR seen in control GL261 plateau phase cells. There is a decrease in survival seen which begins immediately after the end of the first dose and continues to approximately 3 hours after the initial dose. This amounts to fixation of sublethal damage (SLDF). At 3 hours after the initial dose, the fixation of damage reduces survival to approximately 36% of survival seen at 0 hours. At 3 hours, recovery begins to occur but only approximately reaches the level of the recovery seen in the SLDR of plateau phase cells without Tetrac (i.e. approximately 1.2).

Time-Dependent X-Ray Recovery of Exponentially Growing GL261 Cells (PLDR)

The delay in plating of exponentially growing GL261 cells resulted in a decreased extent of PLDR in Tetrac-treated cells as compared to exponentially growing cells (normalized survival is about 2.3 in exponentially growing control cells and about 1.2 in exponential cells) (FIG. 55).

Time-Dependent X-Ray Recovery of Plateau Phase GL261 Cells (PLDR)

The extent of PLDR in plateau phase cells with Tetrac resulted in a decrease in the normalized survival as compared to PLDR in exponentially growing control GL261 cells (the normalized survival at 10 hours post-irradiation was 1.2 in Tetrac-treated cells versus approximately 4 in non-Tetrac-treated plateau phase cells.

Discussion

Tetrac effects on radiation sensitivity and radiation repair. Tetrac treatment reduced the shoulder (Dq) value of the survival curve (FIG. 53). Consequently the effects of Tetrac on repair of sub-lethal radiation damage (SLD) and potentially lethal damage (PLD) were studied. For exponential cells, Tetrac inhibited SLDR, as the maximum recovery in control GL261 cells was 4.2, while that in Tetrac-treated cells was 2.2. (FIG. 54). In plateau phase cells examined for their expression of SLDR, Tetrac not only inhibited SLDR almost completely, but also produced additional cell killing (damage fixation).

The repair of potentially lethal damage repair in exponentially growing cells was also determined. (FIG. 55). Exponentially growing cells did not express a significant amount of PLDR (i.e., about a factor of 2.1). Tetrac decreased PLDR in exponential cells to a factor of about 1.1. PLDR in control plateau phase cells increased by a factor of about 4 from 0 to 8 hours, whereas Tetrac decreased PLDR expression to a factor of 1.1.

Potential Mechanisms of Radiosensitization by Tetrac.

The biochemistry that underlies the Tetrac effects described herein is not yet known. One possibility is that the activity of p53 is altered by Tetrac. There are two reasons to consider a role for p53 here in the action of Tetrac. First, p53 may be activated in the cellular response to ionizing radiation in variable roles, namely, involvement in growth arrest that permits DNA damage repair or promotion of irreversible growth arrest and apoptosis. (See, Fei et al, *Oncogene* 2003. 22:5774-83). Second, thyroid hormone analogs modify actions of p53. It is known that thyroid hormone can cause mitogen-activated protein kinase (MAPK)-dependent Ser-15 phosphorylation of p53 (see Shih et al., *Biochemistry* 2001.40:2870-78) that alters transcriptional activity of the protein. This is the case even when the protein is mutated, except at Ser-15, and the GL261 cells strudied here do bear point mutations in the p53 gene. (See Szatmari et al., *Cancer Sci* 2006. 97: 546-53). It has been shown that agonist thyroid hormone analogs such as T4 are anti-apoptotic in certain cancer cells (see Lin et al., *Carcinogenesis* 2008. 29:62-29; Lin et al., *Steroids* 2007. 72:180-87) by a mechanism that prevents intranuclear activation of p53. Tetrac permits p53-dependent apoptosis to proceed in the presence of T4. (See, Lin et al., *Carcinogenesis* 2008. 29:62-29). The present studies were carried out in the presence of agonist thyroid hormone analogs in fetal calf serum.

Another possible pathway in which Tetrac may have affected the GL261 cells studied here involves the silencing mediator for the thyroid hormone receptor (SMRT) that may be associated with the DNA-protein kinase (PK) repair complex. (See Yu et al., *Cancer Res* 2006. 66:9316-22). SMRT is a deacetylase complex required for recovery from DNA double-strand breaks and whose knockdown by siRNA is importantly rasiosensitizing. (See Yu et al., *Cancer Res* 2006. 66:9316-22). Agonist thyroid hormone analogs liberate SMRT from complexes involving the nuclear thyroid hormone receptor (TR) (see Davis et al., *J Biol Chem* 2000. 275:38032-39) and Tetrac blocks this effect, promoting the association of TR and SMRT. Depending upon the relative affinities of nucleoproteins for SMRT, the effect of Tetrac may be to limit the amount of liberated SMRT available for complexing with DNA-PK and to participate in DNA repair.

Kapiszewska and Lange, *Radiat Res* 1988. 113:458-72 showed that intracellular $NAD^+$ content was reduced in radiosensitive cells, e.g., GL261 cells plus Tetrac. $NAD^+$ is necessary for ADP-ribosylation and subsequent identification of DNA strand breaks. $NAD^+$ usage is linked to signaling reactions in cells. (See Belensky et al., *Trends Biochem Sci* 2007. 32:12-19). If damage fixation is dependent upon the ADP-ribosylation process, and if Tetrac intereferes with this, this could provide an explanation of the fixation seen in x-irradiated cells. Addition of 3-aminobenzamide (3AB), which inhibits ADP-ribosylation, to V-79 cells reduced the size of the Dq value from 3.4 to 1 Gy. (See Ben-Hur et al., *Radiat Res* 1974. 58:38-51). Also, the SLDR responses of V79 cells showed enhanced cell killing (fixation), as did GL261 cells exposed to Tetrac. Thraves et al., have shown about a 70% inhibition of PLDR with 3AB (see *Radiat Res* 1985. 104: 119-27), while Burgman and Konings reported inhibition of PLDR and fixation of PLD with 3AB (see *Radiat Res* 1989. 119: 380-86). Another possible explanation, then, for the action of Tetrac in these studies may be the inhibition of $NAD^+$ synthesis.

While the number of $\alpha v \beta 3$ integrin molecules per GL261 cells has not been measured, other data suggest that the number varies from about 1 to $5 \times 10^5$ per cell. (See Zhang et al., *J. Nucl Med* 2006. 47:113-21). Used in the studies here, Tetrac is present in excess compared to the number of $\alpha v \beta 3$ molecules per cell and would therefore saturate the $\alpha v \beta 3$ response. The results presented herein demonstrate the blockade of the $\alpha v \beta 3$ integrin site by Tetrac. Then, the consequent downstream events may secondarility impact upon radiosensitization and the inhibition of repair of radiation injury.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising a thyroid hormone or thyroid hormone analog wherein the thyroid hormone or thyroid hormone analog is conjugated to a polymer via a linker, wherein said conjugated polymer is a nanoparticle, wherein said nanoparticle is less than 250 nanometers in size, and wherein said thyroid hormone or thyroid hormone analog binds exclusively to a cell surface receptor for thyroid hormone on integrin αvβ3 at a cell membrane level, wherein at least one chemotherapeutic drug is encapsulated in the nanoparticle.

2. The composition of claim 1, wherein the linker is between 4 and 15 atoms long.

3. The composition of claim 1, wherein the polymer is selected from the group consisting of polyvinyl alcohol (PVA), acrylic acid ethylene co-polymer, polyethylene glycol (PEG), methoxypolyethylene glycol-poly(lactide-co-glycolide), polyacrylic acid, polylactic acid, agarose, PEO, m-PEG, PLLA, PGA, poly-L-lysine, Human Serum Albumin, cellulose derivatives (carbomethoxy/ethyl/hydroxypropyl), hyaluronic acid, folate linked cyclodextrin/dextran, sarcosine/amino acid spaced polymer, alginate, carrageenan, polylactic acid pectin/chitosan, chitosan, dextran, collagen, polyamine, poly aniline, poly alanine, polytrytophan, poly tyrosine, polylactide-co-glycolide, poly(lactide-co-glycolic acid) (PLGA), polylysylglycolide, polyglycolide, and co-polymers thereof.

4. The composition of claim 3, wherein the polymer is selected from the group consisting of polyglycolide, polylactide, and co-polymers thereof.

5. The composition of claim 1, wherein the amount of thyroid hormone or thyroid hormone analog in the nanoparticle is between 0.1 and 25%.

6. The composition of claim 1 wherein the composition further comprises one or more pharmaceutically acceptable carriers.

7. The composition of claim 1 wherein the composition further comprises one or more biologically active substances.

8. The composition of claim 7 wherein the biologically active substances are selected from the group consisting of TGF-beta, basic fibroblast growth factor (FGF2), epithelial growth factor (EGF), transforming growth factors alpha and beta (TGF-a and TGF-b), nerve growth factor (NGF), platelet-derived growth factor (PDGF), vascular endothelial growth factor/vascular permeability factor (VEGF/VPF), anti-virals, anti-bacterials, anti-inflammatory, immuno-suppressants, analgesics, vascularizing agents, and cell adhesion molecules.

9. The composition of claim 1, wherein the thyroid hormone analog is selected from the group consisting of tetraiodothyroacetic acid (TETRAC), triiodothyroacetic acid (TRIAC) and a combination thereof.

10. The composition of claim 1, wherein the thyroid hormone analog is TETRAC bound to an OTIPS protecting group.

11. The composition of claim 1, wherein the nanoparticle co-encapsulates two or more chemotherapeutic agents.

12. The composition of claim 1, wherein the at least one chemotherapeutic drug is selected from the group consisting of doxorubicin, atoposide, etoposide, cyclophosphamide, 5-fluorouracil, cisplatin, trichostatin A, paclitaxel, gemcitabine, taxotere, cisplatinum, carboplatinum, irinotecan, topotecan, adriamycin, bortezomib and combinations thereof.

13. A method of producing the composition of claim 1, the method comprising conjugating the thyroid hormone or thyroid hormone analog to the polymer via the linker after forming the nanoparticle.

14. The method of claim 13, wherein the thyroid hormone or thyroid hormone analog is selected from the group consisting of T4, T3, T4 or T3 N-Methyl, T4 or T3 N-Ethyl, T4 or T3 N-Triphenyl, T4 or T3 N-Propyl, T4 or T3 N-Isopropyl, T4 or T3-N-Tertiary butyl, GC-1, DIPTA, Tetrac and Triac.

15. The method of claim 13, wherein the linker is between 4 and 15 atoms long.

16. The method of claim 13 wherein the polymer is selected from the group consisting of polyvinyl alcohol (PVA), acrylic acid ethylene co-polymer, polyethylene glycol (PEG), methoxypolyethylene glycol-poly(lactide-co-glycolide), polyacrylic acid, polylactic acid, agarose, PEO, m-PEG, PLLA, PGA, poly-L-lysine, Human Serum Albumin, cellulose derivatives, carbomethoxy/ethylhydroxypropyl, hyaluronic acid, folate linked cyclodextrinldextran, sarcosine/amino acid spaced polymer, alginate, carrageenan, polylactic acid pectin/chitosan, chitosan, dextran, collagen, polyamine, poly aniline, poly alanine, polytrytophan, poly tyrosine, polylactide-co-glycolide, poly(lactide co-glycolic acid) (PLGA), polylysyl glycolide, polyglycolide, polylactide, and co-polymers thereof.

17. The method of claim 13 wherein the amount of thyroid hormone or thyroid hormone analog in the nanoparticle is between 0.1 and 25%.

18. The method of claim 13, wherein the thyroid hormone or analogs thereof have a protecting group at the NH2 moiety or at the carboxyl moiety.

19. The method of claim 18, wherein the protecting group is selected from the group consisting of N-Methyl, N-Ethyl, N-Triphenyl, N-Propyl, N-Isopropyl, N-tertiary butyl, and other functional groups.

20. A method of producing the composition of claim 1, the method comprising conjugating the thyroid hormone or thyroid hormone analog to the polymer via the linker prior to forming the nanoparticle.

21. The method of claim 20, wherein the thyroid hormone or thyroid hormone analog is selected from the group consisting of T4, T3, T4 or T3 N-Methyl, T4 or T3 N-Ethyl, T4 or T3 N-Triphenyl, T4 or T3 N-Propyl, T4 or T3 N-Isopropyl, T4 or T3-N-Tertiary butyl, GC-1, DIPTA, Tetrac and Triac.

22. The method of claim 20, wherein the linker is between 4 and 15 atoms long.

23. The method of claim 20 wherein the polymer is selected from the group consisting of polyvinyl alcohol (PVA), acrylic acid ethylene co-polymer, polyethylene glycol (PEG), methoxypolyethylene glycol-poly(lactide-co-glycolide), polyacrylic acid, polylactic acid, agarose, PEO, m-PEG, PLLA, PGA, poly-L-lysine, Human Serum Albumin, cellulose derivatives, carbomethoxy/ethyl/hydroxypropyl, hyaluronic acid, folate linked cyclodextrin dextran, sarcosine/amino acid spaced polymer, alginate, carrageenan, poly lactic acid pectin/chitosan, chitosan, dextran, collagen, polyamine, poly aniline, poly alanine, polytrytophan, poly tyrosine, polylactide-co-glycolide, poly(lactide co-glycolic acid) (PLGA), polylysyl glycolide, polyglycolide, polylactide, or co-polymers thereof.

24. The method of claim 20 wherein the amount of thyroid hormone or thyroid hormone analog in the nanoparticle is between 0.1 and 25%.

25. The method of claim 20, wherein the thyroid hormone or analogs thereof have a protecting group at the NH2 moiety or at the carboxyl moiety.

26. The method of claim 25, wherein the protecting group is selected from the group consisting of N-Methyl, N-Ethyl, N-Triphenyl, N-Propyl, N-Isopropyl, N-tertiary butyl, and other functional groups.

27. A pro-angiogenic formulation comprising the composition of claim 1 and a pharmaceutically acceptable carrier, wherein the thyroid hormone or thyroid hormone analog is selected from the group consisting of T4, T3, T4 or T3 N-Methyl, T4 or T3 N-Ethyl, T4 or T3 N-Triphenyl, T4 or T3 N-Propyl, T4 or T3 N-Isopropyl, T4 or T3 N-Tertiary butyl, GC-1, and DIPTA.

28. The formulation of claim 27, further comprising one or more biologically active substances selected from the group consisting of TGF-beta, basic fibroblast growth factor (FGF2), epithelial growth factor (EGF), insulin-like growth factor-1 (IGF-1), transforming growth factors alpha and beta (TGF-α and β), nerve growth factor (NGF), platelet-derived growth factor (PDGF), vascular endothelial growth factor/vascular permeability factor (VEGF/VPF), anti-virals, anti-bacterials, antiinflammatory, immuno-suppressants, analgesics, vascularizing agents, and cell adhesion molecules.

29. An anti-angiogenic formulation comprising the composition of claim 1 and a pharmaceutically acceptable carrier, wherein the thyroid hormone analog is selected from the group consisting of Tetrac and Triac.

30. The formulation of claim 29, further comprising one or more chemotherapeutic drugs selected from a group consisting of doxorubicin, etoposide, cyclophosphamide, 5-fluorouracil, cisplatin, trichostatin A, paclitaxel, gemcitabine, taxotere, cisplatinum, carboplatinum, irinotecan, topotecan, adriamycin, bortezomib, and atoposide.

31. A combination therapy comprising the steps of:
administering the composition of claim 1 and at least one compound selected from the group consisting of thyrotropin (TSH), recombinant human TSH and radioiodine.

* * * * *

UNITED STATES PATENT AND TRADEMARK OFFICE
CERTIFICATE OF CORRECTION

PATENT NO. : 9,220,788 B2
APPLICATION NO. : 12/816287
DATED : December 29, 2015
INVENTOR(S) : Paul J. Davis et al.

It is certified that error appears in the above-identified patent and that said Letters Patent is hereby corrected as shown below:

Title page

Item (56)/references, page 3 (Col. 1 line 33), please change "Endicrinology" to --Endocrinology--

Item (56)/references, page 6 (Col. 1 line 55), please change "Steriods" to --Steroids--

Item (56)/references, page 6 (Col. 2 line 1), please change "1dentification" to --Identification--

Item (56)/references, page 8 (Col. 2 line 5), please change "anit-epidermal" to --anti-epidermal--

Item (56)/references, page 8 (Col. 2 line 50), please change "pages, May 2008" to --pages.--

Specification

Column 2, line 55, please change "that this" to --that--

Column 9, line 4, please change "anti-inflammatory" to --anti-inflammatories,--

Column 17, line 28, please change "correction of" to --correlation of--

Signed and Sealed this
Fifth Day of July, 2016

Michelle K. Lee
*Director of the United States Patent and Trademark Office*

CERTIFICATE OF CORRECTION (continued)
U.S. Pat. No. 9,220,788 B2

Specification

Column 89, line 36, please change
"5 minutes" to --5 minute--

Column 89, line 66, please change
"5 minutes" to --5 minute--

Column 101, line 46, please change
"with eposxy" to --with epoxy--

Column 101, line 48, please change
"expoxy" to --epoxy--

Column 105, line 1, please change
"Steriods" to --Steroids--

Column 107, line 34, please change
"37 C" to --37 C.--

Claims

Column 123, line 46 (claim 8 line 8), please change
"anti-inflammatory" to --anti-inflammatories,--

Column 125, line 16 (claim 28 line 9), please change
"antiinflammatory" to --anti-inflammatories,--